US012466863B2

(12) United States Patent
Yamanaka et al.

(10) Patent No.: US 12,466,863 B2
(45) Date of Patent: *Nov. 11, 2025

(54) NUCLEAR REPROGRAMMING FACTOR AND INDUCED PLURIPOTENT STEM CELLS

(71) Applicant: Kyoto University, Kyoto (JP)

(72) Inventors: Shinya Yamanaka, Kyoto (JP); Kazutoshi Takahashi, Kyoto (JP); Masato Nakagawa, Kyoto (JP)

(73) Assignee: Kyoto University, Kyoto (JP)

( * ) Notice: Subject to any disclaimer, the term of this patent is extended or adjusted under 35 U.S.C. 154(b) by 1122 days.

This patent is subject to a terminal disclaimer.

(21) Appl. No.: 17/445,282

(22) Filed: Aug. 17, 2021

(65) Prior Publication Data

US 2022/0048963 A1 Feb. 17, 2022

Related U.S. Application Data

(63) Continuation of application No. 15/474,855, filed on Mar. 30, 2017, now abandoned, which is a continuation of application No. 12/289,873, filed on Nov. 6, 2008, now abandoned, which is a continuation-in-part of application No. 12/213,035, filed on Jun. 13, 2008, now Pat. No. 8,278,104, which is a continuation-in-part of application No. PCT/JP2006/324881, filed on Dec. 6, 2006.

(60) Provisional application No. 60/996,289, filed on Nov. 9, 2007, provisional application No. 61/001,108, filed on Oct. 31, 2007.

(30) Foreign Application Priority Data

Dec. 13, 2005 (JP) ................................ 2005-359537

(51) Int. Cl.
*C12N 15/86* (2006.01)
*C07K 14/47* (2006.01)
*C12N 5/074* (2010.01)

(52) U.S. Cl.
CPC ........ *C07K 14/4702* (2013.01); *C12N 5/0696* (2013.01); *C12N 2501/60* (2013.01); *C12N 2501/602* (2013.01); *C12N 2501/603* (2013.01); *C12N 2501/604* (2013.01); *C12N 2501/606* (2013.01); *C12N 2510/00* (2013.01); *C12N 2740/15043* (2013.01)

(58) Field of Classification Search
CPC ............. C07K 14/4702; C12N 5/0696; C12N 2501/60; C12N 2501/602; C12N 2501/603; C12N 2501/604; C12N 2501/606; C12N 2510/00; C12N 2740/15043
See application file for complete search history.

(56) References Cited

U.S. PATENT DOCUMENTS

| | | | |
|---|---|---|---|
| 4,650,764 | A | 3/1987 | Temin et al. |
| 4,861,719 | A | 8/1989 | Miller |
| 4,937,190 | A | 6/1990 | Palmenberg et al. |
| 5,225,348 | A | 7/1993 | Nagata et al. |
| 5,266,491 | A | 11/1993 | Nagata et al. |
| 5,268,290 | A | 12/1993 | Hasegawa et al. |
| 5,288,514 | A | 2/1994 | Ellman |
| 5,324,645 | A | 6/1994 | Takahara et al. |
| 5,449,614 | A | 9/1995 | Danos et al. |
| 5,519,134 | A | 5/1996 | Acevedo et al. |
| 5,525,735 | A | 6/1996 | Gallop et al. |
| 5,549,974 | A | 8/1996 | Holmes |
| 5,591,624 | A | 1/1997 | Barber et al. |
| 5,637,456 | A | 6/1997 | Roth et al. |
| 5,652,122 | A | 7/1997 | Frankel et al. |
| 5,674,980 | A | 10/1997 | Frankel |
| 5,707,618 | A | 1/1998 | Armentano et al. |
| 5,716,832 | A | 2/1998 | Barber et al. |
| 5,744,320 | A | 4/1998 | Sherf et al. |

(Continued)

FOREIGN PATENT DOCUMENTS

| | | | |
|---|---|---|---|
| AU | 2008/201280 A1 | 4/2008 | |
| CN | 101250502 A | 8/2008 | |

(Continued)

OTHER PUBLICATIONS

Maherali and Hochedlinger et al. "Guidelines and techniques for the generation of induced pluripotent stem cells." Cell Stem Cell. Dec. 4, 2008;3(6):595-605. (Year: 2008).*

(Continued)

*Primary Examiner* — Titilayo Moloye

(74) *Attorney, Agent, or Firm* — Knobbe, Martens, Olson & Bear, LLP

(57) ABSTRACT

A recombinant vector for producing an induced pluripotent stem cell, including an Oct family gene, a Klf family gene, and a Myc family gene, wherein the genes are inserted in the vector and an induced pluripotent stem cell including the recombinant vector. Also disclosed is a method for preparing a recombinant vector for producing an induced pluripotent stem cell, including inserting each of the three genes into a vector such that the genes are capable of expression. Also disclosed are a first recombinant vector for preparing a second recombinant vector for producing an induced pluripotent stem cell, said first recombinant vector including at least two of the following four genes: an Oct family gene, a Klf family gene, a Myc family gene and a Sox family gene. Also disclosed is a method for preparing the first recombinant vector, including inserting the at least two genes into a vector.

23 Claims, 70 Drawing Sheets

Specification includes a Sequence Listing.

(56) References Cited

U.S. PATENT DOCUMENTS

| | | | |
|---|---|---|---|
| 5,817,491 | A | 10/1998 | Yee et al. |
| 5,817,492 | A | 10/1998 | Saito et al. |
| 5,830,725 | A | 11/1998 | Nolan et al. |
| 5,834,256 | A | 11/1998 | Finer et al. |
| 5,858,740 | A | 1/1999 | Finer et al. |
| 5,910,434 | A | 6/1999 | Rigg et al. |
| 5,955,331 | A | 9/1999 | Danos et al. |
| 6,013,517 | A | 1/2000 | Respess et al. |
| 6,017,735 | A | 1/2000 | O'hare |
| 6,017,761 | A | 1/2000 | Rigg et al. |
| 6,025,192 | A | 2/2000 | Beach et al. |
| 6,140,111 | A | 10/2000 | Riviere et al. |
| 6,146,874 | A | 11/2000 | Zolotukhin et al. |
| 6,153,432 | A | 11/2000 | Halvorsen et al. |
| 6,153,745 | A | 11/2000 | Williams et al. |
| 6,203,975 | B1 | 3/2001 | Wilson et al. |
| 6,251,398 | B1 | 6/2001 | O'Hare et al. |
| 6,255,071 | B1 | 7/2001 | Beach et al. |
| 6,312,948 | B1 | 11/2001 | Cohen-haguenauer |
| 6,312,949 | B1 | 11/2001 | Sakurada et al. |
| 6,333,195 | B1 | 12/2001 | Respess et al. |
| 6,365,352 | B1 | 4/2002 | Yerramilli et al. |
| 6,395,546 | B1 | 5/2002 | Zobel et al. |
| 6,451,595 | B1 | 9/2002 | Kim et al. |
| 6,485,959 | B1 | 11/2002 | Demetriou et al. |
| 6,521,453 | B1 | 2/2003 | Crameri et al. |
| 6,521,455 | B2 | 2/2003 | O'Hare et al. |
| 6,605,275 | B1 | 8/2003 | Boyse et al. |
| 6,660,514 | B1 | 12/2003 | Zolotukhin et al. |
| 6,773,920 | B1 | 8/2004 | Dalby et al. |
| 6,833,269 | B2 | 12/2004 | Carpenter |
| 6,835,567 | B1 | 12/2004 | Sah et al. |
| 6,841,535 | B2 | 1/2005 | Divita et al. |
| 6,872,528 | B2 | 3/2005 | Klatzmann et al. |
| 6,875,578 | B2 | 4/2005 | Giuliano et al. |
| 6,881,825 | B1 | 4/2005 | Robbins et al. |
| 6,910,434 | B2 | 6/2005 | Lundgren et al. |
| 6,995,009 | B1 | 2/2006 | Kitamura et al. |
| 7,029,913 | B2 | 4/2006 | Thomson |
| 7,030,292 | B2 | 4/2006 | Yan et al. |
| 7,070,994 | B2 | 7/2006 | Barber et al. |
| 7,250,255 | B2 | 7/2007 | Yamanaka |
| 7,439,064 | B2 | 10/2008 | Thomson et al. |
| 8,048,999 | B2 | 11/2011 | Yamanaka et al. |
| 8,058,065 | B2 | 11/2011 | Yamanaka et al. |
| 8,129,187 | B2 | 3/2012 | Yamanaka et al. |
| 8,211,697 | B2 | 7/2012 | Sakurada et al. |
| 8,257,941 | B2 | 9/2012 | Sakurada et al. |
| 8,298,825 | B1 | 10/2012 | Hochedlinger et al. |
| 8,440,461 | B2 | 5/2013 | Thomson et al. |
| 9,499,797 | B2 | 11/2016 | Yamanaka et al. |
| 9,714,433 | B2 | 7/2017 | Sakurada et al. |
| 2002/0142397 | A1 | 10/2002 | Collas et al. |
| 2003/0044976 | A1 | 3/2003 | Dominko et al. |
| 2004/0137460 | A1 | 7/2004 | Yamanaka et al. |
| 2004/0235031 | A1 | 11/2004 | Schultz et al. |
| 2005/0019801 | A1 | 1/2005 | Rubin et al. |
| 2005/0026133 | A1 | 2/2005 | Nakatsuji et al. |
| 2005/0079606 | A1 | 4/2005 | Tamaki et al. |
| 2005/0130144 | A1 | 6/2005 | Nakatsuji et al. |
| 2005/0162419 | A1 | 7/2005 | Kim et al. |
| 2006/0030041 | A1 | 2/2006 | Furcht et al. |
| 2006/0084172 | A1 | 4/2006 | Muller et al. |
| 2006/0088599 | A1 | 4/2006 | Prasad et al. |
| 2006/0095319 | A1 | 5/2006 | Cardwell |
| 2006/0110830 | A1 | 5/2006 | Dominko et al. |
| 2006/0222636 | A1 | 10/2006 | Rambukkana |
| 2006/0246064 | A1 | 11/2006 | Boyle |
| 2006/0292620 | A1 | 12/2006 | Yamanaka et al. |
| 2007/0033061 | A1 | 2/2007 | Patten et al. |
| 2007/0053884 | A1 | 3/2007 | Suda et al. |
| 2007/0155013 | A1 | 7/2007 | Akaike et al. |
| 2007/0202592 | A1 | 8/2007 | Kitagawa et al. |
| 2007/0254884 | A1 | 11/2007 | Chen et al. |
| 2007/0269790 | A1 | 11/2007 | Amit et al. |
| 2008/0003560 | A1 | 1/2008 | Nakatsuji et al. |
| 2008/0076176 | A1 | 3/2008 | Dominko et al. |
| 2008/0085555 | A1 | 4/2008 | Asahara et al. |
| 2008/0132803 | A1 | 6/2008 | Friedlander |
| 2008/0171358 | A1 | 7/2008 | Perrault |
| 2008/0171385 | A1 | 7/2008 | Bergendahl et al. |
| 2008/0206865 | A1 | 8/2008 | Zhang et al. |
| 2008/0233610 | A1 | 9/2008 | Thomson et al. |
| 2008/0274914 | A1 | 11/2008 | Yamanaka et al. |
| 2008/0280362 | A1 | 11/2008 | Jaenisch et al. |
| 2008/0293143 | A1 | 11/2008 | Lin et al. |
| 2008/0299548 | A1 | 12/2008 | Yamanaka |
| 2009/0047263 | A1 | 2/2009 | Yamanaka et al. |
| 2009/0068742 | A1 | 3/2009 | Yamanaka |
| 2009/0191171 | A1 | 7/2009 | Mack |
| 2009/0227032 | A1 | 9/2009 | Yamanaka et al. |
| 2009/0246875 | A1 | 10/2009 | Yamanaka et al. |
| 2009/0304646 | A1 | 12/2009 | Sakurada et al. |
| 2010/0003757 | A1 | 1/2010 | Mack |
| 2010/0021437 | A1 | 1/2010 | Isacson |
| 2010/0062533 | A1 | 3/2010 | Yamanaka |
| 2010/0062534 | A1 | 3/2010 | Hochedlinger |
| 2010/0075421 | A1 | 3/2010 | Yamanaka |
| 2010/0093090 | A1 | 4/2010 | Deng |
| 2010/0105100 | A1 | 4/2010 | Sakurada et al. |
| 2010/0120069 | A1 | 5/2010 | Sakurada et al. |
| 2010/0144031 | A1 | 6/2010 | Jaenisch |
| 2010/0184051 | A1 | 7/2010 | Hochedlinger |
| 2010/0184227 | A1 | 7/2010 | Thomson |
| 2010/0210014 | A1 | 8/2010 | Yamanaka |
| 2010/0216236 | A1 | 8/2010 | Yamanaka |
| 2010/0221827 | A1 | 9/2010 | Jaenisch |
| 2010/0233804 | A1 | 9/2010 | Zhou |
| 2010/0240090 | A1 | 9/2010 | Sakurada et al. |
| 2010/0267135 | A1 | 10/2010 | Sakurada et al. |
| 2010/0279404 | A1 | 11/2010 | Yamanaka et al. |
| 2011/0014164 | A1 | 1/2011 | Huangfu et al. |
| 2011/0039332 | A1 | 2/2011 | Sakurada et al. |
| 2013/0059386 | A1 | 3/2013 | Yamanaka et al. |
| 2014/0057355 | A1 | 2/2014 | Thomson et al. |
| 2015/0072417 | A1 | 3/2015 | Yamanaka et al. |

FOREIGN PATENT DOCUMENTS

| | | | |
|---|---|---|---|
| CN | 101550428 | A | 10/2009 |
| EP | 1254211 | A1 | 11/2002 |
| EP | 1384775 | A1 | 1/2004 |
| EP | 1403366 | A1 | 3/2004 |
| EP | 1970446 | A1 | 9/2008 |
| EP | 2096169 | A1 | 9/2009 |
| EP | 2213727 | A1 | 4/2010 |
| JP | 2-227075 | | 9/1990 |
| JP | 2002-065261 | A | 3/2002 |
| JP | 2002-511248 | A | 4/2002 |
| JP | 2003-009854 | A | 1/2003 |
| JP | 2004-161682 | A | 6/2004 |
| JP | 2005-095027 | A | 4/2005 |
| JP | 2005-198546 | | 7/2005 |
| JP | 2006-526409 | | 11/2006 |
| JP | 2008-515435 | | 5/2008 |
| JP | 2008-283972 | A | 11/2008 |
| WO | WO 1995/010619 | A2 | 4/1995 |
| WO | WO 1995/010619 | A3 | 7/1995 |
| WO | WO 1997/005265 | A1 | 2/1997 |
| WO | WO 1998/02529 | A1 | 1/1998 |
| WO | WO 1999/055841 | A2 | 11/1999 |
| WO | WO 1999/64568 | A1 | 12/1999 |
| WO | WO 2000/018885 | A1 | 4/2000 |
| WO | WO 2000/023567 | A2 | 4/2000 |
| WO | WO 2000/27995 | A1 | 5/2000 |
| WO | WO 2000/023567 | A3 | 7/2000 |
| WO | WO 2000/073423 | A1 | 12/2000 |
| WO | WO 2001/021767 | A2 | 3/2001 |
| WO | WO 2001/34776 | A1 | 5/2001 |
| WO | WO 2001/51616 | A2 | 7/2001 |
| WO | WO 2001/021767 | A3 | 8/2001 |
| WO | WO 2001/81549 | A2 | 11/2001 |
| WO | WO 2001/098463 | A1 | 12/2001 |
| WO | WO 2002/000871 | A2 | 1/2002 |

(56) References Cited

FOREIGN PATENT DOCUMENTS

| | | | |
|---|---|---|---|
| WO | WO 2002/061033 | A2 | 8/2002 |
| WO | WO 2002/000871 | A3 | 10/2002 |
| WO | WO 2002/086129 | A1 | 10/2002 |
| WO | WO 2002/086134 | A2 | 10/2002 |
| WO | WO 2002/097090 | A1 | 12/2002 |
| WO | WO 2003/018780 | A1 | 3/2003 |
| WO | WO 2003/042405 | A2 | 5/2003 |
| WO | WO 2002/086134 | A3 | 12/2003 |
| WO | WO 2004/081205 | A1 | 9/2004 |
| WO | WO 2005/017149 | | 2/2005 |
| WO | WO 2005/035741 | A1 | 4/2005 |
| WO | WO 2005/080598 | A1 | 9/2005 |
| WO | WO 2005/090557 | A1 | 9/2005 |
| WO | WO 2006/035741 | A1 | 4/2006 |
| WO | WO 2006/083331 | | 8/2006 |
| WO | WO 2006/084229 | A2 | 8/2006 |
| WO | WO 2006/088867 | A2 | 8/2006 |
| WO | WO 2007/014162 | | 2/2007 |
| WO | WO 2007/019398 | A1 | 2/2007 |
| WO | WO 2007/026255 | A2 | 3/2007 |
| WO | WO 2007/054720 | A1 | 5/2007 |
| WO | WO 2007/069666 | A1 | 6/2007 |
| WO | WO 2007/097494 | A1 | 8/2007 |
| WO | WO 2008/030610 | A2 | 3/2008 |
| WO | WO 2008/035110 | A1 | 3/2008 |
| WO | WO 2008/038148 | A2 | 4/2008 |
| WO | WO 2008/089351 | A1 | 7/2008 |
| WO | WO 2008/105566 | A1 | 9/2008 |
| WO | WO 2008/105630 | A1 | 9/2008 |
| WO | WO 2008/116213 | A1 | 9/2008 |
| WO | WO 2008/118820 | A2 | 10/2008 |
| WO | WO 2008/124133 | A1 | 10/2008 |
| WO | WO 2008/118820 | A3 | 11/2008 |
| WO | WO 2008/150814 | A2 | 12/2008 |
| WO | WO 2008/151058 | A2 | 12/2008 |
| WO | WO 2008/151058 | A3 | 1/2009 |
| WO | WO 2009/006930 | A1 | 1/2009 |
| WO | WO 2009/006997 | A1 | 1/2009 |
| WO | WO 2009/007852 | A2 | 1/2009 |
| WO | WO 2008/150814 | A3 | 2/2009 |
| WO | WO 2009/023161 | A1 | 2/2009 |
| WO | WO 2009/032194 | A1 | 3/2009 |
| WO | WO 2009/032456 | A2 | 3/2009 |
| WO | WO 2009/032456 | A3 | 4/2009 |
| WO | WO 2009/057831 | A1 | 5/2009 |
| WO | WO 2009/061442 | A1 | 5/2009 |
| WO | WO 2009/067563 | A1 | 5/2009 |
| WO | WO 2009/007852 | A3 | 8/2009 |
| WO | WO 2009/096614 | A1 | 8/2009 |
| WO | WO 2009/102983 | A2 | 8/2009 |
| WO | WO 2009/115295 | A1 | 9/2009 |
| WO | WO 2009/133971 | A1 | 11/2009 |
| WO | WO 2009/102983 | A3 | 12/2009 |
| WO | WO 2009/144008 | A1 | 12/2009 |
| WO | WO 2009/149233 | A1 | 12/2009 |
| WO | WO 2010/013359 | A1 | 2/2010 |
| WO | WO 2010/048567 | A1 | 4/2010 |

OTHER PUBLICATIONS

Kim et al. "Reprogrammed pluripotent stem cells from somatic cells." Int J Stem Cells. Jun. 2011;4(1):1-8. (Year: 2011).*
Extended European Search Report in European Patent Application No. 18174008.5 issued Sep. 24, 2018.
Keller, Gordon, "Embryonic stem cell differentiation: emergence of a new era in biology and medicine," Genes & Development 19:1129-1155 (2005).
First Examination Report in Indian Patent Application No. 1636/CHENP/2009 issued Nov. 30, 2018.
Hearing Notice issued in Indian Patent Application No. 1636/CHENP/2009 issued Sep. 2, 2019.
Golan-Mashiach, M., et al., "Design principle of gene expression used by human stem cells: implication for pluripotency," The FASEB Journal, Published online on Oct. 21, 2004.
Zhang et al. "Sox2, a key factor in the regulation of pluripotency and neural differentiation ." World J Stem Cells Jul. 26, 2014; 6(3): 305-311 (Year: 2014).
Chen et al. "BMPs functionally replace Klf4 and support efficient reprogramming of mouse fibroblasts by Oct4 alone." Cell Research (2011) 21:205-212 (Year: 2011).
Wei et al. "Klf4 interacts directly with Oct4 and Sox2 to promote reprogramming." Stem Cells .Dec. 2009;27(12):2969-78. doi: 10.1002/stem.231. (Year: 2009).
Schmidt et al. "The roles of the reprogramming factors Oct4, Sox2 and Klf4 in resetting the somatic cell epigenome during induced pluripotent stem cell generation." Genome Biol. 2012; 13(10): 251. (Year: 2012).
Yamanaka, et al., Nuclear Reprogramming to a Pluripotent State by Three Approaches Nature 465(7299):704-712, Jun. 10, 2010.
Maherali et al. "Guidelines and techniques for the generation of induced pluripotent stem cells." Cell Stem Cell. Dec. 4, 2008;3(6):595-605. (Year: 2008).
Kang et al. "Disease-specific pluripotent stem cells." Korean J Pediatr. Aug. 2010;53(8):786-9. (Year: 2010).
Li et al. "Advances in understanding the cell types and approaches used for generating induced pluripotent stem cells." J Hematol Oneal. Jul. 19, 2014;7:50.pp. 1-18. (Year: 2014).
Raab et al. "A Comparative View on Human Somatic Cell Sources for iPSC Generation." Stem Cells Int. 2014;2014:768391 (Year: 2014).
Mosteiro et al. "Tissue damage and senescence provide critical signals for cellular reprogramming in vivo." Science. Nov. 25, 2016; 354(6315). (Year: 2016).
Johnson et al. "Understanding pluripotency—how embryonic stem cells keep their options open." Mol Hum Reprod. Sep. 2008;14(9): 513-20 (Year: 2008).
Au et al., 1978 "Cytogenetic toxicity of gentian violet and crystal violet on mammalian cells in vitro" *Mutation Research*, 58; 269-276.
Dhanaraj et al., 1996 "Characterization of c-myc-transformed rat fibroblasts resistant to apoptosis induced by growth factor deprivation" *Experimental Cell Research*, 224; 52-62.
Ekwall, et al., "Chapter 7: Toxicity tests with mammalian cell cultures" in *Short-term Toxicity Tests for Non-genotoxic Effects*, edited by P Bourdeau et al., 1990, Scope, pp. 75-98.
Examination Report dated Jun. 1, 2016, in corresponding European patent application No. 10 154 821.2-1410.
Gandarillas et al., 1997 "c-Myc promotes differentiation of human epidermal stem cells" *Genes & Development*, 11; 2869-2882.
Grignani et al., 1990 "Negative autoregulation of c-myc gene expression is inactivated in transformed cells" *The EMBO Journal* 9(12); 3913-3922.
Hearing Notice dated Oct. 5, 2017 in related Indian patent application No. 8308/DELNP/2009.
Jain et al., 2001 "Cell therapy attenuates deleterious ventricular remodeling and improves cardiac performance after myocardial infarction" *Circulation*, 103; 1920-1927.
Niwa, H. 2007 "How is pluripotency determined and maintained?" *Development*, 134(4); 635-646.
Office Action dated Dec. 30, 2015 in related U.S. Appl. No. 14/195,698.
Perkins et al., 1997 "Anemia and perinatal death results from loss of the murine ecotropic retrovirus reception mCAT-1" *Genes & Development* 11: 914-925.
Roche et al., 2004 "Generation of new islets from stem cells" *Cell Biochemistry and Biophysics*, pp. 113-123.
Soria et al., 2001 "From stem cells to beta cells: new strategies in cell therapy of diabetes mellitus" *Diabetologia*, 44; 407-415.
Summons to Attend Oral Proceedings dated Sep. 4, 2017 in corresponding European Patent Appln.No. 10154821.2-1410.
Summons to Attend Oral Proceedings dated Sep. 6, 2017 in corresponding European Patent Appln.No. 10154817.0-1410.
Yamanaka, et al., 2006 "Induction of Pluripotent Stem Cells From Mouse Fibroblast Cultures" *Protein, Nucleic Acid and Enzyme* 51(15):2346-51.
Extended European Search Report for European Patent Application No. 09738908.4, dated Jan. 28, 2013.

(56) References Cited

OTHER PUBLICATIONS

European Office Action for Application No. 07856194.1 dated May 9, 2012.
Office Action issued in connection with European Patent Application No. EP 10154819.6, Nov. 8, 2013.
Office Action issued in European Patent Application No. 10154821.2, on Jun. 1, 2016.
Office Action issued in GB0922013.8, dated Aug. 4, 2011.
Office Action issued in Indian Patent Application No. 3564/CHENP/2008, dated Dec. 27, 2016.
Office Action mailed on Mar. 13, 2012, issued in connection with Japanese Patent Application No. 2007-550210.
Office Action dated Jun. 20, 2007, issued in connection with U.S. Appl. No. 10/861,040.
Office Action dated Oct. 4, 2010, issued in connection with U.S. Appl. No. 12/157,967.
Alberts, et al., Molecular Biology of the Cell, Fourth Ed., Garland Science, 2002, p. 22.
Aoi, T., et al., Generation of Pluripotent Stem Cells From Adult Mouse Liver and Stomach Cells, Science, vol. 321, pp. 699-702, Corrected Aug. 1, 2008.
Asai, et al., Modulation of Tumor Immunogenicity of Rat Glioma Cells by s-Mys Expression: Eradication of Rat Gliomas in Vivo, Cell Growth & Differentiation 5(11):1153-1158, Nov. 1984.
Catalog of ES Cell Culture Medium, Cosmo Bio News 49:5, 2005.
Chiba Medical Journal 84(1):17, Feb. 2006.
Clerc, et al., The B-cell-Specific Oct-2 Protein Contains POU box-and Homeo Box-Type Domains, Genes Dev. 2(12A):1570-1581, Dec. 1988.
Cowan et al., Nuclear Reprogramming of Somatic Cells After Fusion With Human Embryonic Stem Cells, Science 309:1369-73, 2005.
Cyranoski et al., Simple Switch Turns Cells Embryonic (Correction), Nature, Jun. 21, 2007, vol. 447, pp. 897.
Duinsbergen (Experimental Cell Res. Jul. 9, 2008, vol. 314, p. 3255-3263).
Ekwall et al., "Toxicity Tests with Mammalian Cell Cultures," Short-term Toxicity Tests for Non-genotoxic Effects, Edited by P. Bourdeau et al., Scope, John Wiley & Sons Ltd., pp. 75-97 (1990).
Eminli (Stem Cells, Jul. 17, 2008, vol. 26, p. 2467-2474).
Feng (Cell Stem Cell, Apr. 3, 2009, vol. 4, p. 301-312).
Gandarillas et al., "c-Myc promotes differentiation of human epidermal stem cells," Genes & Dev., vol. 11, pp. 2869-2882 (1997). (Retrieved from the Internet: URL:http://genesdev.cshlp.org/content/11/21/2869.full [retrieved on May 18, 2016]).
Grignani et al., "Negative autoregulation of c-myc gene expression is inactivated in transformed cells," The EMBO Journal, vol. 9(12), pp. 3913-3922 (1990).
Ingvarsson, et al., Structure and Expression of B-myc, A New Member of the myc Gene Family, Mol. Cell. Biol. 8(8):3168-3174, Aug. 1988.
Kanai-Azuma, et al., "Depletion Of Definitive Gut Endoderm In Sox17-Null Mutant Mice" Development (2002) 129: 2367-2379.
Kim et al., Pluripotent Stem Cells Induced From Adult Neural Stem Cells by Reprogramming with Two Factors, Nature 454:646-650, 2008.
Klf1 description, Wikipedia, 2014.
Lee, Molecular and Cell. Biol., Oct. 2004, vol. 24, No. 19, p. 8428-8436.
Luke, G.A., 2012, Translating 2A Research into Practice, Innovations in Biotechnology, Agbo, E.C. (Ed.), InTech, available from: http://www.intechopen.com/booksinnovations-in-biotechnology/translating/translating-2a-research, 2012.
Mimeault et al. Concise Review: Recent Advances on the Significance of Stem Cells in Tissue Regeneration and Cancer Therapies. Stem Cells, 2006, vol. 24, pp. 2319-2345.
Niwa, et al., Phenotypic Complementation Establishes Requirements for Specific POU Domain and Generic Transactivation Function of Oct-3/4 in Embryonic Stem Cells, Molecular and Cellular Biology, 22:1526-1536, 2002.
Okita et al., An Efficient Nonviral Method to Generate Integration-Free Human-Induced Pluripotent Stem Cells from Cord blood and Peripheral Blood Cells. Stem Cells, vol. 31, pp. 458-466 (2013).
Oshima et al., "Mechanosensitive Hair Cell-like Cells from Embryonic and Induced Pluripotent Stem Cells," Cell, vol. 141, pp. 704-716 (May 14, 2010).
Park, In-Hyun, et al., "Reprogramming of Human Somatic Cells to Pluripotency With Defined Factors," Nature 451:141-146, 2008.
Perkins et al. Anemia and perinatal death result from loss of the murine ecotropic retrovirus receptor mCAT-1.Genes & Development, 1997, vol. 11, pp. 914-925.
Rybkin, et al., Journal of Biological Chemistry 278:15927-15934, 2003.
Rybouchkin, A., et al., Role of Histone Acetylation in Reprogramming of Somatic Nuclei Following Nuclear Transfer, Biology of Reproduction 74:1083-1089, 2006.
Schöler, et al., A Family of Octamer-Specific Proteins Present During Mouse Embryogenesis: Evidence for Germline-Specific Expression of an Oct Factor, Embo J. 8(9):2543-2550, Sep. 1989.
Sperger et al., "Gene expression patterns in human embryonic stem cells and human pluripotent germ cell tumors," PNAS, vol. 100(23), p. 13350-13355 (Nov. 11, 2003).
Stoykova, et al., Mini-Oct and Oct-2c: Two Novel, Functionally Diverse murine Oct-2 Gene Products are Differentially Expressed in the CNS, Neuron 8(3):541-58, Mar. 1992.
Tomioka et al., "Identification of Sox-2 regulatory region which is under the control of Oct-3/4-Sox-2 complex," Nucleic Acids Research, vol. 30(14), pp. 3202-3213 (2002).
Ulloa-Montoya et al., "Culture Systems for Pluripotent Stem Cells," Journal of Bioscience And Bioengineering, vol. 100(1), pp. 12-27 (2005).
van Viet, et al., Human KLF17 is a New Member of the Sp/KLF Family of Transcription Factors, Genomics 87(4):474-482, Apr. 2006; Epub Feb. 7, 2006.
Vennstrom, et al., Isolation and Characterization of c-myc, a Cellular Homolog of the Oncogene (v-myc) of Avian Myelocytomatosis Virus Strain 29, J. of Virol. 42(3):773-779, Jun. 1982.
Wei et al., "Sumoylation of Oct4 Enhances Its Stability, DNA Binding, and Transactivation," Journal of Biological Chemistry, vol. 282(29), pp. 21551-21560 (2007).
Wernig et al., c-Myc is Dispensable for Direct Reprogramming of Mouse Fibroblasts, Cell Stem Cell 2(1):10-12 (Jan. 2008), published online Dec. 13, 2007.
Yan et al. (Stem Cells and Development, 2010, vol. 19, No. 4, p. 469-480).
Ying, microRNA, Jikken Purotokoru (microRNA Experimental Protocol), Yodosha Col. Ltd. 2008 pp. 2035.
Zhao et al., "A human peripheral blood monocyte-derived subset acts as pluripotent stem cells," PNAS, vol. 100(5), pp. 2426-2431 (Mar. 4, 2003).
Zhu et al., "Three-Color Flow Cytometry Analysis of Tricistronic Expression of eBFP, eGFP, and eYFP Using EMCV-IRES Linkages," Cytometry, vol. 37, pp. 51-59 (1999).
Extended European Search Report issued in connection with European Patent Application No. EP 06834636.0, Mar. 11, 2009.
Extended European Search Report mailed on Feb. 21, 2012 in corresponding European patent app. No. 09763772.2 in 6 pages.
Extended European Search Report issued in connection with European Patent Application No. EP 10154817.0, Jun. 10, 2010.
Extended European Search Report issued in connection with European Patent Application No. 10154819.6, Jun. 10, 2010.
Extended European Search Report issued in connection with European Patent Application No. EP 10154821.2, Jun. 10, 2010.
International Search Report issued with respect to PCT/JP2009/058873, mailed Jul. 7, 2009.
Examination Report issued in Australian Patent Application No. 2006325975, Apr. 18, 2011.
Office Action dated Feb. 10, 2012, issued in connection with Canadian Patent Application No. 2,632, 142.
Office Action issued in connection with Chinese Patent Application No. 200680048227.7, Sep. 14, 2010.

(56) References Cited

OTHER PUBLICATIONS

Notification of the Second Office Action dated Feb. 24, 2012, issued in connection with Chinese Patent Application No. 200880000834.5, 9 pages.
Official Action issued in connection with Eurasian Patent Application No. 200870046, Nov. 9, 2009.
Official Action issued in connection with Eurasian Patent Application No. 201000858, Jul. 14, 2010.
Office Action issued in connection with European Patent Application No. EP 06834636.0, Apr. 30, 2010.
Office Action issued in connection with European Patent Application No. EP 06834636.0, Oct. 25, 2010.
Notice of Opposition dated May 3, 2012, issued in connection with European Patent Application No. 06834636.0, 32 pages.
Examination Report dated Sep. 28, 2011, issued in connection with European Patent Application No. 07856194.1.
Examination report dated Dec. 11, 2012 and issued to related European application No. 10154817.0.
Examination Report dated Oct. 23, 2012, issued in connection with European Patent Application No. 10154819.6.
Examination Report dated Oct. 15, 2012, issued in connection with European Patent Application No. 10154821.2.
Office Action issued in connection with Israeli Patent Application No. 191903, Aug. 19, 2010.
Office Action issued in connection with Japanese Patent Application No. JP 2009-056747, mailed Jun. 2, 2009.
Office Action issued in connection with Japanese Patent Application No. JP 2009-056748, mailed Jun. 2, 2009.
Official Action issued in connection with Japanese Patent Application No. JP 2009-056748, mailed Nov. 4, 2009.
Official Rejection issued in connection with Japanese Patent Application No. JP 2009-056748, mailed Feb. 23, 2010.
Office Action issued in connection with Japanese Patent Application No. JP 2009-056749, mailed Jun. 4, 2009.
Official Rejection issued in connection with Japanese Patent Application No. JP 2009-056749, mailed Nov. 4, 2009.
Office Action issued in connection with Japanese Patent Application No. JP 2009-056750, mailed Jun. 2, 2009.
Office Action issued in Japanese Patent Application No. 2010-506477, on Apr. 9, 2013.
Office Action issued in connection with New Zealand Patent Application No. 569530, Apr. 20, 2010.
Examination Report dated Feb. 9, 2012, issued in connection with New Zealand Patent Application No. 582018.
Office Action issued in connection with Singapore Patent Application No. 200804231-9, Apr. 13, 2010.
Office Action issued in connection with Singapore Patent Application No. 200901803-7, Jan. 22, 2010.
A reprogramming rush, Editorial, Nature 452:388, Mar. 27, 2008. (Published online Mar. 26, 2008.).
Adachi, et al., Role of SOX2 in Maintaining Pluripotency of Human Embryonic Stem Cells, Genes Cells 15(5):455-70, May 2010.
Adewumi et al., Characterization of Human Embryonic Stem Cell Lines by the International Stem Cell Initiative, Nat. Biotechnol. 25(7):803-16, 2007.
Adhikary, et al., Transcriptional Regulation and Transformation by Myc Proteins, Nat. Rev. Mol. Cell Biol. 6(8):635-45, Aug. 2005.
Akimov, et al., Bypass of Senescence, Immortalization, and Transformation of Human Hematopoietic Progenitor Cells, Stem Cells 23:1423-33, 2005.
Allergucci, et al., Differences Between Human Embryonic Stem Cell Lines, Hum. Reprod. Update 13(2):103-20, Mar.-Apr. 2007.
Altschul, et al., Gapped BLAST and PSI-BLAST: A New Generation of Protein Database Search Programs, Nucleic Acids Research 25(17): 3389-3402, 1997.
Amit, et al., Clonally Derived Human Embryonic Stem Cell Lines Maintain Pluripotency and Proliferative Potential for Prolonged Periods of Culture, Dev. Biol. 227:271-78, 2000.
Amsellem, et al., Ex Vivo Expansion of Human Hematopoietic Stem Cells by Direct Delivery of the HOXB4 Homeoprotein, Nat. Med. 9(11):1423-27, 2003.
Anderson, et al., Transgenic Enrichment of Cardiomyocytes From Human Embryonic Stem Cells, Mol. Ther. 15(11):2027-36, Nov. 2007.
Anisimov, et al., SAGE Identification of Gene Transcripts with Profiled Unique to Pluripotent Mouse R1 Embryonic Stem Cells, Genomics 79(2):69-176, Feb. 2002.
Aoi et al., Generation of Pluripotent Stem Cells From Adult Mouse Liver and Stomach Cells, Science 321(5889):699-702, published online Feb. 14, 2008.
Assady, et al., Insulin Production by Human Embryonic Stem Cells, Diabetes 50(8):16911697, Aug. 2001.
Assou, et al., A Meta-Analysis of Human Embryonic Stem Cells Transcriptome Integrated into a Web-Based Expression Atlas, Stem Cells 25(4):961-73, Apr. 2007.
Avilion, et al., Multipotent Cell Lineages in Early Mouse Development Depend on SOX2 Function, Genes Dev. 17:126-40, 2003.
Bader, et al., Leukemia Inhibitory Factor Modulates Cardiogenesis in Embryoid Bodies in Opposite Fashions, Circ. Res. 86(7):787-94, Apr. 14, 2000.
Bagutti, et al., Differentiation of Embryonal Stem Cells Into Keratinocytes: Comparison of Wild-Type and Beta 1 Integrin-Deficient Cells Dev. Biol. 179(1):184-96, Oct. 10, 1996.
Bang, et al., Deconstructing Pluripotency, Science 320:58-59, 2008.
Barrett, et al., Activation Domains of L-Myc and c-Myc Determine Their Transforming Potencies in Rat Embryo Cells, Mol. Cell. Biol. 12(7):3130-37, 1992.
Barrett, et al., NCBI GEO: Mining Tens of Millions of Expression ProfilesDatabase and Tools Update, Nucleic Acids Res. 35(Database issue):D760-S, Jan. 2007.
Bayani, et al., Multi-Color FISH techniques, Curr. Protoc. Cell Biol., Chapter 22, Unit 22.5, 2004.
Bayer Team Makes Stem Cells From Skin, The Japan Times, Apr. 12, 2008. Available at http://search.japantimes.co.jp/cgi-bin/nn20080412a5.html. Accessed May 19, 2009.
Becker-Hapak, et al., Protein Transduction: Generation of Full-Length Transducible Proteins Using the TAT System, Curr. Protoc. Cell Biol., Chapter 20, Unit 20.2, May 2003.
Belmonte, et al., Induced Pluripotent Stem Cells and Reprogramming: Seeing the Science Through the Hype, Nat. Rev. Genet., 10(12):878-83, Dec. 2009 (Epub Oct. 27, 2009).
Ben-Shushan, et al., Rex-1, A Gene Encoding a Transcription Factor Expressed in the Early Embryo, Is Regulated via Oct-3/4 and Oct-6 Binding to an Octomer Site and a Novel Protein, Rox-1, Binding to an Adjacent Site, Mol. Cell Biol. 18(4):1866-78, 1998.
Bendall, et al., IGF and FGF Cooperatively Establish the Regulatory Stem Cell Niche of Pluripotent Human Cells In Vitro, Nature 448(7157):1015-21, Aug. 30, 2007.
Benetti, et al., A Mammalian microRNA Cluster Controls DNA Methylation and Telomere Recombination Via Rbl2-Dependent Regulation of DNA Methyltransferases, Nat. Struct. Mol. Biol. 15(3):268-79, published online Mar. 2, 2008.
Berg, et al., An argument Against a Role for Oct4 in Somatic Stem Cells, Cell Stem Cell 1(4):359-60, Oct. 11, 2007.
Bibel, et al., Differentiation of Mouse Embryonic Stem Cells Into a Defined Neuronal Lineage, Nature Neuroscience 7:1003-1009, 2004.
Bigdeli et al., Adaptation of Human Embryonic Stem Cells to Feeder-Free and Matrix-Free Culture Conditions Directly on Plastic Surfaces. J. Biotec., 2008, vol. 133, pp. 146-153.
BioPorterTM Gene Therapy System, Inc., Wako Bio Window 40:7, 2002.
BioPorterTM Protein Delivery Reagent From www.biocarta.com [2002].
Birnbaum, et al., Slicing Across Kingdoms: Regeneration in Plants and Animals, Cell. 132(4):697-710, Feb. 22, 2008.
Birrer et al., L-myc Cooperates With ras to Transform Primary Rat Embryo Fibroblasts, Mol. Cell. Biol. 8(6):2668-73, 1988.
Blackwood et al., "Max: A Helix-Loop-Helix Zipper Protein That Forms a Sequence-Specific DNA-Binding Complex with Myc," Science, vol. 251, pp. 1211-1217 (1991).

(56) References Cited

OTHER PUBLICATIONS

Blelloch, et al., Generation of Induced Pluripotent Stem Cells in the Absence of Drug Selection, Cell Stem Cell. 1(3):245-247, 2007.
Block, et al., Population Expansion, Clonal Growth, and Specific Differentiation Patterns in Primary Cultures of Hepatocytes Induced by HGF/SF, EGF and TGFα in a Chemically Defined (HGM) Medium, J. Cell Biol. 132(6):1133-49, 1996.
Blow, N., Stem Cells: In Search of Common Ground, Nature 451(7180):855-8, Feb. 14, 2008.
Bonetta, L., European Stem Cell Patents: Taking the Moral High Road? Cell 132(4):SI4-S16, Feb. 22, 2008.
Bongso, A., et al., Isolation and Culture of Inner Cell Mass Cells From Human Blastocysts, Human Reproduction 9(11):2110-2117, 1994.
Boquest, et al., Epigenetic Programming of Mesenchymal Stem Cells From Human Adipose Tissue, Stem Cell Rev. 2(4):319-29, 2006.
Bortvin, et al., Incomplete Reactivation of Oct4-Related Genes in Mouse Embryos Cloned From Somatic Nuclei, Development 130:1673-80, 2003.
Bosman et al., Progress Toward the Clinical Application of Autologous Induced Pluripotent Stem Cells and Gene Repair Therapy for Treatment of Familial Hypercholesterolemia. The International Liver Congress 2011, 2011, abstract.
Boyer et al., "Core Transcriptional Regulatory Circuitry in Human Embryonic Stem Cells," Cell, vol. 122(6), pp. 947-956 (2005).
Brambrink et al., Sequential Expression of Pluripotency Markers During Direct Reprogramming of Mouse Somatic Cells, Cell Stem Cell 2(2):151-59, 2008.
Brena et al. Quantitative assessment of DNA methylation: Potential applications for disease diagnosis, classification, and prognosis in clinical settings. J Mol Med. May 2006;84(5):365-77.
Brimble, et al., Karyotypic Stability, Genotyping, Differentiation, Feeder-Free Maintenance, and Gene Expression Sampling in Three Human Embryonic Stem Cell Lines Derived Prior to Aug. 9, 2001, Stem Cells Develop. 13:585-596, 2004.
Brough, D.E., et al., An Essential Domain of the c-Myc Protein Interacts with a Nuclear Factor That is Also Required for E1A-Mediated Transformation, Molecular and Cellular Biology 15(3):1536-1544, 1995.
Brüstle, et al., Embryonic Stem Cell-Derived Glial Precursors: A Source of Myelinating Transplants, Science. 285(5428):754-756, Jul. 30, 1999.
Burns, et al., Diabetes Mellitus: A Potential Target for Stem Cell Therapy, Curr. Stem Cell Res. Ther. 1(2):255-66, May 2006.
Buttery, et al., Differentiation of Osteoblasts and In Vitro Bone Formation From Murine Embryonic Stem Cells, Tissue Eng. 7(1):89-99, Feb. 2001.
Cai et al. Directed differentiation of human embryonic stem cells into functional hepatic cells. Hepatology. May 2007;45(5): 1229-39.
Campbell, et al., Phosphonate Ester Synthesis Using a Modified Mitsunobu Condensation, J. Org. Chem.59:658-660, 1994.
Carey, et al., Reprogramming of Murine and Human Somatic Cells Using a Single Polycistronic Vector, Proc. Natl. Acad. Sci. USA 106(1):157-162, Jan. 6, 2009, Epub. Dec. 24, 2008; Erratum in: Proc. Natl. Acad. Sci. USA (13):5449, Mar. 31, 2009.
Carpenter, et al., Characterization and Differentiation of Human Embryonic Stem Cells, Cloning and Stem Cells 5(1) 169-176, Nov. 1, 2003.
Cartwright, et al., LIF/STAT3 Controls ES Cell Self-Renewal and Pluripotency by a Myc-Dependent Mechanism, Development. 132(5):885-896, Mar. 2005.
Cauffman, et al., Oct-4 mRNA and Protein Expression During Human Preimplantation Development, Molecular Human Reproduction 11(3) 173-180, Feb. 4, 2005.
Chadwick, et al., Cytokines and BMP-4 Promote Hematopoietic Differentiation of Human Embryonic Stem Cells, Blood 102(3):906-915, Aug. 1, 2003.
Chambers, et al., Functional Expression Cloning of Nanog, A Pluripotency Sustaining Factor in Embryonic Stem Cells, Cell 113:643-55, 2003.
Chang, et al., The c-Myc Transactivation Domain is a Direct Modulator of Apoptotic Versus Proliferative Signals, Mol. Cell Biol. 20(12):4309-4319, Jun. 2000.
Chang, C.-W., et al., Polycistronic Lentiviral Vector for "Hit and Run" Reprogramming of Adult Skin Fibroblasts to Induced Pluripotent Stem Cells, Stem Cells 27:1042-1049, 2009.
Check, E., Simple Recipe Gives Adult Cells Embryonic Powers, Nature 442:11, Jul. 6, 2006.
Chen et al. Analogous Organic-Synthesis of Small-Compound Libraries—Validation of Combinatorial Chemistry in Small-Molecule Synthesis. Journal of the American Chemical Society. 1994;116(6): 2661-2662.
Chen, et al., From Stem Cells to Oligodendrocytes: Prospects for Brain Therapy, Stem Cell Rev. 3(4):280-288, Dec. 2007.
Cheng, et al., Mammalian Grb2 Regulates Multiple Steps in Embryonic Development and Malignant Transformation, Cell 95:793-803, 1998.
Childs, et al., Regression of Metastatic Renal-Cell Carcinoma After Nonmyeloablative Allogeneic Peripheral-Blood Stem-Cell Transplantation, N. Engl. J. Med. 343(11):750-758, Sep. 14, 2000.
Chin, et al., Induced Pluripotent Stem Cells and Embryonic Stem Cells are Distinguished by Gene Expression Signatures, Cell Stem Cell. 5(1):111-123, Jul. 2, 2009.
Cho, et al., An Unnatural Biopolymer, Science, 261(5126):1303-5, Sep. 3, 1993.
Cinalli, et al., Germ Cells Are Forever, Cell. 132(4):559-562, Feb. 22, 2008.
CIRM: Summaries of Review for Applications to RFA 07-05. California Institute for Regenerative Medicine Web site. 2007. Available at: http://www.cirm.ca.gov/RFAIrfa_07-05/. Accessed Jul. 1, 2008.
CIRM Public Release. $24 Million in New Stem Cell Research Funding Awarded to 25 California Institutions. California Institute for Regenerative Medicine (4 pages). Jun. 27, 2008.
Cline, et al., Randomize Gene Sequences with New PCR Mutagenesis Kit, Strategies Newsletter 13:157-161, 2000.
Cohen, et al., Ooplasmic Transfer in Mature Human Oocytes, Molecular Human Reproduction 4:269-280, 1998.
Correction printed in Nature 447:897, Jun. 21, 2007.
Cosmo Bio News 49:5, 2005 (catalog of ES cell culture medium).
Coutts et al. Stem cells for the treatment of spinal cord injury. Exp Neurol. Feb. 2008;209(2):368-77.
Cowan, et al., Derivation of Embryonic Stem-Cell Lines From Human Blastocysts, N. Engl. J. Med. 350:1353-56, 2004.
Cowling, et al., Mechanism of Transcriptional Activation by the Myc Oncoproteins, Semin. Cancer Biol. 16(4):242-252, Aug. 2006.
Crouch, D.H., et al., Multiple Phenotypes Associated With Myc-Induced Transformation of Chick Embryo Fibroblasts Can Be Dissociated By a Basic Region Mutation, Nucleic Acids Research 24(16):3216-3221, 1996.
Cyranoski et al., Simple Switch Turns Cells Embryonic, Nature 447:618-619, Jun. 7, 2007.
Cyranoski, D., Stem Cells: 5 Things to Know Before Jumping on the iPS Bandwagon, Nature. 452(7186)406-408, 2008.
Cyranoski, Japan Ramps Up Patent Effort to Keep iPS lead, Nature 453(7198):962-963, 2008.
Daley, et al., Prospects for Stem Cell Based Therapy, Cell 132(4):544-548, Feb. 22, 2008.
Daley, et al., "Broader implications of defining standards for the pluripotency of iPSCs." Cell Stem Cell. Mar. 6, 2009;4(3):200-1; author reply 202.
D'Amour, et al., Efficient Differentiation of Human Embryonic Stem Cells to Definitive Endoderm, Nat Biotechnol. 23(12):1534-1541, Dec. 2005.
D'Amour, et al., Production of Pancreatic Hormone-Expressing Endocrine Cells From Human Embryonic Stem Cells, Nat. Biotechnol. 24(11): 1392-1401, Nov. 2006.
Dang et al., The Biology of the Mammalian Kruppel-Like Family of Transcription Factors, Int. J. Biochem. Cell Biol. 32:1103-21, 2000.

(56) References Cited

OTHER PUBLICATIONS

Dani, et at Differentiation of embryonic stem cells into adipocytes in vitro. J Cell Sci. Jun. 1997;110 (Pt 11):1279-85.
Deb, et al., Embryonic Stem Cells: From Markers to Market 11(1):19-37, Feb. 2008.
Denker, H.W., Human Embryonic Stem Cells: The Real Challenge for Research as Well as for Bioethics is Still Ahead of US, Cells Tissues Organs 187(4):250-256, 2008.
Dewitt, et al., Diversomers: An Approach to Nonpeptide, Nonoligomeric Chemical Diversity, Proc. Natl Acad. Sci. USA 90(15):6909-6913, Aug. 1, 1993.
Dimos, et al., Induced Pluripotent Stem Cells Generated From Patients With ALS Can be Differentiated Into Motor Neurons, Science 321(5893):1218-1221, Aug. 29, 2008.
D'Ippolito, et al., Marrow-Isolated Adult Multilineage Inducible (MIAMI) Cells, A Unique Population of Postnatal Young and Old Human Cells With Extensive Expansion and Differentiation Potential, J. Cell Sci. 117(Pt. 14):2971-2981, Jun. 15, 2004.
Do, et al., Nuclei of Embryonic Stem Cells Reprogram Somatic Cells, Stem Cells 22:941949, 2004.
Doetschman, et al., Establishment of Hamster Blastocyst-Derived Embryonic Stem Cells, 127 Development 224 (1988).
Durcova-Hills, et al., Induced Reprogramming of Human Somatic Cells Into Pluripotency: A New Way How to Generate Pluripotent Stem Cells, Differentiation 76(4):323-325, Apr. 2008.
Ebert, et al., Induced Pluripotent Stem Cells from a Spinal Muscular Atrophy Patient, Nature 457(7227):277280, Jan. 15, 2009.
Ebert, L., Yamanaka Scooped on iPS (Stem Cell) patent?! TMCNews, Jan. 4, 2009, available at http://ipbiz.blogspot.com/2009/01/yamanaka-scooped-on-ips-stemcell.html, accessed May 19, 2009.
Ehrich, et al., Quantitative High-Throughput Analysis of DNA Methylation Patterns by Base-Specific Cleavage and Mass Spectrometry, Proc. Natl. Acad. Sci. USA.102(44):15785-15790, Nov. 1, 2005.
Eisen, et al., Cluster Analysis and Display of Genome-Wide Expression Patterns 95(25):1486314868, Dec. 8, 1998.
Elefanty, A., Ed., In this Issue . . . , Stem Cell Research. 1:87, 2008.
Essentials of Stem Cell Biology, R. Lanza et al. Ed., 2006, Elsevier Academic Press, pp. 266-267.
Evans et al., Establishment in Culture of Pluripotential Cells From Mouse Embryos, Nature 292:154-56, 1981.
Evans, et al., Krüppel-Like Factor 4 is Acetylated by p300 and Regulates Gene Transcription via Modulation of Histone Acetylation, J. Biol. Chem. 282(47):33994-4002, Nov. 23, 2007.
Felgner, et al., Lipofection: A Highly Efficient, Lipid-Mediated DNA-Transfection Procedure. Proc. Natl. Acad. Sci. USA 84(21):7413-7417, Nov. 1987.
Feng, et al., Reprogramming of Fibroblasts Into Induced Pluripotent Stem Cells With Orphan Nuclear Receptor Esrrb, Nature Cell Biology 11:197-203, 2009.
Ferrer-Costa, et al., PMUT: A Web-Based Tool for the Annotation of Pathological Mutations on Proteins, Bioinformatics 21(14):3176-3178, Jul. 15, 2005.
Forsyth, et al., Human Embryonic Stem Cell Telomere Length Impacts Directly on Clonal Progenitor Isolation Frequency, Rejuvenation Research 11(1):5-17, Feb. 2008.
Furler, et al., Recombinant AAV Vectors Containing the Foot and Mouth Disease Virus 2A Sequence Confer Efficient Bicostronic Gene Expression in Cultured Cells and Rat Substantia Nigra Neurons, Gene Therapy 8:864-873, 2001.
Fusaki, N., et al., Efficient Induction of Transgene-Free Human Pluripotent Stem Cells Using a Vector Based on Sendai Virus, an RNA Virus That Does Not Integrate Into the Host Genome, Proc. Jpn. Acad., Ser. B, 85:348-362, 2009.
Gallop, et al., Applications of Combinatorial Technologies to Drug Discovery. 1. Background and Peptide Combinatorial Libraries, J. Med. Chem. 37(9):1233-1251, Apr. 29, 1994.
Ghaleb, et al., Krüppel-Like Factors 4 and 5: The Yin and Yang Regulators of Cellular Proliferation, Cell Res. 15(2):92-96, Feb. 2005.
Gonzalez, et al., "Generation of mouse-induced pluripotent stem cells by transient expression of a single nonviral polycistronic vector," PNAS, vol. 106(22), pp. 8919-8922 (Jun. 2, 2009).
Goswami, et al., Embryonic Stem Cell Therapy, IDrugs 10(10):713-719, Oct. 2007.
Griffiths-Jones, et al., miRBase: Tools for microRNA Genomics, Nucleic Acids Research 36:D154-D158, published online Nov. 8, 2007.
Gu, et al., Opposite Regulation of Gene Transcription and Cell Proliferation by c-Myc and Max, Proc. Natl Acad. Sci. USA 90(7):2935-2939, Apr. 1, 1993.
Ha, et al., Cryopreservation of Human Embryonic Stem Cells Without the Use of a Programmable Freezer, Hum. Reprod. 20(7):1779-1785, Jul. 2005.
Hakelien, et al., Reprogramming Fibroblasts to Express T-Cell Functions Using Cell Extracts, Nature Biotechnology 20:460-466, May 2002.
Hanna, et al., Direct Reprogramming of Terminally Differentiated Mature B Lymphocytes to Pluripotency, Cell 133:250-264, Apr. 18, 2008; Erratum in Cell. 134(2):365, 2008.
Hanna, et al., Treatment of Sickle Cell Anemia Mouse Model With iPS Cells Generated From Autologous Skin, Science 318(5858):1920-1923, published online Dec. 6, 2007.
Hasegawa, K., Efficient Multicistronic Expression of a Transgene in Human Embryonic Stem Cells, Stem Cells 25(7), 1707-1712, 2007.
Hatfield, et al., Stem Cell Division is Regulated by the microRNA Pathway, Nature 435(7044):974-978, 2005.
Heng, et al., Incorporating Protein Transduction Domains (PTD) Within Intracellular Proteins Associated With the 'Stemness' Phenotype. Novel Use of Such Recombinant 'Fusion' Proteins to Overcome Current Limitations of Applying Autologous Adult Stem Cells in Regenerative Medicine? Med. Hypotheses 64(5):992-996, 2005.
Hermann, et al., Efficient Generation of Neural Stem Cell-Like Cells From Adult Human Bone Marrow Stromal Cells, J. Cell Sci. 117(Pt. 19):4411-4422, Sep. 1, 2004.
Herold, S., et al., Negative Regulation of the Mammalian UV Response by Myc Through Association with Miz-1, Molecular Cell 10(3):509-521, 2002.
Highfield, R., Dolly Creator Proflan Wilmut Shuns Cloning, available at http://www.telegraph.co.uk/earth/main.jhtml?XML=/earth/2007/11/16/scidolly116.XML. Accessed Nov. 12, 2008.
Hockemeyer, et al., A Drug-Inducible System for Direct Reprogramming of Human Somatic Cells to Pluripotency, Cell Stem Cell 3(3):346-353, Sep. 11, 2008.
Hoffman, L., and M. Carpenter, Characterization and Culture of Human Embryonic Stem Cells, Nature Biotechnology 23:699, 2005.
Holt, et al., Regulation of Telomerase Activity in Immortal Cell Lines, Molecular and Cellular Biology, Jun. 1996, pp. 2932-2939.
Hong, et al., Suppression of Induced Pluripotent Stem Cell Generation by the p53-p21 Pathway, Nature 460(7259):1132-1135, Aug. 27, 2009; epub Aug. 9, 2009.
Horikawa, et al., Differential Cis-Regulation of Human Versus Mouse TERT Gene Expression In Vivo: Identification of a Human-Specific Repressive Element, Proc. Natl. Acad. Sci. U.S.A. 102(51):18437-18442, 2005.
Hotta et al., "Retroviral Vector Silencing During iPS Cell Induction: An Epigenetic Beacon that Signals Distinct Pluripotent States," Journal of Cellular Biochemistry, vol. 105, pp. 940-948 (2008).
Houbaviy et al., Embryonic Stem Cell-Specific MicroRNAs, Developmental Cell 5(2):351-58, 2003.
Hsiao, et al., Marking Embryonic Stem Cells With a 2A Self-Cleaving Peptide: A NKX2-5 Emerald GFP BAC Reporter, PLoS One 3(7):e2532, 2008.
Huangfu et al. Efficient Induction of Pluripotent Stem Cells Using Small Molecule Compounds. Companion manuscript to U.S. Appl. No. 61/029,287 [2008].
Huangfu, et al., Induction of Pluripotent Stem Cells by Defined Factors is Greatly Improved by Small-Molecule Compounds, Nature Biotechnology 26(7):795-797, 2008.
Huangfu, et al., Induction of Pluripotent Stem Cells From Primary Human Fibroblasts With Only Oct4 and Sox 2, Nature Biotechnology 26:1269-1275, 2008.

(56) References Cited

OTHER PUBLICATIONS

Humphries, C., Reprogrammed Stem Cells Work on Parkinson's: A Study in Rodents Suggests That Skin Cells Can Be Transformed Into Neurons to Treat Neurodegeneration, Technology Review published by MIT, http://www.technologyreview.com/printer_friendly_article.aspx?id=20530, Apr. 8, 2008.
Hwang, et al., Evidence of Pluripotent Human Embryonic Stem Cell Line Derived From a Cloned Blastocyst, Science 303:1669-1674, 2004.
Hwang, et al., Patient-Specific Embryonic Stem Cells Derived From Human SCNT Blastocysts, Science 308:1777-1783, 2005.
Hyun, et al., New Advances in iPS Cell Research Do Not Obviate the Need for Human Embryonic Stem Cells, Cell Stem Cell 1(4):367-368, Oct. 11, 2007.
Iannaccone, et al., Pluripotent Embryonic Stem Cells From the Rat Are Capable of Producing Chimeras, Developmental Biology 163(288), 1994.
Ingvarsson, The myc Gene Family Proteins and Their Role in Transformation and Differentiation, Seminars in Cancer Biology vol. 1:359-369, 1990.
Itskovitz-Eldor, et al., Differentiation of Human Embryonic Stem Cells Into Embryoid Bodies Comprising the Three Embryonic Germ Layers, Mol. Med. 6(2):88-95, 2000.
Itsykson, et al., Derivation of Neural Precursors From Human Embryonic Stem Cells in the Presence of Noggin, Mol. Cell Neurosci. 30(1):24-36, Sep. 2005.
Jaenisch, et al., Stem Cells, The Molecular Circuitry of Pluripotency and Nuclear Reprogramming, Cell 132(4):567-582, Feb. 22, 2008.
Jahagirdar, et al., Multipotent Adult Progenitor Cell and Stem Cell Plasticity, Stem Cell Rev. 1(1):53-59, 2005.
Janssens, et al., Autologous Bone Marrow-Derived Stem-Cell Transfer in Patients With STSegment Elevation Myocardial Infarction: Double-Blind, Randomised Controlled Trial, Lancet, 367(9505):113-121, Jan. 14, 2006.
Jiang, et al., Pluripotency of Mesenchymal Stem Cells Derived From Adult Marrow, Nature 418(6893):41-49, Jul. 4, 2002.
Jiang, et al., In vitro Derivation of Functional Insulin-Producing Cells From Human Embryonic Stem Cells, Cell Res. 17(4):333-344, Apr. 2007.
Jiang, et al., A Core Klf Circuitry Regulates Self-Renewal of Embryonic Stem Cells, Nat. Cell Biol. 10(3):353-360, Mar. 2008.
Jikken Igaku (Experimental Medicine) 24:814-819, 2006, along with an English language translation thereof.
Johnston, et al., Minimum Requirements for Efficient Transduction of Dividing and Nondividing Cells by Feline Immunodeficiency Virus Vectors, J. Virol. 73(6):4991-5000, Jun. 1999.
Kaji, K., et al., Virus-Free Induction of Pluripotency and Subsequent Excision of Reprogramming Factors, Nature, 458:771-775, 2009.
Kamachi, et al., Mechanism of Regulatory Target Selection by the SOX High-Mobility-Group Domain Proteins as Revealed by Comparison of SOX1/2/3 and SOX9, Mol. Cell Biol. 19(1):107-120, Jan. 1999.
Kanegae, et al., Efficient Gene Activation in Mammalian Cells by Using Recombinant Adenovirus Expressing Site-Specific Cre Recombinase, Nucleic Acids Res. 23(19):3816- 3821, Oct. 11, 1995.
Kanellopoulou, et al., Dicer-Deficient Mouse Embryonic Stem Cells Are Defective in Differentiation and Centromeric Silencing, Genes & Development 19:489-501, 2005.
Kawasaki, et al., Induction of Midbrain Dopaminergic Neurons From ES cells by Stromal Cell-Derived Inducing Activity, Neuron. 28(1):31-40, Oct. 2000.
Kehat et al. Human embryonic stem cells can differentiate into myocytes with structural and functional properties of cardiomyocytes. J Clin Invest. Aug. 2001; 108(3):407-14.
Kim, et al., Ex Vivo Characteristics of Human Amniotic Membrane-Derived Stem Cells, Cloning Stem Cells 9(4):581-594, Winter 2007.
Kim et al., Generation of Human Induced Pluripotent Stem Cells by Direct Delivery of Reprogramming Proteins, Cell Stem Cell 4:472-476, 2009.
Kim, et al., Oct4-Induced Pluripotency in Adult Neural Stem Cells, Cell 136:411-419, 2009.
Kishi et al., Requirement of Sox2-Mediated Signaling for Differentiation of Early Xenopus Neuroectoderm, Development 127:791-800, 2000.
Kitamura, et al., Retrovirus-Mediated Gene Transfer and Expression Cloning: Powerful Tools in Functional Genomics, Exp. Hematol. 31(11):1007-1014, Nov. 2003.
Kitamura, T., New Experimental Approaches in Retrovirus-Mediated Expression Screening. Int. J. Hematol. 67(4):351-359, Jun. 1998.
Klingemann, H., Discarded Stem Cells With a Future? Expert Opin. Biol. Ther. 6(12):1251-1254, Dec. 2006.
Knoblich, J.A., Mechanisms of Asymmetric Stem Cell Division, Cell 132(4):583-597, Feb. 22, 2008.
Koch, et al., Transduction of Human Embryonic Stem Cells by Ecotropic Retroviral Vectors. Nucl. Acids Res. 34:e120, 2006.
Kohge, et al., Promotion of Antigen-Specific Antibody Production in Murine B Cells by a Moderate Increase in Histone Acetylation, Biochem. Pharmacol. 56(10):1359-1364, Nov. 15, 1998.
Kohlhase, et al., Cloning and Expression Analysis of SalI4, The Murine Homologue of the Gene Mutated in Okihiro Syndrome, Cytogenet. Genome Res. 98:274-277, 2002.
Kopsidas, et al., RNA Mutagenesis Yields Highly Diverse mRNA Libraries for In Vitro Protein Evolution, BMC Biotechnol. 7:18, Apr. 11, 2007.
Koyanagi, et al., Screening and Functional Analysis of microRNAs Which Involve in Reprogramming, of Murine Somatic Cells, The Journal of Biochemistry 79(11), Abstract, 1T7-7 From the 80th Annual Meeting of the Japanese Biochemical Society, Nov. 25, 2007, along with an English language translation thereof.
Kozarsky et al., Adenovirus-Medicated Correction of the Genetic Defect in Hepatocytes from Patients with Familial Hypercholesterolemia Somatic Cell Molecular Genetics, 1993, vol. 19 pp. 449-458.
Kramer, et al., Embryonic Stem Cell-Derived Chondrogenic Differentiation In Vitro: Activation by BMP-2 and BMP-4, Mech. Dev. 92(2):193-205, Apr. 2000.
Krausz, E., High-Content siRNA Screening, Mol. Biosyst. 3(4):232-240, Apr. 2007.
Krosl, et al., In vitro Expansion of Hematopoietic Stem Cells by Recombinant TAT-HOXB4 Protein, Nat. Med 9(11):1428-32, 2003.
Kubicek, et al., Reversal of H3K9me2 by a Small-Molecule Inhibitor for the G9a Histone Methyltransferase, Molecular Cell 25:473-481, 2007.
Kunath, et al., FGF Stimulation of the Erk1/2 Signalling Cascade Triggers Transition of Pluripotent Embryonic Stem Cells From Self-Renewal to Lineage Commitment, Development. 134(16):2895-2902, Aug. 2007.
Kuroda, et al., Octamer and Sox Elements Are Required for Transcriptional cis Regulation of Nanog Gene Expression, Mol. Cell. Biol. 25(6):2475-2485, Mar. 2005.
Kyoto Shimbun (Japanese Newspaper) article of Apr. 16, 2008, cols. 1-3, along with a partial English language translation thereof.
Laflamme, et al., Cardiomyocytes Derived From Human Embryonic Stem Cells in Pro-Survival Factors Enhance Function of Infarcted Rat Hearts, Nat. Biotechnol. 25(9):1015-1024, 2007.
Laird, et al., Stem Cell Trafficking in Tissue Development, Growth, and Disease, Cell 132(4):612-630, Feb. 22, 2008.
Lanza et al. (Eds.) Essentials of Stem Cell Biology. Elsevier Academic Press. 2006. (Table of Contents only).
Lebkowski, et al., Human Embryonic Stem Cells: Culture, Differentiation, and Genetic Modification for Regenerative Medicine Applications, The Cancer Journal 7(S.2):S83-S94, 2001.
Lee, et al., Efficient Generation of Midbrain and Hindbrain Neurons From Mouse Embryonic Stem Cells, Nat. Biotechnol. 18(6):675-679, Jun. 2000.
Lemken, et al., Evidence for Intercellular Trafficking of VP22 in Living cells, Mol. Ther. 15(2):310-319, Feb. 2007.
Lengner, et al., The Pluripotency Regulator Oct4: A Role in Somatic Stem Cells? Cell Cycle 7(6):725-728, Mar. 2008.

(56) References Cited

OTHER PUBLICATIONS

Lewitzky, et al., Reprogramming Somatic Cells Towards Pluripotency by Defined Factors, Curr. Opin. Biotechnol. 18(5):467-473, Oct. 2007.
Li, Huawei et al., Pluripotent Stem Cells From the Adult Mouse Inner Ear, Nature Medicine 9(10):1293-1299, Oct. 2003.
Li, Jiayin et al., Leukaemia Disease Genes: Large-Scale Cloning and Pathway Predictions, Nat. Genet. 23(3):348-353, 1999.
Li, Long-Cheng et al. Small dsRNAs induce transcriptional activation in human cells. Proc Natl Acad Sci. 2006; 103, 17337-17342.
Li, Yan, Expansion of Human Embryonic Stem Cells in Defined Serum-Free Medium Devoid of Animal-Derived Products, published online Jun. 21, 2005 in Wiley InterScience, www.interscience.wiley.com.
Li, Yanjun et al., "Murine embryonic stem cell differentiation is promoted by SOCS-3 and inhibited by the zinc finger transcription factor Klf4," Blood, vol. 105, No. 2, pp. 635-637, Jan. 15, 2005.
Li, Ying et al., Transduction of Passaged Human Articular Chondrocytes with Adenoviral, Retroviral, and Lentiviral Vectors and the Effects of Enhanced Expression of Sox9, Tissue Eng. 10:575-584, 2004.
Liao et al., Enhanced Efficiency of Generating Induced Pluripotent Stem (iPS) Cells From Human Somatic Cells by a Combination of Six Transcription Factors, Cell Research 18:600- 603, doi: 10.1038/cr.2008.51, published online Apr. 15, 2008.
Lieschke, et al., Development of Functional Macrophages From Embryonal Stem Cells In Vitro, Exp. Hematol. 23(4):328-334, Apr. 1995.
Lin, et al., Mir-302 Reprograms Human Skin Cancer Cells Into a Pluripotent ES-Cell-Like State, RNA 14:1-10, 2008.
Lin-Goerke, et al., PCR-Based Random Mutagenesis Using Manganese and Reduced dNTP Concentration, Biotechniques 23(3):409-412, Sep. 1997.
Link, et al., Therapeutic Protein Transduction of Mammalian Cells and Mice by Nucleic Acid-Free Lentiviral Nanoparticles, Nucleic Acids Res. 34(2):e16, Jan. 2006.
Littlewood, et al., A Modified Oestrogen Receptor Ligand-Binding Domain as an Improved Switch for the Regulation of Heterologous Proteins, Nucleic Acids Res. 23(10):1686-1690, May 25, 1995.
Liu, S., iPS Cells: A More Critical Review, Stem Cells and Development 17(3):391-397, Jun. 2008, in 11 pages.
Loh, et al., The Oct4 and Nanog Transcription Network Regulates Pluripotency in Mouse Embryonic Stem Cells, Nat. Genet.38(4):431-440, Apr. 2006.
Loriot, et al., Five New Human Cancer-Germline Genes Identified Among 12 Genes Expressed in Spermatogonia, Int. J. Cancer 105:371-76, 2003.
Loudig, et al., Transcriptional Co-Operativity Between Distant Retinoic Acid Response Elements in Regulation of Cyp26A1 Inducibility, Biochem. J. 392(Pt. 1):241-248, Nov. 15, 2005.
Lowry, et al., Generation of Human Induced Pluripotent Stem Cells From Dermal Fibroblasts, Proc. Natl. Acad. Sci. USA 105(8):2883-2888, Feb. 26, 2008.
Ludwig, et al., Derivation of Human Embryonic Stem Cells in Defined Conditions, Nat. Biotechnol. 24(2):185-187, Feb. 2006.
Lumelsky, et al., Differentiation of Embryonic Stem Cells to Insulin-Secreting Structures Similar to Pancreatic Islets, Science 292(5520):1389-1394, May 18, 2001.
Lunde, et al., Zebrafish pou5f1/pou2, Homolog of Mammalian Oct4, Functions in the Endoderm Specification Cascade, Curr. Biol. 14(1):48-55, Jan. 6, 2004.
Lungwitz, et al., Polyethylenimine-Based Non-Viral Gene Delivery Systems, Eur. J. Pharm. Biopharm. 60(2):247-266, Jul. 2005.
Maherali, et al., A high-Efficiency System for the Generation and Study of Human Induced Pluripotent Stem Cells, Cell Stem Cell 3(3):340-345, Sep. 11, 2008.
Maherali, N., et al., "Directly Reprogrammed Fibroblasts Show Global Epigenetic Remodeling and Widespread Tissue Contribution," Cell Stem Cell 1:55-70, 2007.
Mali, et al., Improved Efficiency and Pace of Generating Induced Pluripotent Stem Cells From Human Adult and Fetal Fibroblasts, Stem Cells 26(8):1998-2005, 2008.
Marchetto, et al., Transcriptional Signature and Memory Retention of Human-Induced Pluripotent Stem Cells, PLoS One 4(9):e7076, Sep. 18, 2009.
Marson, et al., Wnt Signaling Promotes Reprogramming of Somatic Cells to Pluripotency, Cell Stem Cell 3:132-35, 2008.
Martin, Isolation of a Pluripotent Cell Line From Early Mouse Embryos Cultured in Medium Conditioned by Teratocarcinoma Stem Cells, Proc. Natl. Acad. Sci. U.S.A. 78(12):7634-38, 1981.
Maruyama et al., Differential Roles for Sox15 and Sox2 in Transcriptional Control in Mouse Embryonic Stem Cells, J. Biol., Chem. 280(26):24371-79, 2005.
Maruyama, "Functional Analysis of Sox15 and Sox2," Ph.D. Thesis, Nara Institute of Science and Technology, Jan. 31, 2005, in 121 pages.
Masaki, et al., Heterogeneity of Pluripotent Marker Gene Expression in Colonies Generated in Human iPS Cell Induction Culture, Stem Cell Research 1:105-115, 2008.
Masaki, et al., Tendency of Pluripotential Marker Gene Expression in Colonies Derived From Human Neonatal Fibroblasts Induced by the Human iPS Cell Method, Stem Cell Research, 2008 (accepted manuscript).
Mathe, et al., Computational Approaches for Predicting the Biological Effect of p53 Missense Mutations: A Comparison of Three Sequence Analysis Based Methods, Nucleic Acids Res. 34(5):1317-1325, Mar. 6, 2006.
Matsuda, et al., STAT3 Activation is Sufficient to Maintain an Undifferentiated State of Mouse Embryonic Stem Cells, EMBO J.18(15):4261-4269, Aug. 2, 1999.
Mcmahon, et al., The Wnt-1 (int-1) Proto-Oncogene Is Required for Development of a Large Region of the Mouse Brain, Cell 62:1073-1085, 1990.
Meiner, et al., Disruption of the Acyl-CoA: Cholesterol Acyltransferase Gene in Mice: Evidence Suggesting Multiple Cholesterol Esterification Enzymes in Mammals, Proc. Natl. Acad. Sci. U.S.A. 93:14041-14046, 1996.
Meissner, et al., Direct Reprogramming of Genetically Unmodified Fibroblasts Into Pluripotent Stem Cells, Nat. Biotechnol. 25(10):1177-1181, published online Aug. 27, 2007.
MicroRNA Jikken Purotokoru (microRNA Experimental Protocol), Yodosha col. Ltd., 2008, pp. 20-35.
Mikkelsen, et al., Dissecting Direct Reprogramming Through Integrative Genomic Analysis, Nature 454(7200):49-55, Jul. 3, 2008; Erratum in Nature 454(7205):794, 2008.
Mitsui, et al., The Homeoprotein Nanog Is Required for Maintenance of Pluripotency in Mouse Epiblast and ES Cells, Cell 113:631-42, 2003.
Miura, et al., Variation in the Safety of Induced Pluripotent Stem Cell Lines, Nat. Biotechnol. 27(8):743-745, Aug. 2009, Epub Jul. 9, 2009.
Miyagishi, et al., Strategies for Generation of an siRNA Expression Library Directed Against the Human Genome, Oligonucleotides 13(5):325-333, 2003.
Miyamoto, et al., Reprogramming Events of Mammalian Somatic Cells Induced by Xenopus Laevis Egg Extracts Molecular Reproduction and Development 74:1268-1277, 2007.
Miyoshi, et al., Development of a Self-Inactivation Lentivirus Vector, J. Virol. 72(10):8150-8157, Oct. 1998.
More California Dough—$23 Million—Rolls Out the Door for Stem Cell Research. California Stem Cell Report Web Site. 2005. Available at: http://californiastemcellreport.blogspot.com/2008/06/more-dough-25-million-rolls-out-door-in.html. Accessed Jul. 1, 2008.
Morgenstern, et al., Advanced Mammalian Gene Transfer: High Titre Retroviral Vectors With Multiple Drug Selection Markers and a Complementary Helper-Free Packaging Cell Line, Nucleic Acids Res. 18(12):3587-3596, Jun. 25, 1990.
Morita, S., et al., Plat-E: An Efficient and Stable System for Transient Packaging of Retroviruses, Gene Therapy 7:1063-1066, 2000.

(56) References Cited

OTHER PUBLICATIONS

Morizane, et al., From Bench to Bed: The Potential of Stem Cells for the Treatment of Parkinson's Disease, Cell Tissue Res. 331(1):323-336, Jan. 2008.
Morling, et al., Enhanced Transduction Efficiency of Retroviral Vectors Coprecipitated With Calcium Phosphate, Gene Ther. 2(7):504-548, Sep. 1995.
Morrison, S.J., Stem Cells and Niches: Mechanisms That Promote Stem Cell Maintenance Throughout Life, Cell. 132(4):598-611, Feb. 22, 2008.
Mummery, et al., Differentiation of Human Embryonic Stem Cells to Cardiomyocytes: Role of Coculture With Visceral Endoderm-Like Cells, Circulation 107(21):2733-2740, Jun. 3, 2003.
Murry, et al., Differentiation of Embryonic Stem Cells to Clinically Relevant Populations: Lessons From Embryonic Development, Cell 132(4):661-680, Feb. 22, 2008.
Nagano et al., "Large-Scale Identification of Proteins Expressed in Mouse Embryonic Stem Cells," Proteomics 5:1346-1361, 2005.
Nagy, et al., Embryonic Stem Cells Alone Are Able to Support Fetal Development in the Mouse, Development 110(3):815-821, Nov. 1990.
Nakagawa et al., "Generation of induced pluripotent stem cells without Myc from mouse and human fibroblasts," Nature Biotechnology, vol. 26(1), pp. 101-106 (Jan. 2008).
Nakagawa, M., et al., Promotion of Direct Reprogramming by Transformation-Deficient Myc., Proc. Natl. Acad. Sci. USA 107(32):14152-14157, Aug. 2010.
Nakatake, et al., Klf4 Cooperates With Oct3/4 and Sox2 to Activate the Lefty1 Core Promoter in Embryonic Stem Cells, Mol. Cell Biol. 26(20):7772-7782, Oct. 2006.
Naldini, et al., In Vivo Gene Delivery and Stable Transduction of Nondividing Cells by a Lentiviral Vector, Science 272(5259):263-267, Apr. 12, 1996.
Needleman, et al., A General Method Applicable to the Search for Similarities in the Amino Acid Sequence of Two Proteins, J. Mol. Biol. 48(3):443-453, Mar. 1970.
Négre, et al., Lentiviral Vectors Derived From Simian Immunodeficiency Virus, Curr. Top Microbiol. Immunol. 261:53-74, 2002.
Newton, Attracting World's Attention. Pluripotent Cells Are Generated From Human Skin. What is the 'iPS Cell' That Can Be Used Not Only in the Regeneration Therapy but Also in the Tailor-Made Therapy, pp. 70-75, Feb. 2008, along with a partial English translation thereof.
Ng, et al., Predicting the Effects of Amino Acid Substitutions on Protein Function, Annu. Rev. Genomics, Hum. Genet. 7:61-80, 2006.
Nichols, et al., Formation of Pluripotent Stem Cells in the Mammalian Embryo Depends on the POU Transcription Factor Oct4, Cell 95:379-391, 1998.
Nienhuis, et al., Genotoxicity of Retroviral Integration in Hematopoietic Cells, Mol. Ther. 13(6):1031-1049, 2006.
Niwa, et al., Efficient Selection for High-Expression Transfectants With a Novel Eukaryotic Vector, Gene 108(2):193-199, 1991.
Niwa, et al., Self-Renewal of Pluripotent Embryonic Stem Cells is Mediated Via Activation of STAT3, Genes Dev. 12(13):2048-2060, Jul. 1, 1998.
Nolta, et al., Transduction of Pluripotent Human Hematopoietic Stem Cells Demonstrated by Clonal Analysis After Engraftment in Immune-Deficient Mice, Proc. Natl. Acad. Sci. USA 93(6):2414-2419, 1996.
Obinata, Conditionally Immortalized Cell Lines With Differentiated Functions Established From Temperature-Sensitive T-Antigen Transgenic Mice, Genes to Cells 2:235-244, 1997.
Ohnuki, et al., Generation and Characterization of Human Induced Pluripotent Stem Cells, Curr. Protoc Stem Cell Biol., Chapter 4:Unit 4A.2, Jun. 2009.
Okabe et al., Green Mice as a Source of Ubiquitous Green Cells, FEBS Letters, 1997, vol. 407, pp. 313-319.
Okamoto, et al., A Novel Octamer Binding Transportation Factor is Differentially Expressed in Mouse Embryonic Cells, Cell 60:461-72, 1990.
Okita, et al., Intracellular Signaling Pathways Regulating Pluripotency of Embryonic Stem Cells, Current Stem Cell Research & Therapy 1:103-111, 2006.
Okita et al., Generation of Germline-Competent Induced Pluripotent Stem Cells, Nature 448:313-17, 2007.
Okita et al., Generation of Mouse Induced Pluripotent Stem Cells Without Viral Vectors, Science 322(5903):949-53, published online Oct. 9, 2008.
Okita et al., Generation of Mouse-Induced Pluripotent Stem Cells With Plasmid Vectors, Nat. Protoc. 5(3):418-428, 2010; Epub Feb. 11, 2010.
Okita et al., "Induction of pluripotency by defined factors." Exp Cell Res. Oct. 1, 2010;316(16):2565-70. Epub Apr. 24, 2010.
Okita et al., A more efficient method to generate integration-free human iPS cells. Nat. Methods, vol. 8, No. 5, pp. 409-412 (2011).
Okuda et al., UTF1, A Novel Transcriptional Coactivator Expressed in Pluripotent Embryonic Stem Cells and Extra-Embryonic Cells, Embo J. 17(7):2019-32, 1998.
Okumura-Nakanishi, et al., Oct-3/4 and Sox2 Regulate Oct-3/4 Gene in Embryonic Stem Cells, The Journal of Biological Chemistry 280(7):5307-5317, Feb. 18, 2006.
Onishi, et al., Applications of Retrovirus-Mediated Expression Cloning, Exp. Hematol. 24(2):324-329, Feb. 1996.
Orkin, et al., Hematopoiesis: An Evolving Paradigm for Stem Cell Biology, Cell 32(4):631-644, Feb. 22, 2008.
Osuna, et al., Protein Evolution by Codon-Based Random Deletions, Nucleic Acids Res. 32(17):e136, Sep. 30, 2004.
Padmanabhan, et al., Visualization of Telomerase Reverse Transcriptase (hTERT) Promoter Activity Using a Trimodality Fusion Reporter Construct, J. Nucl. Med. 47(2):270-277, Feb. 2006.
Park, Alice, Stem-cell Research: The Quest Resumes, Time Magazine, Feb. 9, 2009; available at http://www.time.com/time/health/article/0,8599,1874717,00.html; accessed Jun. 3, 2009.
Park, In-Hyun, et al., Reprogramming of Human Somatic Cells to Pluripotency With Defined Factors, Nature 451:141-46, published online Dec. 23, 2007.
Park, In-Hyun, et al., Disease-Specific Induced Pluripotent Stem Cells, Cell 134(5):877-886, Sep. 5, 2008.
Parson, A.B., Stem Cell Biotech: Seeking a Piece of the Action, Cell 132(4):511-513, Feb. 22, 2008.
Pear et al. Production of high-titer helper-free retroviruses by transient transfection. Proc. Natl. Acad. Sci. USA, vol. 90, pp. 8392-8396 (1993).
Pearson, et al., Improved Tools for Biological Sequence Comparison, Proc. Natl. Acad. Sci. USA 85(8):24442448, Apr. 1988.
Pearson, W.R., Rapid and Sensitive Sequence Comparison With FASTP and FASTA Methods Enzymol. 183:63-98, 1990.
Peister, et al., Stable Transfection of MSCs by Electroporation, Gene Ther. 11(2):224-228, Jan. 2004.
Pera, M.F., On the Road to Reprogramming, Stem Cell Research 1:103-104, 2008.
Pomp, et al., Generation of Peripheral Sensory and Sympathetic Neurons and Neural Crest Cells From Human Embryonic Stem Cells, Stem Cells 23(7):923-930, Aug. 2005.
Postic, et al., Dual Roles for Glucokinase in Glucose Homeostasis as Determined by Liverand Pancreatic β Cell-Specific Gene Knock-Outs Using Cre Recombinase, J. Biol. Chem. 274(1):305-315, 1999.
Pralong, et al., Cell Fusion for Reprogramming Pluripotency: Toward Elimination of the Pluripotent Genome, Stem Cell Rev. 2(4):331-340, 2006.
Prelle, et al., Overexpression of Insulin-Like Growth Factor-II in Mouse Embryonic Stem Cells Promotes Myogenic Differentiation, Biochem. Biophys. Res. Commun. 277(3):631-638, Nov. 2, 2000.
Qin, et al., Direct Generation of ES-Like Cells From Unmodified Mouse Embryonic Fibroblasts by Oct4/Sox2/Myc/Klf4, Cell Res. 17(11):959-962, 2007.
Quenneville, et al., Nucleofection of Muscle-Derived Stem Cells and Myoblasts with phiC31 Integrase: Stable Expression of a Full-Length-Dystrophin Fusion Gene by Human Myoblasts, Mol. Ther. 10(4):679-687, Oct. 2004.

(56) References Cited

OTHER PUBLICATIONS

Rambhatla, et al., Generation of Hepatocyte-Like Cells From Human Embryonic Stem Cells, Cell Transplant. 12(1):1-11, 2003.
Rao, M., Conserved and Divergent Paths That Regulate Self-Renewal in Mouse and Human Embryonic Stem Cells, Dev. Biol. 275(2):269-286, Nov. 15, 2004.
Ratajczak, et al., Bone-Marrow-Derived Stem Cells—Our Key to Longevity? J. Appl. Genet. 48(4):307-319, 2007.
Reubinoff, et al., Neural Progenitors from Human Embryonic Stem Cells, Nat. Biotechnol. 19(12):1134-1140, Dec. 2001.
Riviére, et al., Effects of Retroviral Vector Design on Expression of Human Adenosine Deaminase in Murine Bone Marrow Transplant Recipients Engrafted With Genetically Modified Cells, Proc. Natl. Acad. Sci. USA. 92(15):6733-6737, Jul. 18, 1995.
Rodda, et al., Transcriptional Regulation of Nanog by OCT4 and SOX2, J. Biol. Chem. 280(26):24731-24737, Jul. 1, 2005.
Rodriguez, et al., Manipulation of OCT4 Levels in Human Embryonic Stem Cells Results in Induction of Differential Cell Types, Exp. Biol. Med (Maywood) 232(10):1368-1380, Nov. 2007.
Root, et al., Genome-Scale Loss-of-Function Screening with a Lentiviral RNAi Library, Nat. Methods 3(9):715-719, Sep. 2006.
Rosenfeld, et al., Adenovirus-Mediated Transfer of a Recombinant Alpha 1-Antitrypsin Gene to the Lung Epithelium In Vivo, Science 252(5004):431-434, Apr. 19, 1991.
Rossant, J., Stem Cells: The Magic Brew, Nature 448:260-262, Jul. 19, 2007.
Rossant, J., Stem Cell and Early Lineage Development, Cell 132(4):527-531, Feb. 22, 2008.
Rossi, et al., Stem Cells and the Pathways to Aging and Cancer, Cell 132(4):681-696, Feb. 22, 2008.
Rubin, L., Stem Cell and Drug Discovery: The Beginning of a New Era? Cell 132(4):549-552, Feb. 22, 2008.
Ryan, et al., POU Domain Family Values: Flexibility, Partnerships, and Developmental Codes, Genes Dev. 11:1207-25, 1997.
Sadowski, et al., GAL4-VP16 is an Unusually Potent Transcriptional Activator, Nature 335(6190):563-564, Oct. 6, 1998.
Sakai, et al., A Transgenic Mouse Line That Retains Cre Recombinase Activity in Mature Oocytes Irrespective of the cre Transgene Transmission, Biochem. Biophys. Res. Commun. 237(2):318-324, 1997.
Saldanha, et al., Assessment of Telomere Length and Factors That Contribute to its Stability, Eur. J. Biochem. 270(3):389-403, Feb. 2003.
Salmon, et al., Reversible Immortalization of Human Primary Cells by Lentivector-Mediated Transfer of Specific Genes, Mol. Ther. 2(4):404-414, 2000.
Sarid, J., et al., Evolutionary Conserved Regions of the Human c-Myc Protein Can Be Uncoupled From Transforming Activity, Proc. Natl. Acad. Sci. USA 84(1):170-173, 1987.
Sato, et al., Maintenance of Pluripotency in Human and Mouse Embryonic Stem Cells Through Activation of Wnt Signaling by a Pharmacological GSK-3-Specific Inhibitor, Nat. Med. 10(1):55-63, 2004.
Schepers, et al., Twenty Pairs of Sox: Extent, Homology, and Nomenclature of the Mouse and Human Sox Transcription Factor Gene Families, Dev. Cell 3:167-170, 2002.
Scherr, et al., Gene Silencing by Small Regulatory RNAs in Mammalian Cells, Cell Cycle 6(4):444-449, Feb. 1, 2007.
Schuldiner, et al., Induced Neuronal Differentiation of Human Embryonic Stem Cells, Brain Res. 913(2):201-205, Sep. 21, 2001.
Schwenk, et al., Hybrid Embryonic Stem Cell-Derived Tetraploid Mice Show Apparently Normal Morphological, Physiological, and Neurological Characteristics, Mol Cell Biol. 23(11):3982-3989, Jun. 2003.
Science Magazine Names Top 10 Breakthroughs of 2008; available at http://arstechnica.com/old/content/2008/12/isciencei-names-top-10-scientific-breakthroughs-of-2008.ars; accessed May 19, 2009.
Shah, R., Pharmacogenetics in Drug Regulation: Promise, Potential and Pitfalls, Philos. Trans. R. Soc. Lond. B. Biol. Sci. 360(1460):1617-1638, Aug. 29, 2005.
Shao, et al., Generation of iPS Cells Using Defined Factors Linked Via the Self-Cleaving 2A Sequences in a Single Open Reading Frame, Cell Res. 19(3):296-312, Mar. 2009.
Shi, Y., et al., A Combined Chemical and Genetic Approach for the Generation of Induced Pluripotent Stem Cells, Cell Stem Cell 2:525-528, 2008.
Shi, Y., et al., Induction of Pluripotent Stem Cells From Mouse Embryonic Fibroblasts by Oct4 and Klf4 With Small-Molecule Compounds, Cell Stem Cell 3:568-574, 2008.
Silva, et al., Profiling Essential Genes in Human Mammary Cells by Multiplex RNAi Screening, Science 319(5863):617-620, Feb. 1, 2008.
Silva, et al., Capturing Pluripotericy, Cell. 132(4):532-536, Feb. 22, 2008.
Silva, et al., Promotion of Reprogramming to Ground State Pluripotency by Signal Inhibition, PLoS Biology 6(10):2237-2247, 2008.
Sinkkonen, et al., MicroRNAs Control de novo DNA Methylation Through Regulation of Transcriptional Repressors in Mouse Embryonic Stem Cells, Nat. Struct. Mol. Biol. 15(3):259-267, published online Mar. 2, 2008.
Skottman, et al., Culture Conditions for Human Embryonic Stem Cells, Reproduction 132(5):691-698, Nov. 2006.
Soldner, et al., Parkinson's Disease Patient-Derived Induced Pluripotent Stem Cells Free of Viral Reprogramming Factors, Cell 136(5):964-977, Mar. 6, 2009.
Sottile, et al., In vitro Osteogenic Differentiation of Human ES Cells, Cloning Stem Cells 5(2):149-155, 2003.
Spencer, et al., E-Cadherin Inhibits Cell Surface Localization of the Pro-Migratory 5T4 Oncofetal Antigen in Mouse Embryonic Stem Cells, Mol. Biol. Cell 18:2838-2851, 2007.
Spivakov, et al., Epigenetic Signatures of Stem-Cell Identity, Nat. Rev. Genet. 8(4):263271, 2007.
Stadler, et al., Small RNAs: Keeping Stem Cells in Line, Cell. 132(4):563-566, Feb. 22, 2008.
Stadtfeld, M., Defining Molecular Cornerstones During Fibroblast to iPS Cell Reprogramming in Mouse, Cell Stem Cell 2(3):230-240, Mar. 6, 2008.
Stadtfeld, et al., Induced Pluripotent Stem Cells Generated Without Viral Integration, Science 322(5903):945-949, published online Sep. 25, 2008.
Stadtfeld, et al., Induced Pluripotency: History, Mechanisms, and Applications, Genes & Development 24:2239-2263, 2010.
Stem Cells Made to Mimic Disease, BBC News, http://newsvote.bbc.co.uk/mpapps/pagetools/print/news.bbc.co.uk/2/hi/health/7334365.stm, Apr. 7, 2008.
Stewart, et al., Mechanisms of Self-Renewal in Human Embryonic Stem Cells, Eur. J. Cancer 42(9):1257-1272, Jun. 2006.
Stojkovic, et al., Derivation, Growth and Applications of Human Embryonic Stem Cells. Reproduction 128(3):259-267, Sep. 2004.
Strelchenko, et al., Embryonic Stem Cells from Morula. Methods in Enzymology 418:93-108, 2006.
Strelchenko, N., Bovine Pluripotent Stem Cells, Theriogenology 45:131, 1996.
Suh, et al., Human Embryonic Stem Cells Express a Unique Set of microRNAs, Developmental Biology 270:488-498, 2004.
Sumi, et al., Apoptosis and Differentiation of Human Embryonic Stem Cells Induced by Sustained Activation of c-Myc, Oncogene 26(38):5564-5576, Aug. 16, 2007.
Surani, et al., A New Route to Rejuvenation, Nature 443:284-285, Sep. 21, 2006.
Swift, et al., Rapid Production of Retroviruses for Efficient Gene Delivery to Mammalian Cells Using 293T Cell-Based System, Current Protocols in Immunology 31(Supp.):10.17.1410.17.29, 1999.
Szymczak, A., et al., Correction of Multi-Gene Deficiency in vivo Using a Single 'Self-Cleaving' 2A Peptide-Based Retroviral Vector, Nature Biotechnology 22:589-594, 2002.
Tada, et al., Nuclear Reprogramming of Somatic Cells By in vitro Hybridization With ES Cells, Current Biology 11(19):1553-58, 2001.
Takahashi, K., et al., Human Induced Pluripotent Stem Cells on Autologous Feeders, PLoS One 4(12):e8067, Dec. 2, 2009.
Takahashi, et al., Induced Pluripotent Stem Cells, Jikken Igaku (Experimental Medicine) 26(5):35-40, 2008.

(56) References Cited

OTHER PUBLICATIONS

Takahashi et al., "Induction of Pluripotent Stem Cells from Mouse Embryonic and Adult Fibroblast Cultures by Defined Factors," Cell, vol. 126, pp. 663-676 (Aug. 25, 2006).
Takahashi et al., Induction of Pluripotent Stem Cells From Adult Human Fibroblasts by Defined Factors, Cell 131(5):861-72, published online Nov. 20, 2007.
Takahashi et al., Induction of Pluripotent Stem Cells From Fibroblast Cultures, Nat. Protocols 2(12):3081-89, published online Nov. 29, 2007.
Takahashi et al., Role of ERas in Promoting Tumour-Like Properties in Mouse Embryonic Stem Cells, Nature 423:541-45, 2003.
Takeda, et al., Characterization of Dental Pulp Stem Cells of Human Tooth Germs, Journal of Dental Research 87:676-681, 2008.
Takeda, et al., Human Oct3 Gene Family: cDNA Sequences, Alternative Splicing, Gene Organization, Chromosomal Location, and Expression at Low Levels in Adult Tissues, Nucleic Acids Research 20(17):4613-4620, 1992.
Tan, et al., Changing Viral Tropism Using Immunoliposomes Alters the Stability of Gene Expression: Implications for Viral Vector Design, Mol. Med. 13(3-4):216-226, Mar-Apr. 2007.
Tantin, et al., High-Throughput Biochemical Analysis of in vivo Location Data Reveals Novel Distinct Classes of POU5FI(Oct4)/DNA Complexes, Genome Res. 18(4):631-639, Apr. 2008.
Taranger, et al., Induction of Dedifferentiation, Genomewide Transcriptional Programming, and Epigenetic Reprogramming by Extracts of Carcinoma and Embryonic Stem Cells, Mol. Biol. Cell 16:5719-5735, 2005.
Tateno, et al., Heterogeneity of Growth Potential of Adult Rat Hepatocytes in vitro, Hepatology 31(1):65-74, 2000.
The Top 10 Everything of 2008—1. First Neurons Created from ALS Patients, Time, Available at http://www.time.com/time/specials/2008/top10/article/0,30583,1855948_1863993,00.html. Accessed Dec. 15, 2008.
Thomson, et al., Embryonic Stem Cell Lines Derived From Human Blastocysts, Science 282(5391):1145-1147, Erratum in: Science 282(5395):1827, Dec. 4, 1998.
Thomson, et al., Isolation of a Primate Embryonic Stem Cell Line, 92 Proc. Natl. Acad. Sci. 7844 (1995).
Tokusumi, T., et al., Recombinant Sendai Viruses Expressing Different Levels of a Foreign Reporter Gene, Virus Research 86:33-38, 2002.
Tokuzawa, et al., Fbx15 Is a Novel Target of Oct3/4 but is Dispensible for Embryonic Stem Cell Self-Renewal and Mouse Development, Mol. Cell Biol. 23(8):2699-2718, 2003.
Tokuzawa, et al., Utilization of Digital Differential Display to Identify Novel Targets of Oct3/4. In: Turksen, K., ed., Embryonic Stem Cell Protocols: vol. I: Isolation and Characterization. Humana Press; 2nd ed., Feb. 15, 2006, pp. 223-231.
Trompeter, et al., Rapid and Highly Efficient Gene Transfer into Natural Killer Cells by Nucleofection, J. Immunol. Methods 274(1-2):245-256, Mar. 1, 2003.
Troyanskaya, et al., Nonparametric Methods for Identifying Differentially Expressed Genes in Microarray Data, Bioinformatics 18(11):1454-1461, 2002.
Tsai, et al., In vivo Immunological Function of Mast Cells Derived From Embryonic Stem Cells: An Approach for the Rapid Analysis of Even Embryonic Lethal Mutations in Adult Mice in vivo, Proc. Natl. Acad. Sci. USA 97(16):9186-9190, Aug. 1, 2000.
Tsubooka, et al., Roles of SalI4 in the Generation of Pluripotent Stem Cells From Blastocysts and Fibroblasts, Genes Cells 4(6):683-694, Jun. 2009; Epub May 19, 2009.
Tsunoda, Y., et al., The Recent Progress on Nuclear Transfer in Mammals, Zoological Science 17:1177-1184, 2000.
Tzukerman, et al., Identification of a Novel Transcription factor Binding Element Involved in the Regulation by Differentiation of the Human Telomerase (hTERT) Promoter, Mol. Biol. Cell. 11(12):4381-4391, Dec. 2000.
Ulloa-Montoya, et al., Comparative Transcriptome Analysis of Embryonic and Adult Stem Cells With Extended and Limited Differentiation Capacity, Genome Biol. 8(8):R163, 2007.
Vallier, et al., Activin/Nodal and FGF Pathways Cooperate to Maintain Pluripotency of Human Embryonic Stem Cells, J. Cell Sci. 118(Pt 19):4495-4509, Oct. 1, 2005.
Vector (in biotechnology), IUPAC Compendium of Chemical Terminology, 2nd Edition (1997).
Vermeesch, et al., Guidelines for Molecular Karyotyping in Constitutional Genetic Diagnosis, Eur. J. Hum. Genet. 15(11):1105-1114, Nov. 2007.
Verrey, et al., CATs and HATs: The SLC7 Family of Amino Acid Transporters, Pflugers Archive-European Journal of Physiology, DOI 10.1007/s00424-003-1086-Z, pp. 1-23, published online Jun. 11, 2003.
Vintersten, et al., Mouse in Red: Red Fluorescent Protein Expression in Mouse ES Cells, Embryos, and Adult Animals, Genesis 40:241-46, 2004.
Viswanathan, et al., Selective Blockade of MicroRNA Processing by Lin28, Science 320:97-100, 2008.
Vogel, G., Breakthrough of the Year. Reprogramming Cells, Science 322(5909):1766-1767, Dec. 19, 2008.
Wadia, et al., Protein Transduction Technology, Curr. Opin. Biotechnol. 13:52-56, 2002.
Wagner, et al., Mesenchymal Stem Cell Preparations—Comparing Apples and Oranges, Stem Cell Rev. 3(4):239-248, Dec. 2007.
Wakao, et al., Multilineage-Differentiating Stress-Enduring (Muse) Cells are a Primary Source of Induced Pluripotent Stem Cells in Human Fibroblasts, Available at www.pnas.org/cgi/content/short/1100816108.
Wakayama, et al., Full-Term Development of Mice From Enucleated Oocytes Injected With Cumulus Cell Nuclei, Nature 394:369-374, 1998.
Wakayama, et al., Differentiation of Embryonic Stem Cell Lines Generated From Adult Somatic Cells by Nuclear Transfer, Science 292:740-43, 2001.
Wang et al., A Protein Interaction Network for Pluripotency of Embryonic Stem Cells, Nature 444:364-368, 2006.
Wang, et al., Inhibition of Caspase-Mediated Anoikis is Critical for bFGF-Sustained Culture of Human Pluripotent Stem Cells, J. Biol. Chem. 284(49):34054-34064, Dec. 4, 2009; Epub Oct. 13, 2009.
Watanabe, et al., A Rock Inhibitor Permits Survival of Dissociated Human Embryonic Stem Cells, Nat. Biotechnol. 25:681-686, 2007.
Watson, et al., Identifying Genes Regulated in a Myc-Dependent Manner, J. Biol. Chem. 277(40):36921-36930, Oct. 4, 2002.
Werbowetski-Ogilvie, et al., Characterization of Human Embryonic Stem Cells With Features OF Neoplastic Progression, Nat. Biotechnol. 27(1):91-97, Jan. 2009.
Wernig, et al. In vitro Reprogramming of Fibroblasts into a Pluripotent ES-Cell-Like State, Nature 448:318-324, Jul. 19, 2007.
Wernig, et al., Neurons Derived From Reprogrammed Fibroblasts Functionally Integrate Into the Fetal Brain and Improve Symptoms of Rats With Parkinson's Disease, Proc. Natl. Acad. Sci. USA 105(15):5856-5861, Apr. 15, 2008.
What are adult stem Cells? Stem Cell Information. The National Institutes of Health resource for stem cell research. 2007. Available at: http://stemcells.nih.gov/info/basics/basics4.asp. Accessed Jun. 4, 2007.
Wilmut, et al., Viable Offspring Derived From Fetal and Adult Mammalian Cells, Nature 385:810-813, 1997.
Woltjen, et al., PiggyBac Transposition Reprograms Fibroblasts to Induced Pluripotent Stem Cells, Nature 458(7239):766-770, Mar. 1, 2009.
Wu et al., SalI4 Interacts With Nanog and Co-Occupies Nanog Genomic Sites in Embryonic Stem Cells, J. Biol., Chem., 281(34):24090-24094, 2000.
Wu, et al. Origins and Fates of Cardiovascular Progenitor Cells, Cell 132(4):537-543, Feb. 22, 2008.
Xu, et al. Random Mutagenesis Libraries: Optimization and Simplification by PCR, Biotechniques 27(6):1102, 1104, 1106, 1108, Dec. 1999.

(56) References Cited

OTHER PUBLICATIONS

Xu, et al., BMP4 Initiates Human Embryonic Stem Cell Differentiation to Trophoblast, Nature Biotechnol. 20(12):1261-1264, Dec. 2002.
Xu et al., Basic FGF and Suppression of BMP Signaling Sustain Undifferentiated Proliferation of Human ES Cells, Nat. Methods 2(3):185-90, 2005.
Yamanaka, et al. "Kekkan," Japanese Journal of Circulation Research, vol. 28(2), pp. 33-38 (2005).
Yamanaka, et al., Mouse Sen'iga Saibo Kara Yudo Tansosei Kansaibo o Tsukuru (Induction of Pluripotent Stem Cells From Mouse Fibroblast Cultures) Tanpakushitsu Kakusan Koso (Protein, Nucleic Acid and Enzyme) 51(15):2346-51, 2006.
Yamanaka, S., Strategies and New Developments in the Generation of Patient-Specific Pluripotent Stem Cells, Cell Stem Cell 1(1):39-49, Jun. 7, 2007.
Yamanaka, Pluripotency of Differentiation and miRNA, The Journal of Biochemistry 79(11):Abstract 3BT17, from the 80th Annual Meeting of the Japanese Biochemical Society, Nov. 25, 2007.
Yamanaka, S., The Novel Pluripotent Cells Established by Professor Yamanaka of Kyoto University May Change Medical Care, Asahi Shimbun Weekly AERA, Dec. 24, 2007, pp. 72-73.
Yamanaka, S., Induction of Pluripotent Stem Cells From Mouse Fibroblasts by Four Transcription Factors, Cell Proliferation 41 (Suppl. 1):51-56, 2008.
Yamanaka, S., Symposium: Nuclear Reprogramming and the Control of Differentiation in Mammalian Embryos, Introduction, Reprod. Biomed Online 16(1):11-12, Jan. 2008.
Yamanaka, S., Pluripotency and Nuclear Reprogramming, Philos. Trans. R. Soc. Lond. B. Biol. Sci. 363(1500):2079-2087, Jun. 27, 2008.
Yamanaka, S., A Fresh Look at iPS Cells, Cell 137(1):13-17, Apr. 3, 2009.
Yamanaka, S., Elite and Stochastic Models for Induced Pluripotent Stem Cell Generation, Nature 460(7251):49-52, Jul. 2, 2009.
Yamanaka, S., Ekiden to iPS Cells. Nat. Med. 15(10):1145-1148, Oct. 2009.
Yamanaka, S., "Induction of Pluripotency by Defined Factors—The History of iPS Cells", Gairdner Award acceptance speech, presented on or about Oct. 29, 2009.
Yamanaka, S., An interview with . . . Shinya Yamanaka. Interview by Mary Muers. Nat. Rev. Genet. 11(6):390, Jun. 2010.
Yamanaka, S., Patient-Specific Pluripotent Stem Cells Become Even More Accessible Cell Stem Cell 7(1):1-2, Jul. 2, 2010.
Yamane, et al., Derivation of Melanocytes From Embryonic Stem Cells in Culture, Dev. Dyn. 216:450-458, 1999.
Yamashita, et al., Flk1-Positive Cells Derived From Embryonic Stem Cells Serve as Vascular Progenitors, Nature 408(6808):92-96, Nov. 2, 2000.
Yang et al., Nuclear Reprogramming of Cloned Embryos and Its Implications for Therapeutic Cloning, Nat. Genet. 39(3):295-302, 2007.
Yee, et al. Generation of High-Titer Pseudotyped Retroviral Vectors With Very Broad Host Range, Methods Cell Biol. 43(Pt. A):99-112, 1994.
Ying et al., BMP Induction of ID Proteins Suppresses Differentiation and Sustains Embryonic Stem Cell Self-Renewal in Collaboration With STAT3, Cell 115:281-292, 2003.
Ying et al., The MicroRNA: Overview of the RNA Gene That Modulates Gene Functions, Methods in Molecular Biology, MicroRNA Protocols, vol. 342, pp. 1-18, Humana Press, 2006.
Yoshida et al. Hypoxia Enhances the Generation of Induced Pluripotent Stem Cells, Cell Stem Cell 5(3):237-241, Sep. 4, 2009; Epub Aug. 27, 2009.
Yoshida, et al., Recent Stem Cell Advances: Induced Pluripotent Stem Cells for Disease Modeling and Stem Cell-Based Regeneration, Circulation 122(1):80-87, Jul. 6, 2010.
Yu et al., Induced Pluripotent Stem Cell Lines Derived From Human Somatic Cells, Science 318(5858):1917-20, published online Nov. 20, 2007.
Yu, et al., Human Induced Pluripotent Stem Cells Free of Vector and Transgene Sequences, Science 324:797-801, Mar. 2009.
Yuasa, et al. Transient Inhibition of BMP Signaling by Noggin Induces Cardiomyocyte Differentiation of Mouse Embryonic Stem Cells, Nat. Biotechnol. 23(5):607-611, May 2005.
Zhan, et al., Conservation and Variation of Gene Regulation in Embryonic Stem Cells Assessed by Comparative Genomics, Cell Biochem. Biophys. 43(3):379-405, 2005.
Zhang, et al. In vitro Differentiation of Transplantable Neural Precursors From Human Embryonic Stem Cells, Nat. Biotechnol. 19:1129-1133, Dec. 2001.
Zhang et al., MicroRNA: A New Player in Stem Cells, Journal of Cellular Physiology 209:266-269, 2006.
Zhao, et al. Mechanisms and Functional Implications of Adult Neurogenesis, Cell 132(4):645-660, Feb. 22, 2008.
Zhao et al., "Two Supporting Factors Greatly Improve the Efficiency of Human iPSC Generation" Cell Stem Cell 3:475-79, 2008.
Zhou et al., "Adenoviral Gene Delivery Can Reprogram Human Fibroblasts to Induced Pluripotent Stem Cells," Stem Cells, vol. 27, pp. 2667-2674 (2009).
Zhou et al., Generation of Induced Pluripotent Stem Cells Using Recombinant Proteins, Cell Stem Cell 4:381-384, 2009.
Ziegler et al., The Cationic Cell-Penetrating Peptide CPPTAT Derived From the HIV-1 Protein TAT is Rapidly Transported into Living Fibroblasts: Optical, Biophysical, and Metabolic Evidence, Biochemistry 44:138-148, published online Dec. 14, 2004.

* cited by examiner

A

B

Colony

After passages（Passage 2)

A

B

B

A

B

C

A

B

C

| (ml) | Mock | Oct3/4 | Sox2 | Klf4 | cMyc | mSall4 | mSall1 | DsRed | day 30 ES like | day 30 non ES |
|---|---|---|---|---|---|---|---|---|---|---|
| DsRed | | | | | | | | 2 | 0 | 0 |
| Mock | 2 | | | | | | | | 0 | 0 |
| Y3F + Mock | 0.5 | 0.5 | 0.5 | 0.5 | | | | | 0 | 0 |
| + Mock x2 | 0.8 | 0.4 | 0.4 | 0.4 | | | | | 0 | 1 |
| + DsRed | | 0.5 | 0.5 | 0.5 | | | | 0.5 | 0 | 0 |
| + DsRed x2 | | 0.4 | 0.4 | 0.4 | | | | 0.8 | 0 | 0 |
| + mSall4 | | 0.5 | 0.5 | 0.5 | | 0.5 | | | 7 | 1 |
| + mSall1 | | 0.5 | 0.5 | 0.5 | | | 0.5 | | 0 | 0 |
| + mSall1 + mSall4 | | 0.4 | 0.4 | 0.4 | | 0.4 | 0.4 | | 5 | 0 |
| Y4F + Mock | 0.4 | 0.4 | 0.4 | 0.4 | | | | | 5 | 30 |
| + DsRed | | 0.4 | 0.4 | 0.4 | 0.4 | | | 0.4 | 7 | 21 |
| + mSall4 | | 0.4 | 0.4 | 0.4 | 0.4 | 0.4 | | | 16 | 23 |
| + mSall1 | | 0.4 | 0.4 | 0.4 | 0.4 | | 0.4 | | 6 | 33 |
| + mSall1 + mSall4 | | 0.33 | 0.33 | 0.33 | 0.33 | 0.33 | 0.33 | | 19 | 12 |

NUCLEAR REPROGRAMMING FACTOR AND INDUCED PLURIPOTENT STEM CELLS

PRIOR RELATED APPLICATIONS

This application is a continuation application of U.S. application Ser. No. 15/474,855, filed Mar. 30, 2017, which is a continuation application of U.S. application Ser. No. 12/289,873, filed Nov. 6, 2008, which is a continuation-in-part of U.S. application Ser. No. 12/213,035, filed Jun. 13, 2008, which is a continuation-in-part of PCT/JP2006/324881, filed Dec. 6, 2006, which claims priority to Japanese Application No. 2005-359537, filed Dec. 13, 2005, and also claims priority to U.S. Provisional Application No. 61/001,108, filed Oct. 31, 2007, and U.S. Provisional Application No. 60/996,289, filed Nov. 9, 2007. The entire disclosures of each of the above-cited applications are considered as being part of this application and are expressly incorporated by reference herein in their entireties.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 54537867_1.TXT, the date of creation of the ASCII text file is Nov. 8, 2021, and the size of the ASCII text file is 107 KB.

FIELD OF THE INVENTION

The present invention relates to a nuclear reprogramming factor having an action of reprogramming a somatic cell to derive an induced pluripotent stem (iPS) cell. The present invention also relates to the aforementioned iPS cells, methods of generating, and maintaining iPS cells, and methods of using iPS cells, including screening and testing methods as well as methods of stem cell therapy. The present invention also relates to somatic cells derived by inducing differentiation of the aforementioned iPS cells.

BACKGROUND OF THE INVENTION

Embryonic stem cells (ES cells) are stem cells established from human or mouse early embryos which have a characteristic feature that they can be cultured over a long period of time while maintaining pluripotent ability to differentiate into all kinds of cells existing in living bodies. Human embryonic stem cells are expected for use as resources for cell transplantation therapies for various diseases such as Parkinson's disease, juvenile diabetes, and leukemia, taking advantage of the aforementioned properties. However, transplantation of ES cells has a problem of causing rejection in the same manner as organ transplantation. Moreover, from an ethical viewpoint, there are many dissenting opinions against the use of ES cells which are established by destroying human embryos.

Embryonic stem (ES) cells, derived from the inner cell mass of mammalian blastocysts, have the ability to grow indefinitely while maintaining pluripotency (Evans et al. *Nature* 292:154-156, 1981; Martin *P.N.A.S. USA* 78:7634-7638, 1981). These properties have led to expectations that human ES cells might be useful to understand disease mechanisms, to screen effective and safe drugs, and to treat patients of various diseases and injuries, such as juvenile diabetes and spinal cord injury (Thomson et al. *Science*

282:1145-1147, 1998). Use of human embryos, however, faces ethical controversies that hinder the applications of human ES cells. In addition, it is difficult to generate patient-or disease-specific ES cells, which are required for their effective application. Therefore, if dedifferentiation of a patient's own somatic cells could be induced to establish cells having pluripotency and growth ability similar to those of ES cells (in this specification, these cells are referred to as "induced pluripotent stem cells (iPS cells)", though they are sometimes called "embryonic stem cell-like cells" or "ES-like cells"), it is anticipated that such cells could be used as ideal pluripotent cells, free from rejection or ethical difficulties.

Methods for nuclear reprogramming of a somatic cell nucleus have been reported. One technique for nuclear reprogramming which has been reported involves nuclear transfer into oocytes (Wakayama et al. *Nature* 394:369-374, 1998; Wilmut et al. *Nature* 385:810-813, 1997). Another method, for example, a technique of establishing an embryonic stem cell from a cloned embryo, prepared by transplanting a nucleus of a somatic cell into an egg, was reported (Hwang et al. *Science* 303:1669-74, 2004; Hwang et al. *Science* 308:1777-83, 2005): these articles were, however, proved to be fabrications and later withdrawn. Others have reported techniques for nuclear reprogramming of a somatic cell nucleus by fusing a somatic cell and an ES cell (Tada et al. *Curr. Biol.* 11:1553-1558, 2001; Cowan et al. *Science* 309:1369-73, 2005). Another reported technique for reprogramming a cell nucleus involves treatment of a differentiated cell with an undifferentiated human carcinoma cell extract (Taranger et al. *Mol. Biol. Cell* 16:5719-35, 2005). However, these methods all have serious drawbacks. Methods of nuclear transfer into oocytes and techniques which involve the fusion of ES and differentiated cells both comprise the use of ES cells, which present ethical problems. In addition, cells generated by such methods often lead to problems with rejection upon transplantation into an unmatched host. Furthermore, the use of cell extracts to treat differentiated cells is technically unreliable and unsafe, in part because the cell extract components responsible for the nuclear programming are mixed in solution with other unknown factors.

A method for screening a nuclear reprogramming factor having an action of reprogramming differentiated somatic cells to derive induced pluripotent stems cell was proposed in International Publication WO2005/80598, which is incorporated by reference in its entirety. This method comprises the steps of: contacting somatic cells containing a marker gene under expression regulatory control of an ECAT (ES cell associated transcript) gene expression control region with a test substance; examining presence or absence of the appearance of a cell that expresses the marker gene; and choosing a test substance inducing the appearance of said cell as a candidate nuclear reprogramming factor for somatic cells. A method for reprogramming a somatic cell is disclosed in Example 6 and the like of the above publication. However, this publication fails to report an actual identification of a nuclear reprogramming factor.

In view of these problems, there remains a need in the art for nuclear reprogramming factors capable of generating pluripotent stem cells from somatic cells. There also remains a need for pluripotent stem cells, which can be derived from a patient's own somatic cells, so as to render ethical issues and avoid problems with rejection. Such cells would have enormous potential for both research and clinical applications.

SUMMARY OF THE INVENTION

The present invention provides induced pluripotent stem (iPS) cells derived by nuclear reprogramming of a somatic cell. The present invention also provides methods for reprogramming of a differentiated cell without using eggs, embryos, or embryonic stem (ES) cells. The present invention also provides nuclear reprogramming factors for induction of pluripotent stem cells. The disclosed methods and nuclear reprogramming factors may be used to conveniently and highly reproducibly establish iPS cells having pluripotency and growth ability similar to that of ES cells. More specifically, the present invention provides for inducing reprogramming of a differentiated cell without using eggs, embryos, or ES cells to conveniently and highly reproducibly establish the iPS cells having pluripotency and growth ability similar to that of ES cells.

The invention provides a pluripotent stem cell induced by reprogramming a somatic cell in the absence of eggs, embryos, or embryonic stem (ES) cells. The somatic cell can be a mammalian cell, for example a mouse cell or a human cell. The present invention also provides such a pluripotent stem cell, wherein the reprogramming comprises contacting the somatic cell with a nuclear reprogramming factor.

The nuclear reprogramming factor can comprise at least one gene product, for example a protein. The nuclear reprogramming factor can comprise a gene product of an Oct family gene, a Klf family gene, a Myc family gene, or a Sox family gene. The nuclear reprogramming factor can comprise one or more gene products of each of: an Oct family gene, a Klf family gene, and a Sox family gene. The nuclear reprogramming factor can comprise one or more gene products of each of: an Oct family gene, a Klf family gene, a Myc family gene, and a Sox family gene. Furthermore, the nuclear reprogramming factor can comprise one or more gene products of each of: an Oct family gene, a Klf family gene, together with a cytokine. The cytokine can be at least one of basic fibroblast growth factor (bFGF) and stem cell factor (SCF).

The invention also provides a method for preparing an induced pluripotent stem cell by nuclear reprogramming of a somatic cell, which comprises contacting a nuclear reprogramming factor with the somatic cell to obtain an induced pluripotent stem cell. The invention also provides such a method which is performed in the absence of eggs, embryos, or embryonic stem (ES) cells. The present invention also provides an induced pluripotent stem cell obtained by such a method. The present invention also provides a pluripotent stem cell induced by reprogramming a somatic cell, wherein the reprogramming comprises contacting the somatic cell with a nuclear reprogramming factor.

The present invention also provides such a method wherein the nuclear reprogramming factor comprises one or more gene products of each of: an Oct family gene, a Klf family gene, and a Sox family gene. The present invention also provides such a method wherein the nuclear reprogramming factor comprises one or more gene products of each of: Oct3/4, Klf4, and Sox2. The present invention also provides such a method wherein the nuclear reprogramming factor further comprises one or more gene products of a Sall4 gene. The present invention also provides pluripotent stem cells prepared by such methods.

The present invention also provides such a method wherein the nuclear reprogramming factor comprises one or more gene products of each of: wherein the nuclear reprogramming factor comprises one or more gene products of each of: an Oct family gene, a Klf family gene, a Myc family gene, and a Sox family gene. The present invention also provides such a method wherein the nuclear reprogramming factor comprises one or more gene products of each of: Oct3/4, Klf4, c-Myc, and Sox2. The present invention also provides such a method wherein the nuclear reprogramming factor further comprises one or more gene products of a Sall4 gene. The present invention also provides pluripotent stem cells prepared by such methods.

The present invention also provides such a method wherein the nuclear reprogramming factor comprises one or more gene products of each of: Klf4, c-Myc, Oct3/4, Sox2, Nanog, and Lin28. The present invention also provides pluripotent stem cells prepared by such a method.

The present invention also provides a method of inducing a somatic cell to become a pluripotent stem cell comprising contacting the somatic cell with a nuclear reprogramming factor under conditions to obtain a pluripotent stem cell free of rejection.

The present invention also provides a somatic cell derived by inducing differentiation of an induced pluripotent stem cell as disclosed herein.

The present invention also provides a pluripotent stem cell induced by reprogramming a somatic cell, wherein the reprogramming is performed in the absence of eggs, embryos, or embryonic stem (ES) cells and comprises contacting the somatic cell with a nuclear reprogramming factor comprising one or more gene products of a Sall1 gene and/or a Sall4 gene.

The present invention also provides a pluripotent stem cell induced by reprogramming a somatic cell, wherein the reprogramming is performed in the absence of eggs, embryos, or embryonic stem (ES) cells and comprises contacting the somatic cell with a nuclear reprogramming factor comprising one or more gene products of: an L-Myc gene, an N-Myc gene, and/or a c-Myc gene.

The present invention also provides a pluripotent stem cell induced by reprogramming a somatic cell, wherein the reprogramming is performed in the absence of eggs, embryos, or embryonic stem (ES) cells and comprises contacting the somatic cell with a nuclear reprogramming factor comprising one or more gene products of a Lin28 gene.

The present invention also provides a method for preparing an induced pluripotent stem cell by nuclear reprogramming of a somatic cell, which comprises contacting a nuclear reprogramming factor comprising one or more gene products of a Sall1 gene and/or a Sall4 gene with the somatic cell to obtain an induced pluipotent stem cell.

The present invention also provides a method for preparing an induced pluripotent stem cell by nuclear reprogramming of a somatic cell, which comprises contacting a nuclear reprogramming factor comprising one or more gene products of: an L-Myc gene, an N-Myc gene, and/or a c-Myc gene with the somatic cell to obtain an induced pluipotent stem cell.

The present invention is also directed to a method for preparing an induced pluripotent stem cell by nuclear reprogramming of a somatic cell, which comprises contacting a nuclear reprogramming factor comprising one or more gene products of a Lin28 gene with the somatic cell to obtain an induced pluipotent stem cell.

The present invention also provides induced pluripotent stem cells obtained by methods disclosed herein.

The somatic cell can be a human cell or a mouse cell.

The nuclear reprogramming factor can comprise one or more gene products of a human or mouse Sall4 gene.

The nuclear reprogramming factor can comprise one or more gene products of each of: an Oct family gene, a Klf family gene, and a Sox family gene.

The nuclear reprogramming factor can comprise one or more gene products of a Myc family gene.

The nuclear reprogramming factor can comprise Oct3/4, Klf4, and Sox2, and at least one of Sall1 and Sall4.

The nuclear reprogramming factor can comprise Oct3/4, Klf4, Sox2, and c-Myc, and at least one of Sall1 and Sall4.

The nuclear reprogramming factor can comprise one or more gene products of each of: an Oct family gene, a Sox family gene, and a Nanog family gene.

The nuclear reprogramming factor can comprise one or more gene products of a Lin28 family gene.

The nuclear reprogramming factor can comprise Oct3/4, Sox2, and Nanog, and at least one of Sall1 and Sall4.

The nuclear reprogramming factor can comprise Oct3/4, Sox2, Nanog, and Lin28, and at least one of Sall1 and Sall4.

The L-Myc gene, the N-Myc gene, and/or the c-Myc gene can be a chimera or mutant gene.

The nuclear reprogramming factor can comprise Ms-cL-Myc or its human homolog.

The nuclear reprogramming factor can comprise amino acids 1-144 of c-Myc or its human homolog.

The nuclear reprogramming factor can comprise amino acids 105-277 of L-Myc or its human homolog.

The nuclear reprogramming factor can comprise amino acids 347-439 of c-Myc, amino acids 278-368 of L-Myc, or their human homolog.

The nuclear reprogramming factor can comprise one or more gene products of: an Oct family gene, and a Klf family gene.

The nuclear reprogramming factor can comprise one or more gene products of a Sox family gene.

The nuclear reprogramming factor can comprise one or more gene products of a Lin28 family gene.

The nuclear reprogramming factor can comprise Oct3/4, Klf4, and L-Myc.

The nuclear reprogramming factor can comprise Oct3/4, Klf4, Sox2, and L-Myc.

The nuclear reprogramming factor can comprise Oct3/4, Klf4, Sox2, L-Myc, and Lin28.

The present invention also provides a method for stem cell therapy comprising: (1) isolating and collecting a somatic cell from a patient; (2) inducing said somatic cell from the patient into an iPS cell (3) inducing differentiation of said iPS cell, and (4) transplanting the differentiated cell from (3) into the patient.

The present invention also provides a method for evaluating a physiological function of a compound comprising treating cells obtained by inducing differentiation of an induced pluripotent stem cell as disclosed herein with the compound.

The present invention also provides a method for evaluating the toxicity of a compound comprising treating cells obtained by inducing differentiation of an induced pluripotent stem cell as disclosed herein with the compound.

Other features and advantages of the present invention will be set forth in the description of the invention that follows, and will be apparent, in part, from the description or may be learned by practice of the invention. The invention will be realized and attained by the compositions, products, and methods particularly pointed out in the written description and claims hereof.

DETAILED DESCRIPTION OF THE INVENTION

Figure 1:
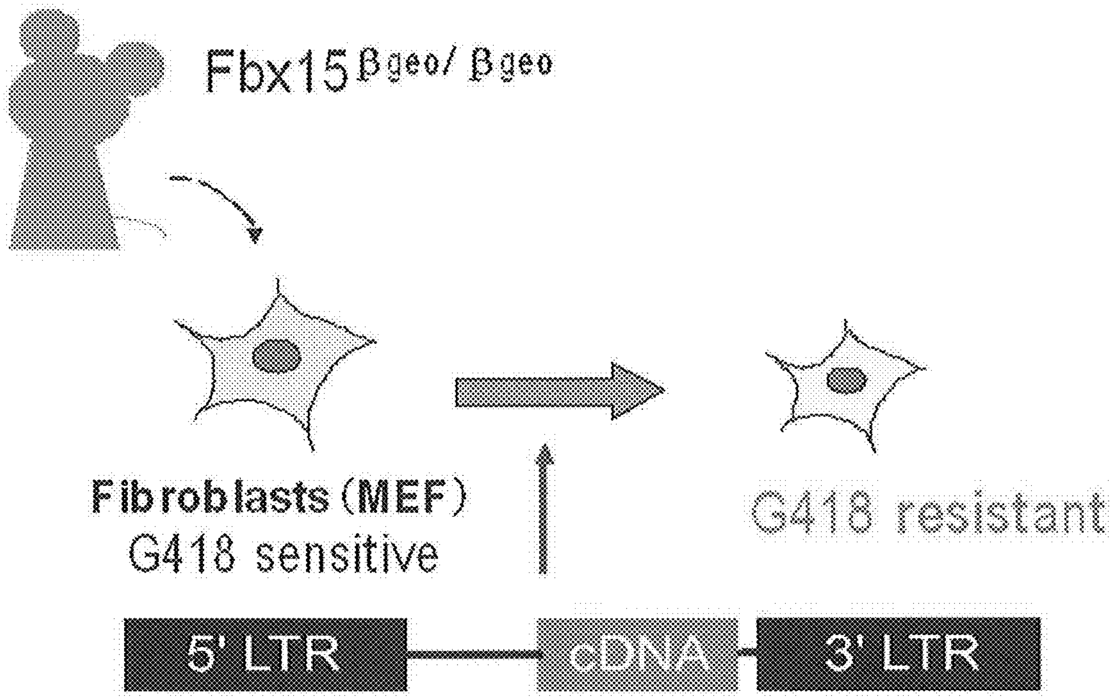
FIG. 1 shows a screening method for reprogramming factors using embryonic fibroblasts (MEFs) of a mouse having βgeo knock-in Fbx15 gene.

Various investigations were conducted to address the aforementioned need for pluripotent stem cells which can be derived from a patient's own somatic cells, and for nuclear reprogramming factors capable of generating pluripotent stem cells from somatic cells. Investigations were also conducted to identify nuclear reprogramming factors by using the screening method for a nuclear reprogramming factor disclosed in International Publication WO2005/80598. While International Publication WO 2005/80598 discloses a screening method, this document fails to disclose any nuclear reprogramming factor. Furthermore, this document fails to specify any nuclear reprogramming factor or candidate nuclear reprogramming factor which would be capable of generating an induced pluripotent stem cell.

Ultimately, 24 kinds of candidate genes were found as genes relating to nuclear reprogramming, and among them, three kinds of the genes were found as particularly preferred for nuclear reprogramming: sometimes these genes are referred to as essential in certain embodiments. As further discussed throughout the specification, the nuclear reprogramming factor of the present invention may contain one or more factors relating to differentiation, development, proliferation or the like and factors having other physiological activities, as well as other gene products which can function as a nuclear reprogramming factor. The present invention was achieved on the basis of these findings.

The present invention provides at least the following advantages and features: induced pluripotent stem (iPS) cells derived by nuclear reprogramming of a somatic cell, including methods for reprogramming of a differentiated cell without using eggs, embryos, or embryonic stem (ES) cells.

As further discussed herein with respect to the general guidance for the reprogramming of differentiated cells and the examples, the present invention also provides various nuclear reprogramming factors capable of generating pluripotent stem cells from somatic cells. The nuclear reprogramming factor may comprise one or more gene products. The nuclear reprogramming factor may also comprise a combination of gene products. Each nuclear reprogramming factor may be used alone or in combination with other nuclear reprogramming factors as disclosed herein. In addition, nuclear reprogramming may be performed with small molecules, compounds, or other agents such that iPS cells are obtained.

In a preferred embodiment, the nuclear reprogramming factor comprises a gene product of each of the following three kinds of genes: an Oct family gene, a Klf family gene, and a Sox family gene. According to a more preferred embodiment of the invention, there is provided the aforementioned factor comprising a gene product of each of the following three kinds of genes: Oct3/4, Klf4, and Sox2.

In another embodiment of the invention, there is provided a nuclear reprogramming factor comprising a gene product of each of the following three kinds of genes: an Oct family gene, a Klf family gene, and a Myc family gene. According to a preferred embodiment of the invention, there is provided the aforementioned factor comprising a gene product of each of the following three kinds of genes: Oct3/4, Klf4 and c-Myc.

According to another preferred embodiment, there is provided the aforementioned factor, which further comprises a gene product of the following gene: a Sox family gene, and as a more preferred embodiment, there is provided the aforementioned factor, which comprises a gene product of Sox2.

According to still another preferred embodiment, there is provided the aforementioned factor, which comprises a cytokine together with the gene product of the Myc family gene, or alternatively, instead of the gene product of the Myc family gene. As a more preferred embodiment, there is provided the aforementioned factor, wherein the cytokine is basic fibroblast growth factor (bFGF) and/or stem cell factor (SCF). Accordingly, it is understood that the nuclear reprogramming factor can be with or without the Myc family gene.

According to particularly preferred embodiments, there is provided a nuclear reprogramming factor for a somatic cell, which comprises a gene product of the TERT gene in addition to a gene product of each of an Oct family gene, a Klf family gene, a Myc family gene, and a Sox family gene; and the aforementioned factor, which comprises a gene product or gene products of one or more kinds of genes selected from the group consisting of the following genes: SV40 Large T antigen (SEQ ID NO: 23), HPV16 E6 (SEQ ID NO: 24), HPV16 E7 (SEQ ID NO: 25), and Bmil, in addition to a gene product of each of the Oct family gene, the Klf family gene, the Myc family gene, the Sox family gene, and the TERT gene.

In addition to these factors, there is provided the aforementioned factor, which further comprises a gene product or gene products of one or more kinds of genes selected from the group consisting of the following: Fbx15, Nanog, ERas, ECAT15-2, Tell, and β-catenin.

There is also provided the aforementioned factor, which comprises a gene product or gene products of one or more kinds of genes selected from the group consisting of the following: ECAT1, Esg1, Dnmt3L, ECAT8, Gdf3, Sox15, ECAT15-1, Fthl17, Sall4, Rex1, UTF1, Stella, Stat3, and Grb2.

The present invention also provides a nuclear reprogramming factor comprising a gene product or gene products of one or more kinds of the following genes: Oct3/4, Sox2, Klf4, Nanog, Lin-28, and c-Myc.

The present invention also provides a nuclear reprogramming factor comprising any combination of gene products, small molecules and/or substances as described herein, further comprising one or more factors improving the efficiency of iPS cell induction, such as one or more gene products of a Sall1 and/or Sall4 gene, a Myc gene (including c-Myc, N-Myc, and/or L-Myc, as well as mutants and chimeras thereof), and/or a Lin28 gene. The one or more gene products capable of improving iPS cell induction, such as a Sall1, Sall4, Myc, Lin28, and/or Nanog gene may be derived from a mammal, e.g. mouse, rat, or human.

In another aspect, the present invention provides a method for preparing an induced pluripotent stem cell by nuclear reprogramming of a somatic cell, which comprises the step of contacting the aforementioned nuclear reprogramming factor with the somatic cell.

There is also provided the aforementioned method, which comprises the step of adding the aforementioned nuclear reprogramming factor to a culture of the somatic cell; the aforementioned method, which comprises the step of introducing a gene encoding the aforementioned nuclear reprogramming factor into the somatic cell; the aforementioned method, which comprises the step of introducing said gene into the somatic cell by using a recombinant vector containing at least one kind of gene encoding the aforementioned nuclear reprogramming factor; and the aforementioned method, wherein a somatic cell isolated from a patient is used as the somatic cell.

In another aspect, the present invention provides an induced pluripotent stem cell obtained by the aforementioned method. The present invention also provides a somatic cell derived by inducing differentiation of the aforementioned induced pluripotent stem cell.

The present invention further provides a method for stem cell therapy, which comprises the step of transplanting a somatic cell, wherein said cell is obtained by inducing differentiation of an induced pluripotent stem cell obtained by the aforementioned method using a somatic cell isolated and collected from a patient, into said patient. Several kinds of, preferably approximately 200 kinds of iPS cells prepared from somatic cells derived from healthy humans can be stored in an iPS cell bank as a library of iPS cells, and one kind or more kinds of the iPS cells in the library can be used for preparation of somatic cells, tissues, or organs that are free of rejection by a patient to be subjected to stem cell therapy.

The present invention further provides a method for evaluating a physiological function or toxicity of a compound, a medicament, a poison or the like by using various cells obtained by inducing differentiation of an induced pluripotent stem cell obtained by the aforementioned method.

The present invention also provides a method for improving ability of differentiation and/or growth of a cell, which comprises the step of contacting the aforementioned nuclear reprogramming factor with the cell, and further provides a cell obtained by the aforementioned method, and a somatic cell derived by inducing differentiation of a cell obtained by the aforementioned method.

By using the nuclear reprogramming factor provided by the present invention, reprogramming of a differentiated cell nucleus can be conveniently and highly reproducibly induced without using embryos or ES cells, and an induced pluripotent stem cell, as an undifferentiated cell having differentiation ability, pluripotency, and growth ability similar to those of ES cells, can be established. For example, an induced pluripotent stem cell having high growth ability and differentiation pluripotency can be prepared from a patient's own somatic cell by using the nuclear reprogramming factor of the present invention. Cells obtainable by differentiating said cell (for example, cardiac muscle cells, insulin producing cells, nerve cells and the like) are extremely useful, because they can be utilized for stem cell transplantation therapies for a variety of diseases such as cardiac insufficiency, insulin dependent diabetes mellitus, Parkinson's disease and spinal cord injury, thereby the ethical problem concerning the use of human embryo and rejection after transplantation can be avoided. Further, various cells obtainable by differentiating the induced pluripotent stem cell (for example, cardiac muscle cells, hepatic cells and the like) are highly useful as systems for evaluating efficacy or toxicity of compounds, medicaments, poisons and the like.

As noted above, transplantation of ES cells has a problem of causing rejection in the same manner as organ transplantation. Moreover, from an ethical viewpoint, there are many dissenting opinions against the use of ES cells, which are established by destroying human embryos.

The present invention provides at least the following advantages and features:

Identification of Nuclear Reprogramming Factors

As will be further disclosed below, the nuclear reprogramming factor of the present invention may contain one or more factors relating to differentiation, development, proliferation or the like and factors having other physiological activities, as well as other gene products which can function as a nuclear reprogramming factor. It is understood that such embodiments fall within the scope of the present invention, and the present invention is, in other words, directed to factors inducing pluripotent stem cells and various methods of obtaining induced pluripotent stem cells, including various manners of reprogramming differentiated cells as well as various manners of culturing, maintaining, and differentiating the induced pluripotent stem cells.

Furthermore, by using somatic cells in which only one or two genes among the three kinds of genes Oct3/4, Klf4, and c-Myc are expressed, other gene products which can function as a nuclear reprogramming factor can be identified by, for example, performing screening for a gene product which can induce nuclear reprogramming of said cells. For example, depending on the kinds of genes expressed in a differentiated cell, one or more genes useful as a reprogramming factor can be determined using the guidance herein provided. According to the present invention, the aforementioned screening method is also provided as a novel method for screening for a nuclear reprogramming factor. In other words, the present invention is not limited to any particular combination of nuclear reprogramming factors and the nuclear reprogramming factors of the present invention can be identified by screening methods, for example, the aforementioned screening method.

In one embodiment, the nuclear reprogramming factor of the present invention is characterized in that it comprises one or more gene products. As a means for confirming the nuclear reprogramming factor of the present invention, for example, the screening method for nuclear reprogramming factors disclosed in International Publication WO 2005/80598 can be used. The entire disclosure of the aforementioned publication is incorporated into the disclosure of the specification by reference. By referring to the aforementioned publication, those skilled in the art can perform screening of nuclear reprogramming factors to confirm the existence and the action of the reprogramming factor of the present invention.

For example, as an experimental system allowing for observation of the reprogramming phenomenon, a mouse can be used in which the βgeo (a fusion gene of the β galactosidase gene and the neomycin resistance gene) is knocked into the Fbx15 locus (Tokuzawa et al. *Mol. Cell Biol.* 23:2699-708, 2003). The details are described in the examples of the specification. The mouse Fbx15 gene is a gene specifically expressed in differentiation pluripotent cells such as ES cells and early embryos. In a homomutant mouse in which βgeo is knocked into the mouse Fbx15 gene so as to be deficient in the Fbx15 function, abnormal phenotypes including those relating to differentiation pluripotency or generation are not generally observed. In this mouse, the expression of the βgeo is controlled by the enhancer and promoter of the Fbx15 gene, and differentiated somatic cells in which βgeo is not expressed have sensitivity to G418. In contrast, βgeo knockin homomutant ES cells have resistance against G418 at an extremely high concentration (higher than 12 mg/ml). By utilizing this phenomenon, an experimental system can be constructed to visualize reprogramming of somatic cells.

By applying the aforementioned experimental system, fibroblasts ($Fbx15^{\beta geo/\beta geo}$ MEFs) can be first isolated from an embryo of the βgeo knockin homomutant mouse (13.5 days after fertilization). The MEFs do not express the Fbx15 gene, and accordingly also do not express βgeo to give sensitivity to G418. However, when the MEFs are fused with genetic manipulation-free ES cells (also have sensitivity to G418), βgeo is expressed and the cells become G418-resistant as a result of reprogramming of nuclei of MEFs. Therefore, by utilizing this experimental system, the reprogramming phenomenon can be visualized as G418 resistance.

Nuclear reprogramming factors can be selected by using the aforementioned experimental system. As candidates of genes relevant to nuclear reprogramming factors, a plurality of genes can be selected which show specific expression in ES cells or of which important roles in the maintenance of pluripotency of ES cells are suggested, and it can be confirmed whether or not each candidate gene can induce nuclear reprogramming alone or in an appropriate combination thereof. For example, a combination of all of the selected primary candidate genes is confirmed to be capable of inducing the reprogramming of differentiated cells into a state close to that of ES cells. Combinations are then prepared by withdrawing each individual gene from the aforementioned combination, and the same actions of the combinations are confirmed in order to select each secondary candidate gene whose absence causes a reduction of the reprogramming induction ability or loss of the reprogramming induction ability. By repeating similar steps for the secondary candidate genes selected as described above, an essential combination of nuclear reprogramming genes can be selected, and it can be confirmed that a combination of gene products of each of the three kinds of genes, e.g., an Oct family gene, a Klf family gene, and a Myc family gene, acts as a nuclear reprogramming factor. It can be further confirmed that a combination of a gene product of a Sox family gene additionally with the gene products of the aforementioned three kinds of genes has extremely superior characteristics as a nuclear reprogramming factor. Specific examples of the selection method for the nuclear reprogramming factors are demonstrated in the examples of the specification.

Therefore, by referring to the above general explanations and specific explanations of the examples, those skilled in the art can readily confirm that the combination of these three kinds of genes induces the reprogramming of somatic cells, and that the combination of these three kinds of gene products is essential for nuclear reprogramming in certain embodiments. Thus, the embodiments herein illustrate various combinations of gene products and/or nuclear reprogramming factors which can provide iPS cells. In other words, based on the disclosure provided herein, one of ordinary skill in the art would know from the disclosed examples and/or readily determine which combination and/or combinations of nuclear reprogramming factors, including gene products, can generate pluripotent stem cells.

Nuclear Reprogramming Factor (NRF)

In a preferred embodiment, the NRF comprises a gene product. The nuclear reprogramming factor can be used to induce reprogramming of a differentiated cell without using eggs, embryos, or ES cells, to conveniently and highly reproducibly establish an induced pluripotent stem cell having pluripotency and growth ability similar to those of ES cells. For example, the nuclear reprogramming factor can be introduced into a cell by transducing the cell with a recombinant vector comprising a gene encoding the nuclear reprogramming factor. Accordingly, the cell can express the nuclear reprogramming factor expressed as a product of a gene contained in the recombinant vector, thereby inducing reprogramming of a differentiated cell.

The nuclear reprogramming factor may comprise a protein or peptide. The protein may be produced from the aforementioned gene, or alternatively, in the form of a fusion gene product of said protein with another protein, peptide or the like. The protein or peptide may be a fluorescent protein and/or a fusion protein. For example, a fusion protein with green fluorescence protein (GFP) or a fusion gene product with a peptide such as a histidine tag can also be used. Further, by preparing and using a fusion protein with the TAT peptide derived form the virus HIV, intracellular uptake of the nuclear reprogramming factor through cell membranes can be promoted, thereby enabling induction of reprogramming only by adding the fusion protein to a medium thus avoiding complicated operations such as gene transduction. Since preparation methods of such fusion gene products are well known to those skilled in the art, skilled artisans can easily design and prepare an appropriate fusion gene product depending on the purpose.

Nuclear reprogramming may also be accomplished with one or more small molecules, compounds, including inorganic and organic compounds, or mixtures thereof, extracts, epigenetic factors, and/or other components of the cytoplasm of a pluripotent cell.

In a particularly preferred embodiment, the nuclear reprogramming factor may comprise one or more gene products of each of the following three kinds of genes: an Oct family gene, a Klf family gene, and a Sox family gene.

In another preferred embodiment, the nuclear reprogramming factor may comprise one or more gene products of each of: an Oct family gene, a Klf family gene, and a Myc family gene.

The nuclear reprogramming factor may also comprise one or more gene products of each of: an Oct family gene, a Klf family gene, a Myc family gene, and a Sox family gene.

The nuclear reprogramming factor may also comprise one or more gene products of each of: an Oct family gene, a Klf family gene, and a cytokine. In one exemplary embodiment, the above-referenced nuclear reprogramming factor may further comprise one or more gene products of a Myc family gene. In another exemplary embodiment, the above referenced nuclear reprogramming factor may further comprise one or more gene products of a Sox family gene.

The cytokines of the present invention are not particularly limited. For example, the cytokine may comprise basic fibroblast growth factor (bFGF/FGF2) or stem cell factor (SCF).

With regard to gene family members, the nuclear reprogramming factor may comprise any combination of members from one or more gene families. For example, a combination of one or more gene products of Oct3/4, Klf4, and c-Myc. Examples of the Oct family gene include, for example, Oct3/4, Oct1A, Oct6, and the like. Oct3/4 is a transcription factor belonging to the POU family, and is reported as a marker of undifferentiated cells (Okamoto et al. *Cell* 60:461-72, 1990). Oct3/4 is also reported to participate in the maintenance of pluripotency (Nichols et al. *Cell* 95:379-91, 1998). Examples of the Klf family gene include Klf1, Klf2, Klf4, Klf5 and the like. Klf4 (Kruppel like factor-4) is reported as a tumor repressing factor (Ghaleb et al. *Cell Res.* 15:92-96, 2005). Examples of the Myc family gene include c-Myc, N-Myc, L-Myc and the like. c-Myc is a transcription control factor involved in differentiation and proliferation of cells (Adhikary & Eilers, *Nat. Rev. Mol. Cell Biol.* 6:635-45, 2005), and is also reported to be involved in the maintenance of pluripotency (Cartwright et al. *Development* 132:885-96, 2005). L-Myc, which as noted is a Myc family member, was revealed to have much lower transformation activity than c-Myc, i.e., 1% to 10% of the transformation activity of c-Myc (Birrer et al. *Molecular and Cellular Biology* 8 (6): 2668-2673, 1988); Barrett et al. *Molecular and Cellular Biology* 12 (7): 3130-3137, 1992, both of which are hereby incorporated by reference in their entireties). The NCBI accession numbers of the genes of the families other than Oct3/4, Klf4 and c-Myc are set in TABLE 1 as follows:

TABLE 1

| | | Mouse | Human |
|---|---|---|---|
| Klf1 | Kruppel-like factor 1 (erythroid) | NM_010635 | NM_006563 |
| Klf2 | Kruppel-like factor 2 (lung) | NM_008452 | NM_016270 |
| Klf5 | Kruppel-like factor 5 | NM_009769 | NM_001730 |
| c-Myc | myelocytomatosis oncogene | NM_010849 | NM_002467 |
| N-Myc | v-Myc myelocytomatosis viral related oncogene, neuroblastoma derived (avian) | NM_008709 | NM_005378 |
| L-Myc | v-Myc myelocytomatosis viral oncogene homolog 1, lung carcinoma derived (avian) | NM_008506 | NM_005376 |

TABLE 1-continued

| | | Mouse | Human |
|---|---|---|---|
| Oct1A | POU domain, class 2, transcription factor 1 | NM_198934 | NM_002697 |
| Oct6 | POU domain, class 3, transcription factor 1 | NM_011141 | NM_002699 |

All of these genes are those commonly existing in mammals including human, and for use of the aforementioned gene products in the present invention, genes derived from arbitrary mammals (those derived from mammals such as mouse, rat, bovine, ovine, horse, and ape) can be used. In addition to wild-type gene products, mutant gene products including substitution, insertion, and/or deletion of several (for example, 1 to 10, preferably 1 to 6, more preferably 1 to 4, still more preferably 1 to 3, and most preferably 1 or 2) amino acids and having similar function to that of the wild-type gene products can also be used. For example, as a gene product of c-Myc, a stable type product (T58A) may be used as well as the wild-type product. The above explanation may be applied similarly to the other gene products.

The nuclear reprogramming factor of the present invention may comprise a gene product other than the aforementioned three kinds of gene products. An example of such gene product includes a gene product of a Sox family gene. Examples of the Sox family genes include, for example, Sox1, Sox3, Sox7, Sox15, Sox17 and Sox18, and a preferred example includes Sox2. A nuclear reprogramming factor comprising at least a combination of the gene products of four kinds of genes, an Oct family gene (for example, Oct3/4), a Klf family gene (for example, Klf4), a Myc family gene (for example, c-Myc), and a Sox family gene (for example, Sox2) is a preferred embodiment of the present invention from a viewpoint of reprogramming efficiency, and in particular, a combination of a gene product of a Sox family gene is sometimes preferred to obtain pluripotency. Sox2, expressed in an early development process, is a gene encoding a transcription factor (Avilion et al. *Genes Dev.* 17:126-40, 2003). The NCBI accession numbers of Sox family genes other than Sox2 are in TABLE 2 as follows.

TABLE 2

| | | Mouse | Human |
|---|---|---|---|
| Sox1 | SRY-box containing gene 1 | NM_009233 | NM_005986 |
| Sox3 | SRY-box containing gene 3 | NM_009237 | NM_005634 |
| Sox7 | SRY-box containing gene 7 | NM_011446 | NM_031439 |
| Sox15 | SRY-box containing gene 15 | NM_009235 | NM_006942 |
| Sox17 | SRY-box containing gene 17 | NM_011441 | NM_022454 |
| Sox18 | SRY-box containing gene 18 | NM_009236 | NM_018419 |

Further, a gene product of a Myc family gene may be replaced with a cytokine. As the cytokine, for example, SCF, bFGF or the like is preferred. However, cytokines are not limited to these examples.

The nuclear reprogramming factor of the present invention may comprise a gene product of a Lin family gene. Examples of the Lin family genes include, for example, Lin28 and Lin28b, and a preferred example includes Lin28. The NCBI accession numbers of Lin family genes are as follows:

Lin28: NM_145833 (mouse), NM_024674 (human); and

Lin28b: NM_001031772 (mouse), NM_001004317 (human).

As a more preferred embodiment, an example includes a factor which induces immortalization of cells, in addition to the aforementioned three kinds of gene products, preferably, the four kinds of gene products. For example, an example includes a combination of a factor comprising a gene product of the TERT gene. In another exemplary embodiment, the nuclear reprogramming factor comprises any of the aforementioned gene products in combination with a factor comprising a gene product or gene products of one or more kinds of the following genes: SV40 Large T antigen, HPV16 E6, HPV16 E7, and Bmil. TERT is essential for the maintenance of the telomere structure at the end of chromosome at the time of DNA replication, and the gene is expressed in stem cells or tumor cells in humans, whilst it is not expressed in many somatic cells (Horikawa et al. *P.N.A S. USA* 102:18437-442, 2005). SV40 Large T antigen, HPV16 E6, HPV16 E7, or Bmil was reported to induce immortalization of human somatic cells in combination with Large T antigen (Akimov et al. *Stem Cells* 23:1423-33, 2005; Salmon et al. *Mol. Ther.* 2:404-14, 2000). These factors are extremely useful particularly when iPS cells are induced from human cells. The NCBI accession numbers of TERT and Bmil genes are listed in TABLE 3 as follows.

TABLE 3

| | | Mouse | Human |
|---|---|---|---|
| TERT | telomerase reverse transcriptase | NM_009354 | NM_198253 |
| Bmi1 | B lymphoma Mo-MLV insertion region 1 | NM_007552 | NM_005180 |

Furthermore, a gene product or gene products of one or more kinds of genes selected from the group consisting of the following: Fbx15, Nanog, ERas, ECAT15-2, Tcl1, and β-catenin may be combined. As a particularly preferred embodiment from a viewpoint of reprogramming efficiency, an example includes a nuclear reprogramming factor comprising a total of ten kinds of gene products, wherein gene products of Fbx15, Nanog, ERas, ECAT15-2, Tcl1, and β-catenin are combined with the aforementioned four kinds of gene products. Fbx15 (Tokuzawa et al. *Mol. Cell Biol.* 23:2699-708, 2003), Nanog (Mitsui et al. *Cell* 113:631-42, 2003), ERas (Takahashi et al. *Nature* 423:541-45, 2003), and ECAT15-2 (Bortvin et al. *Development* 130:1673-80, 2003) are genes specifically expressed in ES cells. Tell is involved in the activation of Akt (Bortvin et al. *Development* 130: 1673-80, 2003), and β-catenin is an important factor constituting the Wnt signal transmission pathway, and also reported to be involved in the maintenance of pluripotency (Sato et al. *Nat. Med.* 10:55-63, 2004).

Further, the nuclear reprogramming factor of the present invention may comprise, for example, a gene product or gene products of one or more kinds of genes selected from the group consisting of the following: ECAT1, Esg1, Dnmt3L, ECAT8, Gdf3, Sox15, ECAT15-1, Fthl17, Sall4, Rex1, UTF1, Stella, Stat3, and Grb2. ECAT1, Esg1, ECAT8, Gdf3, and ECAT15-1 are genes specifically expressed in ES cells (Mitsui et al. *Cell* 113:631-42, 2003). Dnmt3L is a DNA methylating enzyme-related factor, and Sox15 is a class of genes expressed in an early development process and encoding transcription factors (Maruyama et al. *J. Biol. Chem.* 280:24371-79, 2005). Fthl17 encodes ferritin heavy polypeptide-like 17 (colLoriot et al. *Int. J. Cancer* 105:371-76, 2003), Sall4 encodes a Zn finger protein abundantly expressed in embryonic stem cells (Kohlhase et al. *Cytogenet. Genome Res.* 98:274-77, 2002), and Rex1 encodes a transcription factor locating downstream from Oct3/4 (Ben-Shushan et al. *Mol. Cell Biol.* 18:1866-78, 1998). UTF1 is a transcription cofactor locating downstream from Oct3/4, and it is reported that the suppression of the proliferation of ES cells is induced when this factor is suppressed (Okuda et al. *EMBO J.* 17:2019-32, 1998). Stat3 is a signal factor for proliferation and differentiation of cells. The activation of Stat3 triggers the operation of LIF, and thereby the factor plays an important role for the maintenance of pluripotency (Niwa et al. *Genes Dev.* 12:2048-60, 1998). Grb2 encodes a protein mediating between various growth factor receptors existing in cell membranes and the Ras/MAPK cascade (Cheng et al. *Cell* 95:793-803, 1998).

However, as noted above, the gene products which may be included in the nuclear reprogramming factor of the present invention are not limited to the gene products of the genes specifically explained above. The nuclear reprogramming factor of the present invention may contain one or more factors relating to differentiation, development, proliferation or the like and factors having other physiological activities, as well as other gene products which can function as a nuclear reprogramming factor. It is understood that such embodiments fall within the scope of the present invention. By using somatic cells in which only one or two genes among the three kinds of the gene Oct3/4, Klf4, and c-Myc are expressed, the other gene products which can function as a nuclear reprogramming factor can be identified by, for example, performing screening for a gene product which can induce nuclear reprogramming of said cells. According to the present invention, the aforementioned screening method is also provided as a novel method for screening for a nuclear reprogramming factor.

Examples of nuclear reprogramming factors containing an Oct family factor, a Klf family factor, and a Myc family factor include:

(1) a combination comprising Oct3/4, Klf4, and L-Myc;

(2) a combination comprising Oct 3/4, Klf4, L-Myc, and Sox2; and (3) a combination comprising Oct 3/4, Klf4, L-Myc, Sox2, and Lin28.

While any number of combinations of gene products or factors can be used to establish iPS cells, some combinations of factors have been found to establish iPS cells with higher efficiency than others. For example, a higher efficiency of iPS cell establishment can be achieved by using L-Myc instead of c-Myc. In particular, human iPS cell can be established with higher efficiency when using L-Myc instead of c-Myc. Accordingly, it is preferred to use L-Myc for the preparation of iPS cells, especially human iPS cells.

Furthermore, the combinations of factors are not limited to the use of wild-type genes or gene products. For example, Myc chimeras or other Myc variants can be used instead of wild-type Myc. In particular, examples of Myc chimeras or variants include Ms-cL-Myc, Ms-cLc-Myc as shown in Example 29, and human homologs thereof. Other examples of Myc variants include mutants of c-Myc comprising nucleic acid and/or amino acid deletions, substitutions, or additions.

Human homologs of mouse chimeric Myc or mouse Myc variants can be readily prepared by one of ordinary skill in the art on the basis of the information of the nucleotide and amino acid sequences of human c-Myc (GenBank Acc. No. NM_002467) and human L-Myc (GenBank Acc. No. NM_005376), as well as that of the nucleotide and amino acid sequences of mouse Myc chimeras and/or mouse Myc variants disclosed in the instant specification.

Cells of the Invention and Methods of Generating the Same 1

By using the nuclear reprogramming factor of the present invention, the nucleus of a somatic cell can be reprogrammed to obtain an induced pluripotent stem cell. In the specification, the term "induced pluripotent stem cells" means cells having properties similar to those of ES cells, and more specifically, the term encompasses undifferentiated cells having pluripotency and growth ability. However, the term should not be construed narrowly in any sense, and should be construed in the broadest sense. The method for preparing induced pluripotent stem cells by using a nuclear reprogramming factor is explained in International Publication WO2005/80598 (the term "ES-like cells" is used in the publication), and a means for isolating induced pluripotent stem cells is also specifically explained. Therefore, by referring to the aforementioned publication, those skilled in the art can easily prepare induced pluripotent stem cells by using the nuclear reprogramming factor of the present invention. Methods for preparing induced pluripotent stem cells from somatic cells by using the nuclear reprogramming factor of the present invention are not particularly limited. Any method may be employed as long as the nuclear reprogramming factor can contact with somatic cells under an environment in which the somatic cells and induced pluripotent stem cells can proliferate. An advantage of the present invention is that an induced pluripotent stem cell can be prepared by contacting a nuclear reprogramming factor with a somatic cell in the absence of eggs, embryos, or embryonic stem (ES) cells.

For example, a gene product contained in the nuclear reprogramming factor of the present invention may be added to a medium. Alternatively, by using a vector containing a gene that is capable of expressing the nuclear reprogramming factor of the present invention, a means of transducing said gene into a somatic cell may be employed. When such vector is used, two or more kinds of genes may be incorporated into the vector, and each of the gene products may be simultaneously expressed in a somatic cell. When one or more of the gene products contained in the nuclear reprogramming factor of the present invention are already expressed in a somatic cell to be reprogrammed, said gene products may be excluded from the nuclear reprogramming factor of the present invention. It is understood that such embodiments fall within the scope of the present invention.

Specific means for using a retrovirus as a vector is disclosed in WO 2007/69666; Takahashi et al. *Cell* 126:663-676, 2006; and Takahashi et al. *Cell* 131:861-872, 2007, which are herein incorportated by reference in their entireties. Specific means for using a lentivirus as a vector is disclosed in Yu et al. *Science* 318:1917-1920, 2007, which is herein incorporated by reference in its entirety. Specific means for using adenovirus as a vector is disclosed in Stadtfeld et al. (*Science* published online: Sep. 25, 2008, 10.1126/science.1162494), which is herein incorporated by reference in its entirety. Specific means for using a plasmid as a non-viral vector is disclosed in Okita et al. (*Science*, published online: Oct. 9, 2008, 10.1126/science.1164270), which is herein incorporated by reference in its entirety. One of ordinary skill in the art could choose and use an appropriate means from among the above known means, or from any of the other known means available in the prior art.

As indicated above, the nuclear reprogramming factor of the present invention can be used to generate iPS cells from differentiated adult somatic cells. In the preparation of induced pluripotent stem cells by using the nuclear reprogramming factor of the present invention, types of somatic cells to be reprogrammed are not particularly limited, and any kind of somatic cells may be used. For example, matured somatic cells may be used, as well as somatic cells of an embryonic period. Other examples of cells capable of being generated into iPS cells and/or encompassed by the present invention include mammalian cells such as fibroblasts, B cells, T cells, dendritic cells, ketatinocytes, adipose cells, epithelial cells, epidermal cells, chondrocytes, cumulus cells, neural cells, glial cells, astrocytes, cardiac cells, esophageal cells, muscle cells, melanocytes, hematopoietic cells, pancreatic cells, hepatocytes, macrophages, monocytes, mononuclear cells, and gastric cells, including gastric epithelial cells. The cells can be embryonic, or adult somatic cells, differentiated cells, cells with an intact nuclear membrane, non-dividing cells, quiescent cells, terminally differentiated primary cells, and the like.

Induced pluripotent stem cells may express any number of pluripotent cell markers, including: alkaline phosphatase (AP); ABCG2; stage specific embryonic antigen-1 (SSEA-1); SSEA-3; SSEA-4; TRA-1-60; TRA-1-81; Tra-2-49/6E; ERas/ECAT5, E-cadherin; βIII-tubulin; α-smooth muscle actin (α-SMA); fibroblast growth factor 4 (Fgf4), Cripto, Dax1; zinc finger protein 296 (Zfp296); N-acetyltransferase-1 (Nat1); (ES cell associated transcript 1 (ECAT1); ESG1/DPPA5/ECAT2; ECAT3; ECAT6; ECAT7; ECAT8; ECAT9; ECAT10; ECAT15-1; ECAT15-2; Fthl17; Sall4; undifferentiated embryonic cell transcription factor (Utf1); Rex1; p53; G3PDH; telomerase, including TERT; silent X chromosome genes; Dnmt3a; Dnmt3b; TRIM28; F-box containing protein 15 (Fbx15); Nanog/ECAT4; Oct3/4; Sox2; Klf4; c-Myc; Esrrb; TDGF1; GABRB3; Zfp42, FoxD3; GDF3; CYP25A1; developmental pluripotency-associated 2 (DPPA2); T-cell lymphoma breakpoint 1 (Tcl1); DPPA3/Stella; DPPA4; other general markers for pluripotency, etc. Other markers can include Dnmt3L; Sox15; Stat3; Grb2; SV40 Large T Antigen; HPV16 E6; HPV16 E7, β-catenin, and Bmi1. Such cells can also be characterized by the down-regulation of markers characteristic of the differentiated cell from which the iPS cell is induced. For example, iPS cells derived from fibroblasts may be characterized by down-regulation of the fibroblast cell marker Thy1 and/or up-regulation of SSEA-1. It is understood that the present invention is not limited to those markers listed herein, and encompasses markers such as cell surface markers, antigens, and other gene products including ESTs, RNA (including microRNAs and antisense RNA), DNA (including genes and cDNAs), and portions thereof.

When induced pluripotent stem cells are used for therapeutic treatment of diseases, it is desirable to use somatic cells isolated from patients. For example, somatic cells involved in diseases, somatic cells participating in therapeutic treatment of diseases and the like can be used. A method for selecting induced pluripotent stem cells that appear in a medium according to the method of the present invention is not particularly limited, and a well-known means may be suitably employed, for example, a drug resistance gene or the like can be used as a marker gene to isolate induced pluripotent stem cells using drug resistance as an index. Various media that can maintain undifferentiated state and pluripotency of ES cells and various media which cannot maintain such properties are known in this field, and induced pluripotent stem cells can be efficiently isolated by using a combination of appropriate media. Differentiation and proliferation abilities of isolated induced pluripotent stem cells can be easily confirmed by those skilled in the art by using confirmation means widely applied to ES cells.

Thus, another preferred embodiment of the invention comprises a pluripotent stem cell induced by reprogramming a somatic cell in the absence of eggs, embryos, or embryonic stem (ES) cells. The pluripotent stem cell can be a mammalian cell, for example a mouse, human, rat, bovine, ovine, horse, hamster, dog, guinea pig, or ape cell. For example, direct reprogramming of somatic cells provides an opportunity to generate patient- or disease-specific pluripotent stem cells. Mouse iPS cells are indistinguishable from ES cells in morphology, proliferation, gene expression, and teratoma formation. Furthermore, when transplanted into blastocysts, mouse iPS cells can give rise to adult chimeras, which are competent for germline transmission (Maherali et al. *Cell Stem Cell* 1:55-70, 2007; Okita et al. *Nature* 448: 313-17, 2007; Wernig et al. *Nature* 448:318-324, 2007). Human iPS cells are also expandable and indistinguishable from human embryonic stem (ES) cells in morphology and proliferation. Furthermore, these cells can differentiate into cell types of the three germ layers in vitro and in teratomas.

The present invention also provides for the generation of somatic cells derived by inducing differentiation of the aforementioned pluripotent stem cells. The present invention thus provides a somatic cell derived by inducing differentiation of the aforementioned induced pluripotent stem cell.

In another embodiment, there is disclosed a method for improving differentiation ability and/or growth ability of a cell, which comprises contacting a nuclear reprogramming factor with a cell.

In a particularly preferred embodiment, the present invention comprises a method for stem cell therapy comprising: (1) isolating and collecting a somatic cell from a patient; (2) inducing said somatic cell from the patient into an iPS cell; (3) inducing differentiation of said iPS cell, and (4) transplanting the differentiated cell from step (3) into the patient.

In another preferred embodiment, the present invention includes a method for evaluating a physiological function of a compound comprising treating cells obtained by inducing differentiation of an induced pluripotent stem cell with the compound.

A method for evaluating the toxicity of a compound comprising treating cells obtained by inducing differentiation of an induced pluripotent stem cell in the presence of the compound.

EXAMPLES

Various terms, abbreviations and designations for the raw materials and tests used in the following Examples are explained as follows:

Abbreviations

- iPS cell (induced pluripotent stem cell)
- NRF (nuclear reprogramming factor)
- ES cell (embryonic stem cell)
- TTF (tail tip fibroblast)
- MEF (mouse embryonic fibroblast)
- HDF (human dermal fibroblast)
- bFGF (basic fibroblast growth factor)
- SCF (stem cell factor)
- GFP (green fluorescent protein)

The present invention will be more specifically explained with reference to examples. However, the scope of the present invention is not limited to the following examples.

Example 1: Selection of A Nuclear Reprogramming Factor

In order to identify reprogramming factors, an experimental system for easy observation of the reprogramming phenomenon is required. As an experimental system, a mouse in which βgeo (a fusion gene of β-galactosidase gene and neomycin resistance gene) was knocked into the Fbx15 locus (Tokuzawa et al. *Mol. Cell Biol.* 23:2699-708, 2003) was used. The mouse Fbx15 gene is a gene specifically expressed in differentiation pluripotent cells such as ES cells and early embryos. However, in a homomutant mouse in which βgeo was knocked into the mouse Fbx15 gene so as to delete the function of Fbx15, no abnormal phenotypes including those concerning differentiation pluripotency or development were observed. In this mouse, expression control of βgeo is attained by the enhancer and promoter of the Fbx15 gene. Specifically, βgeo is not expressed in differentiated somatic cells, and they have sensitivity to G418. In contrast, the βgeo knockin homomutant ES cells have resistance against G418 at an extremely high concentration (higher than 12 mg/ml). By utilizing the above phenomenon, an experimental system for visualizing the reprogramming of somatic cells was constructed.

In the aforementioned experimental system, fibroblasts ($Fbx15^{\beta geo/\beta geo}$ MEFs) were first isolated from an embryo of the βgeo knockin homomutant mouse (13.5 days after fertilization). Since MEFs do not express the Fbx15 gene, the cells also do not express βgeo and thus have sensitivity to G418. Whilst when the MEFs are fused with ES cells that have not been gene-manipulated (also having sensitivity to G418), the nuclei of MEFs are reprogrammed, and as a result, βgeo is expressed to give G418-resistance. The reprogramming phenomenon can thus be visualized as G418 resistance by using this experimental system (International Publication WO2005/80598). Searches for reprogramming factors were performed by using the aforementioned experimental system (FIG. 1), and total 24 kinds of genes were selected as candidate reprogramming factors, including genes showing specific expression in ES cells and genes suggested to have important roles in the maintenance of differentiation pluripotency of ES cells. These genes are shown in TABLES 4 and 5 below. For β-catenin (#21) and c-Myc (#22), active type mutants (catenin: S33Y, c-Myc: T58A) were used.

TABLE 4

| Number | Name of Gene | Explanation of Gene |
|---|---|---|
| 1 | ECAT1 | ES cell associated transcript 1 (ECAT1) |
| 2 | ECAT2 | developmental pluripotency associated 5 (DPPA5), ES cell specific gene 1 (ESG1) |
| 3 | ECAT3 | F-box protein 15 (Fbx15), |
| 4 | ECAT4 | homeobox transcription factor Nanog |
| 5 | ECAT5 | ES cell expressed Ras (ERas) |
| 6 | ECAT7 | DNA (cytosine-5-)-methyltransferase 3-like (Dnmt3l), valiant 1 |
| 7 | ECAT8 | ES cell associated transcript 8 (ECAT8) |
| 8 | ECAT9 | growth differentiation factor 3 (Gdf3) |
| 9 | ECAT10 | SRY-box containing gene 15 (Sox15) |
| 10 | ECAT15-1 | developmental pluripotency associated 4 (Dppa4), variant 1 |
| 11 | ECAT15-2 | developmental pluripotency associated 2 (Dppa2) |
| 12 | Fthl17 | ferritin, heavy polypeptide-like 17 (Fthl17) |
| 13 | Sall4 | sal-like 4 (Drosophila) (Sall4), transcript variant a |
| 14 | Oct3/4 | POU domain, class 5, transcription factor 1 (Pou5f1) |
| 15 | Sox2 | SRY-box containing gene 2 (Sox2) |
| 16 | Rex1 | zinc finger protein 42 (Zfp42) |
| 17 | Utf1 | undifferentiated embryonic cell transcription factor 1 (Utf1) |
| 18 | Tcl1 | T-cell lymphoma breakpoint 1 (Tcl1) |
| 19 | Stella | developmental pluripotency-associated 3 (Dppa3) |
| 20 | Klf4 | Kruppel-like factor 4 (gut) (Klf4) |
| 21 | β-catenin | catenin (cadherin associated protein), beta 1, 88kDa (Ctnnb1) |
| 22 | c-Myc | myelocytomatosis oncogene (Myc) |
| 23 | Stat3 | signal transducer and activator of transcription 3 (Stat3), transcript variant 1 |
| 24 | Grb2 | growth factor receptor bound protein 2 (Grb2) |

TABLE 5

| Number | Name of Gene | Characteristic Feature | NCBI accession number Mouse | NCBI accession number Human |
|---|---|---|---|---|
| 1 | ECAT1 | Gene specifically expressed in ES cell | AB211060 | AB211062 |
| 2 | ECAT2 | Gene specifically expressed in ES cell | NM_025274 | NM_001025290 |
| 3 | ECAT3 | Gene specifically expressed in ES cell | NM_015798 | NM_152676 |
| 4 | ECAT4 | Transcription factor having homeodomain, essential factor for differentiation pluripotency maintenance | AB093574 | NM_024865 |
| 5 | ECAT5 | Ras family protein, ES cell growth promoting factor | NM_181548 | NM_181532 |
| 6 | ECAT7 | DNA methylation enzyme-related factor, essential for imprinting | NM_019448 | NM_013369 |
| 7 | ECAT8 | Gene specifically expressed in ES cell, having Tudor domain | AB211061 | AB211063 |
| 8 | ECAT9 | Gene specifically expressed in ES cell, belonging to TGFβ family | NM_008108 | NM_020634 |
| 9 | ECAT10 | Gene specifically expressed in ES cell, SRY family transcription factor | NM_009235 | NM_006942 |
| 10 | ECAT15-1 | Gene specifically expressed in ES cell | NM_028610 | NM_018189 |
| 11 | ECAT15-2 | Gene specifically expressed in ES cell | NM_028615 | NM_138815 |

TABLE 5-continued

Figure 2:
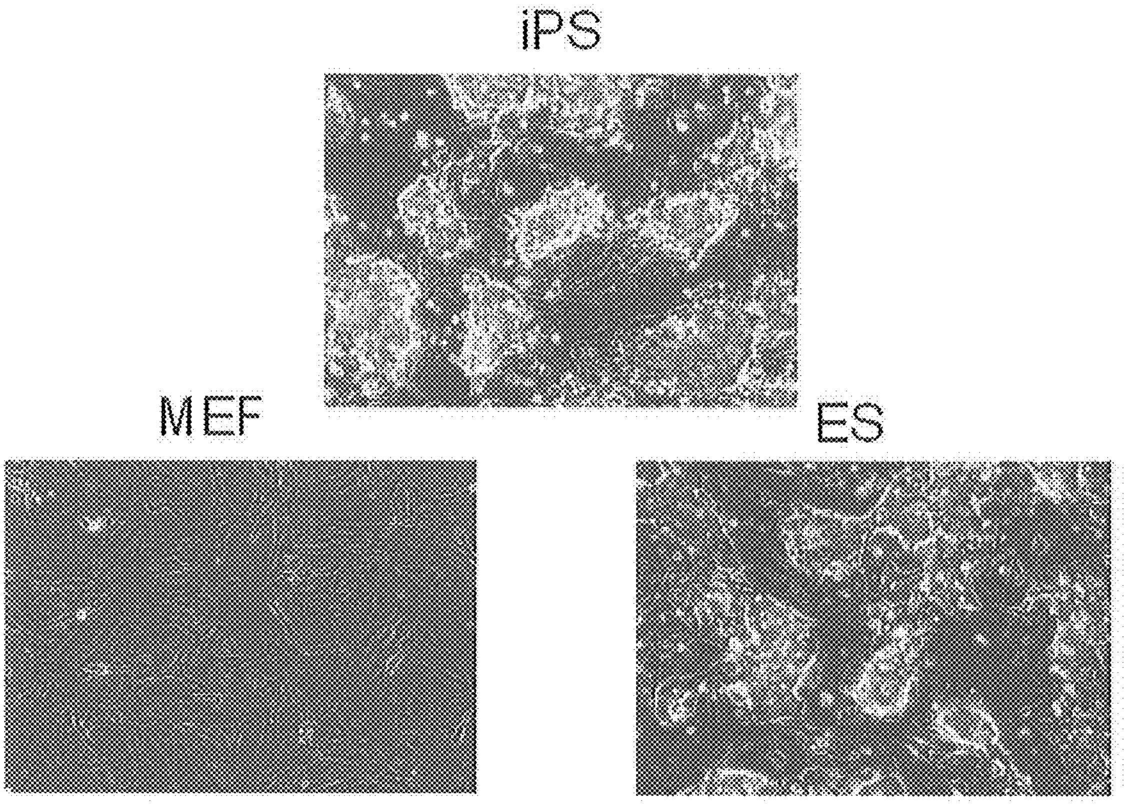
FIG. 2 depicts photographs showing morphology of iPS cells obtained by introducing the 24 genes shown in TABLE 4. Morphologies of differentiated cells (MEF) and of normal embryonic stem cells (ES) are also shown as a reference.

| | | | NCBI accession number | |
|---|---|---|---|---|
| Number | Name of Gene | Characteristic Feature | Mouse | Human |
| 12 | Fthl17 | Gene specifically expressed in ES cell, similar to ferritin heavy chain | NM_031261 | NM_031894 |
| 13 | Sall4 | Gene specifically expressed in ES cell, Zn finger protein | NM_175303 | NM_020436 |
| 14 | Oct3/4 | POU family transcription factor, essential for pluripotency maintenance | NM_013633 | NM_002701 |
| 15 | Sox2 | SRY family transcription factor, essential for pluripotency maintenance | NM_011443 | NM_003106 |
| 16 | Rex1 | Gene specifically expressed in ES cell, Zn finger protein | NM_009556 | NM_174900 |
| 17 | Utf1 | Transcription regulation factor highly expressed in ES cell, promoting growth of ES | NM_009482 | NM_003577 |
| 18 | Tcl1 | Oncogene activating AKT, abundantly expressed in ES cell | NM_009337 | NM_021966 |
| 19 | Stella | Gene specifically expressed in ES cell | NM_139218 | NM_199286 |
| 20 | Klf4 | Abundantly expressed in ES cell, both actions as antioncogene and oncogene are reported | NM_010637 | NM_004235 |
| 21 | β-catenin | Transcription factor activated by Wnt signal, involvement in pluripotency maintenance is reported | NM_007614 | NM_001904 |
| 22 | c-Myc | Transcription control factor participating in cell proliferation and differentiation and oncogene, involvement in pluripotency maintenance is reported | NM_010849 | NM_002467 |
| 23 | Stat3 | Transcription factor activated by LIF signal, considered essential for pluripotency maintenance of mouse ES cells | NM_213659 | NM_139276 |
| 24 | Grb2 | Adapter protein mediating growth factor receptors and Ras/MAPK cascade | NM_008163 | NM_002086 |

cDNAs of these genes were inserted into the retroviral vector pMX-gw by the Gateway technology. First, each of the 24 genes was infected into Fbx15$^{\beta geo/\beta geo}$ MEFs, and then G418 selection was performed under ES cell culture conditions. However, no G418-resistant colony was obtained. Next, the retroviral vectors of all of the 24 genes were simultaneously infected into Fbx15$^{\beta geo/\beta geo}$ MEFs. When G418 selection was performed under ES cell culture conditions, a plurality of drug resistant colonies were obtained. These colonies were isolated, and cultivation was continued. It was found that cultivation of these cells over a long period of time could be performed, and that these cells had morphology similar to that of ES cells (FIG. 2). In the figure, iPS cells represent induced pluripotent stem cells (also called "ES like cells", "ES-like cells", or "ESL cells"), ES represents embryonic stem cells, and MEF represents differentiated cells (embryonic fibroblasts).

Figure 3:
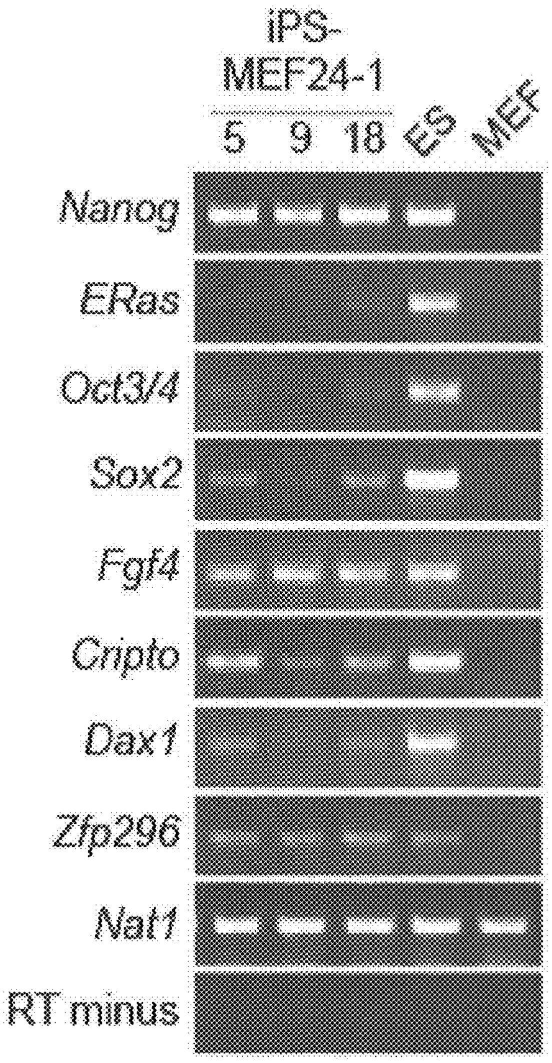
FIG. 3 shows expression profiles of marker genes in iPS cells. The results of RT-PCR using total RNAs extracted from iPS cells, ES cells and MEF cells as templates are shown.
Figure 4:
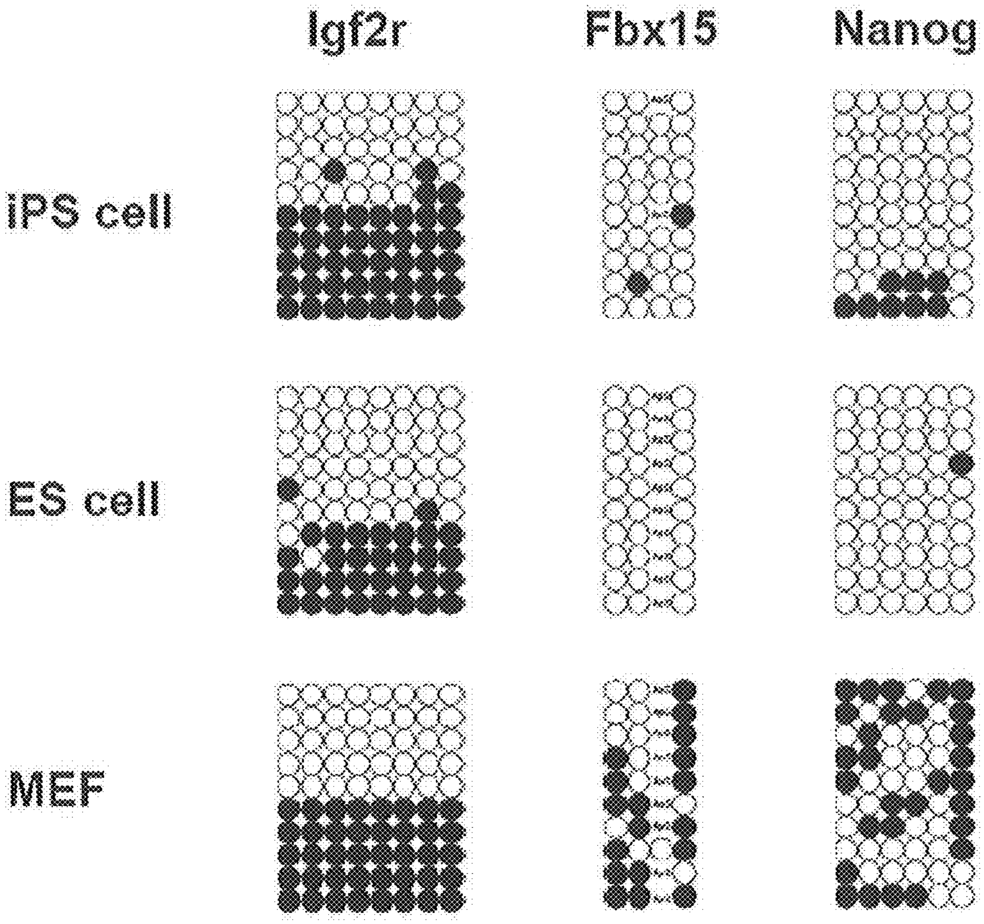
FIG. 4 shows methylation status of DNA in iPS cells. Genomic DNAs extracted from iPS cells, ES cells, and MEF cells were treated with bisulfite. The target DNAs were amplified by PCR and then inserted into plasmid. Ten clones of plasmid were isolated for each of the genes, and sequenced. Methylated CpGs are indicated with closed circles, and unmethylated CpGs with open circles.

When expression profiles of the marker genes were examined by RT-PCR, undifferentiation markers such as Nanog and Oct3/4 were found to be expressed (FIG. 3). It was found that the expression of Nanog was close to that of ES cells, whereas the expression of Oct3/4 was lower than that of ES cells. When DNA methylation status was examined by the bisulfite genomic sequencing, it was found that the Nanog gene and Fbx15 gene were highly methylated in MEFs, whereas they were demethylated in the iPS cells (FIG. 4). About 50% of IGF2 gene, an imprinting gene, was methylated both in the MEF and iPS cells. Since it was known that the imprinting memory was deleted and the IGF2 gene was almost completely demethylated in the primordial germ cells at 13.5 days after fertilization, from which the Fbx15$^{\beta geo/\beta geo}$ MEFs were isolated, it was concluded that iPS cells were not derived from primordial germ cells contaminated in the Fbx15$^{\beta geo/\beta geo}$ MEFs. The above results demonstrated that reprogramming of the differentiated cells (MEFs) into a state close to that of ES cells was able to be induced with the combination of the 24 kinds of factors.

Figure 5:
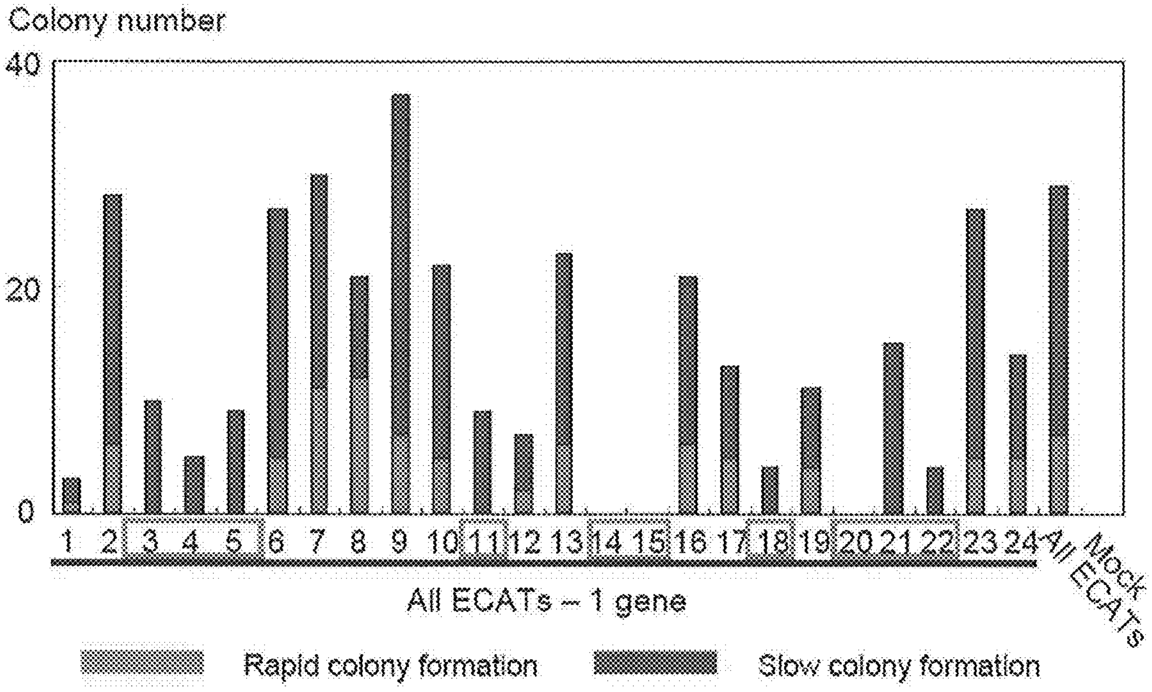
FIG. 5 shows colony numbers of G418-resistant cells obtained by transduction of 24-gene group and 23-gene groups wherein each individual gene was withdrawn from the 24-gene group. The lower parts of the graph show colony numbers obtained in one week after the G418 selection, and the upper parts of the graph show numbers of clones obtained in three weeks. When each boxed gene (the reference number for each gene is the same as that indicated in TABLE 4) was withdrawn, no colonies were obtained at all, or only a few colonies were observed after 3 weeks.

Then, studies were made as to whether or not all of the 24 kinds of genes were required for the reprogramming. With withdrawal of each individual gene, 23 genes were transfected into the Fbx15$^{\beta geo/\beta geo}$ MEFs. As a result, for 10 genes, colony formation was found to be inhibited with each withdrawal thereof (FIG. 5, the gene numbers correspond to the gene numbers shown in TABLE 4, and the genes are the following 10 kinds of genes: #3, #4, #5, #11, #14, #15, #18, #20, #21, and #22). When these ten genes were simultaneously transfected into the Fbx15$^{\beta geo/\beta geo}$ MEFs, G418-resistant colonies were significantly more efficiently obtained as compared to simultaneous transfection with the 24 genes.

Figure 6:
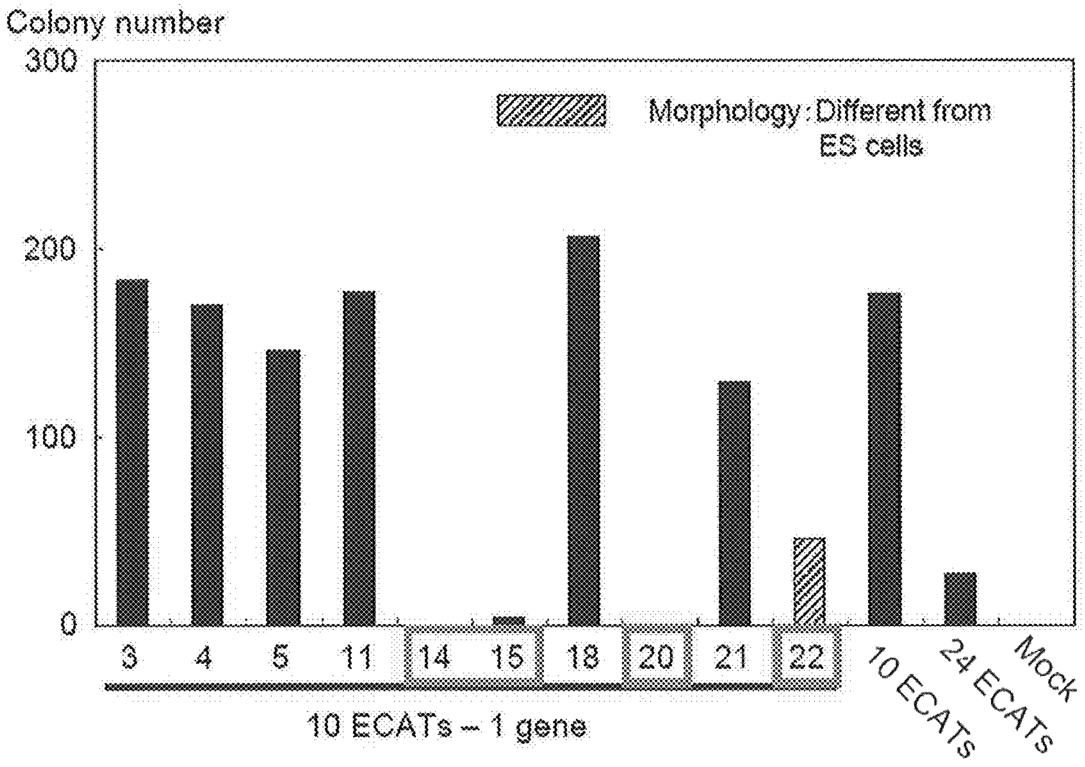
FIG. 6 shows colony numbers of G418-resistant cells obtained by transduction of 10-gene group and 9-gene groups wherein each individual gene was withdrawn from the 10-gene group. When each of genes #14, #15 or #20 was withdrawn, no colony was obtained. When gene #22 was withdrawn, a few G418-resistant colonies were obtained. However, the cells gave differentiated morphology which was apparently different from that of iPS cells.

Furthermore, 9 genes, with withdrawal of each individual gene from the 10 genes, were transfected into Fbx15$^{\beta geo/\beta geo}$ MEFs. As a result, it was found that G418-resistant iPS cell colonies were not formed when each of 4 kinds of genes (#14, #15, #20, or #22) was withdrawn (FIG. 6). Therefore, it was suggested that these four kinds of genes, among the ten genes, had particularly important roles in the induction of reprogramming.

Example 2: Induction of Reprogramming with a Combination of 4 Kinds of Genes

It was examined whether or not induction of reprogramming of somatic cells was achievable with the four kinds of genes of which particular importance was suggested among the 10 genes. By using the combination of the aforementioned 10 kinds of genes, the combination of the aforementioned 4 kinds of genes, combinations of only 3 kinds of genes among the 4 kinds of genes, and combinations of only 2 kinds of genes among the 4 kinds of genes, these sets of genes were retrovirally transduced into the MEF cells as somatic cells in which βgeo was knocked into the Fbx15 gene. As a result, when the 4 kinds of genes were transduced, 160 G418-resistant colonies were obtained. Although this result was almost the same as that obtained by the transduction with the 10 kinds of genes (179 colonies), the colonies obtained by the 4-gene transduction were smaller than those by the 10-gene transduction. When these colonies were passaged, the numbers of colonies having iPS cell morphology was 9 clones among 12 clones in the case of the 10-gene transduction, whereas there was a somewhat lower tendency of 7 clones among 12 clones in the case of the 4-gene transduction. As for the 4 genes, almost the same numbers of iPS cells were obtained with either of those derived from mouse or those derived from human.

Figure 7:
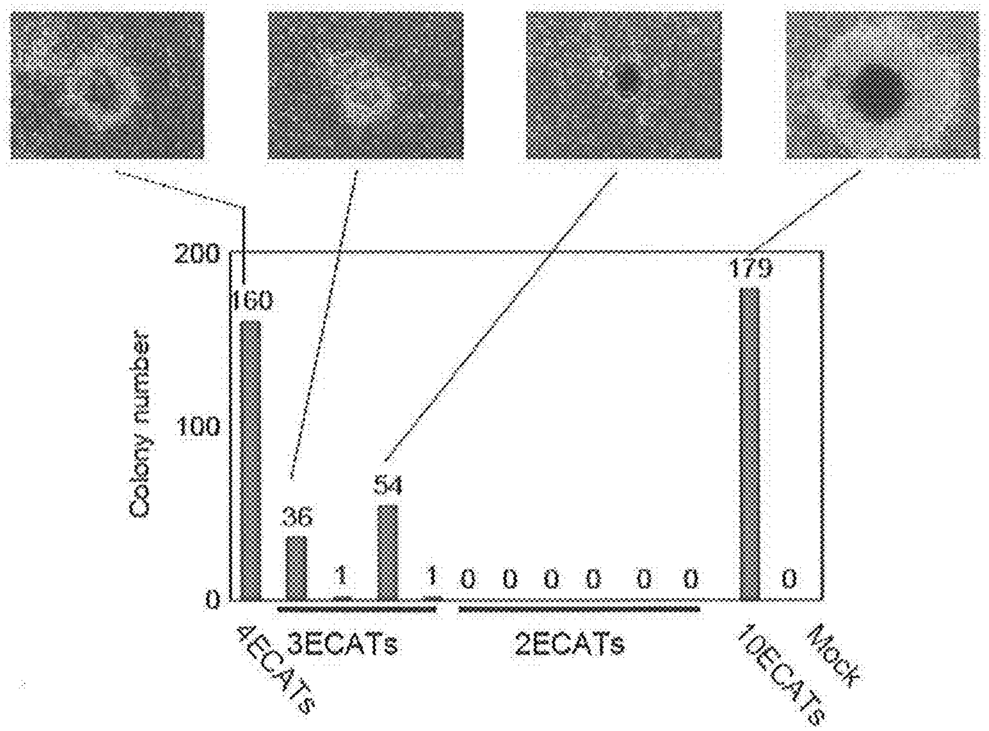
FIG. 7 shows numbers of G418-resistant emerged colonies (reprogrammed colony) with 10-gene group, 4-gene group, 3-gene groups, or 2-gene groups. Typical morphology and sizes of the colonies are shown.

When 3 genes selected from the aforementioned 4 genes were transduced, 36 flat colonies were obtained with one combination (#14 (Oct3/4), #15 (Sox2), and #20 (Klf4)). However, iPS cells were not observed when they were passaged. With another combination (#14 (Oct3/4), #20 (Klf4), and #22 (c-Myc)), 54 small colonies were obtained. When 6 of the relatively large colonies from among those colonies were passaged, cells similar to ES cells were obtained for all these 6 clones. However, it seemed that adhesion of the cells between themselves and to the culture dish was weaker than that of ES cells. The proliferation rate of the cells was also slower than that observed in the case of the transduction with the 4 genes. Further, one colony each was formed with each of the other two kinds of combinations of 3 genes among the 4 genes. However, proliferation of the cells was not observed when the cells were passaged. With any of combinations of 2 genes selected from the 4 genes (6 combinations), no G418-resistant colonies were formed. The above results are shown in FIG. 7.

Figure 10:
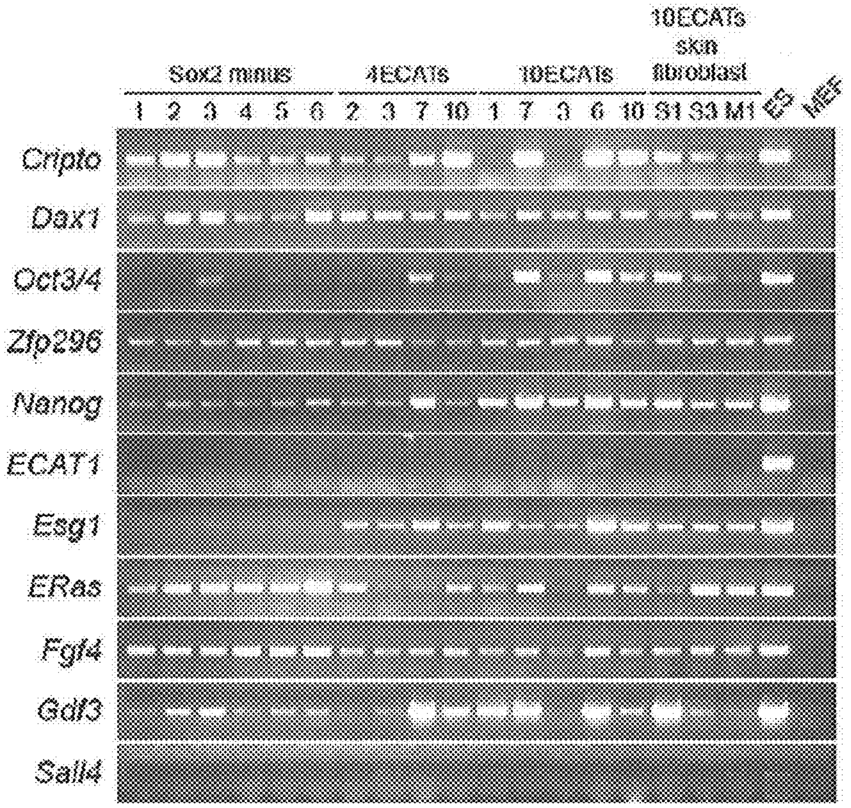
FIG. 10 depicts photographs showing results of RT-PCR confirming the expression of the ES cell marker genes. In the photographs, Sox2 minus indicates iPS cells established by the transduction of 3 genes into MEFs, 4ECATs indicates iPS cells established by the transduction of 4 genes into MEFs, 10ECATs indicates iPS cells established by the transduction of 10 genes into MEFs, 10ECATs Skin fibroblast indicates iPS cells established by the transduction of 10 genes into dermal fibroblasts, ES indicates mouse ES cells, and MEF indicates MEF cells without gene transduction. The numerical values under the symbols indicate clones numbers.

Further, the results of observation of expression profiles of the ES cell marker genes by RT-PCR are shown in FIG. 10. The details of the method are as follows. From iPS cells established by transducing 3 genes (Oct3/4, Klf4, and c-Myc: represented as "Sox2 minus"), 4 genes (Sox2 was added to the three genes: represented as "4ECAT"), and 10 genes (#3, #4, #5, #11, #18, and #21 in TABLE 4 were added to the four genes: represented as "10ECAT") into Fbx $15^{\beta geo/\beta geo}$ MEFs; iPS cells established by transducing 10 genes into fibroblasts established from tail tip of an adult mouse in which βgeo was knocked into the Fbx15 gene (represented as "10ECAT Skin fibroblast"), mouse ES cells, and MEF cells with no gene transduction, total RNAs were purified, and treated with DNaseI to remove contamination of genomic DNA. First strand cDNAs were prepared by a reverse transcription reaction, and expression profiles of the ES cell marker genes were examined by PCR. For Oct3/4, Nanog, and ERas, PCR was performed by using primers which only amplified a transcript product from an endogenous gene, not from the transduced retrovirus. The primer sequences are shown in TABLE 6.

TABLE 6

| | | |
|---|---|---|
| ECAT1 | ECAT1-RT-S | TGT GGG GCC CTG AAA GGC GAG CTG AGA T (SEQ ID NO: 1) |
| | ECAT1-RT-AS | ATG GGC CGC CAT ACG ACG ACG CTC AAC T (SEQ ID NO: 2) |
| Esg1 | pH34-U38 | GAA GTC TGG TTC CTT GGC AGG ATG (SEQ ID NO: 3) |
| | pH34-L394 | ACT CGA TAC ACT GGC CTA GC (SEQ ID NO: 4) |
| Nanog | 6047-S1 | CAG GTG TTT GAG GGT AGC TC (SEQ ID NO: 5) |
| | 6047-AS1 | CGG TTC ATC ATG GTA CAG TC (SEQ ID NO: 6) |
| ERas | 45328-S118 | ACT GCC CCT CAT CAG ACT GCT ACT (SEQ ID NO: 7) |
| | ERas-AS304 | CAC TGC CTT GTA CTC GGG TAG CTG (SEQ ID NO: 8) |
| Gdf3 | Gdf3-U253 | GTT CCA ACC TGT GCC TCG CGT CTT (SEQ ID NO: 9) |
| | GDF3 L16914 | AGC GAG GCA TGG AGA GAG CGG AGC AG (SEQ ID NO: 10) |
| Fgf4 | Fgf4-RT-S | CGT GGT GAG CAT CTT CGG AGT GG (SEQ ID NO: 11) |
| | Fgf4-RT-AS | CCT TCT TGG TCC GCC CGT TCT TA (SEQ ID NO: 12) |
| Cripto | Cripto-S | ATG GAC GCA ACT GTG AAC ATG ATG TTC GCA (SEQ ID NO: 13) |
| | Cripto-AS | CTT TGA GGT CCT GGT CCA TCA CGT GAC CAT (SEQ ID NO: 14) |
| Zfp296 | Zfp296-S67 | CCA TTA GGG GCC ATC ATC GCT TTC (SEQ ID NO: 15) |
| | Zfp296-AS350 | CAC TGC TCA CTG GAG GGG GCT TGC (SEQ ID NO: 16) |
| Dax1 | Dax1-S1096 | TGC TGC GGT CCA GGC CAT CAA GAG (SEQ ID NO: 17) |
| | Dax1-AS1305 | GGG CAC TGT TCA GTT CAG CGG ATC (SEQ ID NO: 18) |
| Oct3/4 | Oct3/4-S9 | TCT TTC CAC CAG GCC CCC GGC TC (SEQ ID NO: 19) |
| | Oct3/4-AS210 | TGC GGG CGG ACA TGG GGA GAT CC (SEQ ID NO: 20) |
| NAT1 | NAT1 U283 | ATT CTT CGT TGT CAA GCC GCC AAA GTG GAG (SEQ ID NO: 21) |
| | NAT1 L476 | AGT TGT TTG CTG CGG AGT TGT CAT CTC GTC (SEQ ID NO: 22) |

The results shown in this figure revealed that, by transduction of the 3 genes, expression of each of ERas and Fgf4 was efficiently induced, but expression of each of Oct3/4 and Nanog, essential factors for the maintenance of pluripotency, was not induced, or was very weak even when induced. However, when the 4 genes were transduced, there was one clone (#7) in which Oct3/4 and Nanog were relatively strongly induced among 4 clones examined. Further, when the 10 genes were transduced, strong induction of each of Oct3/4 and Nanog was observed in 3 clones among 5 clones examined.

These results revealed that a combination of at least 3 genes (#14 (Oct3/4), #20 (Klf4), and #22 (c-Myc)) was essential for reprogramming under these conditions, and in the cases of the 4-gene group and 10-gene group including the 3 kinds of genes, the reprogramming efficiency was increased in proportion to the increasing number of genes. In other words, in accordance with the guidance disclosed herein, the minimum combination of nuclear reprogramming factors required for iPS cell induction under a given set of experimental conditions could be further optimized as evidenced below.

Example 3: Analysis of Pluripotency of Reprogrammed Cells

Figure 8:
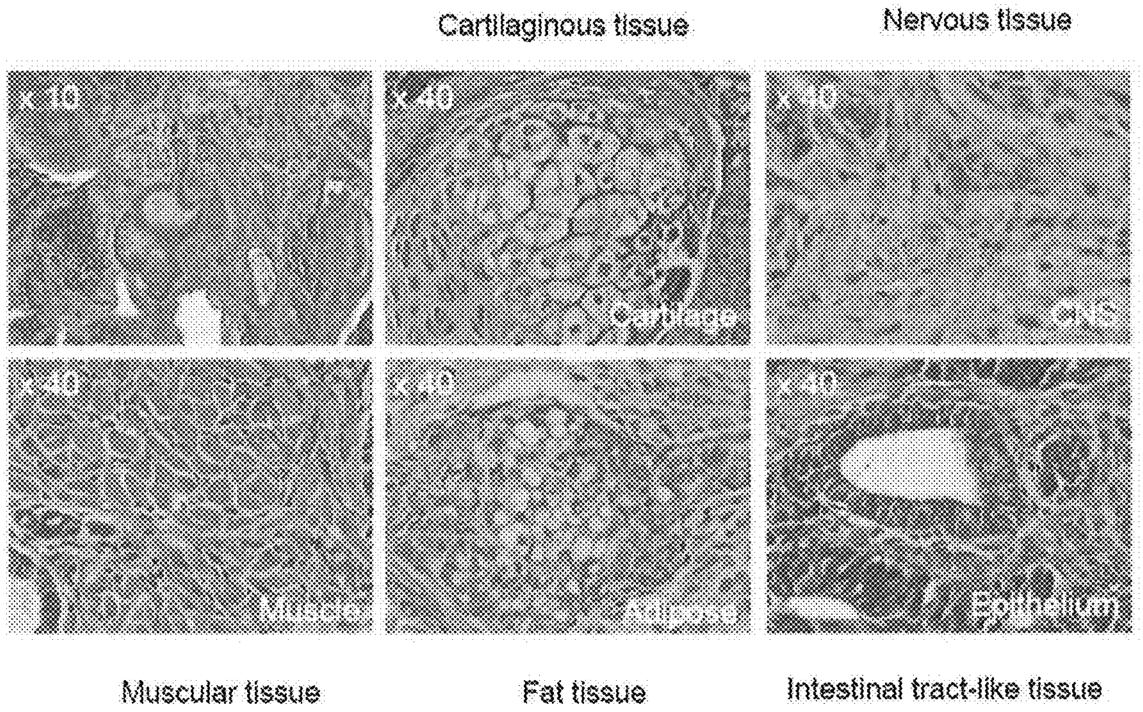
FIG. 8 depicts photographs showing results of hematoxylin-eosin (H & E) staining of tumors formed after subcutaneous transplantation of iPS cells derived from MEFs into nude mice. Differentiation into a variety of tissues in a triploblastic system was observed.

In order to evaluate the differentiation pluripotency of the established iPS cells, the iPS cells established with 24 factors, 10 factors, and 4 factors were subcutaneously transplanted into nude mice. As a result, tumors having a size similar to that observed with ES cells were formed in all animals. Histologically, the tumors consisted of a plurality of kinds of cells, and cartilaginous tissues, nervous tissues, muscular tissues, fat tissues, and intestinal tract-like tissues were observed (FIG. 8), which verified pluripotency of the iPS cells. In contrast, although tumors were formed when the cells established with the 3 factors were transplanted into nude mice, they were formed histologically only from undifferentiated cells. These results suggested that a Sox family gene was essential for the induction of differentiation pluripotency.

Example 4: Reprogramming of Fibroblasts Derived from Tails of Adult Mice

Figure 9:
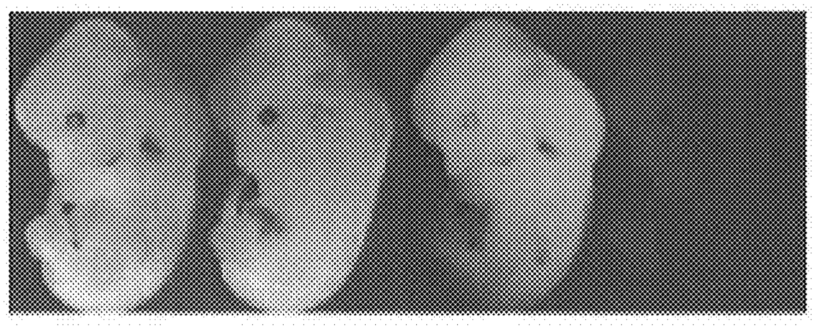
FIG. 9 depicts photographs of embryos prepared by transplanting iPS cells derived from adult dermal fibroblasts into mouse blastocysts and transplanting the cells into the uteri of pseudopregnant mice. It can be observed that, in the upper left embryo, cells derived from the iPS cells (emitting green fluorescence) were systemically distributed. In the lower photographs, it can be observed that almost all cells of the heart, liver, and spinal cord of the embryo were GFP-positive and were derived from the iPS cells.
Figure 9:
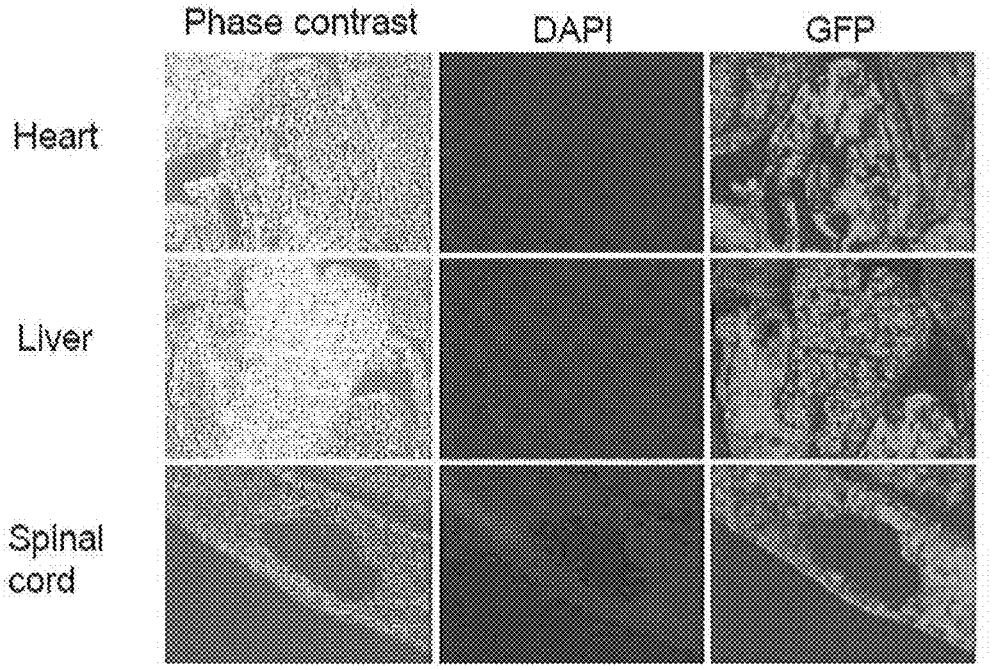

The 4 factors identified in the mouse embryonic fibroblasts (MEFs) were transduced into fibroblasts derived from tails of βgeo knockin Fbx15 adult mice systemically expressing green fluorescence protein (GFP). Then, the cells were cultured on feeder cells under the same conditions as ES cell culture conditions, and G418 selection was performed. In about two weeks after the start of the drug selection, a plurality of colonies of iPS cells were obtained. When these cells were subcutaneously transplanted to nude mice, teratomas consisting of a variety of all three germ layer tissues were formed. Further, when the iPS cells derived from adult dermal fibroblasts were transplanted to the blastocysts, and then transplanted into the uteri of pseudopregnant mice, embryos in which the GFP-positive cells were systemically distributed were observed among those at 13.5 days after fertilization (FIG. 9), demonstrating that the iPS cells had pluripotency and were able to contribute to mouse embryogenesis. These results indicate that the identified class of factors had an ability to induce reprogramming of not only somatic cells in an embryonic period, but also somatic cells of mature mice. Practically, it is extremely important that the reprogramming can be induced in cells derived from adult skin.

Example 5: Effect of Cytokine on iPS Cell Establishment

Figure 11:
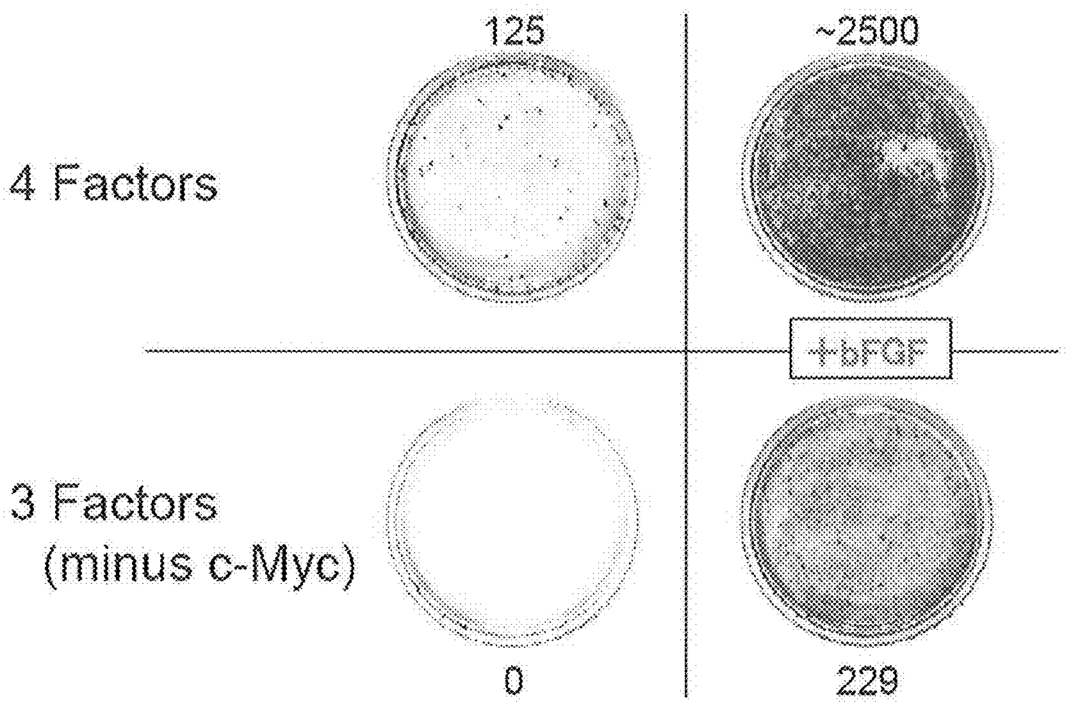
FIG. 11 shows an effect of bFGF on the establishment of iPS cells from MEFs. Four factors (upper row) or three factors except for c-Myc (lower row) were retrovirally transduced into MEFs derived from $Fbx15^{\beta geo/\beta geo}$ mice, and cultured on ordinary feeder cells (STO cells) (left) and bFGF expression vector-introduced STO cells (right). G418 selection was performed for 2 weeks, and cells were stained with crystal blue and photographed. The numerical values indicate the number of colonies.

An effect of cytokine on iPS cell establishment was investigated. Expression vector (pMX retroviral vector) for basic fibroblast growth factor (bFGF) or stem cell factor (SCF) was transduced into feeder cells (STO cells) to establish cells permanently expressing the cytokines. MEFs derived from the Fbx15$^{\beta geo/\beta geo}$ mouse (500,000 cells/100 mm dish) were cultured on these STO cells and transduced with the 4 factors, and then subjected to G418 selection. As a result, the number of formed colonies increased 20 times or higher on the STO cells producing bFGF (FIG. 11) or SCF (data not shown), as compared with the culture on normal STO cells. Further, although no iPS cell colony was formed on the normal STO cells when the 3 factors other than c-Myc were transduced, colony formation was observed on the STO cells producing bFGF (FIG. 11) or SCF (data not shown). These results revealed that stimulation with the cytokine increased the efficiency of the establishment of iPS cells from MEFs, and the nuclear reprogramming was achievable by using a cytokine instead of c-Myc.

Example 6: iPS Cell Generation with Other Oct, Klf, Myc, and Sox Family Members Family genes exist for all of the Oct3/4, Klf4, c-Myc, and Sox2 genes (TABLES 1 and 2). Accordingly, studies were made as to whether iPS cells could be established with the family genes instead of the 4 genes. In TABLE 7, combined experimental results in duplicate are shown. With regard to the Sox family, Sox1 gave almost the same number of G418-resistant colonies formed and iPS cell establishment efficiency as those with Sox2. As for Sox3, the number of G418-resistant colonies formed was about 1/10 of that with Sox2, however, iPS cell establishment efficiency of the colonies picked up was in fact higher than that with Sox2. As for Sox15, both the number of G418-resistant colonies formed and iPS cell establishment efficiency were lower than those with Sox2. As for Sox17, the number of G418-resistant colonies formed was almost the same as that with Sox2, however, iPS cell establishment efficiency was low. With regard to the Klf family, Klf2 gave a smaller number of G418-resistant colonies than Klf4, however, they gave almost the same iPS cell establishment efficiency. With regard to the Myc family, it was found that wild-type c-Myc was almost the same as a T58A mutant both in the number of G418-resistant colonies formed and iPS cell establishment efficiency. Further, each of N-Myc and L-Myc (each wild type) was almost the same as c-Myc in both of the number of G418-resistant colonies formed and iPS cell establishment efficiency.

TABLE 7

| Transduced gene | Number of formed colonies | Number of picked colonies | Number of established iPS cell strain | iPS cell establishment efficiency (%) |
|---|---|---|---|---|
| 4 Factors (cMycT58A) | 85 | 12 | 5 | 42 |
| Sox1 | 84 | 12 | 7 | 58 |
| Sox3 | 8 | 8 | 7 | 92 |
| Sox15 | 11 | 11 | 1 | 8 |
| Sox17 | 78 | 12 | 2 | 17 |
| Klf2 | 11 | 10 | 5 | 50 |
| c-MycWT | 53 | 11 | 8 | 72 |
| N-MycWT | 40 | 12 | 7 | 58 |
| L-MycWT | 50 | 12 | 11 | 92 |
| 3 Factors (-Sox2) | 6 | 6 | 2 | 17 |

Example 7: Use of a Nanog-GFP-Puro$^r$ Reporter to Establish iPS Cells

Figure 12:
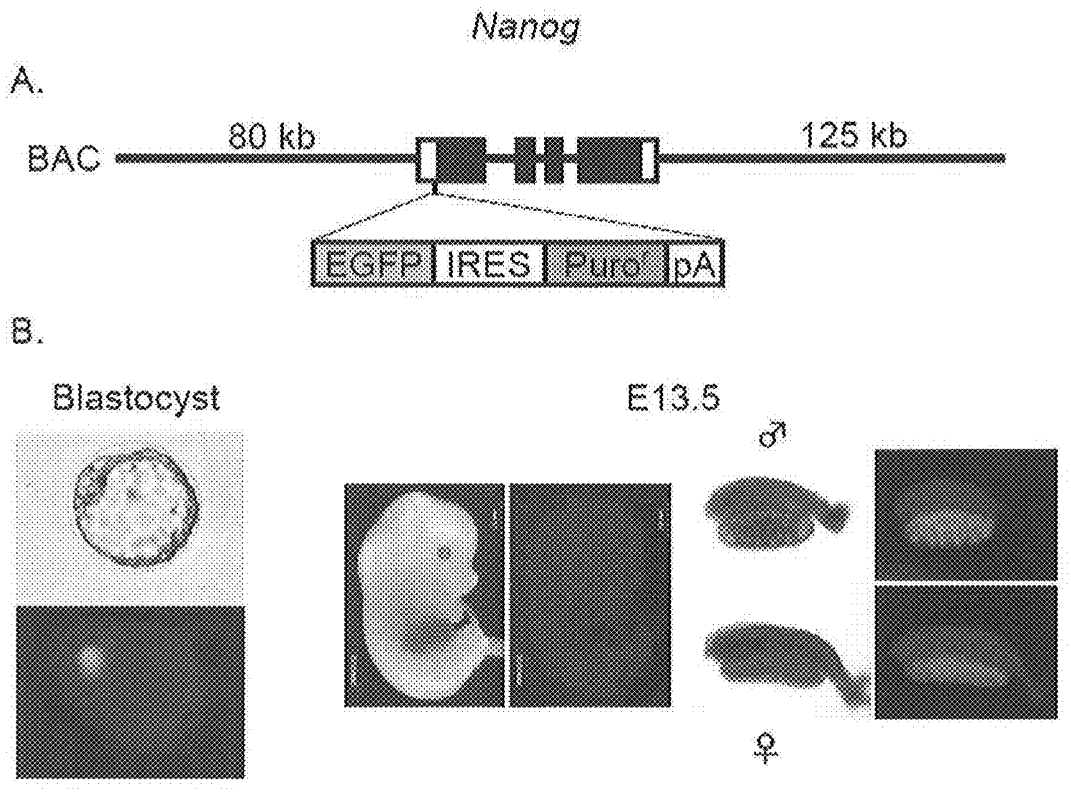
FIG. 12 depicts explanations of the experiments using Nanog-EGFP-IRES-Puro$^r$ mice. (A) *E. coli* artificial chromosome (BAC) containing the mouse Nanog gene in the center was isolated, and the EGFP-IRES-Puro$^r$ cassette was inserted upstream from the coding region of Nanog by recombineering. (B) Transgenic mice were prepared with the modified BAC. GFP expression was observed limitedly in inner cell masses of blastocysts and gonads.
Figure 13:
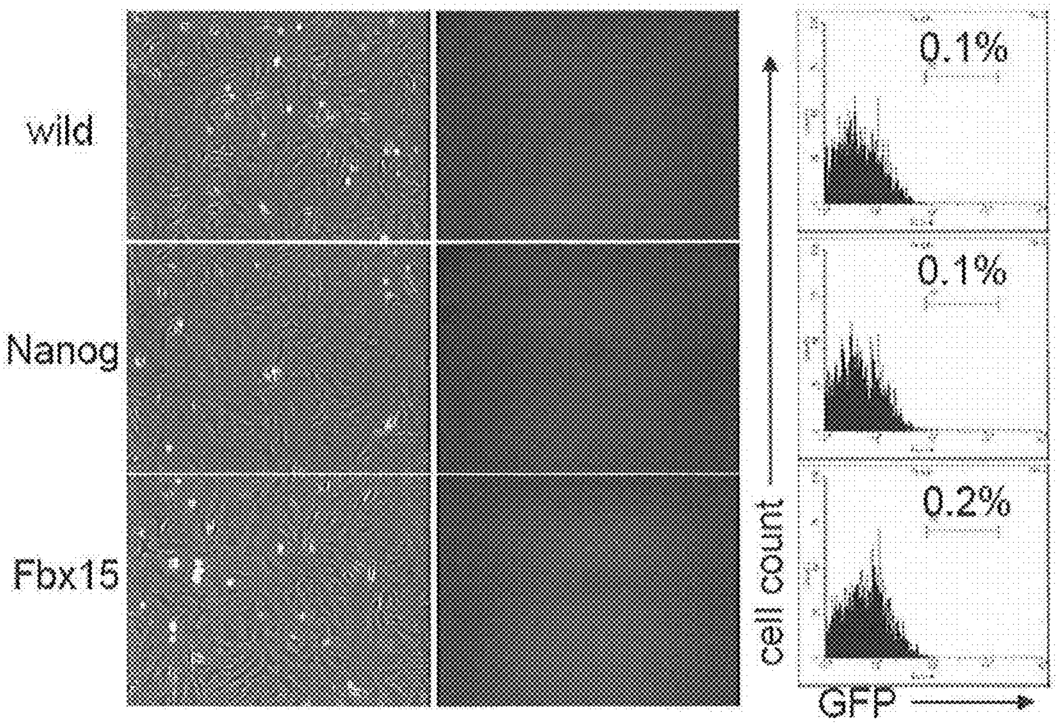
FIG. 13 depicts explanations of the experiments using Nanog-EGFP-IRES-Puro$^r$ mice. From embryos of Nanog-EGFP-IRES-Puro$^r$ mice (13.5 days after fertilization), heads, viscera and gonads were removed to establish MEFs. As a result of analysis with a cell sorter, almost no GFP-positive cells existed in MEFs derived from the Nanog-EGFP-IRES-Puro mice (Nanog) in the same manner as the Fbx15$^{\beta geo/\beta geo}$ mouse-derived MEFs (Fbx15) or wild-type mouse-derived MEFs (Wild).
Figure 14:
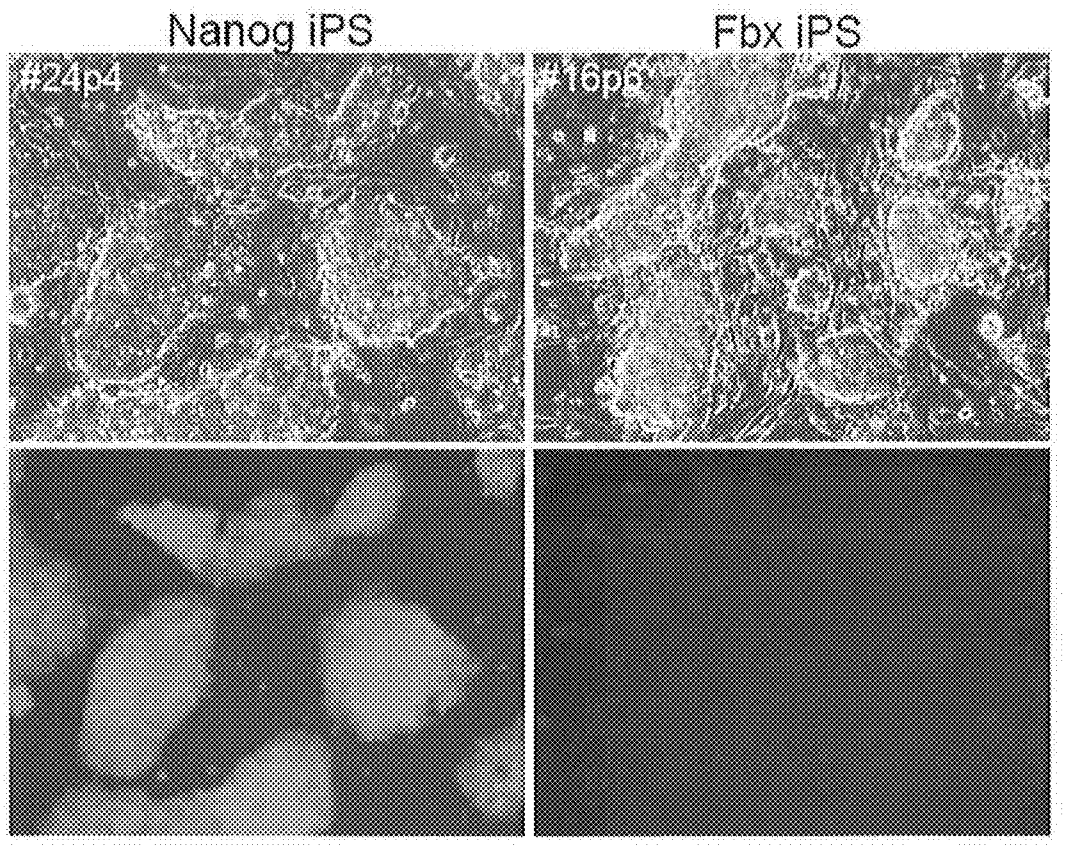
FIG. 14 depicts photographs of iPS cells established from the Nanog-EGFP-IRES-Puro mouse MEFs (left) and the Fbx15$^{\beta geo/\beta geo}$ mouse MEFs (right). The cells were selected with puromycin and G418, respectively.
Figure 15:
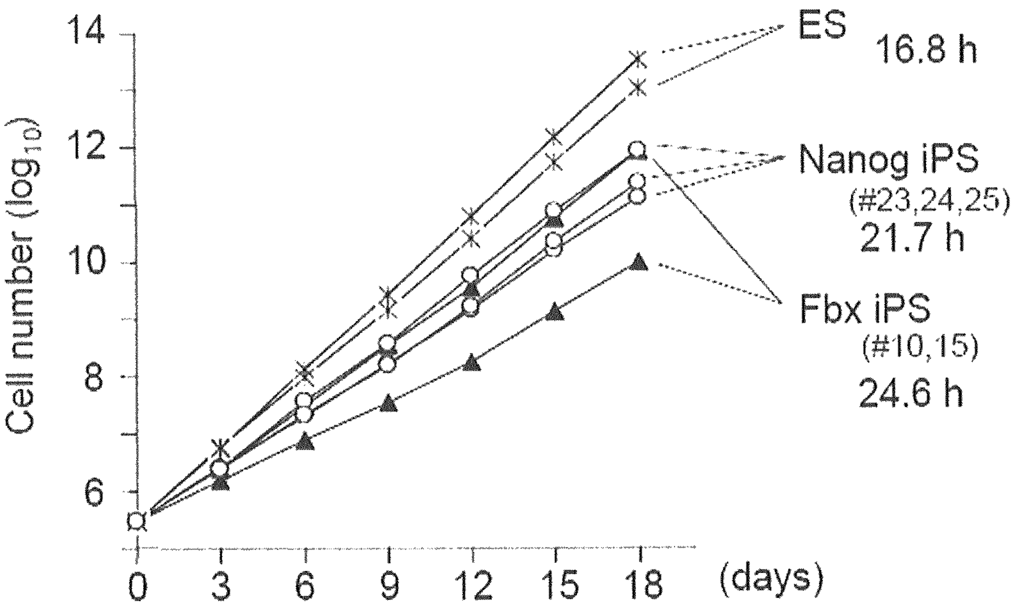
FIG. 15 shows results of growth of iPS cells. 100,000 cells of each of ES cells, iPS cells derived from the Nanog-EGFP-IRES-Puro mouse MEFs (Nanog iPS, left), and iPS cells derived from the Fbx15$^{\beta geo/\beta geo}$ mouse MEFs (Fbx iPS) were seeded on 24-well plates, and passaged every 3 days. Cell count results are shown. The numerical values represent average doubling times.
Figure 16:
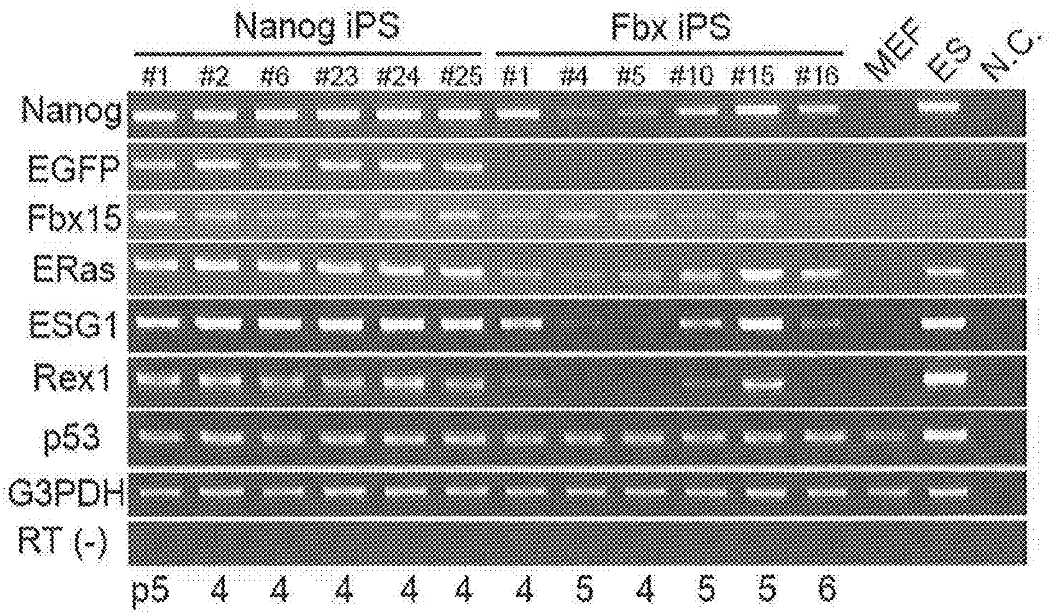
FIG. 16 shows gene expression profiles of iPS cells. Expression of the marker genes in MEFs, ES cells, iPS cells derived from Nanog-EGFP-IRES-Puro mouse MEFs (Nanog iPS, left), and iPS cells derived from Fbx15$^{\beta geo/\beta geo}$, mouse MEFs (Fbx iPS) were analyzed by RT-PCR. The numerical values at the bottom indicate the numbers of passages.
Figure 17:
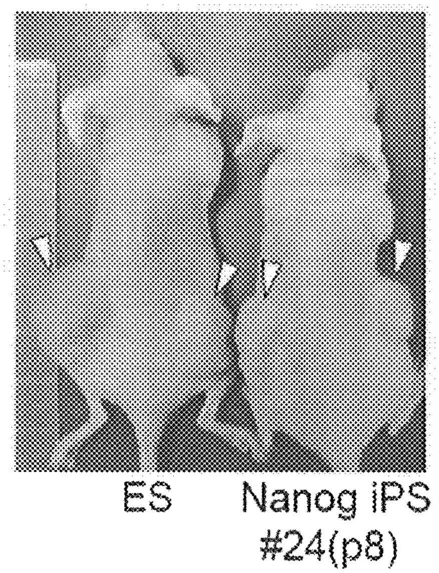
FIG. 17 shows teratoma formation from the Nanog iPS cells. 1,000,000 cells of each of ES cells or Nanog iPS cells #24 (passage 8 times) were subcutaneously injected into the backs of nude mice, and the appearance of tumors formed after 3 weeks (left) and tissue images (right, H & E stained) are shown.
Figure 17:
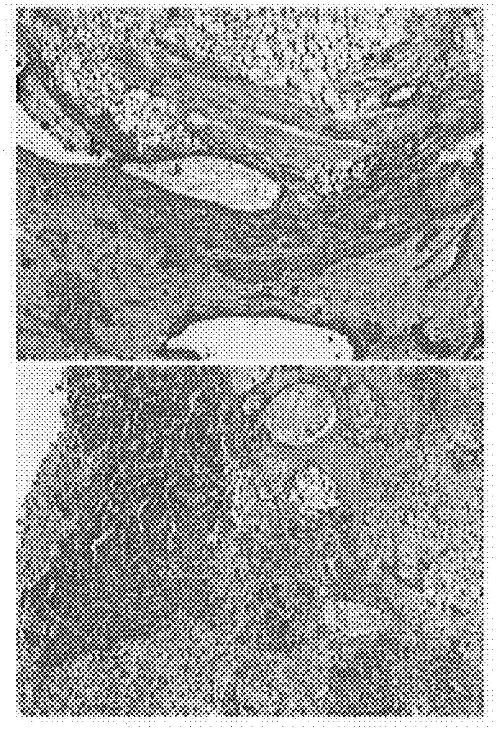
Figure 18:
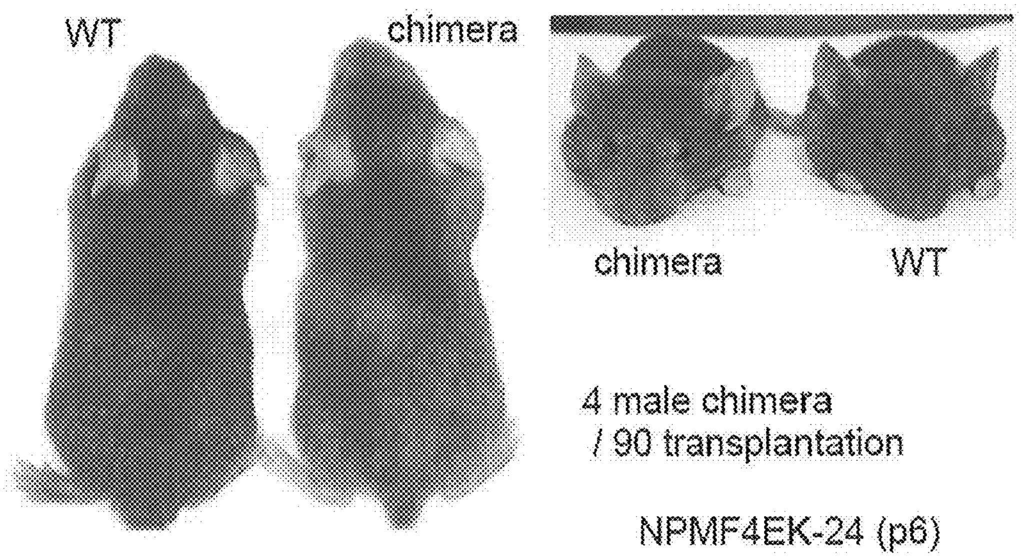
FIG. 18 shows preparation of chimeric mice with the Nanog iPS cells. The chimeric mice that were born after transplantation of the Nanog iPS cells (clone NPMF4EK-24, passaged 6 times) into the blastocysts. Four chimeric mice were born from 90 transplanted embryos.
Figure 19:
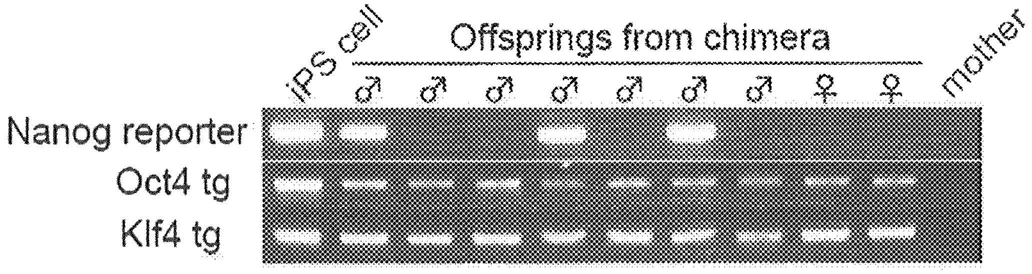
FIG. 19 shows germ-line transmission from the Nanog iPS cells. PCR analysis of genomic DNA of mice, born by mating of the chimeric mice shown in FIGS. 18 and C57BL/6 mice, revealed the existence of transgenes of Oct3/4 and Klf4 in all of the mice, thereby confirming germ-line transmission.

Studies were made as to whether iPS cells could be established with a reporter other than Fbx15-βgeo. *Escherichia coli* artificial chromosome (BAC) containing the Nanog gene in the center was isolated, and then the GFP gene and the puromycin resistance gene were knocked in by recombination in *E. coli* (FIG. 12A). Subsequently, the above modified BAC was introduced into ES cells to confirm that the cells became GFP-positive in an undifferentiated state specific manner (data not shown). Then, these ES cells were transplanted in mouse blastocysts to create transgenic mice via chimeric mice. In these mice, GFP-positive cells were specifically observed in inner cell masses of the blastocysts or gonads of embryos at 13.5 days after fertilization (FIG. 12B). The gonads were removed from the embryos at 13.5 days after fertilization (hybrid of DBA, 129, and C57BL/6 mice), and MEFs were isolated. The isolated MEFs were confirmed to be GFP-negative (FIG. 13) by flow cytometry. These MEFs were retrovirally transduced with the 4 factors and subjected to puromycin selection, and as a result, a plural, number of resistant colonies were obtained. Only about 10 to 20% of the colonies were GFP-positive. When the GFP-positive colonies were passaged, they gave morphology (FIG. 14) and proliferation (FIG. 15) similar to those of ES cells. Examination of the gene expression pattern revealed that the expression pattern was closer to that of ES cells as compared to the iPS cells isolated from Fbx15$^{\beta geo/\beta geo}$ MEFs by G418 selection (FIG. 16). When these cells were transplanted to nude mice, teratoma formation was induced, thereby the cells were confirmed to be iPS cells (FIG. 17). Further, chimeric mice were born by transplanting the iPS cells obtained by Nanog-GFP selection to the blastocysts of C57BL/6 mice (FIG. 18). When these chimeric mice were mated, germ-line transmission was observed (FIG. 19). In these iPS cells established by Nanog-GFP selection, which were closer to ES cells, the expressions of the 4 factors from the retroviruses were almost completely silenced, suggesting that self-replication was maintained by endogenous Oct3/4 and Sox2.

Example 8: In Vitro Differentiation Induction

Figure 20:
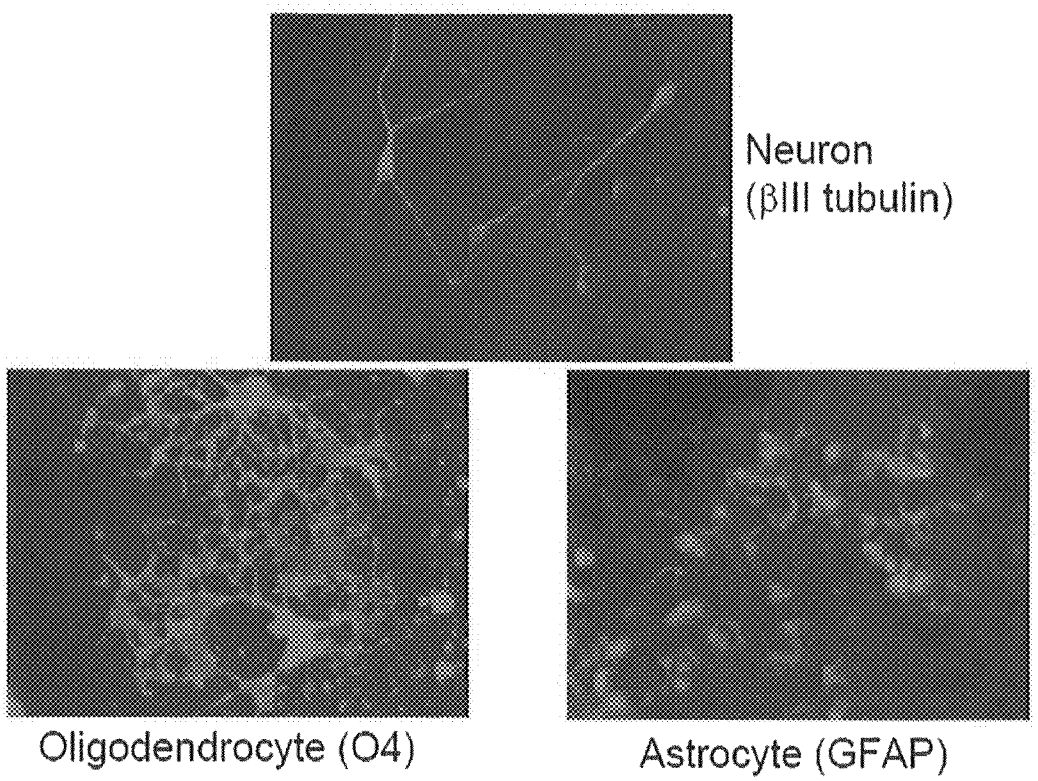
FIG. 20 shows induction of differentiation into nerve cells from iPS cells. Nerve cells (top, βIII tubulin-positive), oligodendrocytes (left, O4-positive), and astrocytes (right, GFAP-positive) differentiated in vitro from dermal fibroblasts-derived iPS cells are shown.

Confluent iPS cells in 10 cm dishes were trypsinized and suspended in ES cell medium (the STO cells were removed by adhesion to a gelatin-coated dish for 10 to 20 minutes after the suspension). 2×10$^6$ cells were cultured for four days in a HEMA (2-hydroxyethyl methacrylate) coated *E. coli* culture dish as a suspension culture to form embryoid bodies (EBs) (day 1 to 4). On the 4th day of EB formation (day 4), all of the EBs were transferred to a 10-cm tissue culture dish, and cultured in ES cell medium for 24 hours to allow adhesion. After 24 hours (day 5), the medium was changed to an ITS/fibronectin-containing medium. The culture was performed for 7 days (medium was exchanged every 2 days), and nestin-positive cells were selected (cells of other pedigrees were dying to some extent in a culture under serum-free condition) (day 5 to 12). A2B5-positive cells were then induced. After 7 days (day 12), the cells were separated by trypsinization, and the remaining EBs were removed. 1×10$^5$ cells were seeded on a poly-L-ornithine/fibronectin-coated 24-well plate, and cultured for 4 days in an N2/bFGF-containing medium (medium was exchanged every 2 days) (day 12 to 16). After 4 days (day 16), the medium was changed to an N2/bFGF/EGF-containing medium, and the culture was continued for 4 days (medium was exchanged every 2 days) (day 16 to 20). After 4 days (day 20), the medium was changed to an N2/bFGF/PDGF-containing medium, and the culture was continued for 4 days (medium was exchanged every 2 days) (day 20 to 24). During this period (day 12 to 24), when the cells had increased excessively and reached confluent, they were passaged at appropriate times, and 1 to 2×10$^5$ cells were seeded (the number of the cells varied depending on the timing of the passage). After 4 days (day 24), the medium was changed to an N2/T3 medium, and the culture was continued for 7 days (day 24 to 31) with medium exchange every 2 days. On day 31, the cells were fixed and subjected to immunostaining. As a result, differentiation of the iPS cells into BIII tubulin-positive nerve cells, 04-positive oligodendrocytes, and GFAP-positive astrocytes was observed (FIG. 20).

Example 9: Establishment of iPS Cells Without Drug Selection

Figure 21:
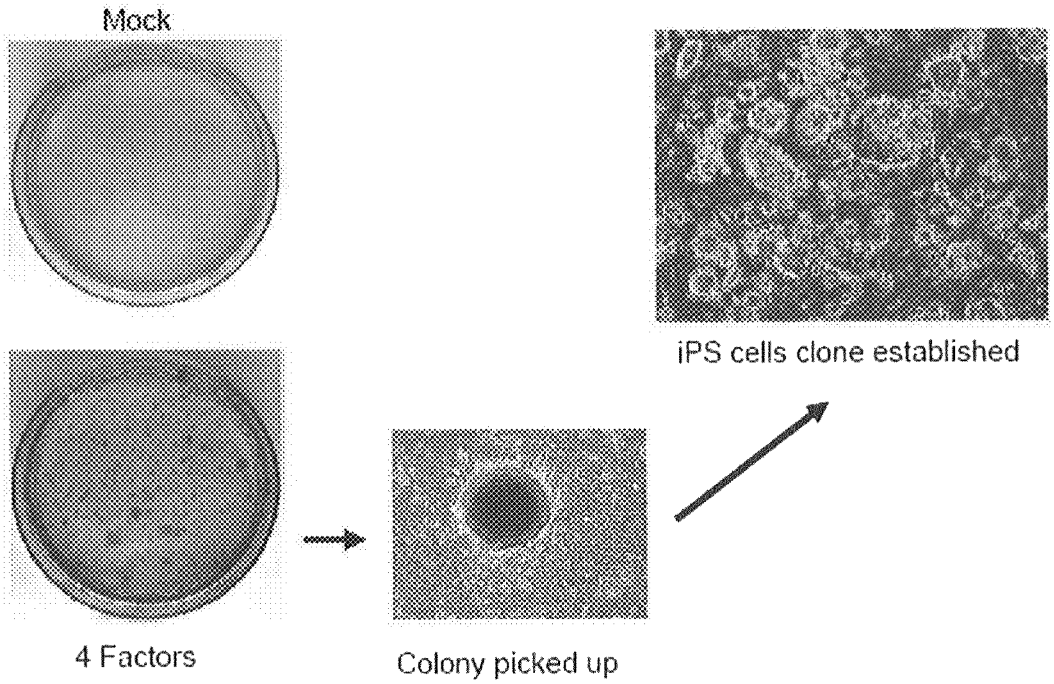
FIG. 21 depicts explanations of establishment of the iPS cells without using drug selection. MEFs at 10,000 to 100,000 cells per 10 cm dish were seeded, and the 4 factors were retrovirally transduced. No colony appeared in the control (Mock, top left), whilst in the dish with the transduction by the 4 factors, swelling colonies similar to those of the iPS cells were obtained (bottom left and center), as well as flat transformant colonies. When the cells were passaged, cells similar to the iPS cells were obtained (right).
Figure 22:
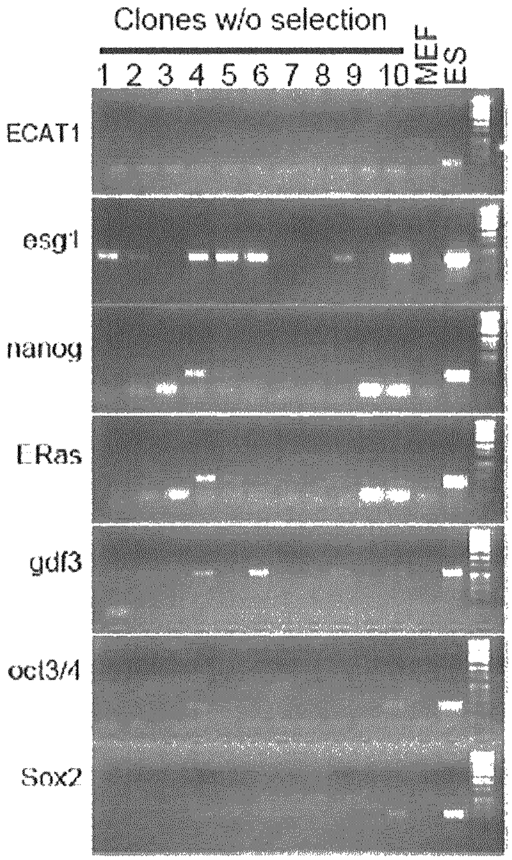
FIG. 22 shows gene expression profiles of cells established without using drug selection. RNA was extracted from the established cells shown in FIG. 21, and expression of the ES cell marker genes was analyzed by RT-PCR.

In order to establish iPS cells from arbitrary mouse somatic cells other than those derived from the Fbx15-βgeo knockin mouse, a method for the establishment without using drug selection was developed. 10,000, 50,000, or 100,000 cells mouse embryo fibroblasts (MEFs) were cultured on a 10 cm dish (on STO feeder cells). This is less than the number of cells used above, Control DNA or the 4 factors were retrovirally transduced. When culture was performed for 2 weeks in the ES cell medium (without G418 selection), no colony formation was observed in the dish in which the control DNA was transduced, whilst in the dish in which the 4 factors were transduced, a plurality of compact colonies were formed as well as flat colonies considered to be transformed (FIG. 21). When 24 colonies were picked up from these colonies and culture was continued, ES cell-like morphology was observed. Gene expression profiles thereof were examined by RT-PCR, and as a result, the expression of Esg1, an ES cell marker, was observed in 7 clones. Induction of many ES cell markers such as Nanog, ERas, GDF3, Oct3/4, and Sox2 was observed in clone 4, and therefore the cells were considered to be iPS cells (FIG. 22). The above results demonstrated that drug selection using Fbx15-βgeo knockin or the like was not indispensable for iPS cell establishment, and iPS cells could be established from arbitrary mouse-derived somatic cells. This also suggested the possibility that iPS cells could be established from somatic cells of a disease model mouse by the aforementioned technique.

Example 10: iPS Cell Generation from Hepatocytes and Gastric Mucous Cells

As cells from which iPS cells were induced, hepatocytes and gastric mucous cells being cells other than fibroblasts were examined. Hepatocytes were isolated from the liver of the Fbx15$^{\beta geo/\beta geo}$ mice by perfusion. These hepatocytes were retrovirally introduced with the 4 factors, and then subjected to G418 selection to obtain plural iPS cell colonies. As a result of gene expression pattern analysis using a DNA microarray, the iPS cells derived from the liver were found to be more similar to ES cells than the iPS cells derived from dermal fibroblasts or embryonic fibroblasts. iPS cells were obtained also from gastric mucous cells in the same manner as those from hepatocytes.

Example 11: Effect of MAP Kinase Inhibitor on iPS Cell Establishment

PD98059 is an inhibitor of MAP kinase which suppresses proliferation of various differentiated cells. However, it is known to promote maintenance of undifferentiated status and proliferation of ES cells. Effects of PD98059 on iPS cell establishment were thus examined. MEFs established from a mouse having the selective markers of Nanog-EGFP-IRES-Puro were retrovirally introduced with the 4 factors and subjected to puromycin selection. When PD98059 was not added, the percentage of GFP-positive colonies was 8% of the iPS cell colonies obtained. However, in the group to which PD98059 (final concentration: 25 μM) was continuously added from the next day of the retroviral transfection, 45% of the colonies obtained were GFP-positive. The results were interpreted to be due to PD98059 promoting the proliferation of the GFP-positive iPS cells, which are closer to ES cells, whilst PD98059 suppressing the proliferation of the GFP-negative iPS cells or differentiated cells. From these results, PD98059 was demonstrated to be able to be used for establishment of the iPS cells closer to ES cells or establishment of iPS cells without using drug selection.

Figure 23:
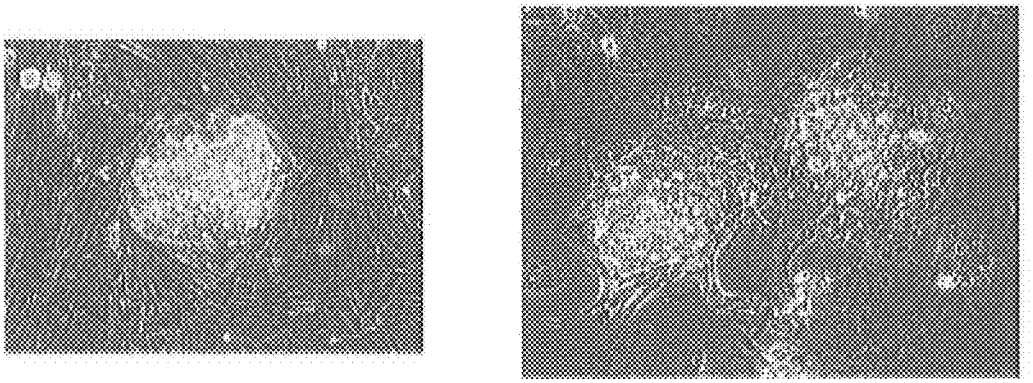
FIG. 23 shows iPS cell-like cells derived from human fibroblasts. The colonies obtained by retroviral transduction with human homologous genes of the 4 factors into fibroblasts derived from human embryos (A), and the cells after two passages (B) are shown.

Example 12: Establishment of iPS Cells from Embryonic HDFs in Mouse ES Cell Medium A plasmid, containing the red fluorescence protein gene downstream from the mouse Oct3/4 gene promoter and the hygromycin resistance gene downstream from the PGK promoter, was introduced by nucleofection into embryonic human dermal fibroblasts (HDFs) in which solute carrier family 7 (Slc7a1, NCBI accession number NM_007513) as a mouse ecotropic virus receptor was expressed by lentiviral transduction. Hygromycin selection was performed to establish strains with stable expression. 800,000 cells were seeded on the STO cells treated with mitomycin, and on the next day, Oct3/4, Sox2, Klf4, and c-Myc (each derived from human) were retrovirally transduced into the cells. 24 colonies were picked up from those obtained after 3 weeks (FIG. 23, left), and transferred on a 24-well plate on which the STO cells were seeded and then cultured. After 2 weeks, one grown clone was passaged on a 6-well plate on which the STO cells were seeded and cultured. As a result, cells morphologically similar to ES cells were obtained (FIG. 23, right), suggesting that the cells were iPS cells. The mouse ES cell medium was used as every medium.

Example 13: Establishment of iPS Cells from Adult HDFs in Mouse ES Cell Medium

Human adult dermal fibroblasts (adult HDFs) or human neonatal foreskin cells (BJ) were transduced with Slc7a1 (mouse retroviral receptor) by using lentivirus, and the resulting cells were seeded on 800,000 feeder cells (mitomycin-treated STO cells). The genes were retrovirally transduced as the following combinations.

1. Oct3/4, Sox2, Klf4, c-Myc, TERT, and SV40 Large T antigen
2. Oct3/4, Sox2, Klf4, c-Myc, TERT, HPV16 E6
3. Oct3/4, Sox2, Klf4, c-Myc, TERT, HPV16 E7
4. Oct3/4, Sox2, Klf4, c-Myc, TERT, HPV16 E6, HPV16 E7
5. Oct3/4, Sox2, Klf4, c-Myc, TERT, Bmil
6. Oct3/4, Sox2, Klf4, c-Myc (Oct3/4, Sox2, Klf4, c-Myc and TERT were Derived from Human, and Bmil was Derived from Mouse)

Figure 24:
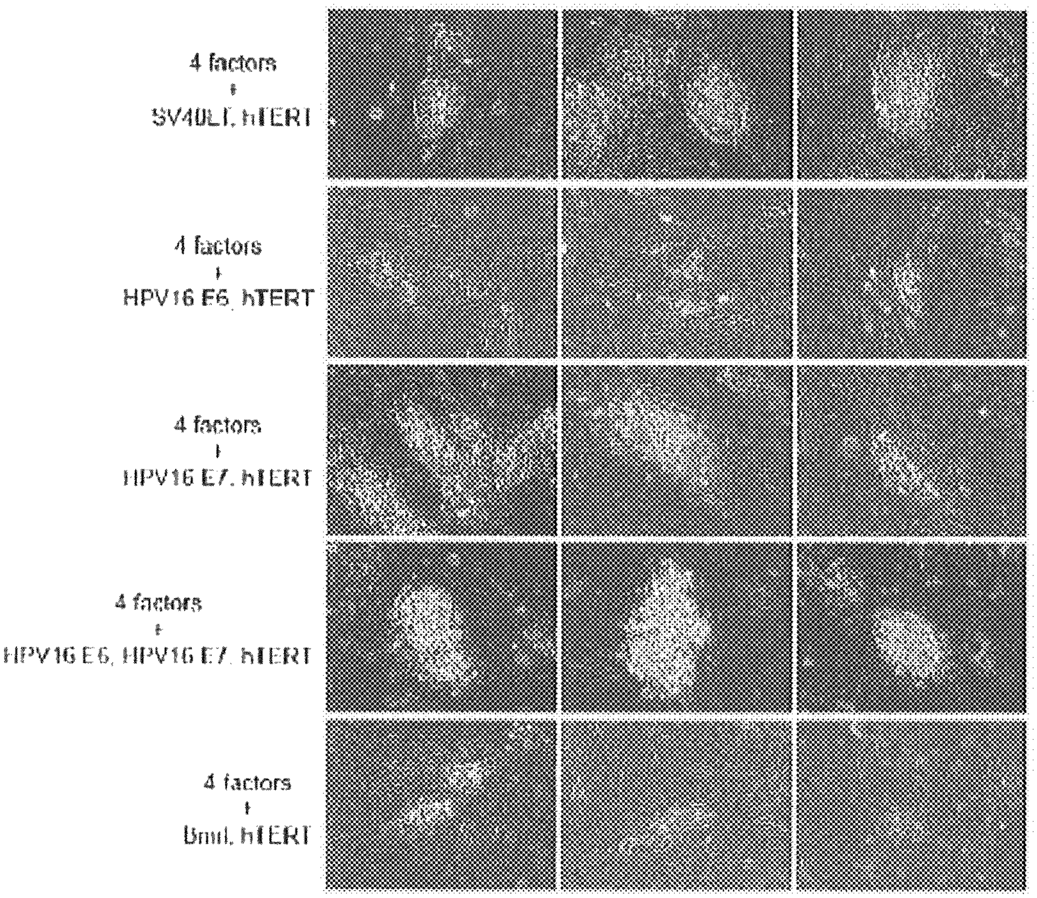
FIG. 24 shows establishment of the iPS cells from human adult dermal fibroblasts. The factors mentioned in the left column were transduced retrovirally into human adult dermal fibroblasts infected with the mouse retroviral receptor with lentivirus. The photographs shows phase contrast images (object×10) on day 8 after the viral infection.
Figure 25:
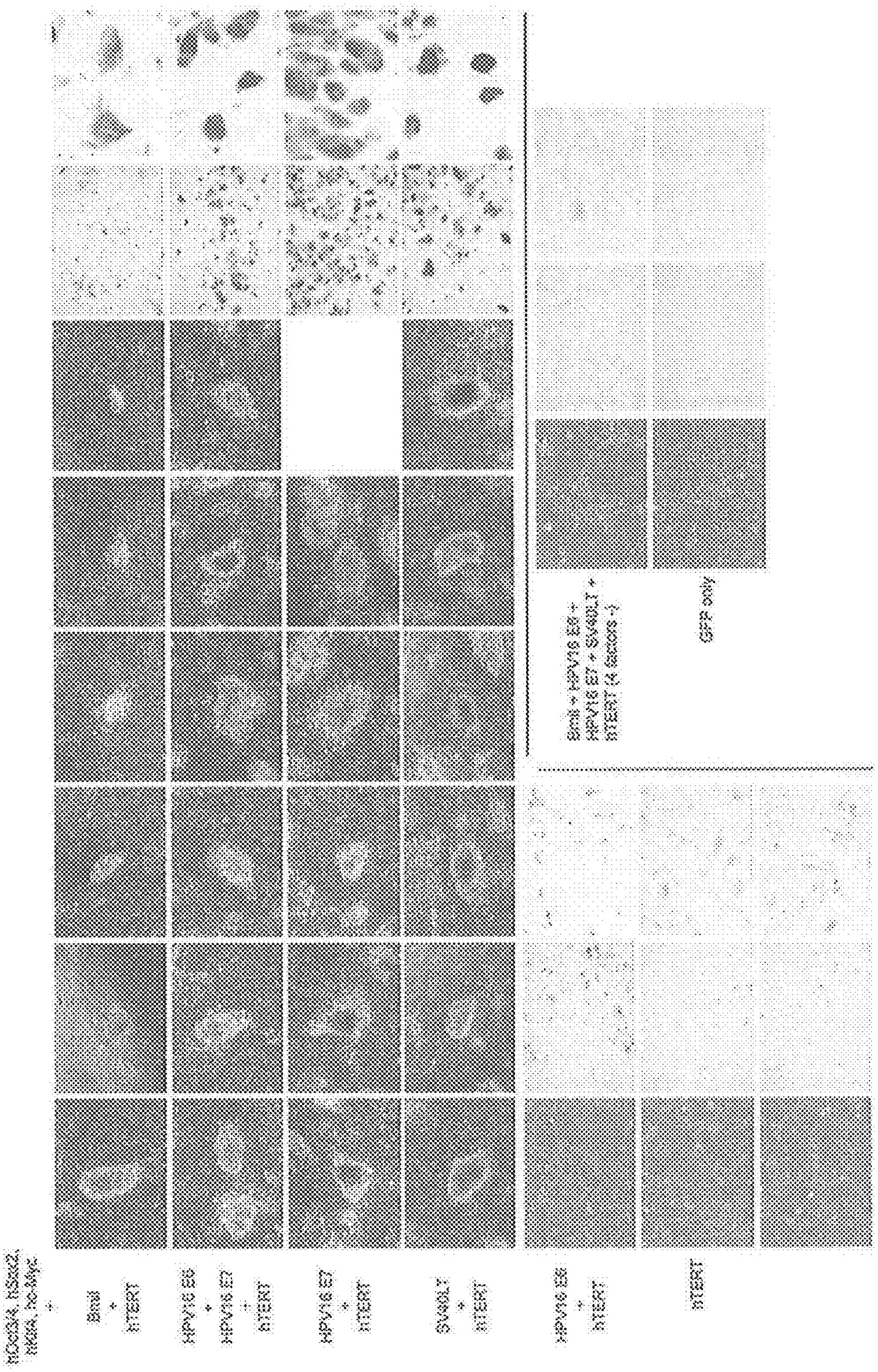
FIG. 25 shows the results of alkaline phosphatase staining of iPS cells from two different experiments. (A) $8\times10^5$ HDFs derived from adult skin expressing mouse Slc7a1 gene and introduced with pMXs encoding the genes indicated were plated on mitomycin C-treated STO cells. The infected cells were cultured in ES medium for 12 days. The cells were stained with alkaline phosphatase. (B) BJ fibroblasts expressing mouse Slc7a1 gene were plated at $8\times10^5$ cells per 100 mm dish on mitomycin C treated STO cells. Next day, the cells were transduced with the genes indicated (left) by retroviral infection. After transduction, the cells were maintained in ES medium for 2 weeks. After picking up the colonies, the cells were stained with alkaline phosphatase.
Figure 25:
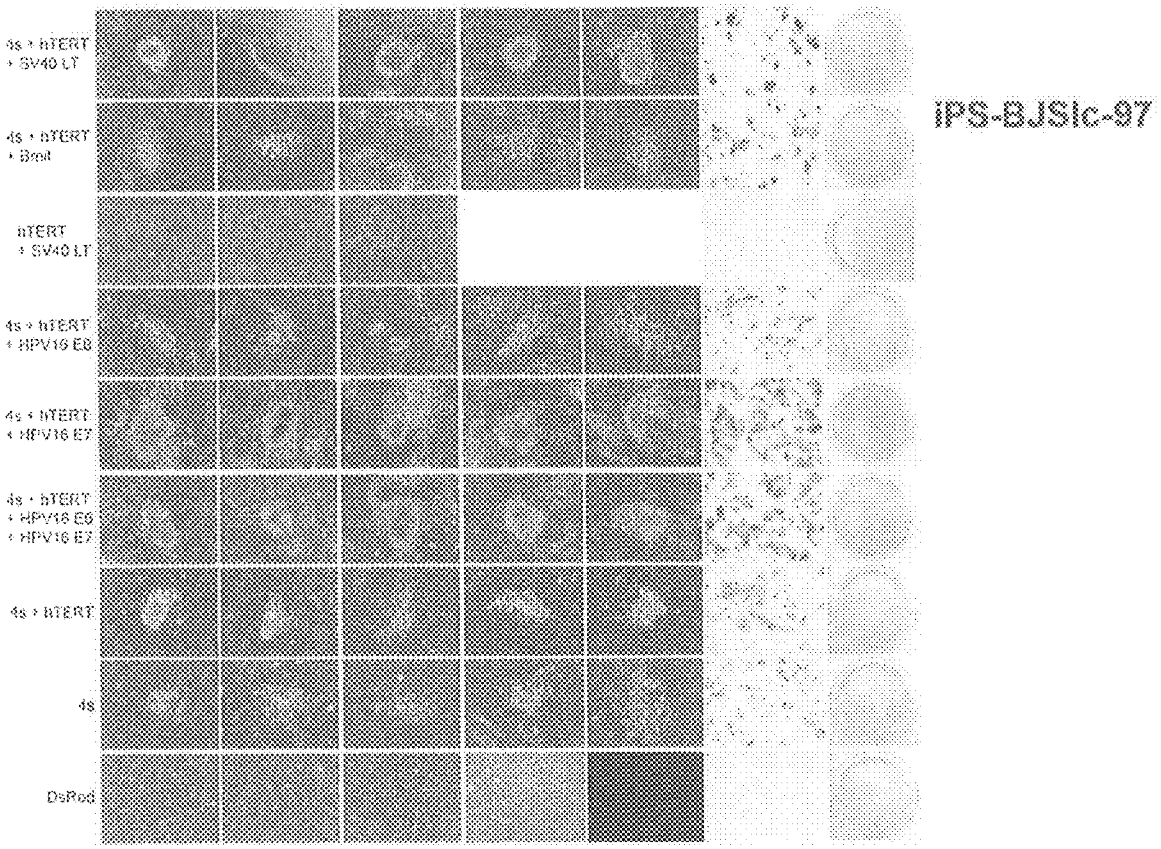

The culture was continued under the culture conditions for mouse ES cells without drug selection. As a result, colonies considered to be those of iPS cells emerged on the 8th day after the virus transfection on the dish in which the factors were introduced according to Combination 1 (FIG. 24). iPS cell-like colonies also emerged with the other combinations (2 to 5), although they were not as apparent when compared to Combination 1. When only the 4 factors were transduced (6), no colonies emerged. However, cells transduced with the four factors under the experimental conditions used in this Example did show staining for alkaline phosphatase (FIG. 25(A)-(B)).

Figure 26:
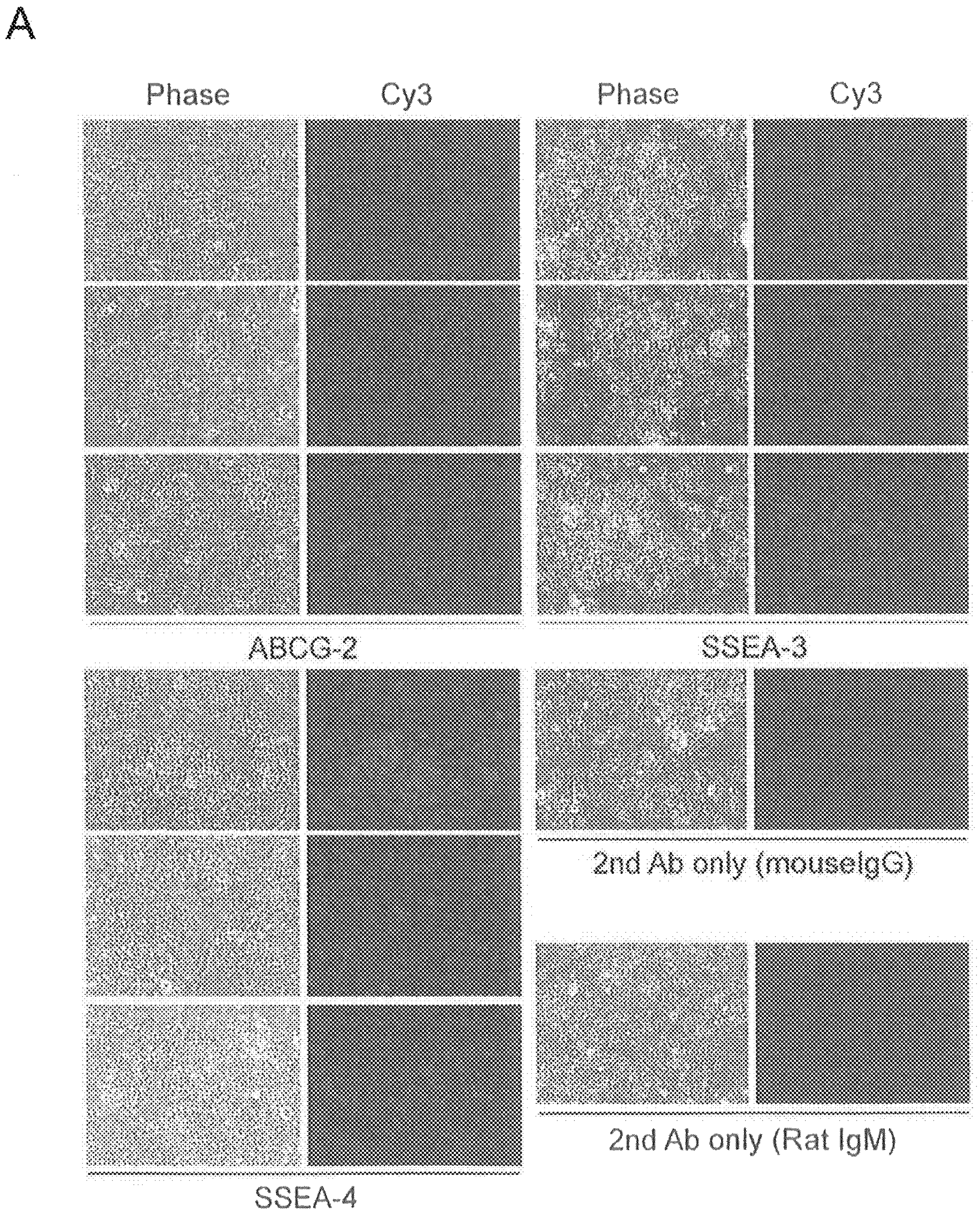
FIG. 26 shows Cyanine 3(Cy-3) staining of iPS (-like) cells with ES cell markers. (A) iPS (-like) cells derived from adult human dermal fibroblasts (HDFs) were plated at $5\times10^4$ cells per well of 6 well plates on mitomycin C-treated STO cells, and grown for 4 days. The cells were fixed with PBS containing 10% formalin, and blocked with blocking buffer (0.1% bovine serum albumin and 10 mg/ml normal donkey serum in PBS) for 45 minutes at room temperature. Primary antibodies indicated above were diluted 1:100 in blocking buffer. Overnight incubation with primary antibody, the cells were washed with PBS, and then incubated with secondary antibody. Cy-3-conjugated anti-mouse IgG (for ABCG-2 and SSEA-4) and anti-rat IgM (for SSEA-3) antibodies were used. (B) iPS (-like) cells derived from adult HDFs (clone 87E3, 87E4 and 87E12) were plated at $5\times10^4$ cells per well of a 6 well plate on mitomycin C-treated STO cells, and grown for 5 days. Parental HDFs also plated on 6 well plate and maintained for 2 days. The cells were fixed with PBS containing 10% formalin, and blocked with blocking buffer (3% BSA in PBS) for 45 minutes at room temperature. Primary antibodies indicated above were diluted 1:100 in blocking buffer. Overnight incubation with primary antibody, the cells were washed with PBS, and then incubated with secondary antibody. Cy-3-conjugated anti-mouse IgG (for ABCG-2, E-cadherin, and SSEA-4) and anti-rat IgM (for SSEA-3) antibodies were used as secondary antibodies.
Figure 26:
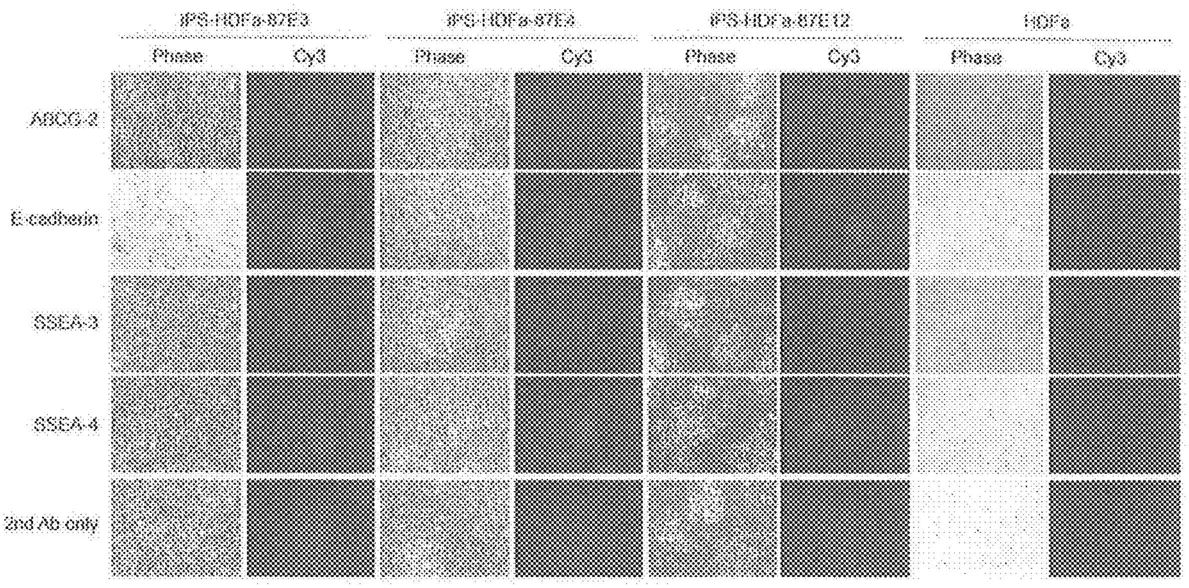
Figure 27:
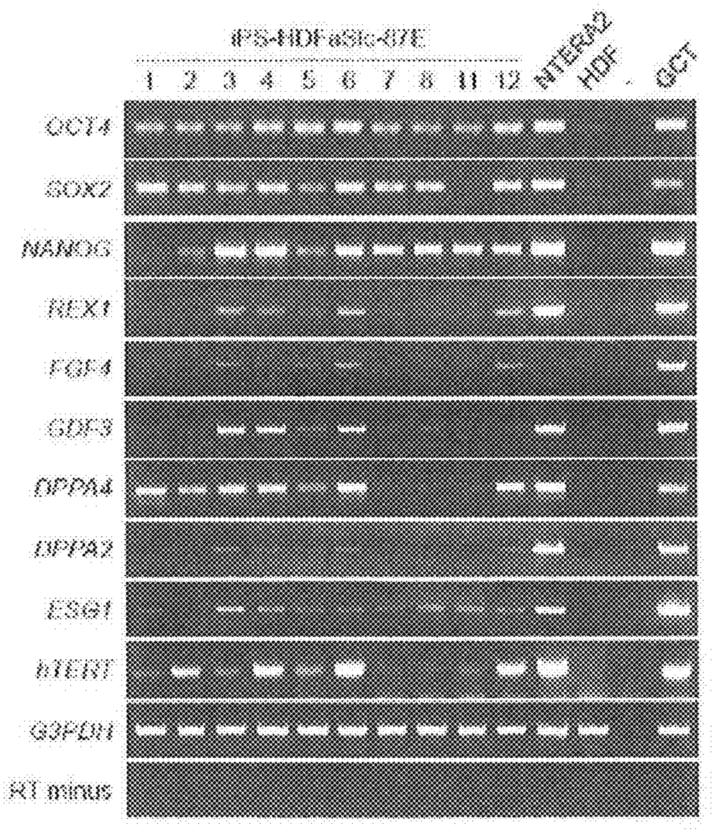
FIG. 27 shows human iPS (-like) cells express ECATs. Total RNA was isolated from human iPS (-like) cells (iPS-HDFaSlc-87E-1~8, 11 and 12), NTERA2 cloneD1 human embryonic carcinoma cells (passage 35) and adult HDFs expressing mouse Slc7a1 gene (passage 6). First-strand cDNA was synthesized by using oligo-dT20 primer and Rever Tra Ace-α-kit (Toyobo) according to manufacturer's protocol. PCR was performed with the primers as follows: hOct4 S1165 and hOct4-AS1283 for endogenous OCT4, hSox2-S1430 and hSox2-AS1555 for endogenous SOX2, ECAT4-macaca-968S and ECAT4-macaca-1334AS for NANOG, hRex1-RT-U and hRex1-RT-L for REX1, hFGF4-RT-U and hFGF4-RT-L for FGF4, hGDF3-S243 and hGDF3-AS850 for GDF3, hECAT15-S532 and hECAT15-AS916 for ECAT15-1, hECAT15-2-S85 and hECAT15-2-AS667 for ECAT15-2, hpH34-S40 and hpH34-AS259 for ESG1, hTERT-S3556 and hTERT-AS3713 for hTERT, and G3PDH-F and G3PDH-R for G3PDH.
Figure 28:
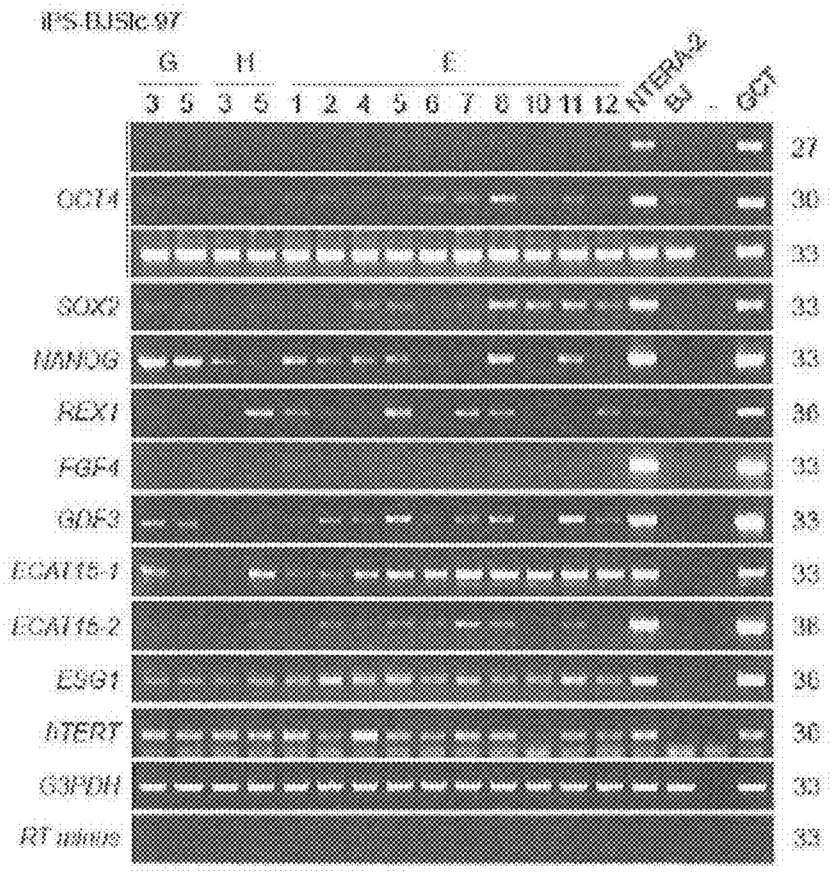
FIG. 28 shows human iPS (-like) cells express ECATs. Total RNA was isolated from human iPS (-like) cells (iPS-BJSlc-97E-1, 2, 4, 5, 6, 7, 8, 10, 11, 12, -97G-3,5, -97H-3, 5), NTERA2 clone DI human embryonic carcinoma cells (passage 35) and BJ fibroblasts expressing mouse Slc7a1 gene (passage 6). First-strand cDNA was synthesized by using oligo-dT20 primer and Rever Tra Ace-α-kit (Toyobo) according to manufacturer's protocol. PCR was performed with the primers as follows: hOct4 S1165 and hOct4-AS1283 for endogenous OCT4, hSox2-S1430 and hSox2-AS1555 for endogenous SOX2, ECAT4-macaca-968S and ECAT4-macaca-1334AS for NANOG, hRex1-RT-U and hRex1-RT-L for REX1, hFGF4-RT-U and hFGF4-RT-L for FGF4, hGDF3-S243 and hGDF3-AS850 for GDF3, hECAT15-S532 and hECAT15-AS916 for ECAT15-1, hECAT15-2-S85 and hECAT15-2-AS667 for ECAT15-2, hpH34-S40 and hpH34-AS259 for ESG1, hTERT-S3556 and hTERT-AS3713 for hTERT, and G3PDH-F and G3PDH-R for G3PDH.
Figure 29:
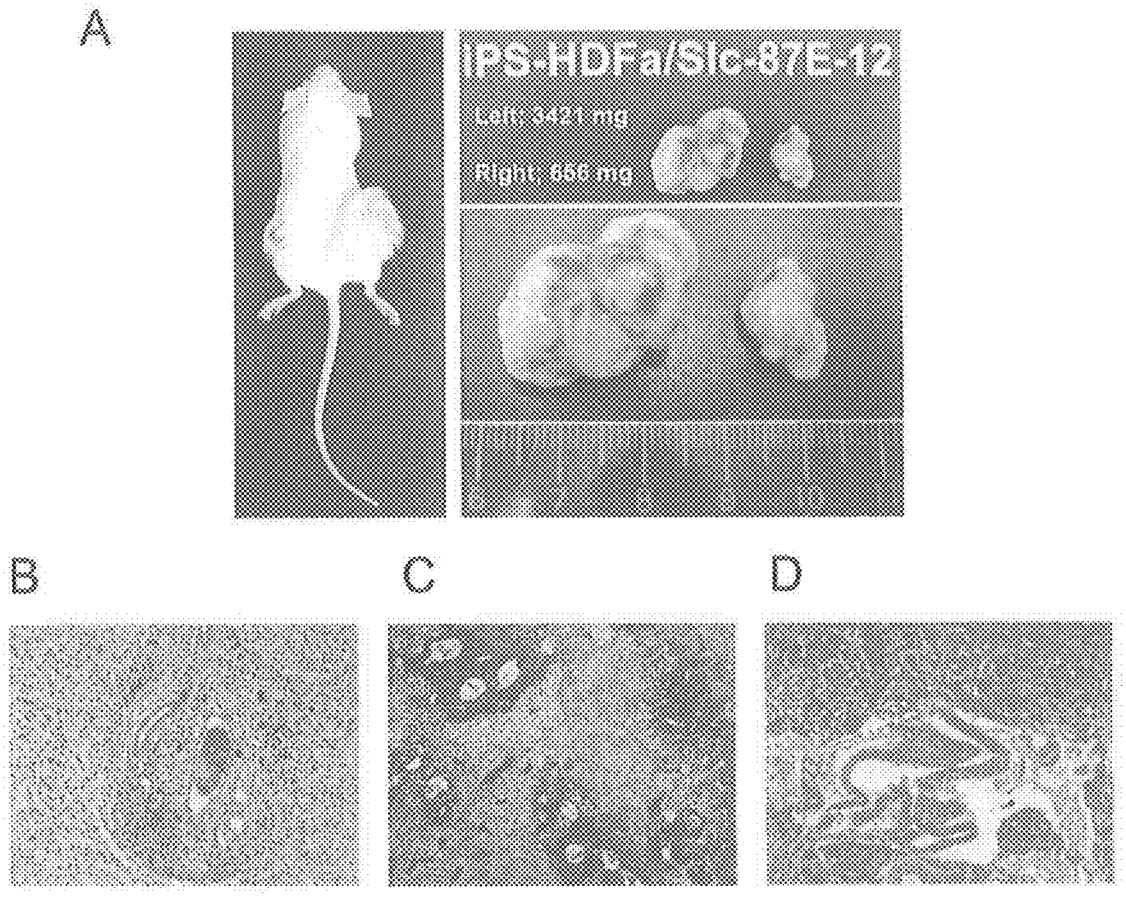
FIG. 29 shows teratoma formation. Five million of hiPS (-like) cells were subcutaneously injected into dorsal flanks of SCID mouse (female, 5 weeks old). Two months after injection, large tumors were observed. Tumors were dissected, weighed and photographed. Then these tumors were fixed with PBS containing 10% formalin. Paraffin-embedded tumor was sliced and then stained with hematoxylin and eosin. (A) Mouse from clone iPS-HDFa/Slc-87E-12. (B)-(D) indicate mouse teratomas from clones iPS-HDFa/Slc-97E-3 (B); iPS-HDFa/Slc-87E-6 (C); and iPS-HDFa/Slc-87E-12 (D).
Figure 30:
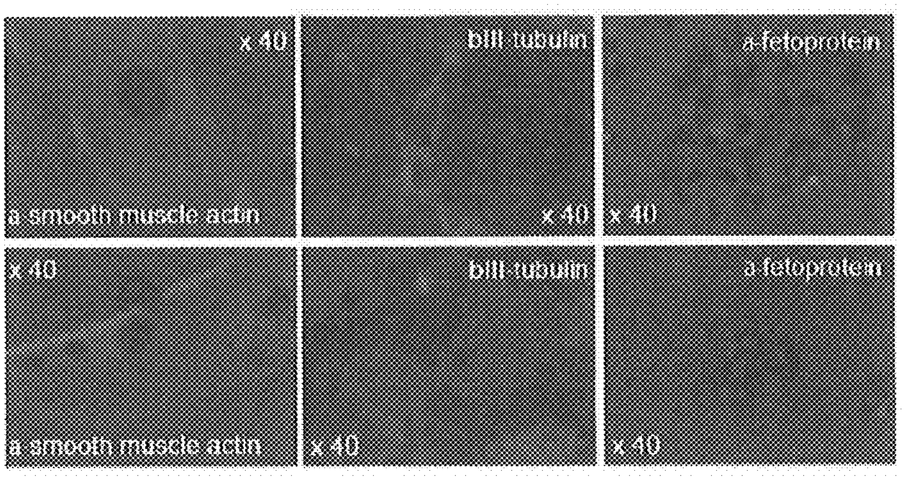
FIG. 30 shows in vitro differentiation of human iPS-like cells. The cells (iPS-HDFaSlc-127F2, E3) were suspended in hES medium (w/o bFGF). $2\times10^6$ cells were transferred to HEMA (2-hydroxyethyl methacrylate)-coated 100 mm tissue culture dish. The medium was changed every other day. After seven days floating culture, the cells were collected, plated to six gelatinized 35 mm dishes and incubated another 7 days. The cells were fixed with PBS containing 10% formalin for 10 min at room temperature, permeabilized with PBS containing 0.5% TritonX-100 for 5 min at room temperature, and blocked with PBS containing 3% BSA for 30 min at room temperature. Primary antibodies used in this experiment were as follows; anti-α-smooth muscle actin (Ms mono, pre-diluted, DAKO), anti-βIII-tubulin (Ms mono, 1:100 in blocking buffer, Chemicon), anti-α-fetoprotein (Rb poly, pre-diluted, DAKO), normal mouse IgG (2 mg/ml, Chemicon), and normal rabbit IgG (2 mg/ml, Chemicon). After incubation with primary antibody (1 hour at room temperature), the cells were washed with PBS, and incubated with secondary antibody (1:300 in blocking buffer).

Optimization of the methods heretofore described revealed successful induction of iPS cell colonies through staining of any number of pluripotent markers, including alkaline phosphatase, ABCG-2, E-cadherin, SSEA-3, and SSEA-4 when adult human dermal fibroblasts expressing mouse Slc7a1 gene were generated into iPS cells by reprogramming with the four factors plus TERT and SV40 Large T antigen (i.e. six factors total: c-Myc, Klf4, Sox2, Oct3/4, TERT, and SV40 Large T antigen) (FIG. 26(A)-(B)). These cells were assessed for pluripotent cell markers (FIG. 27). These cells were found to express ECATS, including Nanog and ESG1. Similarly, BJ fibroblasts expressing mouse Slc7a1 gene were generated into iPS cells by reprogramming with the following same factors. These cells were also tested for pluripotent cell markers (FIG. 28). In addition, iPS cells generated from adult HDFs were selected for subcutaneous injection into the dorsal flanks of SCID mice. Teratoma formation was observed (FIGS. 29(A)-(D)). Human dermal fibroblasts were also shown to differentiate in vitro upon culturing in HEMA-coated plates (7 days) and gelatinized dishes (7 days) (FIG. 30).

Figure 31:
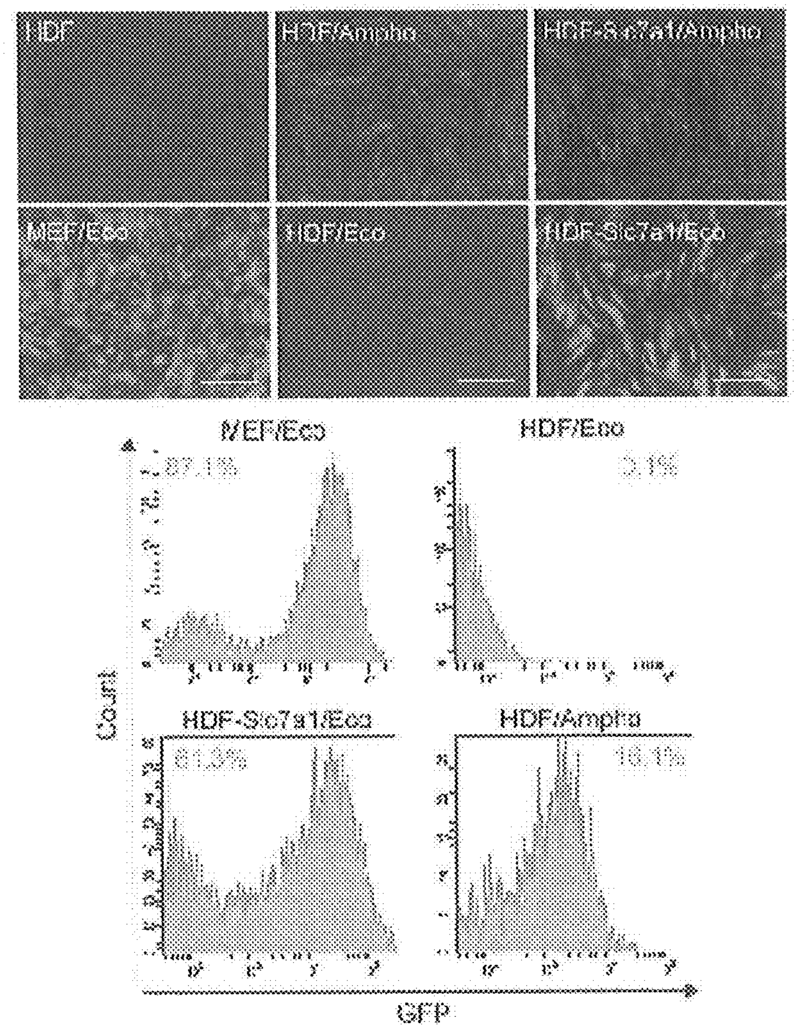
FIG. 31 shows improved transduction efficiency of retroviruses in human HDFs. HDFs or HDFs expressing mouse Slc7a1 gene (HDF-Slc7a1) were introduced with ecotropic (Eco) or amphotropic (Ampho) pMX retroviruses containing the GFP cDNA. Shown are results of fluorescent microscope (upper) and flow cytometry (lower). Bars=100 μm.

Example 14: Optimization of Retroviral Transduction for Generating Human iPS Cells Next, iPS cell generation from adult human somatic cells was further evaluated by optimizing retroviral transduction in human fibroblasts and subsequent culture conditions. Induction of iPS cells from mouse fibroblasts requires retroviruses with high transduction efficiencies (Takahashi et al. *Cell* 126:663-676, 2006). Therefore, transduction methods in adult human dermal fibroblasts (HDFs) were optimized. First, green fluorescent protein (GFP) was introduced into adult HDF with amphotropic retrovirus produced in PLAT-A packaging cells. As a control, GFP was introduced into mouse embryonic fibroblasts (MEF) with ecotropic retrovirus produced in PLAT-E packaging cells (Morita et al. *Gene Ther.* 7:1063-66, 2000). In MEF, more than 80% of cells expressed GFP (FIG. 31). In contrast, less than 20% of HDF expressed GFP with significantly lower intensity than in MEF. To improve the transduction efficiency, the mouse receptor for retroviruses, Slc7a1 (Verrey et al. *Pflugers Arch.* 447:532-542, 2004) (also known as mCAT1), was introduced into HDF with lentivirus. Then GFP was introduced into HDF-Slc7a1 with ecotropic retrovirus. This strategy yielded a transduction efficiency of 60%, with a similar intensity to that in MEF.

Example 15: Generation of iPS Cells from Adult HDFs in Primate ES Cell Culture Medium The protocol for human iPS cell induction is summarized in FIG. 32A. pMXs encoding human Oct3/4, Sox2, Klf4, and c-Myc were introduced into HDF-Slc7a1 cells (FIG. 32B; $8\times10^5$ cells per 100 mm dish). The HDFs were derived from facial dermis of 36-year-old Caucasian female.

Figure 32:
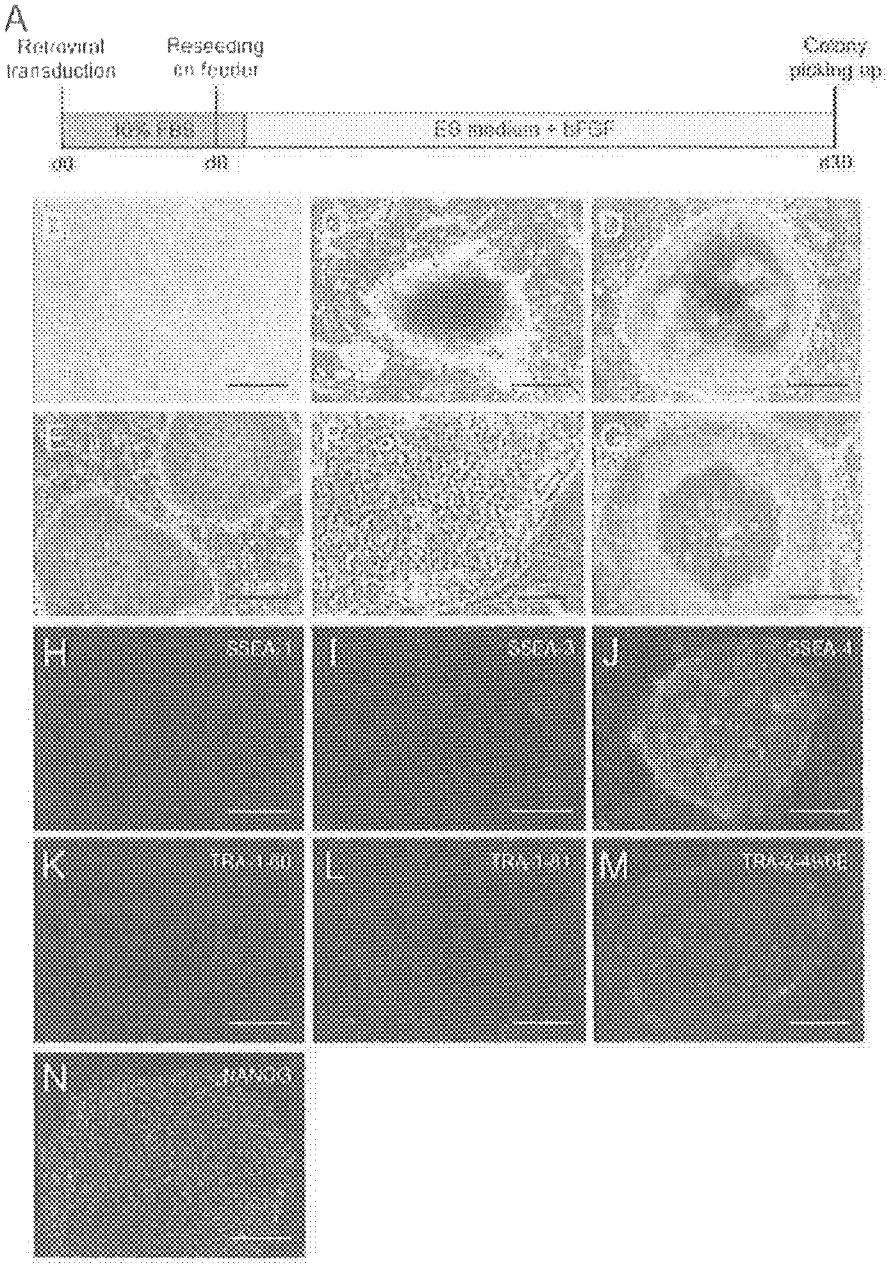
FIG. 32 shows induction of iPS cells from adult HDFs in primate ES cell media. (A) Time schedule of iPS cell generation. (B) Morphology of HDFs. (C) Typical image of non-ES cell-like colony. (D) Typical image of hES cell-like colony. (E) Morphology of established iPS cell line at passage number 6 (clone 201B7). (F) Image of iPS cells with high magnification. (G) Spontaneously differentiated cells in the center part of human iPS cell colonies. (H-N) Immunocytochemistry for SSEA-1 (H), SSEA-3 (I), SSEA-4 (J), TRA-1-60 (K), TRA-1-81 (L), TRA-2-4916E (M), and Nanog (N). Nuclei were stained with Hoechst 33342 (blue). Bars=200 μm (B-E, G), 20 μm (F), and 100 μm (H-N).

Six days after transduction, the cells were harvested by trypsinization and plated onto mitomycin C-treated SNL feeder cells (McMahon et al. *Cell* 62:1073-85, 1990) at $5\times10^4$ or $5\times10^5$ cells per 100 mm dish. The next day, the medium (DMEM containing 10% FBS) was replaced with a medium for primate ES cell culture supplemented with 4 ng/ml basic fibroblast growth factor (bFGF). Approximately two weeks later, some granulated colonies appeared that were not similar to hES cells in morphology (FIG. 32C). Around day 25, distinct types of colonies that were flat and resembled hES cell colonies were observed (FIG. 32D). From $5\times10^4$ fibroblasts, ~10 hES cell-like colonies and ~100 granulated colonies (7/122, 8/84, 8/171, 5/73, 6/122, and 11/213 in six independent experiments, summarized in TABLE 8) were observed.

TABLE 8

Summary of the iPS cell induction experiments

| Exp. ID | Parental cells | Cell No. seeded at d6 | No. of ES-like colony | No. of total colony | No. of picked up colony | No. of established clone |
|---|---|---|---|---|---|---|
| 201B | HDF | 50000 | 7 | 129 | 7 | 5 |
| 243H | HFLS | 500000 | 0 | >1000 | | |
| | | 50000 | 17 | 679 | 6 | 2 |
| 246B | HDF | 500000 | 0 | 420 | | |
| | | 500000 | 2 | 508 | | |
| | | 50000 | 8 | 92 | 6 | 6 |
| 246G | BJ | 50000 | 7 | 10 | 6 | 5 |
| | | 500000 | 86 | 98 | | |
| | | 500000 | 106 | 108 | | |
| 249D | HDF | 500000 | 0 | 320 | | |
| | | 500000 | 0 | 467 | | |
| | | 50000 | 8 | 179 | 6 | 4 |
| 253F | HDF | 50000 | 5 | 78 | 3 | 2 |
| | | 50000 | 6 | 128 | 3 | 3 |
| | | 500000 | 10 | 531 | | |
| | | 500000 | 3 | 738 | | |
| 282C | HDF | 50000 | 11 | 224 | 3 | 1 |
| 282H | BJ | 50000 | 13 | 15 | 3 | 2 |
| 282R | HFLS | 5000 | 31 | 98 | 6 | 2 |

At day 30, hES cell-like colonies were picked up and mechanically disaggregated into small clumps without enzymatic digestion. When starting with $5\times10^5$ fibroblasts, the dish was nearly covered with more than 300 granulated colonies. Occasionally some hES cell-like colonies in between the granulated cells were observed, but it was difficult to isolate hES cell-like colonies because of the high density of granulated cells.

The hES-like cells expanded on SNL feeder cells under the human ES cell culture condition. They formed tightly packed and flat colonies (FIG. 32E). Each cell exhibited morphology similar to that of human ES cells, characterized by large nucleoli and scant cytoplasm (FIG. 32F). As is the case with hES cells, occasionally spontaneous differentiation was observed in the center of the colony (FIG. 32G).

Figure 33:
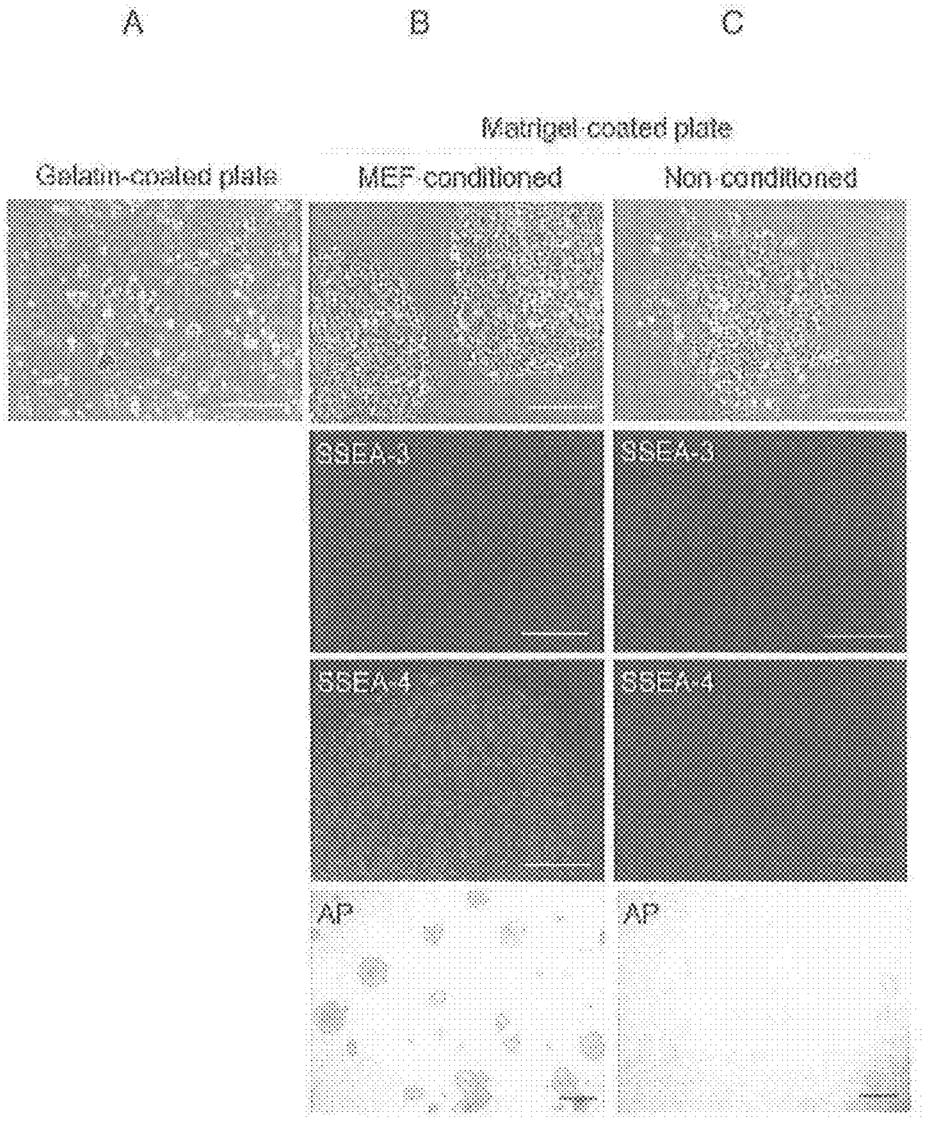
FIG. 33 shows feeder dependency of human iPS cells. (A) Image of iPS cells plated on gelatin-coated plate. (B) Images of iPS cells cultured on Matrigel-coated plates in MEF-conditioned medium (MEF-CCM). (C) Images of iPS cells cultured in ES medium on Matrigel-coated plates with non-conditioned hES medium.

These cells also showed similarity to hES cells in feeder dependency. They did not attach to gelatin-coated tissue-culture plates. By contrast, they maintained an undifferentiated state on Matrigel-coated plates in MEF-conditioned medium (MEF-CM), but not in ES medium (FIG. 33).

Since these cells were indistinguishable from hES cells in morphology and other aspects noted above, the selected cells after transduction of HDFs are referred to as human iPS cells. The molecular and functional evidence for this claim is further described below. Human iPS cells clones established in this study are summarized in TABLE 9.

TABLE 9

Characterization of established clones

| Clone | Source | Marker expression: RT-PCR | Marker expression: IC | Pluripotency: EB | Pluripotency: PA6 | Pluripotency: Cardio-myocyte | Pluripotency: Teratoma |
|---|---|---|---|---|---|---|---|
| 201B1 | HDF | √ | | | | | |
| 201B2 | | √ | √ | √ | √ | √ | |
| 201B3 | | √ | | | | | |
| 201B6 | | √ | √ | √ | √ | √ | |
| 201B7 | | √ | √ | √ | √ | √ | √ |
| 243H1 | HFLS | √ | | √ | | | |
| 243H7 | | √ | | √ | | | |
| 246B1 | HDF | √ | | | | | |
| 246B2 | | √ | | | | | |
| 246B3 | | √ | | | | | |
| 246B4 | | √ | | | | | |
| 246B5 | | √ | | | | | |
| 246B6 | | √ | | | | | |
| 246G1 | BJ | √ | | √ | | | |
| 246G3 | | √ | | √ | | | |
| 246G4 | | √ | | | | | |
| 246G5 | | √ | | | | | |
| 246G6 | | √ | | | | | |
| 253F1 | HDF | √ | | | | | |
| 253F2 | | √ | | | | | |
| 253F3 | | √ | | | | | |
| 253F4 | | √ | | | | | |
| 253F5 | | √ | | | | | |

IC; immunocytochemistry,
EB; embryoid body

Human IPS Cells Express LES Markers

In general, except for a few cells at the edge of the colonies, human iPS cells did not express stage-specific embryonic antigen (SSEA)-1 (FIG. 32H). In contrast, they expressed hES cell-specific surface antigens (Adewumi et al. *Nat. Biotechnol.* 25:803-816, 2007), including SSEA-3, SSEA-4, tumor-related antigen (TRA)-1-60, TRA-1-81, and TRA-2-49/6E (alkaline phosphatase), and NANOG protein (FIG. 32I-N).

Figure 34:
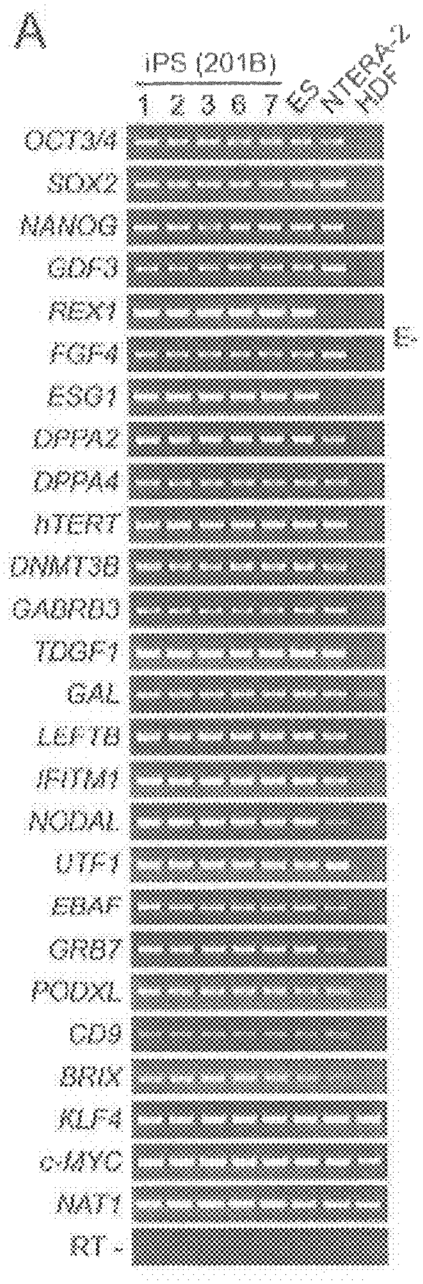
FIG. 34 shows expression of hES cell marker genes in human iPS cells. (A) RT-PCR analysis of ES cell marker genes. (B) Western blot analysis of ES cell marker genes. (C) Quantitative PCR for expression of retroviral transgenes. The graph shows the average of three assays. Bars indicate standard deviation. (D) Bisulfite genomic sequencing of the promoter regions of OCT3/4, REXJ and NANOG. Open and closed circles indicate unmethylated and methylated CpGs. (E) Luciferase assays. The graphs show the average of the results from four assays. Bars indicate standard deviation.
Figure 34:
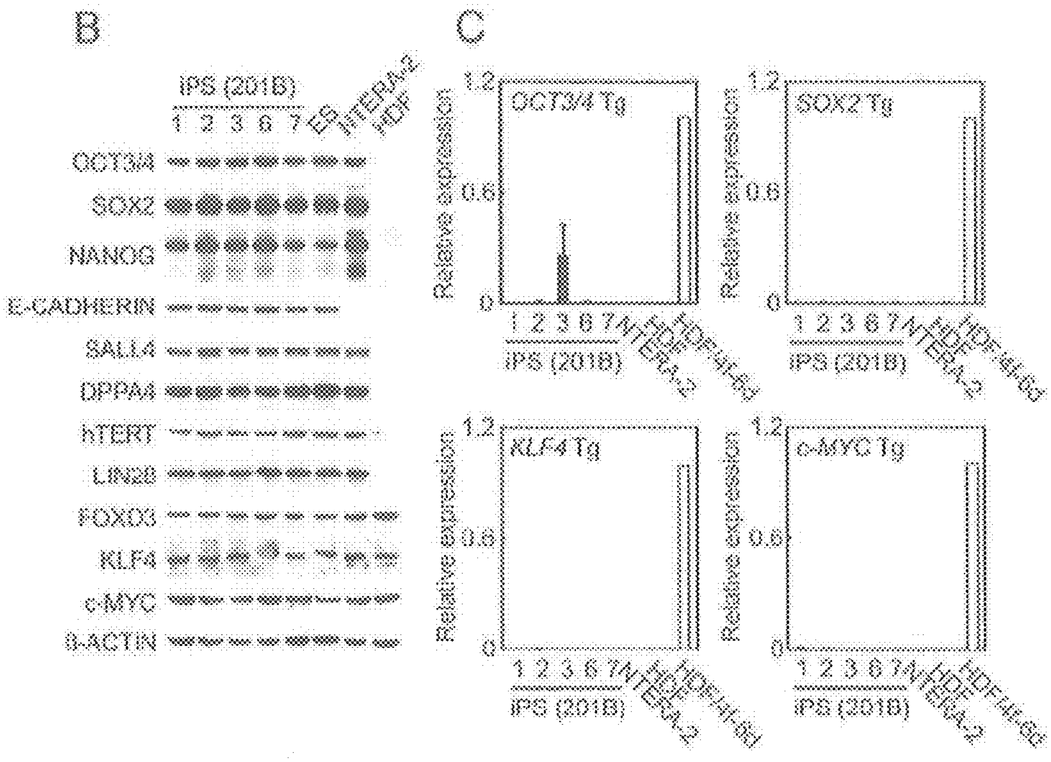
Figure 34:
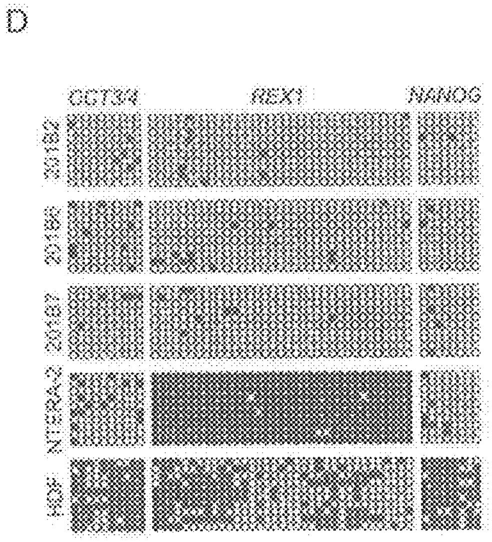
Figure 34:
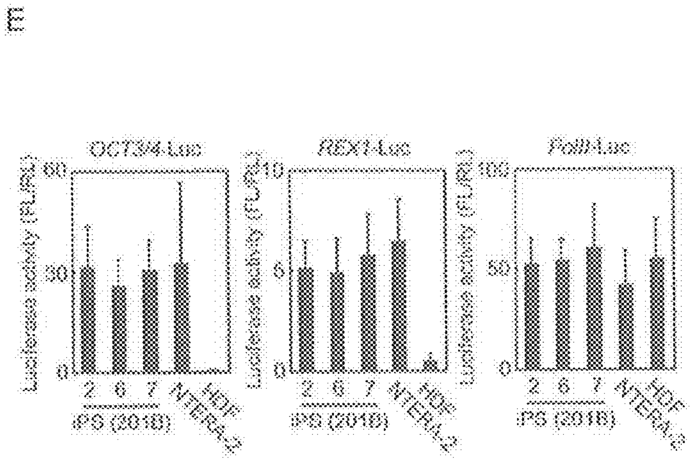

RT-PCR showed human iPS cells expressed many undifferentiated ES cell gene markers (Adewumi et al. *Nat. Biotechnol.* 25:803-816, 2007), such as OCT3/4, SOX2, NANOG, growth and differentiation factor 3 (GDF3), reduced expression 1 (REX1), fibroblast growth factor 4 (FGF4), embryonic cell-specific gene 1 (ESG1), developmental pluripotency-associated 2 (DPPA2), DPPA4, and telomerase reverse transcriptase (hTERT) at levels equivalent to or higher than those in the human embryonic carcinoma cell line, NTERA-2 (FIG. 34A). By western blotting, proteins levels of OCT3/4, SOX2, NANOG, SALL4, E-CADHERIN, and hTERT were similar in human iPS cells and hES cells (FIG. 34B). In human iPS cells, the expression of transgenes from integrated retroviruses was efficiently silenced, indicating that they depend on the endogenous expression of these genes (FIG. 34C).

Promoters of ES Cell-Specific Genes are Active in Human iPS Cells

Bisulfite genomic sequencing analyses evaluating the methylation statuses of cytosine guanine dinucleotides (CpG) in the promoter regions of pluripotent-associated genes, such as OCT3/4, REX1, and NANOG, revealed that they were highly unmethylated, whereas the CpG dinucleotides of the regions were highly methylated in parental HDFs (FIG. 34D). These findings indicate that these promoters are active in human iPS cells.

Luciferase reporter assays also showed that human OCT3/4 and REX1 promoters had high levels of transcriptional activity in human iPS cells, but not in HDF. The promoter activities of ubiquitously expressed genes, such as human RNA polymerase II (PolII), showed similar activities in both human iPS cells and HDF (FIG. 34E).

High Telomerase Activity and Exponential Growth of Human iPS Cells

Figure 35:
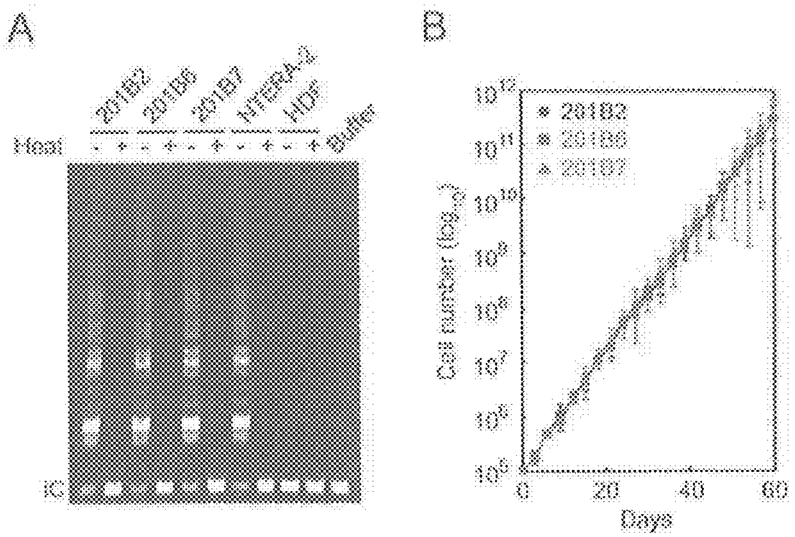
FIG. 35 shows high levels of telomerase activity and exponential proliferation of human iPS cells. (A) Detection of telomerase activities by the TRAP method. Heat-inactivated (+) samples were used as negative controls. IC=internal control. (B) Growth curve of iPS cells. Shown are averages and standard deviations in quadruplicate.

As predicted from the high expression levels of hTERT, human iPS cells showed high telomerase activity (FIG. 35A). They proliferated exponentially for at least 4 months (FIG. 35B). The calculated doubling time of human iPS cells were 46.9±12.4 (clone 201B2), 47.8±6.6 (201B6) and 43.2±11.5 (201B7) hours (FIG. 35B). These times are equivalent to the reported doubling time of hES cells (Cowan et al. *N. Engl. J. Med.* 350:1353-56, 2004).

Human iPS Cells Are Derived from HDF, not Cross-Contamination

Figure 36:
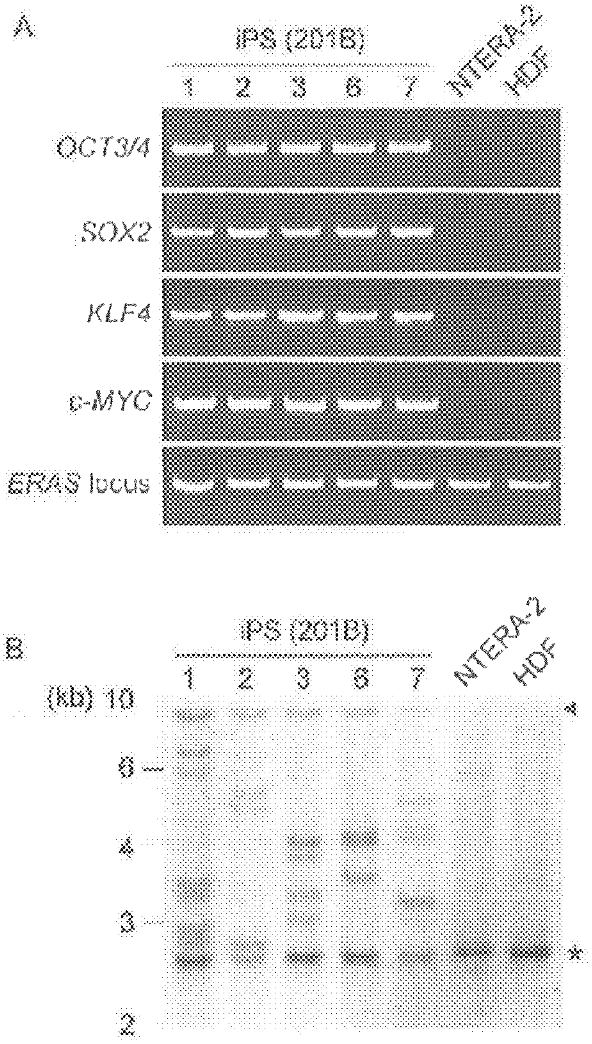
FIG. 36 shows genetic analyses of human iPS cells. (A) Genomic PCR revealed integration of all the four retroviruses in all clones. (B) Southern blot analyses with a c-MYC cDNA probe. Asterisk indicates the endogenous c-MYC alleles (2.7 kb). Arrowhead indicates mouse c-Myc alleles derived from SNL feeder cells (9.8 kb).

PCR of genomic DNA of human iPS cells showed that all clones have integration of all the four retroviruses (FIG. 36A). Southern blot analysis with a c-Myc cDNA probe revealed that each clone had a unique pattern of retroviral integration sites (FIG. 36B). In addition, the patterns of 16 short tandem repeats were completely matched between human iPS clones and parental HDF (TABLE 10).

TABLE 10

STR analyses of HDF-derived iPS cells

| Locus/ Clone | 201B1 | | 201B2 | | 201B3 | | 201B6 | | 201B7 | | NTERA-2 | | HDF | |
|---|---|---|---|---|---|---|---|---|---|---|---|---|---|---|
| D3S1358 | 15 | 17 | 15 | 17 | 15 | 17 | 15 | 17 | 15 | 17 | 15 | | 15 | 17 |
| TH01 | 5 | | 5 | | 5 | | 5 | | 5 | | 9 | | 5 | |
| D21S11 | 28 | | 28 | | 28 | | 28 | | 28 | | 29 | 30 | 28 | |
| D18S51 | 14 | | 14 | | 14 | | 14 | | 14 | | 13 | | 14 | |
| Penta_E | 7 | 19 | 7 | 19 | 7 | 19 | 7 | 19 | 7 | 19 | 5 | 14 | 7 | 19 |
| D5S818 | 11 | | 11 | | 11 | | 11 | | 11 | | 8 | 11 | 11 | |
| D13S317 | 10 | 14 | 10 | 14 | 10 | 14 | 10 | 14 | 10 | 14 | 14 | | 10 | 14 |
| D7S820 | 9 | 10 | 9 | 10 | 9 | 10 | 9 | 10 | 9 | 10 | 12 | | 9 | 10 |
| D16S539 | 11 | 13 | 11 | 13 | 11 | 13 | 11 | 13 | 11 | 13 | 11 | 16 | 11 | 13 |
| CSF1PO | 10 | | 10 | | 10 | | 10 | | 10 | | 9 | 11 | 10 | |
| Penta_D | 8 | 10 | 8 | 10 | 8 | 10 | 8 | 10 | 8 | 10 | 11 | 12 | 8 | 10 |
| AMEL | X | | X | | X | | X | | X | | X | Y | X | |
| vWA | 15 | 18 | 15 | 18 | 15 | 18 | 15 | 18 | 15 | 18 | 19 | | 15 | 18 |
| D8S1179 | 8 | 10 | 8 | 10 | 8 | 10 | 8 | 10 | 8 | 10 | 13 | 15 | 8 | 10 |
| TPOX | 8 | 9 | 8 | 9 | 8 | 9 | 8 | 9 | 8 | 9 | 8 | 9 | 8 | 9 |
| FGA | 20 | 22 | 20 | 22 | 20 | 22 | 20 | 22 | 20 | 22 | 23 | | 20 | 22 |

These patterns differed from any established hES cell lines reported on National Institutes of Health website (http://stemcells.nih.gov/research/nihresearch/scunit/genotyping.htm). In addition, chromosomal G-band analyses showed that human iPS cells had a normal karyotype of 46XX (not shown). Thus, human iPS clones were derived from HDF and were not a result of cross-contamination.

Example 16: Embryoid Body-Mediated Differentiation of Human iPS Cells

Figure 37:
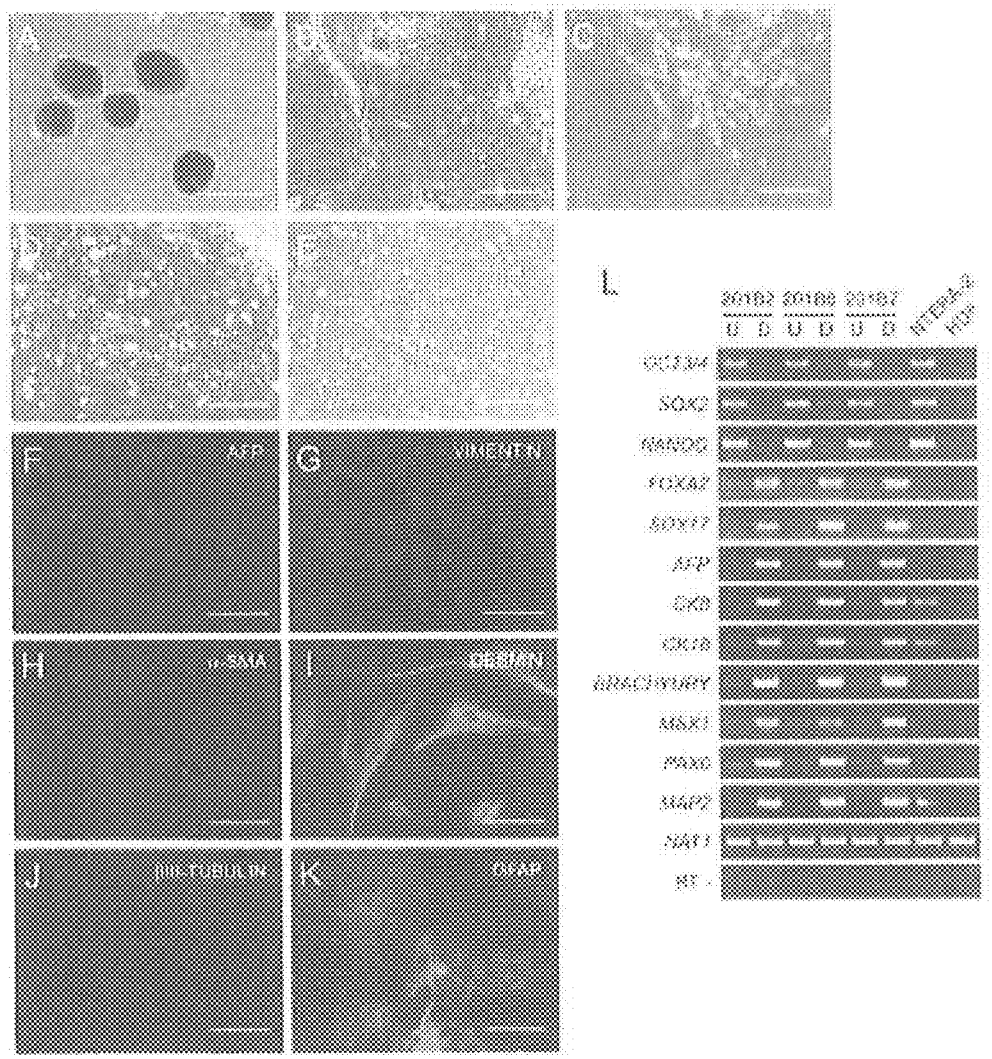
FIG. 37 shows embryoid body-mediated differentiation of human iPS cells. (A) Floating culture of iPS cells at day 8. (B-E) Images of differentiated cells at day 16 (B), neuron-like cells (C), epithelial cells (D), and cobblestone-like cells (E). (F-K) Immunocytochemistry of alpha-fetoprotein (F), vimentin (G), α-smooth muscle actin (H), desmin (I), βIII-tubulin (J), and GFAP (K). Bars=200 μm (A, B) and 100 μm (C-K). Nuclei were stained with Hoechst 33342 (blue). (L) RT-PCR analyses of various differentiation markers for the three germ layers.

To determine the differentiation ability of human iPS cells in vitro, floating cultivation was used to form embryoid bodies (EBs) (Itskovitz-Eldor et al. *Mol. Med.* 6:88-95, 2000). After 8 days in suspension culture, iPS cells formed ball-shaped structures (FIG. 37A). These embryoid body-like structures were transferred to gelatin-coated plates and continued cultivation for another 8 days. Attached cells showed various types of morphologies, such as those resembling neuronal cells, cobblestone-like cells, and epithelial cells (FIG. 37B-E). Immunocytochemistry detected cells positive for βIII-tubulin (a marker of ectoderm), glial fibrillary acidic protein (GFAP, ectoderm), α-smooth muscle actin (α-SMA, mesoderm), desmin (mesoderm), α-fetoprotein (AFP, endoderm), and vimentin (mesoderm and parietal endoderm) (FIG. 37F-K). RT-PCR-confirmed that these differentiated cells expressed forkhead box A2 (FOXA2, a marker of endoderm), AFP (endoderm), cytokeratin 8 and 18 (endoderm), SRY-box containing gene 17 (SOX17, endoderm), BRACHYURY (mesoderm), Msh homeobox 1 (MSX1, mesoderm), microtubule-associated protein 2 (MAP2, ectoderm), and paired box 6 (PAX6, ectoderm) (FIG. 37L). In contrast, expression of OCT3/4, SOX2, and NANOG was significantly decreased. These data demonstrated that iPS cells could differentiate into three germ layers in vitro.

Example 17: Directed Differentiation of Human iPS Cells into Neural Cells

Figure 38:
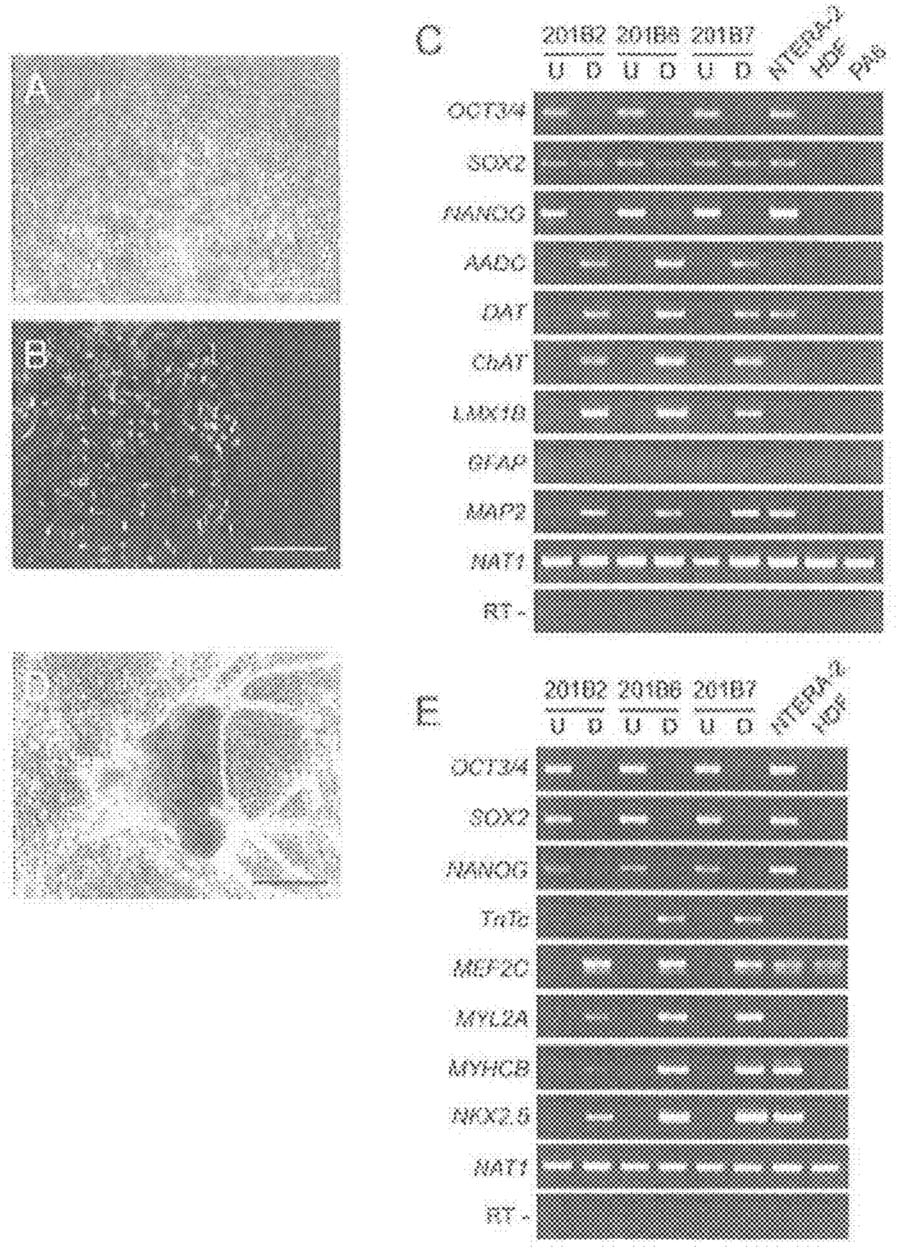
FIG. 38 shows directed differentiations of human iPS cells. (A) Phase contrast image of differentiated iPS cells after 18 days cultivation on PA6. (B) Immunocytochemistry of the cells shown in A with βIII-tubulin (red) and tyrosine hydroxylase (green) antibodies. Nuclei were stained with Hoechst 33342 (blue). (C) RT-PCR analyses of dopaminergic neuron markers. (D) Phase contrast image of iPS cells differentiated into cardiomyocytes. (E) RT-PCR analyses of cardiomyocyte markers. Bars=200 μm (A, D) and 100 μm (B).

Next, it was examined whether lineage-directed differentiation of human iPS cells could be induced by reported methods for hES cells. Human iPS cells were seeded on PA6 feeder layer and maintained under differentiation conditions for 2 weeks (Kawasaki et al. *Neuron* 28:31-40, 2000). Cells spread drastically, and some neuronal structures were observed (FIG. 38A). Immunocytochemistry detected cells positive for tyrosine hydroxylase and BIII tubulin in the culture (FIG. 38B). PCR analysis revealed expression of dopaminergic neuron markers, such as aromatic-L-amino acid decarboxylase (AADC), choline acetyltransferase (ChAT), solute carrier family 6 (neurotransmitter transporter, dopamine), member 3 (DAT), and LIM homeobox transcription factor 1 beta (LMX1B), as well as another neuron marker, MAP2 (FIG. 38C). In contrast, GFAP expression was not induced with this system. On the other hand, expression of OCT3/4, SOX2, and NANOG decreased (FIG. 38C). These data demonstrated that iPS cells could differentiate into neuronal cells, including dopaminergic neurons, by co-culture with PA6 cells.

Example 18: Directed Differentiation of Human iPS Cells into Cardiac Cells

Next directed cardiac differentiation of human iPS cells was examined with the recently reported protocol, which utilizes activin A and bone morphogenetic protein (BMP) 4

(Laflamme et al. *Nat. Biotechnol.* 25:1015-24, 2007). Twelve days after the induction of differentiation, clumps of cells started beating (FIG. 38D). RT-PCR showed that these cells expressed cardiomyocyte markers, such as troponin T type 2 cardiac (TnTc); myocyte enhancer factor 2C (MEF2C); NK2 transcription factor related, locus 5 (NKX2.5) myosin, light polypeptide 7, regulatory (MYL2A), and myosin, heavy polypeptide 7, cardiac muscle, beta (MYHCB) (FIG. 38E). In contrast, the expression of Oct3/4, Sox2, and Nanog markedly decreased. Thus, human iPS cells can differentiate into cardiac myocytes in vitro.

Example 19: Teratoma Formation from Human iPS Cells

Figure 39:
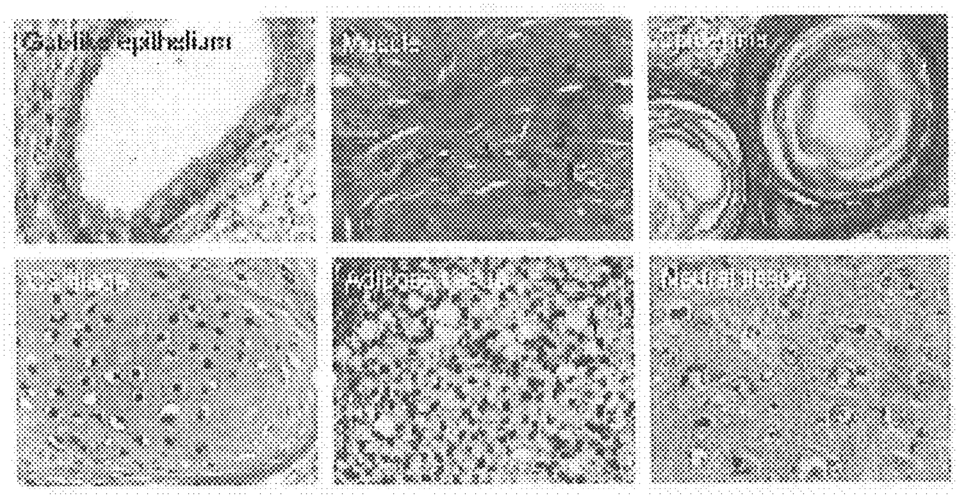
FIG. 39 shows hematoxylin and eosin staining of teratoma derived from human iPS cells (clone 201B7).

To test pluripotency in vivo, human iPS cells (clone 201B7) were transplanted subcutaneously into dorsal flanks of immunodeficient (SCID) mice. Nine weeks after injection, tumor formation was observed. Histological examination showed that the tumor contained various tissues (FIG. 39), including gut-like epithelial tissues (endoderm), striated muscle (mesoderm), cartilage (muscle), neural tissues (ectoderm), and keratin-containing squamous tissues (ectoderm).

Example 20: Generation of iPS Cells from Other Human Somatic Cells

Figure 40:
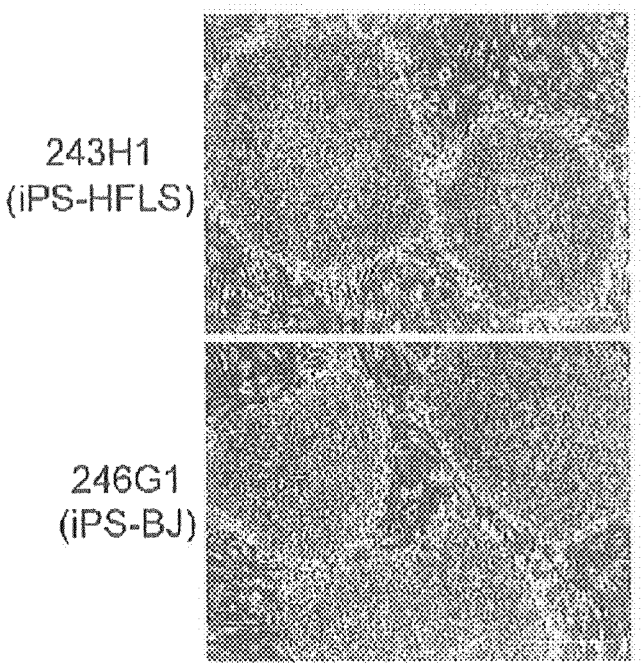
FIG. 40 shows human iPS cells (phase contrast images) derived from fibroblast-like synoviocytes (HFLS, clone 243H1) and BJ fibroblasts (clone 246G1). Bars=200 μm.
Figure 41:
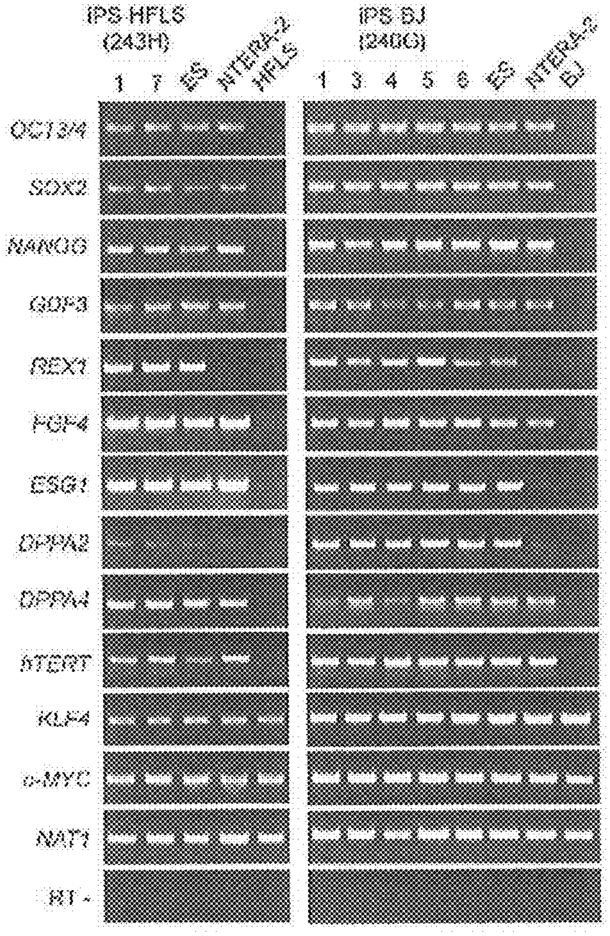
FIG. 41 shows expression of ES cell marker genes in iPS cells derived from HFLS and BJ fibroblasts.
Figure 42:
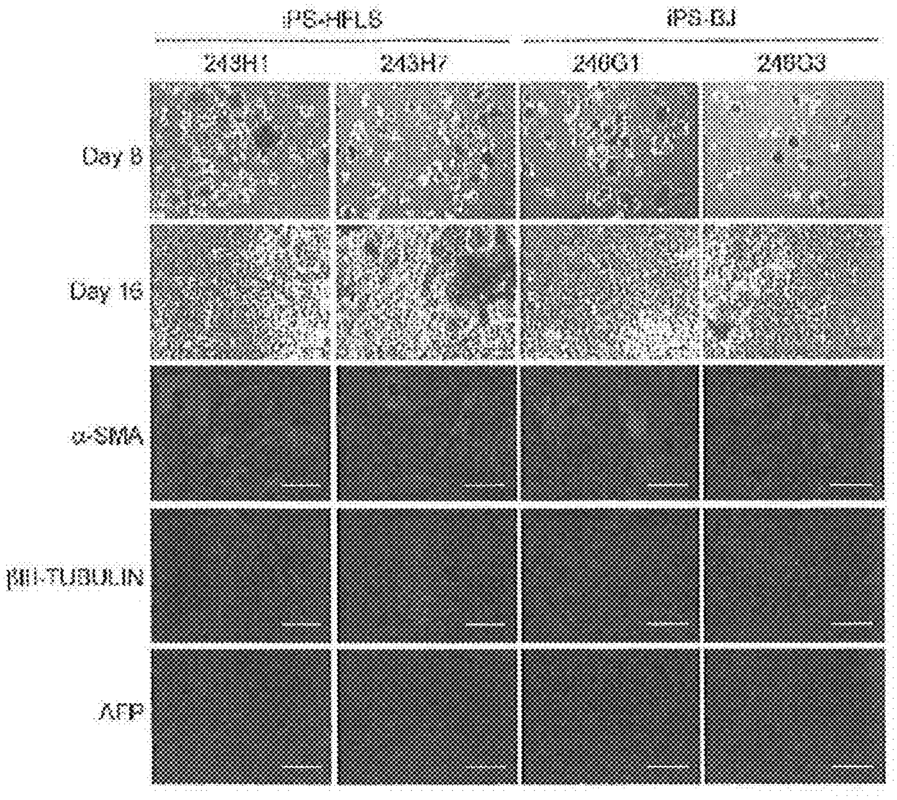
FIG. 42 shows embryoid body-mediated differentiation of iPS cells derived from HFLS and BJ fibroblasts.

In addition to HDF, primary human fibroblast-like synoviocytes (HFLS) from synovial tissue of 69-year-old Caucasian male and BJ cells, a cell line established from neonate fibroblasts, were used (TABLE 8). From $5\times10^4$ HFLS cells per 100 mm dish, more than 600 hundred granulated colonies and 17 hES cell-like colonies were obtained. Six colonies were picked, of which only two were expandable as iPS cells (FIG. 40). Dishes seeded with $5\times10^5$ HFLS were covered with granulated cells, and no hES cell-like colonies were distinguishable. In contrast, 7 to 8 and ~100 hES cell-like colonies were obtained from $5\times10^4$ and $5\times10^5$ BJ cells, respectively, with only a few granulated colonies (TABLE 8). Six hES cell-like colonies were picked and iPS cells were generated from five colonies (FIG. 40). Human iPS cells derived from HFLS and BJ expressed hES cell-marker genes at levels similar to or higher than those in hES cells (FIG. 41). They differentiated into all three germ layers through EBs (FIG. 42). STR analyses confirmed that iPS-HFLS cells and iPS-BJ cells were derived from HFLS and BJ fibroblasts, respectively (TABLE 11 and TABLE 12).

TABLE 11

STR analyses of HFLS-derived iPS cells

| Locus/Clone | 243H1 | | 243H7 | | HFLS | |
|---|---|---|---|---|---|---|
| D3S1358 | 16 | 17 | 16 | 17 | 16 | 17 |
| TH01 | 5 | 9 | 5 | 9 | 5 | 9 |
| D21S11 | 28 | 30 | 28 | 30 | 28 | 30 |
| D18S51 | 14 | 17 | 14 | 17 | 14 | 17 |
| Penta_E | 5 | 12 | 5 | 12 | 5 | 12 |
| D5S818 | 10 | 12 | 10 | 12 | 10 | 12 |
| D13S317 | 13 | | 13 | | 13 | |
| D7S820 | 9 | 12 | 9 | 12 | 8 | 12 |
| D16S539 | 11 | 13 | 11 | 13 | 11 | 13 |
| CSF1PO | 10 | 11 | 10 | 11 | 10 | 11 |
| Penta_D | 9 | 11 | 9 | 11 | 9 | 11 |
| AMEL | X | | X | Y | X | Y |
| vWA | 17 | 19 | 17 | 19 | 17 | 19 |
| D8S1179 | 13 | | 13 | | 13 | |
| TPOX | 8 | 11 | 8 | 11 | 8 | 11 |
| FGA | 21 | 22 | 21 | 22 | 21 | 22 |

TABLE 12

STR analyses of BJ-derived iPS cells

| Locus/Clone | 246G1 | | 246G3 | | 246G4 | | 246G5 | | 246G6 | | BJ | |
|---|---|---|---|---|---|---|---|---|---|---|---|---|
| D3S1358 | 13 | 15 | 13 | 15 | 13 | 15 | 13 | 15 | 13 | 15 | 13 | 15 |
| TH01 | 6 | 7 | 6 | 7 | 6 | 7 | 6 | 7 | 6 | 7 | 6 | 7 |
| D21S11 | 28 | | 28 | | 28 | | 28 | | 28 | | 28 | |
| D18S51 | 16 | 18 | 16 | 18 | 16 | 18 | 16 | 18 | 16 | 18 | 16 | 18 |
| Penta_E | 7 | 17 | 7 | 17 | 7 | 17 | 7 | 17 | 7 | 17 | 7 | 17 |
| D5S818 | 11 | | 11 | | 11 | | 11 | | 11 | | 11 | |
| D13S317 | 9 | 10 | 9 | 10 | 9 | 10 | 9 | 10 | 9 | 10 | 9 | 10 |
| D7S820 | 11 | 12 | 11 | 12 | 11 | 12 | 11 | 12 | 11 | 12 | 11 | 12 |
| D16S539 | 9 | 13 | 9 | 13 | 9 | 13 | 9 | 13 | 9 | 13 | 9 | 13 |
| CSF1PO | 9 | 11 | 9 | 11 | 9 | 11 | 9 | 11 | 9 | 11 | 9 | 11 |
| Penta_D | 11 | 12 | 11 | 12 | 11 | 12 | 11 | 12 | 11 | 12 | 11 | 12 |
| AMEL | X | Y | X | Y | X | Y | X | Y | X | Y | X | Y |
| vWA | 16 | 18 | 16 | 18 | 16 | 18 | 16 | 18 | 16 | 18 | 16 | 18 |
| D8S1179 | 9 | 11 | 9 | 11 | 9 | 11 | 9 | 11 | 9 | 11 | 9 | 11 |
| TPOX | 10 | 11 | 10 | 11 | 10 | 11 | 10 | 11 | 10 | 11 | 10 | 11 |
| FGA | 22 | 23 | 22 | 23 | 22 | 23 | 22 | 23 | 22 | 23 | 22 | 23 |

Thus, with Examples 13-20 it was shown that iPS cells can be generated from adult HDF and other somatic cells by retroviral transduction of the same four transcription factors, namely Oct3/4, Sox2, Klf4, and c-Myc. The established human iPS cells are indistinguishable from hES cells in many aspects, including morphology, proliferation, feeder dependence, surface markers, gene expression, promoter activities, telomerase activities, in vitro differentiation, and teratoma formation. The four retroviruses are nearly completely silenced in human iPS cells, indicating that these cells are fully reprogrammed and do not depend on continuous expression of the transgenes for self-renewal.

hES cells are different from mouse counterparts in many respects (Rao, M., *Dev. Biol.* 275:269-286, 2004). hES cell colonies are flatter and do not override each other. hES cells depend on bFGF for self renewal (Amit et al. *Dev. Biol.* 227:271-78, 2000), whereas mouse ES cells depend on the LIF/Stat3 pathway (Matsuda et al. *EMBO J.* 18:4261-69, 1999; Niwa et al. *Genes Dev.* 12:2048-60, 1998). BMP induces differentiation in hES cells (Xu et al. *Nat. Methods* 2:185-90, 2005) but is involved in self renewal of mouse ES cells (Ying et al. *Cell* 115:281-92, 2003). Because of these differences, it has been speculated that factors required for reprogramming might differ between humans and mice. On the contrary, our data show that the same four transcription factors induce iPS cells in both humans and mouse. The four factors, however, could not induce human iPS cell colonies when fibroblasts were kept under the culture condition for mouse ES cells after retroviral transduction (See Example 13, above), even though these cells stained positive for alkaline phosphatase. These data suggest that the fundamental transcriptional network governing pluripotency is common in human and mice, but extrinsic factors and signals maintaining pluripotency are unique for each species.

Deciphering of the mechanism by which the four factors induce pluripotency in somatic cells remains elusive. The function of Oct3/4 and Sox2 as core transcription factors to determine pluripotency is well documented (Boyer et al. *Cell* 122:947-956, 2005; Loh et al. *Nat Genet* 38:431-440, 2006; Wang et al. *Nature* 444:364-368, 2006). They synergistically upregulate "stemness" genes, while suppressing differentiation-associated genes in both mouse and human ES cells. However, they cannot bind their targets genes in differentiated cells, because of other inhibitory mechanisms, including DNA methylation. It may be speculated that c-Myc and Klf4 modifies chromatin structure so that Oct3/4 and Sox2 can bind to their targets (Yamanaka, *Cell Stem Cell* 1:39-49, 2007). Notably, Klf4 interacts with p300 histone acetyltransferase and regulates gene transcription by modulating histone acetylation (Evans et al. *J Biol Chem,* 2007).

The negative role of c-Myc in the self renewal of hES cells has also been reported (Sumi et al. *Oncogene* 26:5564-5576, 2007). They showed that forced expression of c-Myc induced differentiation and apoptosis of human ES cells. During iPS cell generation, transgenes derived from retroviruses are silenced when the transduced fibroblasts acquire ES-like state. The role of c-Myc in establishing iPS cells may be as a booster of reprogramming, rather than a controller of maintenance of pluripotency.

It has been found that each iPS clone contained 3-6 retroviral integrations for each factor. Thus, each clone had more than 20 retroviral integration sites in total, which may increase the risk of tumorigenesis. In the case of mouse iPS cells, ~20% of chimera mice and their offspring derived from iPS cells developed tumors Okita et al. *Nature* 448: 313-17, 2007). This issue must be overcome to use iPS cells in human therapies. Therefore, non-retroviral methods to introduce the four factors, such as adenoviruses or cell-permeable recombinant proteins, are also contemplated as part of the invention. Alternatively, small molecules may replace the four factors for the induction of iPS cells.

Experimental Procedures for Examples 14-20.

Cell Culture

HDFs from facial dermis of 36-year-old Caucasian female and HFLS from synovial tissue of 69-year-old Caucasian male were purchased from Cell Applications, Inc. BJ fibroblasts from neonatal foreskin and NTERA-2 clone DI human embryonic carcinoma cells were obtained from American Type Culture Collection. Human fibroblasts, NTERA-2, PLAT-E, and PLAT-A cells were maintained in Dulbecco's modified eagle medium (DMEM, Nacalai Tesque, Japan) containing 10% fetal bovine serum (FBS, Japan Serum) and 0.5% penicillin and streptomycin (Invitrogen). 293 FT cells were maintained in DMEM containing 10% FBS, 2 mM L-glutamine (Invitrogen), $1\times10^{-4}$ M non-essential amino acids (Invitrogen), 1 mM sodium pyruvate (Sigma) and 0.5% penicillin and streptomycin. PA6 stroma cells (RIKEN Bioresource Center, Japan) were maintained in α-MEM containing 10% FBS and 0.5% penicillin and streptomycin. iPS cells were generated and maintained in Primate ES medium (ReproCELL, Japan) supplemented with 4 ng/ml recombinant human basic fibroblast growth factor (bFGF, WAKO, Japan). For passaging, human iPS cells were washed once with PBS and then incubated with DMEM/F12 containing 1 mg/ml collagenase IV (Invitrogen) at 37° C. When colonies at the edge of the dish started dissociating from the bottom, DMEF/F12/collangenase was removed and washed with hES cell medium. Cells were scraped and collected into 15 ml conical tube. An appropriate volume of the medium was added, and the contents were transferred to a new dish on SNL feeder cells. The split ratio was routinely 1:3. For feeder-free culture of iPS cells, the plate was coated with 0.3 mg/ml Matrigel (growth-factor reduced, BD Biosciences) at 4° C. overnight. The plate was warmed to room temperature before use. Unbound Matrigel was aspirated off and washed out with DMEM/F12. iPS cells were seeded on Matrigel-coated plate in MEF-CM or ES medium, both supplemented with 4 ng/ml bFGF. The medium was changed daily. For preparation of MEF-CM, MEFs derived from embryonic day 13.5 embryo pool of ICR mice were plated at $1\times10^{6}$ cells per 100 mm dish and incubated overnight. Next day, the cells were washed once with PBS and cultured in 10 ml of ES medium. Twenty-four h after incubation, the supernatant of MEF culture was collected, filtered through a 0.22 μm pore-size filter, and stored at −20° C. until use.

Plasmid Construction

The open reading frame of human OCT3/4 was amplified by RT-PCR and cloned into pCR2.1-TOPO. An EcoRI fragment of pCR2.1-hOCT3/4 was introduced into the EcoRI site of pMXs retroviral vector. To discriminate each experiment, a 20-bp random sequence, designated N20 barcode, was introduced into the NotI/SalI site of Oct3/4 expression vector. A unique barcode sequence was used in each experiment to avoid inter-experimental contamination. The open reading frames of human SOX2, KLF4, and c-MYC were also amplified by RT-PCR and subcloned into pENTR-D-TOPO (Invitrogen). All of the genes subcloned into pENTR-D-TOPO were transferred to pMXs by using the Gateway cloning system (Invitrogen), according to the manufacturer's instructions. Mouse Slc7a1 ORF was also amplified, subcloned into pENTR-D-TOPO, and transferred to pLenti6/UbC/V5-DEST (Invitrogen) by the Gateway system. The regulatory regions of the human OCT3/4 gene and the REX1 gene were amplified by PCR and subcloned into pCRXL-TOPO (Invitrogen). For phOCT4-Luc and phREX1-Luc, the fragments were removed by KpnI/BglII digestion from pCRXL vector and subcloned into the KpnI/BglII site of pGV-BM2. For pPolII-Luc, an AatII (blunted)/NheI fragment of pQBI-polII was inserted into the KpnI (blunted)/NheI site of pGV-BM2. All of the fragments were verified by sequencing. Primer sequences are shown in TABLE 13.

TABLE 13

| Primer Sequences | | | |
|---|---|---|---|
| Primer | SEQ ID NO: | Sequence (5' to 3') | Applications |
| hOCT3/4-S944 | 26 | CCC CAG GGC CCC ATT TTG GTA CC | OCT3/4 Tg PCR |
| hSOX2-S691 | 27 | GGC ACC CCT GGC ATG GCT CTT GGC TC | SOX2 Tg PCR |
| hKLF4-S1128 | 28 | ACG ATC GTG GCC CCG GAA AAG GAC C | KLF4 endo and Tg PCR |
| hMYC-S1011 | 29 | CAA CAA CCG AAA ATG CAC CAG CCC CAG | c-MYC Tg PCR |
| pMXs-AS3200 | 30 | TTA TCG TCG ACC ACT GTG CTG CTG | Tg PCR |
| pMXs-L3205 | 31 | CCC TTT TTC TGG AGA CTA AAT AAA | Tg PCR |
| hOCT3/4-S1165 | 32 | GAC AGG GGG AGG GGA GGA GCT AGG | Endo OCT3/4 RT-PCR |
| hOCT3/4-AS1283 | 33 | CTT CCC TCC AAC CAG TTG CCC CAA AC | |
| hSOX2-S1430 | 34 | GGG AAA TGG GAG GGG TGC AAA AGA GG | Endo SOX2 RT-PCR |
| hSOX2-AS1555 | 35 | TTG CGT GAG TGT GGA TGG GAT TGG TG | |
| ECAT4-macaca-968S | 36 | CAG CCC CGA TTC TTC CAC CAG TCC C | NANOG RT-PCR |
| ECAT4-macaca-1334AS | 37 | CGG AAG ATT CCC AGT CGG GTT CAC C | |
| hGDF3-S243 | 38 | CTT ATG CTA CGT AAA GGA GCT GGG | GDF3 RT-PCR |
| hGDF3-AS850 | 39 | GTG CCA ACC CAG GTC CCG GAA GTT | |
| hREXI-RT-U | 40 | CAG ATC CTA AAC AGC TCG CAG AAT | REX1 RT-PCR |
| hREXI-RT-L | 41 | GCG TAC GCA AAT TAA AGT CCA GA | |
| hFGF4-RT-U | 42 | CTA CAA CGC CTA CGA GTC CTA CA | FGF4 RT-PCR |
| hFGF4-RT-L | 43 | GTT GCA CCA GAA AAG TCA GAG TTG | |
| hpH34-S40 | 44 | ATA TCC CGC CGT GGG TGA AAG TTC | ESG1 RT-PCR |
| hpH34-AS259 | 45 | ACT CAG CCA TGG ACT GGA GCA TCC | |
| hECAT15-1-S532 | 46 | GGA GCC GCC TGC CCT GGA AAA TTC | DPPA4 RT-PCR |
| hECAT15-1-AS916 | 47 | TTT TTC CTG ATA TTC TAT TCC CAT | |
| hECAT15-2-S85 | 48 | CCG TCC CCG CAA TCT CCT TCC ATC | DPPA2 RT-PCR |
| hECAT15-2-AS667 | 49 | ATG ATG CCA ACA TGG CTC CCG GTG | |
| hTERT-S3234 | 50 | CCT GCT CAA GCT GAC TCG ACA CCG TG | hTERT RT-PCR |
| hTERT-AS3713 | 51 | GGA AAA GCT GGC CCT GGG GTG GAG C | |
| hKLF4-AS1826 | 52 | TGA TTG TAG TGC TTT CTG GCT GGG CTC C | Endo KLF4 RT-PCR |
| hMYC-S253 | 53 | GCG TCC TGG GAA GGG AGA TCC GGA GC | Endo c-MYC RT-PCR |
| hMYC-AS555 | 54 | TTG AGG GGC ATC GTC GCG GGA GGC TG | |

TABLE 13-continued

| Primer Sequences | | | |
|---|---|---|---|
| Primer | SEQ ID NO: | Sequence (5' to 3') | Applications |
| hMSX1-S665 | 55 | CGA GAG GAC CCC GTG GAT GCA GAG | MSX1 RT-PCR |
| hMSX1-AS938 | 56 | GGC GGC CAT CTT CAG CTT CTC CAG | |
| hBRACHYURY-S1292 | 57 | GCC CTC TCC CTC CCC TCC ACG CAC AG | BRACHYURY/T RT-PCR |
| hBRACHYURY-AS1540 | 58 | CGG CGC CGT TGC TCA CAG ACC ACA GG | |
| hGFAP-S1040 | 59 | GGC CCG CCA CTT GCA GGA GTA CCA GG | GFAP RT-PCR |
| hGFAP-AS1342 | 60 | CTT CTG CTC GGG CCC CTC ATG AGA CG | |
| hPAX6-S1206 | 61 | ACC CAT TAT CCA GAT GTG TTT GCC CGA G | PAX6 RT-PCR |
| hPAX6-AS1497 | 62 | ATG GTG AAG CTG GGC ATA GGC GGC AG | |
| hFOXA2-S208 | 63 | TGG GAG CGG TGA AGA TGG AAG GGC AC | FOXA2 RT-PCR |
| hFOXA2-AS398 | 64 | TCA TGC CAG CGC CCA CGT ACG ACG AC | |
| hSOX17-S423 | 65 | CGC TTT CAT GGT GTG GGC TAA GGA CG | SOX17 RT-PCR |
| hSOX17-AS583 | 66 | TAG TTG GGG TGG TCC TGC ATG TGC TG | |
| hAADC-S1378 | 67 | CGC CAG GAT CCC CGC TTT GAA ATC TG | AADC RT-PCR |
| hAADC-AS1594 | 68 | TCG GCC GCC AGC TCT TTG ATG TGT TC | |
| hChAT-S1360 | 69 | GGA GGC GTG GAG CTC AGC GAC ACC | ChAT RT-PCR |
| hChAT-AS1592 | 70 | CGG GGA GCT CGC TGA CGG AGT CTG | |
| hMAP2-S5401 | 71 | CAG GTG GCG GAC GTG TGA AAA TTG AGA GTG | MAP2 RT-PCR |
| hMAP2-AS5587 | 72 | CAC GCT GGA TCT GCC TGG GGA CTG TG | |
| hDAT-S1935 | 73 | ACA GAG GGG AGG TGC GCC AGT TCA CG | SLC6A3/DAT RT-PCR |
| hDAT-AS2207 | 74 | ACG GGG TGG ACC TCG CTG CAC AGA TC | |
| hLMX1B-S770 | 75 | GGC ACC AGC AGC AGC AGG AGC AGC AG | LMX1B RT-PCR |
| hLMXIB-AS1020 | 76 | CCA CGT CTG AGG AGC CGA GGA AGC AG | |
| hMYL2A-S258 | 77 | GGG CCC CAT CAA CTT CAC CGT CTT CC | MYL2A RT-PCR |
| hMYL2A-AS468 | 78 | TGT AGT CGA TGT TCC CCG CCA GGT CC | |
| hTnTc-S524 | 79 | ATG AGC GGG AGA AGG AGC GGC AGA AC | TnTc RT-PCR |
| hTnTc-AS730 | 80 | TCA ATG GCC AGC ACC TTC CTC CTC TC | |
| hMEF2C-S1407 | 81 | TTT AAC ACC GCC AGC GCT CTT CAC CTT G | MEF2C RT-PCR |
| hMEF2C-AS1618 | 82 | TCG TGG CGC GTG TGT TGT GGG TAT CTC G | |
| hMYHCB-S5582 | 83 | CTG GAG GCC GAG CAG AAG CGC AAC G | MYHCB RT-PCR |
| hMYHCB-AS5815 | 84 | GTC CGC CCG CTC CTC TGC CTC ATC C | |

TABLE 13-continued

| Primer Sequences | | | |
|---|---|---|---|
| Primer | SEQ ID NO: | Sequence (5' to 3') | Applications |
| $dT_{20}$ | 85 | TTT TTT TTT TTT TTT TTT TT | Reverse transcription |
| hMYC-S857 | 86 | GCC ACA GCA AAC CTC CTC ACA GCC CAC | Southern blot probe |
| hMYC-AS1246 | 87 | CTC GTC GTT TCC GCA ACA AGT CCT CTT C | |
| hOCT3/4-S | 88 | CAC CAT GGC GGG ACA CCT GGC TTC AG | OCT3/4 cloning |
| hOCT3/4-AS | 89 | ACC TCA GTT TGA ATG CAT GGG AGA GC | |
| hSOX2-S | 90 | CAC CAT GTA CAA CAT GAT GGA GAC GGA GCT G | SOX2 cloning |
| hSOX2-AS | 91 | TCA CAT GTG TGA GAG GGG CAG TGT GC | |
| hKLF4-S | 92 | CAC CAT GGC TGT CAG TGA CGC GCT GCT CCC | KLF4 cloning |
| hKLF4-AS | 93 | TTA AAA ATG TCT CTT CAT GTG TAA GGC GAG | |
| hMYC-S | 94 | CAC CAT GCC CCT CAA CGT TAG CTT CAC CAA | c-MYC cloning |
| hMYC-AS | 95 | TCA CGC ACA AGA GTT CCG TAG CTG TTC AAG | |
| Slc7a1-S | 96 | CAC CAT GGG CTG CAA AAA CCT GCT CGG | Mouse Slc7a1 cloning |
| Slc7a1-AS | 97 | TCA TTT GCA CTG GTC CAA GTT GCT GTC | |
| hREX1-pro5K-S | 98 | ATT GTC GAC GGG GAT TTG GCA GGG TCA CAG GAC | Promoter cloning |
| hREXx1-pro5K-AS | 99 | CCC AGA TCT CCA ATG CCA CCT CCT CCC AAA CG | |
| hOCT3/4-pro5K-S | 100 | CACTCG AGG TGG AGG AGC TGA GGG CAC TGT GG | |
| hOCT3/4-pro5K-AS | 101 | CAC AGA TCT GAA ATG AGG GCT TGC GAA GGG AC | |
| mehREX1-F1-S | 102 | GGT TTA AAA GGG TAA ATG TGA TTA TAT TTA | Bisulfite sequencing |
| mehREX1-F1-AS | 103 | CAA ACT ACA ACC ACC CAT CAA C | |
| mehOCT3/4 F2-S | 104 | GAG GTT GGA GTA GAA GGA TTG TTT TGG TTT | |
| mehOCT3/4 F2-AS | 105 | CCC CCC TAA CCC ATC ACC TCC ACC ACC TAA | |
| mehNANOG-FI-S | 106 | TGG TTA GGT TGG TTT TAA ATT TTT G | |
| mehNANOG-FI-AS | 107 | AAC CCA CCC TTA TAA ATT CTC AAT TA | |

Lentivirus Production and Infection

293 FT cells (Invitrogen) were plated at $6\times10^6$ cells per 100 mm dish, and incubated overnight. Cells were transfected with 3 μg of pLenti6/UbC-Sic7a1 along with 9 μg of Virapower packaging mix by Lipofectamine 2000 (Invitrogen), according to the manufacturer's instructions. Forty-eight hours after transfection, the supernatant of transfectant was collected and filtered through a 0.45 μm pore-size cellulose acetate filter (Whatman). Human fibroblasts were seeded at $8\times10^5$ cells per 100 mm dish 1 day before transduction. The medium was replaced with virus-containing supernatant supplemented with 4 μg/ml polybrene (Nacalai Tesque), and incubated for 24 hours.

Retroviral Infection and iPS Cell Generation

PLAT-E packaging cells were plated at $8\times10^6$ cells per 100 mm dish and incubated overnight. Next day, the cells were transfected with pMXs vectors with Fugene 6 transfection reagent (Roche). Twenty-four hours after transfection, the medium was collected as the first virus-containing supernatant and replaced with a new medium, which was collected after 24 hours as the second virus-containing supernatant. Human fibroblasts expressing mouse Slc7a1 gene were seeded at $8\times10^5$ cells per 100 mm dish 1 day before transduction. The virus-containing supernatants were filtered through a 0.45-μm pore-size filter, and supplemented with 4 μg/ml polybrene. Equal amounts of supernatants containing each of the four retroviruses were mixed, transferred to the fibroblast dish, and incubated overnight. Twenty-four hours after transduction, the virus-containing medium was replaced with the second supernatant. Six days after transduction, fibroblasts were harvested by trypsinization and re-plated at $5\times10^4$ cells per 100-mm dish on an SNL feeder layer. Next day, the medium was replaced with hES medium supplemented with 4 ng/ml bFGF. The medium was changed every other day. Thirty days after transduction, colonies were picked up and transferred into 0.2 ml of hES cell medium. The colonies were mechanically dissociated to small clumps by pipeting up and down. The cell suspension was transferred on SNL feeder in 24-well plates. This stage was defined as passage 1.

RNA Isolation and Reverse Transcription

Total RNA was purified with Trizol reagent (Invitrogen) and treated with Turbo DNA-free kit (Ambion) to remove genomic DNA contamination. One microgram of total RNA was used for reverse transcription reaction with ReverTraAce-α (Toyobo, Japan) and $dT_{20}$ primer, according to the manufacturer's instructions. PCR was performed with ExTaq (Takara, Japan). Quantitative PCR was performed with Platinum SYBR Green qPCR Supermix UDG (Invitrogen) and analyzed with the 7300 real-time PCR system (Applied Biosystems). Primer sequences are shown in TABLE 13.

Alkaline Phosphatase Staining and Immunocytochemistry

Alkaline phosphatase staining was performed using the Leukocyte Alkaline Phosphatase kit (Sigma). For immunocytochemistry, cells were fixed with PBS containing 4% paraformaldehyde for 10 min at room temperature. After washing with PBS, the cells were treated with PBS containing 5% normal goat or donkey serum (Chemicon), 1% bovine serum albumin (BSA, Nacalai tesque), and 0.1% Triton X-100 for 45 min at room temperature. Primary antibodies included SSEA1 (1:100, Developmental Studies Hybridoma Bank), SSEA3 (1:10, a kind gift from Dr. Peter W. Andrews), SSEA4 (1:100, Developmental Studies Hybridoma Bank), TRA-2-49/6E (1:20, Developmental Studies Hybridoma Bank), TRA-1-60 (1:50, a kind gift from Dr. Peter W. Andrews), TRA-1-81 (1:50, a kind gift from Dr. Peter W. Andrews), Nanog (1:20, AF1997, R&D Systems), βIII-tubulin (1:100, CB412, Chemicon), glial fibrillary acidic protein (1:500, Z0334, DAKO), α-smooth muscle actin (pre-diluted, N1584, DAKO), desmin (1:100, RB-9014, Lab Vision), vimentin (1:100, SC-6260, Santa Cruz), α-fetoprotein (1:100, MAB1368, R&D Systems), tyrosine hydroxylase (1:100, AB152, Chemicon). Secondary antibodies used were cyanine 3 (Cy3)-conjugated goat anti-rat IgM (1:500, Jackson Immunoresearch), Alexa546-conjugated goat anti-mouse IgM (1:500, Invitrogen), Alexa488-conjugated goat anti-rabbit IgG (1:500, Invitrogen), Alexa488-conjugated donkey anti-goat IgG (1:500, Invitrogen), Cy3-conjugated goat anti-mouse IgG (1:500, Chemicon), and Alexa488-conjugated goat anti-mouse IgG (1:500, Invitrogen). Nuclei were stained with 1 μg/ml Hoechst 33342 (Invitrogen).

In Vitro Differentiation

For EB formation, human iPS cells were harvested by treating with collagenase IV. The clumps of the cells were transferred to poly (2-hydroxyethyl methacrylate)-coated dish in DMEM/F12 containing 20% knockout serum replacement (KSR, Invitrogen), 2 mM L-glutamine, $1\times10^{-4}$ M nonessential amino acids, $1\times10^{-4}$ M 2-mercaptoethanol (Invitrogen), and 0.5% penicillin and streptomycin. The medium was changed every other day. After 8 days as a floating culture, EBs were transferred to gelatin-coated plate and cultured in the same medium for another 8 days. Co-culture with PA6 was used for differentiation into dopaminergic neurons. PA6 cells were plated on gelatin-coated 6-well plates and incubated for 4 days to reach confluence. Small clumps of iPS cells were plated on PA6-feeder layer in Glasgow minimum essential medium (Invitrogen) containing 10% KSR (Invitrogen), $1\times10^{-4}$ M nonessential amino acids, $1\times10^{-4}$ M 2-mercaptoethanol (Invitrogen), and 0.5% penicillin and streptomycin. For cardiomyocyte differentiation, iPS cells were maintained on Matrigel-coated plate in MEF-CM supplemented with 4 ng/ml bFGF for 6 days. The medium was then replaced with RPMI1640 (Invitrogen) plus B27 supplement (Invitrogen) medium (RPMI/B27), supplemented with 100 ng/ml human recombinant activin A (R & D Systems) for 24 hours, followed by 10 ng/ml human recombinant bone morphologenic protein 4 (BMP4, R&D Systems) for 4 days. After cytokine stimulation, the cells were maintained in RPMI/B27 without any cytokines. The medium was changed every other day.

Bisulfite Sequencing

Genomic DNA (1 μg) was treated with CpGenome DNA modification kit (Chemicon), according to the manufacturer's recommendations. Treated DNA was purified with QIAquick column (QIAGEN). The promoter regions of the human Oct3/4, Nanog, and Rex1 genes were amplified by PCR. The PCR products were subcloned into pCR2.1-TOPO. Ten clones of each sample were verified by sequencing with the M13 universal primer. Primer sequences used for PCR amplification were provided in TABLE 13.

Luciferase Assay

Each reporter plasmid (1 μg) containing the firefly luciferase gene was introduced into human iPS cells or HDF with 50 ng of pRL-TK (Promega). Forty-eight hours after transfection, the cells were lysed with 1× passive lysis buffer (Promega) and incubated for 15 min at room temperature. Luciferase activities were measured with a Dual-Luciferase reporter assay system (Promega) and Centro LB 960 detection system (BERTHOLD), according to the manufacturer's protocol.

Teratoma Formation

The cells were harvested by collagenase IV treatment, collected into tubes and centrifuged, and the pellets were suspended in DMEM/F12. One quarter of the cells from a confluent 100 mm dish was injected subcutaneously to dorsal flank of a SCID mouse (CREA, Japan). Nine weeks after injection, tumors were dissected, weighted, and fixed with PBS containing 4% paraformaldehyde. Paraffin-embedded tissue was sliced and stained with hematoxylin and eosin.

Western Blotting

The cells at semiconfluent state were lysed with RIPA buffer (50 mM Tris-HCl, pH 8.0, 150 mM NaCl, 1% Nonidet P-40 (NP-40), 1% sodium deoxycholate, and 0.1% SDS), supplemented with protease inhibitor cocktail (Roche). The cell lysate of MEL-1 hES cell line was purchased from Abcam. Cell lysates (20 μg) were separated by electrophoresis on 8% or 12% SDS-polyacrylamide gel and transferred to a polyvinylidine difluoride membrane (Millipore). The blot was blocked with TBST (20 mM Tris-HCl, pH 7.6, 136 mM NaCl, and 0.1% Tween-20) containing 1% skim milk and then incubated with primary antibody solution at 4° C. overnight. After washing with TBST, the membrane was incubated with horseradish peroxidase (HRP)-conjugated secondary antibody for 1 hour at room temperature. Signals were detected with Immobilon Western chemiluminescent HRP substrate (Millipore) and LAS3000 imaging system (FUJIFILM, Japan). Antibodies used for western blotting were anti-Oct3/4 (1:600, SC-5279, Santa Cruz), anti-Sox2 (1:2000, AB5603, Chemicon), anti-Nanog (1:200, R&D Systems), anti-Klf4 (1:200, SC-20691, Santa Cruz), anti-c-Myc (1:200, SC-764, Santa Cruz), anti-E-cadherin (1:1000, 610182, BD Biosciences), anti-Dppa4 (1:500, ab31648, Abcam), anti-FoxD3 (1:200, AB5687, Chemicon), anti-telomerase (1:1000, ab23699, Abcam), anti-Sall4 (1:400, ab29112, Abcam), anti-LIN-28 (1:500, AF3757, R&D systems), anti-β-actin (1:5000, A5441, Sigma), anti-mouse IgG-HRP (1:3000, #7076, Cell Signaling), anti-rabbit IgG-HRP (1:2000, #7074, Cell Signaling), and anti-goat IgG-HRP (1:3000, SC-2056, Santa Cruz).

Southern Blotting

Genomic DNA (5 μg) was digested with BglII, EcoRI, and NcoI overnight. Digested DNA fragments were separated on 0.8% agarose gel and transferred to a nylon membrane (Amersham). The membrane was incubated with digoxigenin (DIG)-labeled DNA probe in DIG Easy Hyb buffer (Roche) at 42° C. overnight with constant agitation. After washing, alkaline phosphatase-conjugated anti-DIG antibody (1:10,000, Roche) was added to a membrane. Signals were raised by CDP-star (Roche) and detected by LAS3000 imaging system.

Short Tandem Repeat Analysis and Karyotyping

The genomic DNA was used for PCR with Powerplex 16 system (Promega) and analyzed by ABI PRISM 3100 Genetic analyzer and Gene Mapper v3.5 (Applied Biosystems). Chromosomal G-band analyses were performed at the Nihon Gene Research Laboratories, Japan.

Detection of Telomerase Activity

Telomerase activity was detected with a TRAPEZE telomerase detection kit (Chemicon), according to the manufacturer's instructions. The samples were separated by TBE-based 10% acrylamide non-denaturing gel electrophoresis. The gel was stained with SYBR Gold (1:10,000, Invitrogen).

Example 21: Generation of Induced Pluripotent Stem Cells without Myc

The direct reprogramming of somatic cells is considered to provide an opportunity to generate patient- or disease-specific pluripotent stem cells. Such pluripotent stem (iPS) cells are induced from mouse fibroblasts by the retroviral transduction of four transcription factors, Oct3/4, Sox2, Klf4, and c-Myc (Takahashi et al. *Cell* 126:663-76, 2006). Mouse iPS cells are indistinguishable from mouse ES cells in many aspects and give rise to germline-competent chimeras (Wernig et al. *Nature* 448:318-24, 2007; Okita et al. *Nature* 448:313-17, 2007; Maherali et al. *Cell Stem Cell* 1:55-70, 2007). It was noted above that each iPS clone contained 3-6 retroviral integrations for each factor. Thus, each clone had more than 20 retroviral integration sites in total, which may increase the risk of tumorigenesis. In the case of mouse iPS cells, ~20% of chimera mice and their offspring derived from iPS cells developed tumors (Okita et al. *Nature* 448:313-17, 2007). In particular, it was found that the reactivation of the c-Myc retrovirus results in an increased incidence of tumor formation in the chimeras and progeny mice generated with mouse iPS cells, thus hindering the clinical application of this technology (Okita et al. *Nature* 448:313-17, 2007). Therefore, a modified protocol for the induction of iPS cells, which does not require the Myc retrovirus was developed. With this new protocol, significantly fewer non-iPS background cells were obtained. Furthermore, the iPS cells generated without Myc were constantly of high quality. These findings are important for the future clinical application of this iPS cell technology.

Substitution of the Four Factors with Other Family Members

Figure 43:
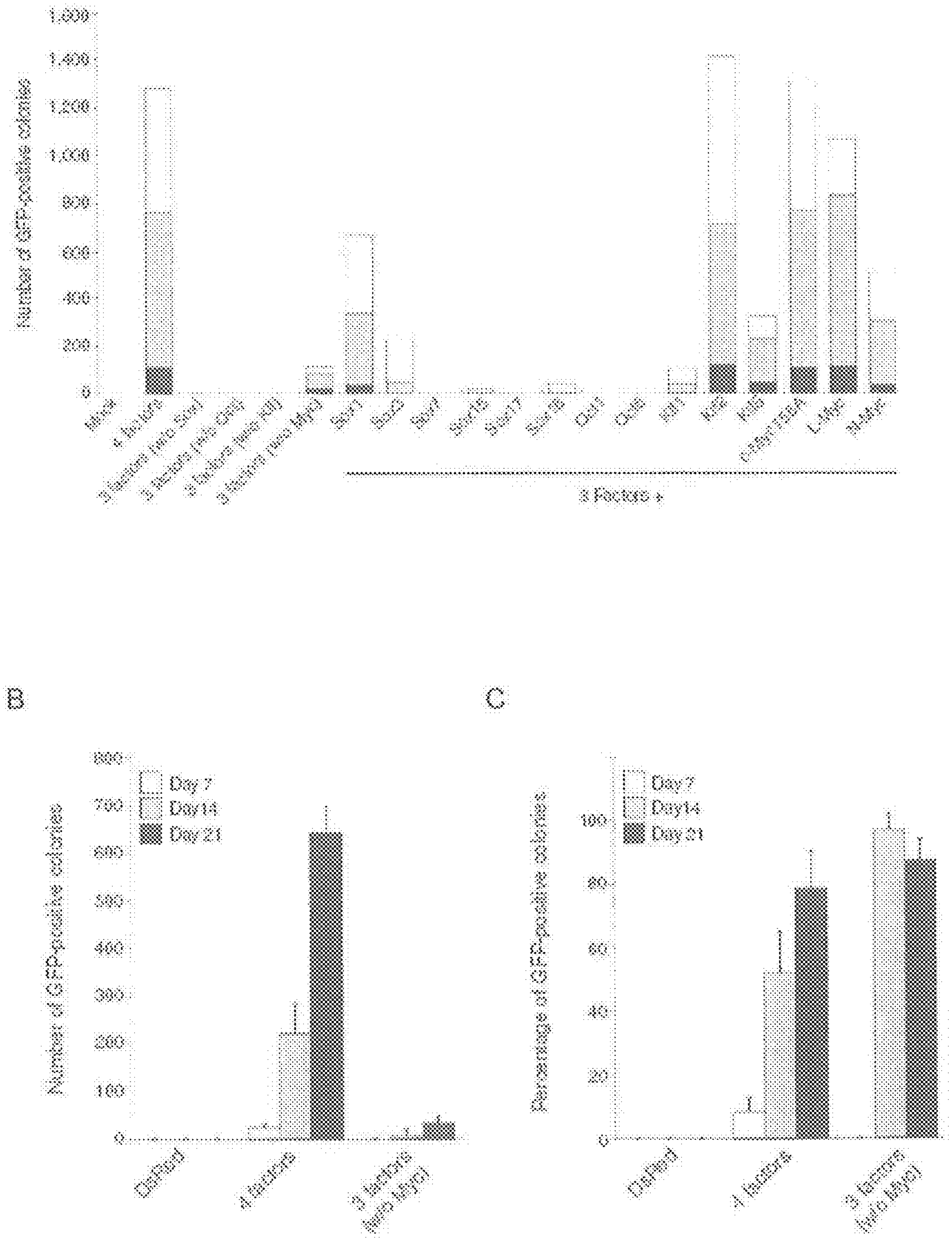
FIG. 43 shows the effect of family factors and the omission of Myc on generation of iPS cells from Nanog-reporter MEFs. (A) Generation of iPS cells with family genes from MEF by Nanog selection. The number of GFP-positive colonies is shown. The results of three independent experiments were shown with different colors (white, gray, and black). The "4 factors" indicate the combination of Oct3/4, Sox2, Klf4, and c-Myc. (B) The effect of puromycin selection timing on iPS cell generation. Shown are GFP-positive colonies observed 28 days after the transduction of the four factors or the three factors devoid of Myc. (C) The effect of puromycin selection timing on the percentage of GFP-positive colonies per all colonies.

This study was initiated to examine whether the family proteins of the four factors could also induce iPS cells. In other words, further investigations were performed to assess which family members of a given gene family could substitute for others as nuclear reprogramming factors. Mouse embryonic fibroblasts (MEF) containing a GFP-IRES-Puro$^r$ transgene driven by the Nanog gene regulatory elements were used (Okita et al. *Nature* 448:313-17, 2007). Nanog is specifically expressed in mouse ES cells and preimplantation embryos (Chambers et al. *Cell* 113:643-55, 2003; Mitsui et al. *Cell* 113:631-42, 2003) and can serve as a selection marker during iPS cell induction. By introducing the aforementioned four factors, iPS cells are induced as GFP-expressing colonies. Nanog-selected iPS cells are indistinguishable from ES cells and have been shown to give rise to germline-competent chimeras (Wernig et al. *Nature* 448:318-24, 2007; Okita et al. *Nature* 448:313-17, 2007; Maherali et al. *Cell Stem Cell* 1:55-70, 2007). Oct3/4 belongs to the Oct family transcription factors, which contain the POU domain (Ryan et al. *Genes Dev* 11:1207-25, 1997). The closest homologs of Oct3/4 are Oct1 and Oct6. Oct3/4, Oct1, or Oct6 were introduced together with the remaining three factors, into the Nanog-reporter MEF by retroviruses. With Oct3/4, many GFP-positive colonies were observed (FIG. 43A). In contrast, no GFP-positive colonies were obtained with Oct1 or Oct6, thus indicating the inability of these two homologs to induce iPS cells.

Sox2 belongs to the Sox (SRY-related HMG-box) transcription factors, characterized by the presence of the high mobility group (HMG) domain (Schepers et al. *Dev Cell* 3:167-70, 2002). Sox1, Sox3, Sox7, Sox15, Sox17, and Sox18 were tested and GFP-positive colonies were obtained with Sox1. In addition, fewer GFP-positive colonies were obtained with Sox3, Sox15, and Sox18 (FIG. 43A). Sox18, however, failed to expand the cells.

Klf4 belongs to Krüppel-like factors (Klfs), zinc-finger proteins that contain amino acid sequences that resemble those of the *Drosophila* embryonic pattern regulator Krüppel (Dang et al. *Int J Biochem Cell Biol* 32:1103-21, 2000). Klf1, Klf2, and Klf5 were tested and GFP-expressing colonies with Klf2 were thus obtained (FIG. 43A). Klf1 and Klf5 were also capable of inducing iPS cells, but with a lower efficiency.

c-Myc has two related proteins, N-Myc and L-Myc (Adhikary et al. *Nat Rev Mol Cell Biol* 6:635-45, 2005). GFP-positive colonies emerged with both N-Myc and L-Myc (FIG. 43A). Therefore, some, but not all family proteins of the four factors can induce iPS cells.

Figure 44:
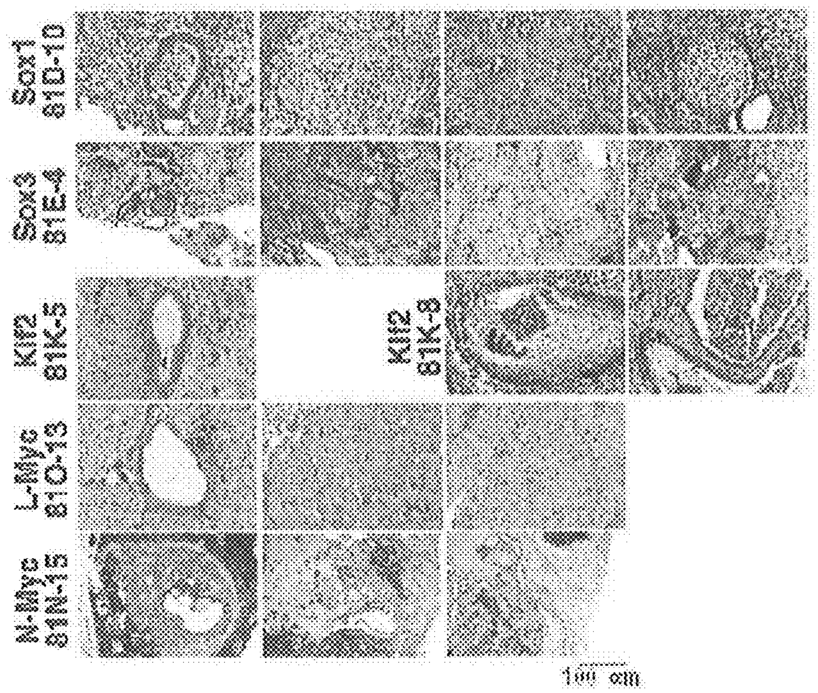
FIG. 44 shows teratomas derived from iPS cells, which were induced from Fbx15-reporter MEFs with family proteins.

The family proteins were also tested for their ability to induce iPS cells from MEFs in which βgeo was knocked into the Fbx15 locus (Tokuzawa et al. *Mol Cell Biol* 23:2699-708, 2003). Similar results to those with the Nanog-based selection were obtained: Sox2 could be replaced by Sox1 and Sox3, Klf4 by Klf2, and c-Myc by N-Myc and L-Myc. The cells generated by the family proteins were expandable and showed a morphology indistinguishable from that of ES cells (not shown). They gave rise to teratomas in nude mice (FIG. 44). Therefore, some family proteins are capable of inducing iPS cells from both Nanog-reporter MEF and Fbx15-reporter MEF.

As has been stated above, iPS cell generation from somatic cells was evaluated by optimizing retroviral transduction and subsequent culture conditions. Furthermore, optimization would be useful for the application of this iPS cell technology to human cells, especially in clinical situations. Unexpectedly, a few ES cell-like and GFP-positive colonies from Nanog-reporter MEF were obtained without any Myc retroviruses (FIG. 43A). This was in contrast to a previous study in which no GFP-positive colonies could be obtained without c-Myc (Okita et al. *Nature* 448:313-17, 2007). Consistent with the efforts toward optimization, one difference between the two studies is the timing of the drug selection: In the previous study, puromycin selection was initiated seven days after the transduction, whereas in this experiment the selection was started at 14 days. This suggests that iPS cell induction without Myc is a slower process than that with Myc. Furthermore, as is further discussed herein, the omission of Myc resulted in a less efficient but more specific induction of iPS cells.

Myc Omission Results in More Specific iPS Cell Induction

Figure 45:
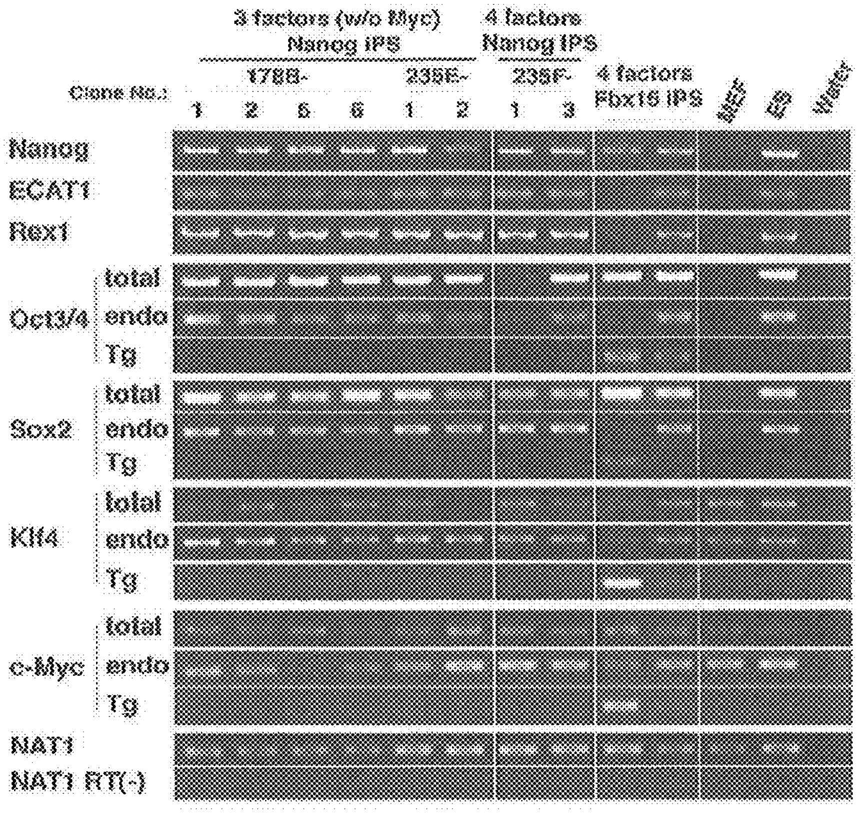
FIG. 45 shows characterization of iPS cells induced from Nanog-reporter MEFs without Myc retroviruses. RT-PCR showing expression levels of ES cell marker genes and the four factors. By using specific primer sets, total transcripts, transcripts from the endogenous genes (endo), and the transcripts from the retroviruses (Tg) were distinguished for the four factors.

To test whether iPS cell induction without Myc is a slower process than that with Myc, Nanog-reporter MEFs were transduced with either the four factors or three factors devoid of Myc, and then puromycin selection was started seven, 14, or 21 days after the transduction (FIG. 43B). With the four factors, GFP-positive colonies were observed in all of the conditions. The colony numbers significantly increased when puromycin selection was delayed. Without Myc, no GFP-colonies were observed when selection was initiated seven days after the transduction. In contrast, GFP-positive colonies did emerge even without Myc when selection was started 14 or 21 days after the transduction. The colony numbers were fewer with the three factors than with the four factors in each condition. Nanog-selected iPS cells generated without Myc retroviruses expressed ES cell marker genes at comparable levels to those in ES cells (FIG. 45), and thus gave rise to adult chimeras when transplanted into blastocysts (TABLE 14).

TABLE 14

Summary of blastocysts injections

| iPS clones | origin-genotype* | selection | injected blastocysts | born mice | chimeras |
|---|---|---|---|---|---|
| 142B-6 | MEF-FB/gfp | G418 | 39 | 7 | 3 |
| 142B-12 | | | 46 | 12 | 5 |
| 178B-1 | MEF-Ng | Puro | 156 | 50 | 5 |
| 178B-2 | | | 142 | 43 | 17 |
| 178B-5 | | | 60 | 20 | 5 |
| 178B-6 | | | 28 | 10 | 4 |
| 256H-4 | TTF-ACTB- | No | 72 | 6 | 5 |
| 256H-13 | DsRed | | 96 | 8 | 5 |
| 256H-18 | | | 90 | 17 | 11 |

All iPS clones were induced with three factors devoid of Myc from MEF or TTF.
*FB, Fbx15-βgeo reporter; Ng, Nanog-GFP-IRES-$Puro^r$ reporter; gfp, CAG-EGFP Another difference is that fewer GFP-negative colonies as well as background cells were observed with the three factors devoid of Myc than with the four factors (FIG. 43C). Therefore, the omission of Myc resulted in a less efficient but more specific induction of iPS cells.

Figure 46:
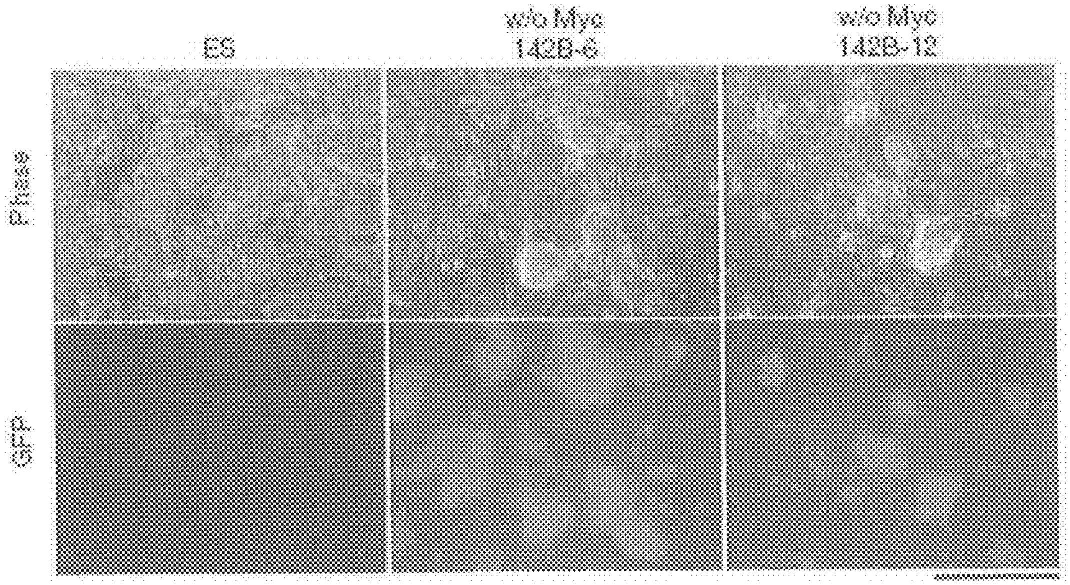
FIG. 46 shows generation of iPS cells without Myc retroviruses from MEFs containing the Fbx15-reporter and the constitutively active GFP-transgene. (A) Morphology of iPS cells generated without Myc retroviruses. The bar indicates 500 μm. (B) RT-PCR analyses of ES marker genes in ES, MEF, and iPS cells induced without Myc. (C) Chimeras derived from iPS cells induced without Myc (clones 142B-6 and -12).
Figure 46:
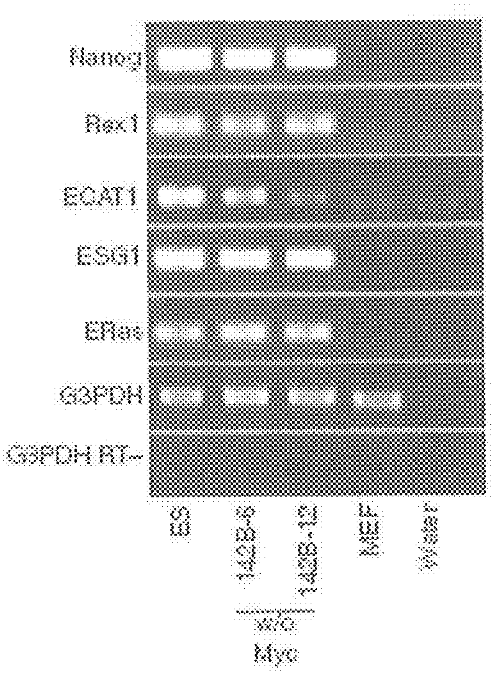
Figure 46:
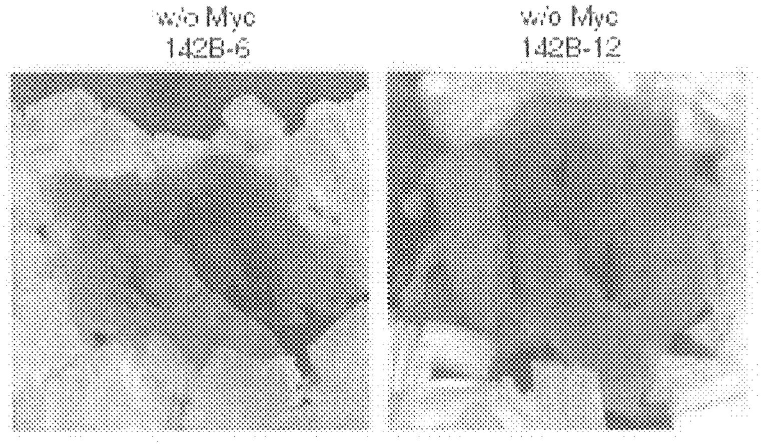

It was also possible to generate a few iPS cells without Myc from MEFs, in which βgeo was knocked into the Fbx15 locus (Tokuzawa et al. *Mol. Cell Biol.* 23:2699-708, 2003). (FIG. 46A). This is again in contrast to the original report, in which no iPS cells were obtained without c-Myc (Takahashi et al. *Cell* 126:663-76, 2006). In the two experiments, G418 selection was initiated with the same timing: three days after the transduction. However, the colonies were selected 14-21 days after the transduction in the previous report, whereas ~30 days were required in the current study. Another difference was that the retroviral transfection efficiency was raised by preparing each of the four or three factors separately in an independent Plat-E (Morita et al. *Gene Ther.* 7:1063-66, 2000) plate in this study. In comparison to the original work in which all the four factors were prepared in a single Plat-E plate, a significant increase in the number of iPS cell colonies was observed (not shown). This is consistent with the notion that iPS cell induction without Myc is a slower and less efficient process than that with Myc.

Fbx15-selected iPS cells, which were generated with the four factors, express lower levels of ES-cell marker genes than ES cells (Takahashi et al. *Cell* 126:663-76, 2006). They cannot produce adult chimeras when microinjected into blastocysts. In contrast, iPS cells generated without Myc expressed ES-cell marker genes at comparable levels to those in ES cells even with the Fbx15 selection (FIG. 46B). Furthermore, adult chimeras were obtained with high iPS cell contribution from these cells (FIG. 46C, TABLE 14). No increased incidence of tumor formation was observed in these chimeras. That is, six of 37 chimeras derived from iPS cells with the four factors died of tumors within 100 d after birth. By contrast, all 26 chimeras gererated without Myc survived this period. Thus, the omission of the Myc retrovirus significantly reduced the risk of tumorigenicity in chimeras.

iPS Cell Induction in the Absence of Drug Selection

Figure 47:
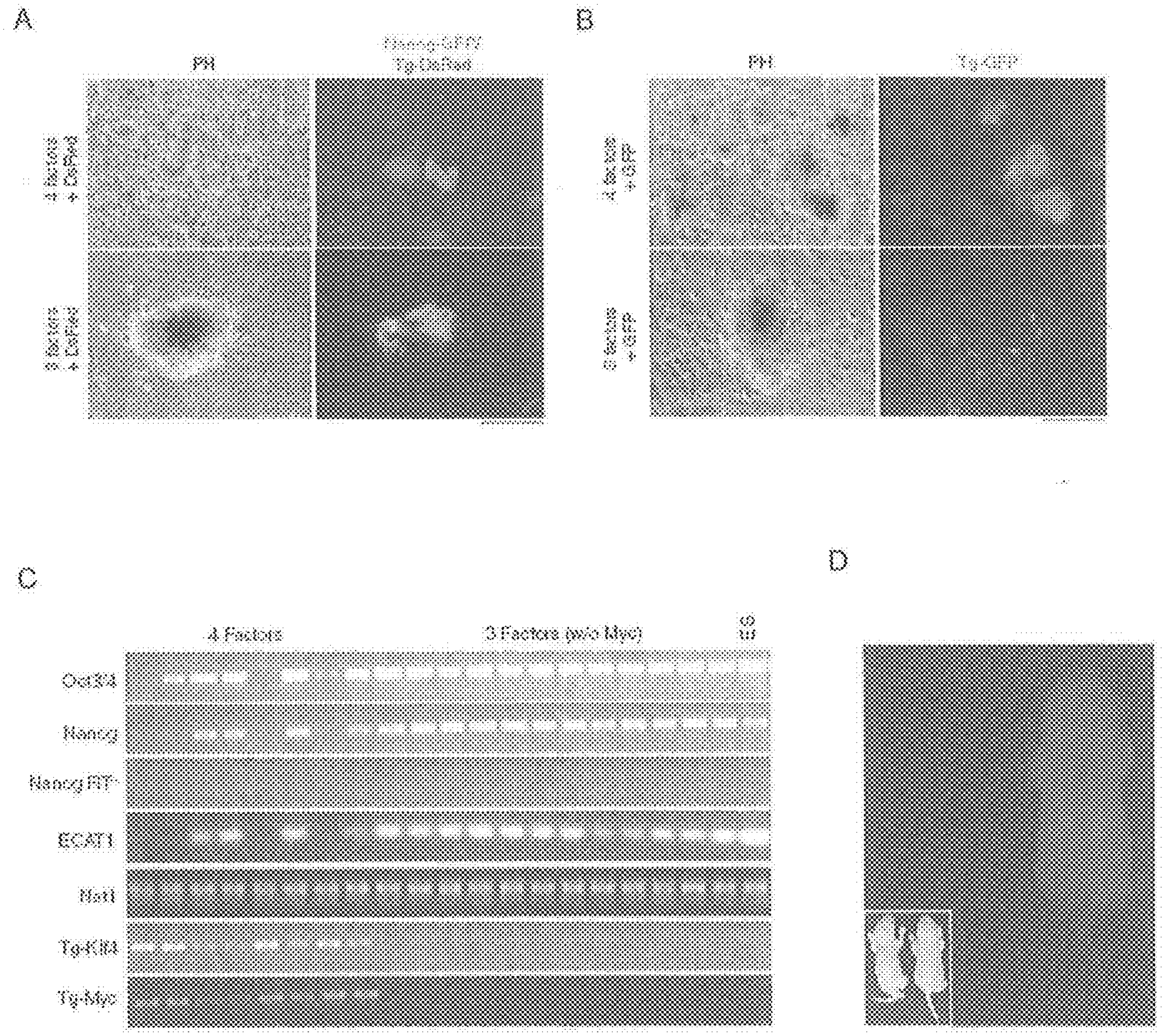
FIG. 47 shows the efficient isolation of iPS cells without drug selection. (A) Morphology of iPS cells induced from adult TTF containing the Nanog-GFP-IRES-Puro$^r$ reporter. Cells were transduced with either the four factors or the three factors devoid of Myc, together with DsRed, and then were cultured for 30 days without drug selection. The expression of the Nanog reporter (Nanog-GFP) and the DsRed retrovirus (Tg-DsRed) was examined by fluorescent microscopy. The bar indicates 500 μm. (B) Morphology of iPS cells induced from adult TTF, which contained a DsRed transgene driven by a constitutively active promoter (ACTB, β-actin gene), but lacking the Nanog- or Fbx15-selection cassettes. The cells were transduced with either the four factors or the three factors devoid of Myc, together with GFP, and then cultured for 30 days without drug selection. The expression of the GFP retrovirus (Tg-GFP) was examined by fluorescent microscopy. The bar indicates 500 μm. (C) RT-PCR analyses of ES maker genes in iPS cells generated from TTF without drug selection and ES cells. (D) Chimeras derived from iPS cells, which were generated from adult TTF without drug selection or the Myc retroviruses.

Next, it was determined whether the omission of Myc would result in efficient isolation of iPS cells without drug selection. The four or three factors were introduced into adult tail tip fibroblasts (TTF) containing the Nanog reporter, but puromycin selection was not applied. DsRed retrovirus was transduced together with the four or three factors to visualize transduced cells. Thirty days after the retroviral transduction, the dishes transduced with the four factors were covered with numerous GFP-negative colonies and background cells (FIG. 47A, TABLE 15).

TABLE 15

Summary of experiments (Nanog-GFP reporter TTF, without selection)

| Experiment Number | Factors | Cell seeded | Total colonies | picked up | established |
|---|---|---|---|---|---|
| 220 | 4 | $5 \times 10^4$ | many (107) | 26(24) | 25(22) |
| 256 | 4 | $5 \times 10^4$ | many (4) | | |
| | 3 | $3.5 \times 10^5$ | 7(4) | 7(4) | 6(5) |
| 272 | 4 | $5.4 \times 10^4$ | many (132) | 6(6) | 5(4) |
| | 3 | $3.1 \times 10^5$ | 21(8) | 4(4) | 2(2) |
| 309 | 4 | $2.3 \times 10^4$ | many (424) | | |
| | 3 | $9.6 \times 10^5$ | 43(24) | | |

Numbers in parentheses indicate number of colonies or clones that were positive for GFP. The ratios of the retroviruses, Oct3/4, Sox2, Klf4, (c-Myc), and DsRed, were 1:1:1:(1):4 in experiment 256 and 1:1:1:(1):1 in experiments 272 and 309. In experiment 220, DsRed was not introduced.

Using fluorescent microscopy, small portions of these colonies (4, 132, and 424 colonies in three independent experiments) were found GFP-positive. Of note, the GFP-positive colonies were negative for DsRed, which was consistent with the retroviral silencing observed in Nanog-selected iPS cells (Okita et al. *Nature* 448:313-17, 2007). In contrast, with the three factors devoid of Myc, a small number (7, 21, and 43 in three independent experiments) of discrete colonies were observed with few background cells. Approximately a half of them expressed GFP in a patchy manner. DsRed was only detected in a small portion of some colonies, indicating that it was largely silenced. No overlap was observed between GFP and DsRed. Most of these colonies were expandable and produced iPS cells, which became positive for GFP and negative for DsRed at passage 2. Therefore, the omission of c-Myc resulted in more specific generation of iPS cells, in which Nanog-GFP is activated whereas the retroviruses are silenced.

Next, generation of iPS cells was attempted from adult TTF that did not have selection markers, but had the DsRed transgene driven by a constitutively active promoter (Vintersten et al. *Genesis* 40:241-46, 2004). The four factors or the three factors devoid of Myc were introduced. In addition, a GFP retrovirus was introduced to monitor silencing. After 30 days without drug selection, ~1000 colonies emerged from $0.5\times10^5$ cells transduced with the four factors. Most of them were positive for GFP, indicating that retroviral silencing did not take place in these cells. In contrast, only 16 colonies (FIG. 47B) emerged from $3.5\times10^5$ cells transduced with the three factors devoid of Myc. Most of these colonies express no GFP, while the remaining expressed GFP in small portions. All of these colonies were expandable and showed iPS- or ES-like morphology at the second passage. They were all negative for GFP, thus indicating retroviral silencing. RT-PCR showed that these cells expressed ES cell marker genes at comparable levels to those in ES cells (FIG. 47C). In addition, RT-PCR confirmed the retroviral silencing of Klf4 and the absence of the Myc transgene in iPS cells generated with the three factors. Furthermore, when transplanted into blastocysts, these cells gave rise to chimeras (FIG. 47D, TABLE 14). Therefore, by omitting Myc, good iPS cells can be efficiently generated from adult TTF without drug selection. These findings should be useful for the application of this iPS cell technology to human cells, especially in clinical situations.

Induction of Human iPS Cells without Myc Retroviruses

Figure 48:
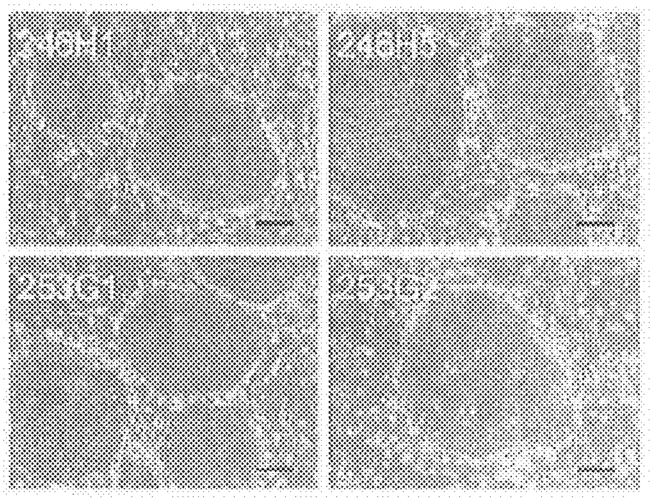
FIG. 48 shows induction of human iPS cells without Myc retroviruses. (A) The retroviruses for Oct3/4, Sox2 and Klf4 were introduced into BJ fibroblasts (246G) or HDF (253G). After 30 days, a few hES cell-like colonies emerged. These cells were expandable and showed hES cell-like morphology. (B) The expression of ES cell marker genes in human iPS cells derived from HDF without Myc retroviruses (253G) or with Myc (253F). (C) Embryoid body-mediated differentiation of human iPS cells generated without Myc retroviruses.
Figure 48:
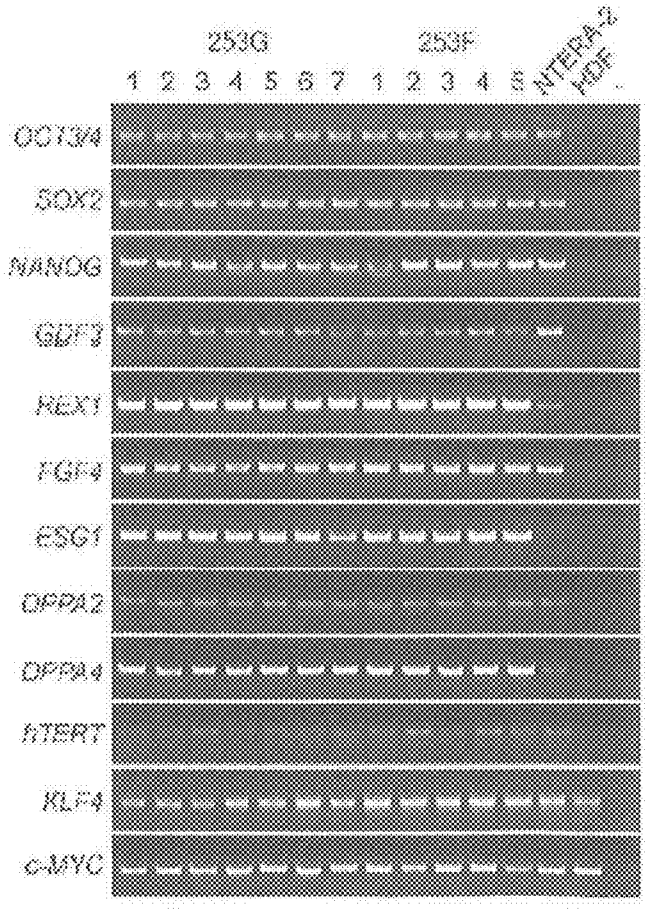
Figure 48:
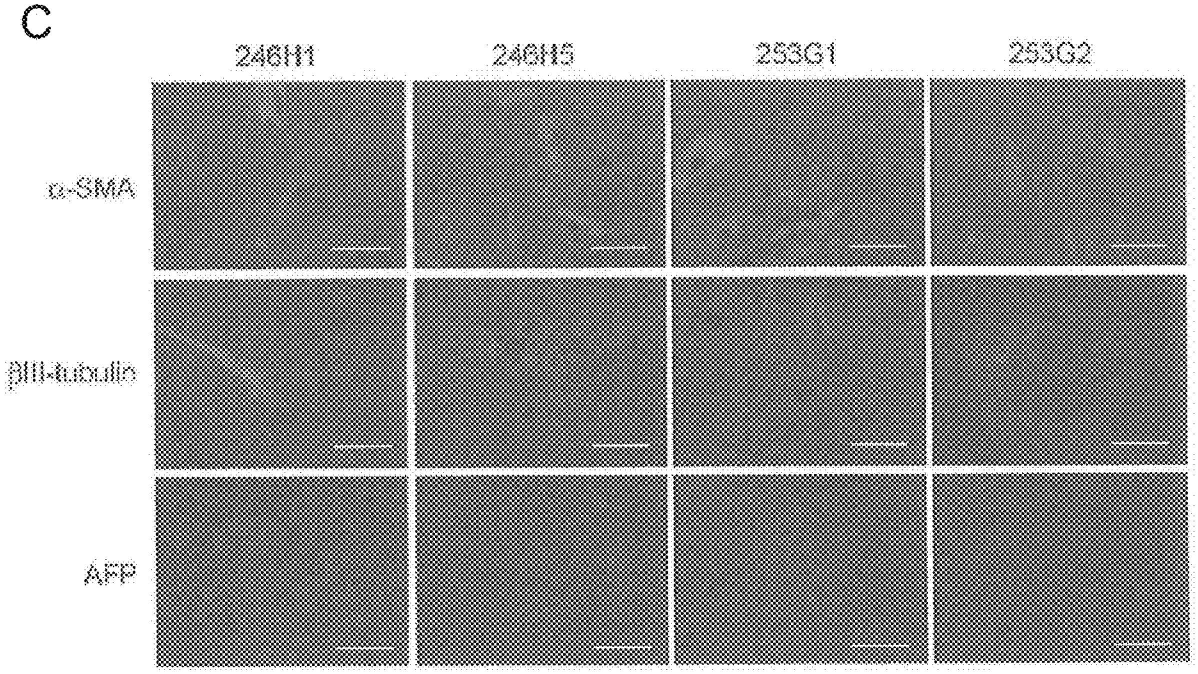

FIGS. 48(A)-(C) show induction of human iPS cells without Myc retroviruses. The retroviruses for Oct3/4, Sox2 and Klf4 were introduced into BJ fibroblasts (246G) or HDF (253G). After 30 days, a few hES cell-like colonies emerged. These cells were expandable and showed hES cell-like morphology (FIG. 48(A)). Results were obtained for the expression of ES cell marker genes in human iPS cells derived from HDF without Myc retroviruses (253G) or with Myc (253F) (FIG. 48(B)), as were results for embryoid body-mediated differentiation of human iPS cells generated without Myc retroviruses (FIG. 48(C)).

Experimental Procedures for Example 21.

Plasmid construction. The coding regions of family genes were amplified by RT-PCR with primers listed in TABLE 16, subcloned into pDONR201 or pENTR-D-TOPO (Invitrogen), and recombined with pMXs-gw by the LR reaction (Invitrogen).

TABLE 16

Primers used for cloning of the family factors

| Genes | Sequences | SEQ ID NO: |
|---|---|---|
| Sox1 | CAC CAT GTA CAG CAT GAT GAT GGA GAC CGA CCT | 108 |
| | CTA GAT ATG CGT CAG GGG CAC CGT GC | 109 |
| Sox3 | CAC CAT GTA CAG CCT GCT GGA GAC TGA ACT CAA | 110 |
| | TCA GAT GTG GGT CAG CGG CAC CGT TCC ATT | 111 |
| Sox7 | CAC CTC GGC CAT GGC CTC GCT GCT GGG | 112 |
| | CTC CAT TCC TCC AGC TCT ATG ACA CAC | 113 |
| Sox15 | CAC CAT GGC GCT GAC CAG CTC CTC ACA A | 114 |
| | TTA AAG GTG GGT TAC TGG CAT GGG | 115 |
| Sox17 | CAC CAG AGC CAT GAG CAG CCC GGA TG | 116 |
| | CGT CAA ATG TCG GGG TAG TTG CAA TA | 117 |
| Sox18 | CAC CAT GCA GAG ATC GCC GCC CGG CTA CG | 118 |
| | CTA GCC TGA GAT GCA AGC ACT GTA ATA GAC | 119 |
| Oct1 | CAC CAT GAA TAA TCC ATC AGA AAC CAA T | 120 |
| | GCT CTG CAC TCA GCT CAC TGT GCC | 121 |
| Oct6 | CAC CAT GGC CAC CAC CGG GCA GTA TCT G | 122 |
| | GGA ACC CAG TCC GCA GGG TCA CTG | 123 |
| Klf1 | CAC CAT GAG GCA GAA GAG AGA GAG GAG GC | 124 |
| | TCA GAG GTG ACG CTT CAT GTG CAG AGC TAA | 125 |
| Klf2 | CAC CAT GGC GCT CAG CGA GCC TAT CTT GCC | 126 |
| | CTA CAT ATG TCG CTT CAT GTG CAA GGC CAG | 127 |
| Klf5 | CAC CAT GCC CAC GCG GGT GCT GAC CAT G | 128 |
| | TCG CTC AGT TCT GGT GGC GCT TCA | 129 |
| L-MycWT | CAC CAT GGA CTT CGA CTC GTA TCA GCA CTA TTT C | 130 |
| | TTA GTA GCC ACT GAG GTA CGC GAT TCT CTT | 131 |
| N-MycWT | CAC CAT GCC CAG CTG CAC CGC GTC CAC CAT | 132 |
| | TTA GCA AGT CCG AGC GTG TTC GAT CT | 133 |

Retroviral transduction. pMXs-based retroviral vectors were transfected into Plat-E cells (Morita et al. *Gene Ther.* 7:1063-66, 2000) using Fugene 6 reagents (Roche) according to manufacturer's instruction. Twenty-four hours after transfection, the medium was replaced. After 24 hours, virus-containing supernatant were used for retroviral infection. In a "mixed" protocol, the mixture of plasmids for the four factors was transfected into a single dish of Plat-E cells. In a "separate" method, each plasmid was transfected into separate dishes of Plat-E cells. Virus-containing supernatant was mixed prior to transduction. Significantly higher transduction efficiency was observed with the separate method.

Induction of iPS cells with drug selection. The induction of iPS cells was performed as previously described (Takahashi et al. *Cell* 126:663-76, 2006; Okita et al. *Nature* 448:313-17, 2007) with some modifications. Briefly, MEFs, which contained either the Nanog-GFP-IRES-Puro$^r$ reporter or the Fbx15-βgeo reporter, or both, were seeded at 1.3 and $8.0\times10^5$ cells/well in 6-well plates and 100 mm dish, respectively, with SNL feeder cells (McMahon et al. *Cell* 62:1073-85, 1990). The transduced cells were cultivated with ES medium containing LIF (Meiner et al. *Proc. Natl. Acad. Sci. U.S.A.* 93:14041-46. (1996). Selection with G418 (300 g/ml) or puromycin (1.5 μg/ml) was started as indicated. Twenty-five to 30 days after transduction, the number of colonies was recorded. Some colonies were then selected for expansion.

iPS cells induction without drug selection. TTFs were isolated from adult Nanog-reporter mice or adult DsRed-transgenic mice (Vintersten et al. *Genesis* 40:241-46, 2004). Retroviral-containing supernatant was prepared in the separated method. For the four-factor transduction, retrovirus-containing supernatants for Klf4, c-Myc, Oct3/4, Sox2 and DsRed, were mixed with the ratio of 1:1:1:1:4. When the three factors were transduced, retrovirus-containing supernatants for Klf4, Oct3/4, Sox2, Mock, and DsRed were mixed with the ratio of 1:1:1:1:4. With DsRed transgenic mice, the GFP retrovirus was used instead of DsRed. For transfection, TTFs were seeded at $8.0\times10^5$ cells per 100-mm dishes, which did not have feeder cells. TTFs were incubated in the virus/polybrene-containing supernatants for 24 hours. Four days after transduction, TTFs transduced with the three factors were reseeded at $3.5\times10^5$ cells per 100-mm dishes with SNL feeder cells and cultured with ES medium. TTFs transduced with the four factors were re-seeded at $0.5\times10^5$ cells per 100-mm dishes with feeder cells. Thirty to 40 days after transduction, the colonies were selected for expansion.

Characterization of iPS cells. RT-PCR and teratoma formation were performed as previously described. For the chimera experiments, 15-20 iPS cells were injected into BDF1-derived blastocysts, which were then transplanted into the uteri of pseudo-pregnant mice.

Example 22: Establishment of Human iPS Cells from Epithelial Cells with Six Factors Among the nuclear reprogramming factors disclosed herein is a nuclear reprogramming factor comprising one or more gene products from the following genes: Klf4, c-Myc, Oct3/4, Sox2, Nanog, and Lin28 (NCBI accession number NM_145833 (mouse) and NM_024674 (human)). Establishment of induced pluripotent stem cells was performed with combinations of these gene products. The results are shown in TABLE 17.

TABLE 17

Summary of Experiments with Six Factors

| | Day 23 | | Day 29 | | Day 23 | |
|---|---|---|---|---|---|---|
| | non ES like | ES like | non ES like | ES like | non ES like | ES like |
| 6F | 59 | 39 | 167 | 42 | 16 | 27 |
| -L | 49 | 5 | 53 | 14 | | |
| -N | 220 | 11 | 216 | 47 | | |
| -M | 2 | 0 | 15 | 0 | | |
| -O | 0 | 0 | 0 | 0 | | |
| -S | 491 | 0 | 489 | 0 | | |
| -K | 61 | 0 | 51 | 0 | | |
| -KS | 1206 | 0 | 1305 | 0 | | |
| -KO | 0 | 0 | 0 | 0 | | |
| -KM | 0 | 0 | 0 | 0 | 0 | 0 |
| -KN | 51 | 0 | 57 | 0 | | |
| -KL | 28 | 0 | 41 | 0 | | |
| -SO | 0 | 0 | 0 | 0 | | |
| -SM | 0 | 0 | 0 | 0 | | |
| -SN | 188 | 0 | 171 | 0 | | |
| -SL | 112 | 0 | 136 | 0 | | |
| -OM | 0 | 0 | 0 | 0 | | |
| -ON | 0 | 0 | 0 | 0 | | |
| -OL | 0 | 0 | 0 | 0 | | |
| -MN | 3 | 0 | 8 | 0 | | |
| -ML | 0 | 0 | 0 | 0 | | |
| -NL | 98 | 1 | 119 | 9 | 17 | 6 |
| GFP | 0 | 0 | 0 | 0 | | |
| KO | 0 | 0 | 0 | 0 | | |
| KS | 0 | 0 | 0 | 0 | | |

$6\times10^6$ 293 FT cells were plated on 10 cm dish and cultured overnight, and then transfected with 3 μg of pLenti6/UbC-Slc7a1 lentiviral vector together with 9 μg of Virapower packaging mix by Lipofectamine 2000 (Invitrogen). After 24 hours, the culture medium was replaced with a fresh medium. After 20 hours, the culture supernatant was collected and filtrated through 0.45-μm pore-size cellulose acetate filter (Whatman). $5\times10^5$ epithelial cells were prepared on the previous day. To the dish which the culture supernatant was removed from, the aforementioned filtrated culture supernatant containing viruses and 4 μg/ml polybrene (Nacalai Tesque) were added. Then, the cells were cultured for 24 hours.

In addition, $1.0\times10^6$ Plat-E cells were plated on 6 cm dish and cultured. On the next day, the cells were transfected with 9.0 μg of pMX-based retrovirus vector incorporating klf4, c-myc, oct3/4, sox2, nanog and/or Lin-28 by using 27 μl of Fugene6 transfection reagent. After 24 hours, the culture medium was replaced with a fresh medium. On the next day, the culture supernatant of Plat-E cells was collected and filtrated through 0.45-μm pore-size cellulose acetate filter (Whatman). Seven days after lentivirus infection, epithelial cells were plated at $3.0\times10^5$ cells per 6 cm dish again, and the aforementioned culture supernatant containing retrovirus and polybrene were added thereto.

The term "6F" in TABLE 17 refers to the six factors (klf4, c-myc, oct3/4, sox2, nanog and Lin-28), the term "L" refers to Lin-28, the term "N" refers to nanog, the term "M" refers to c-Myc, the term "O" refers to Oct3/4, the term "S" refers to Sox2, and the term "K" refers to Klf4, respectively. The symbol "-" refers to colonies obtained by subtracting from the six factors those factors shown by the term subsequent to the symbol "-". For example, the term "-L" shows the colonies obtained with the remaining five factors other than lin-28, and the term "-KS" shows the colonies obtained with the remaining four factors other than Klf4 and Sox2, respectively.

The numbers in TABLE 17 refer to the number of colonies. The term "non-ES like" refers to shows colonies having a non-ES cell like morphology, and the term "ES like" refers to colonies having an ES like cell morphology.

Two experimental results are shown. The first experiment shows the number of colonies from cells introduced with various combinations of factors 23 days or 29 days after gene introduction and the second experiment shows the number of "6F," "-KM," and "—NL." According to these experimental results, the number of colonies from cells not-introduced with lin-28 such as "-L" was smaller than that of cell transduced with lin-28, suggesting that Lin-28 plays an important role to improve the efficiency of establishment of iPS cells.

Figure 49:
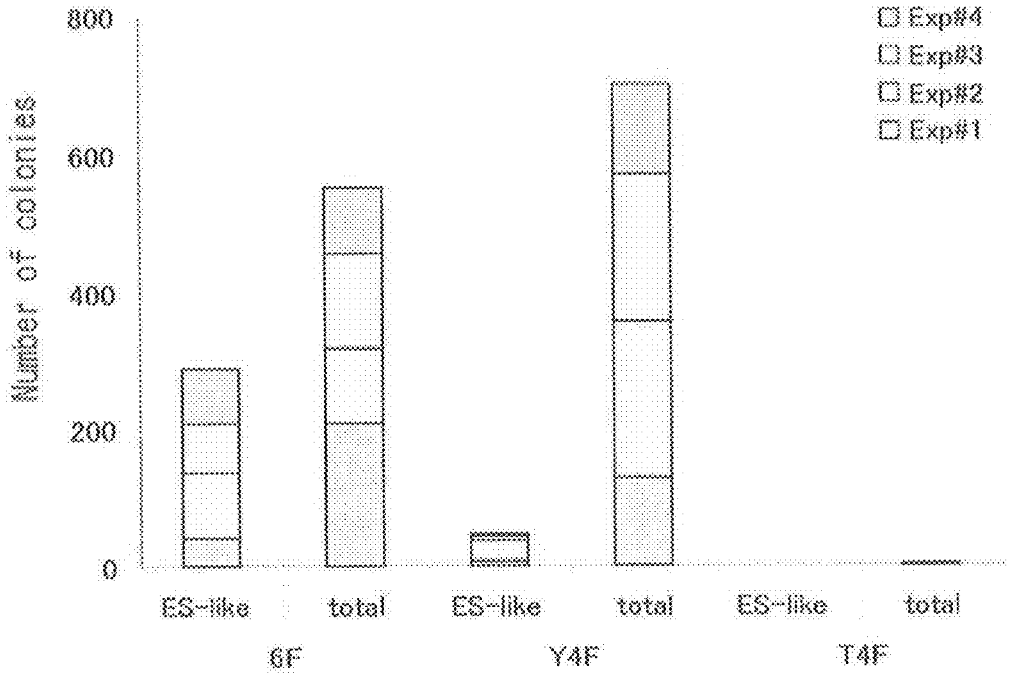
FIG. 49 shows results from experiments using six factors and two different combinations of four factors. The vertical axis shows the number of colonies. The term "6F" refers to the six factors (klf4, c-myc, oct3/4, sox2, nanog and Lin-28), the term "Y4F" refers to the first combination of four factors (klf4, c-myc, oct3/4 and sox2), and the term "T4F" refers to the second combination of four factors (oct3/4, sox2, nanog and Lin-28), respectively. The term "ES like" refers to ES-like cell colony morphologically, and the term "total" shows total number of ES-like cell colonies and non-ES like cell colonies. Exp #1, Exp #2, Exp #3, and Exp #4 show individual experimental results, respectively.
Figure 50:
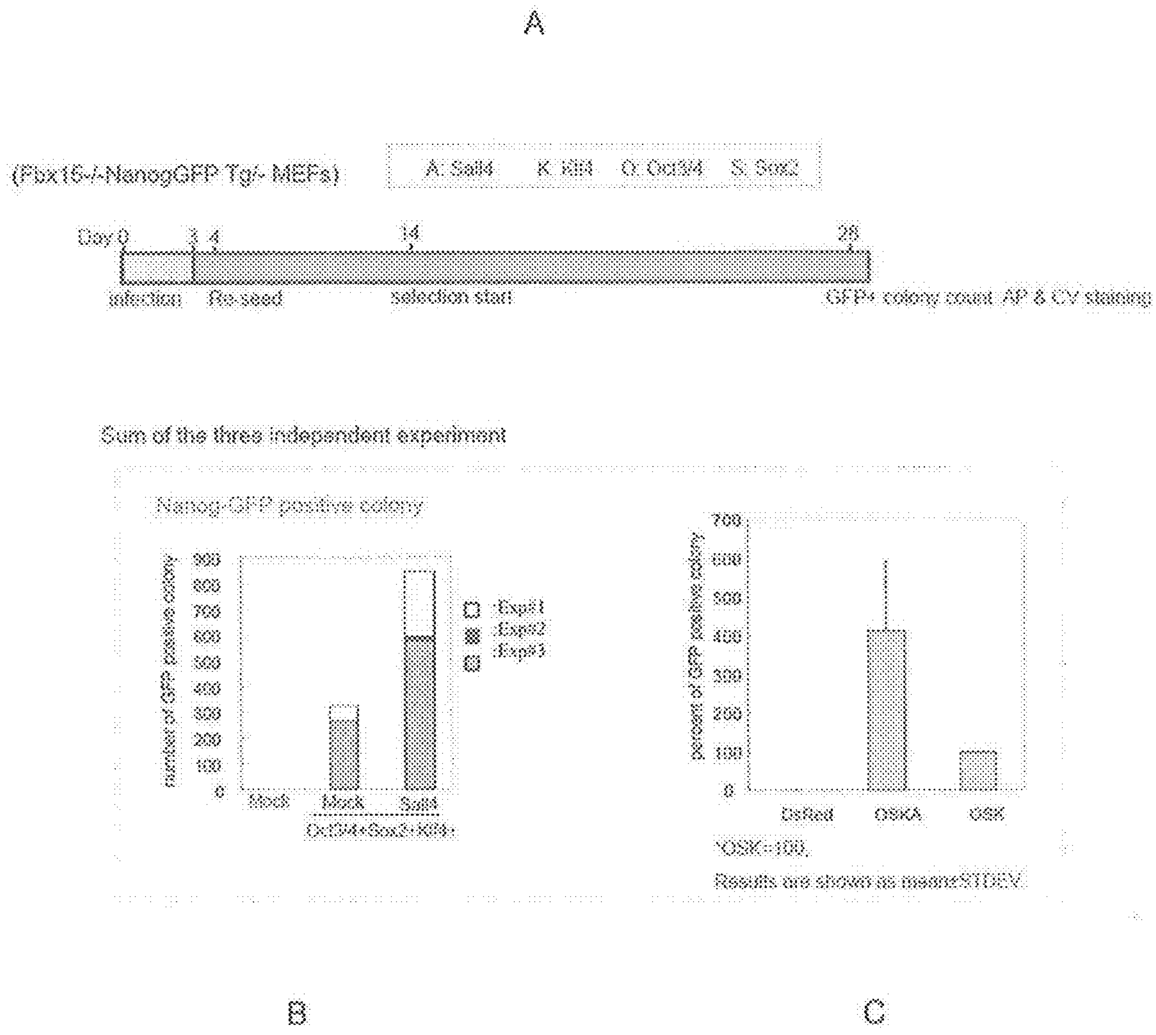
FIG. 50 shows a summary of data from experiments performed with mouse embryonic fibroblasts (MEFs). (A) $1.0\times10^5$ MEF cells obtained from Nanog $GFP^{tg/-}Fbx15^{-/-}$ mouse were seeded on gelatin coated 6 well plates. Next day, four factors (Oct3/4, Klf4, Sox2, c-Myc) or three factors (Oct3/4, Klf4, Sox2) were retrovirally transduced into the cells. After 4 days of the infection, cells were re-seeded 1 to 2 or 1 to 6-ratio on 6 well plates covered with mitomycin C-treated STO cells. Drug selection was started at 14 days or 21 days. At day 28, GFP positive cells were counted and cells were stained for alkaline phosphatase (AP) and crystal violet(CV). (B) Summary of the number of the GFP positive colonies from three independent experiments, Exp. #1, 2, and 3. (C) Percentage of GFP positive colonies from three independent iPS experiments, Exp. #1, 2, and 3.
Figure 51:
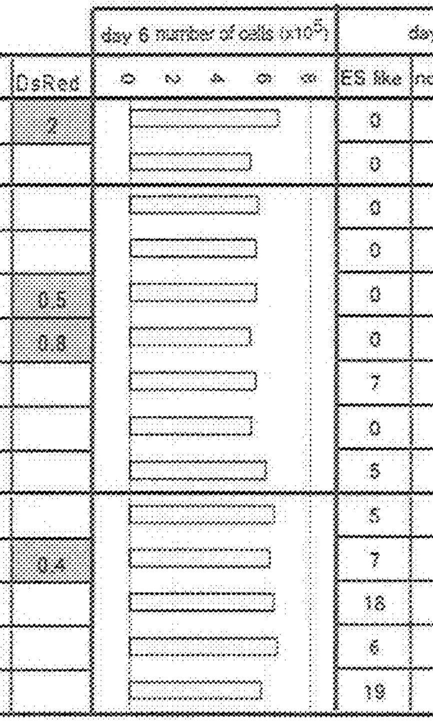
FIG. 51 shows a summary of data from experiments performed with adult human dermal fibroblasts. $1.0\times10^5$ adult HDF cells expressing slc7a were seeded on 6 well plates. Next day, four factors (Oct3/4, Klf4, Sox2, c-Myc) or three factors (Oct3/4, Klf4, Sox2) were retrovirally transduced into the cells. After 6 days of the infection, $5.0\times10^5$ cells were re-seeded on 100 mm plates covered with $1.5\times10^6$ of mitomycin C-treated STO cells. At day 7 the medium was replaced with Primate ES cell medium supplemented with 4 ng/ml bFGF. This figure shows colony numbers at 30 days after infections.
Figure 51:
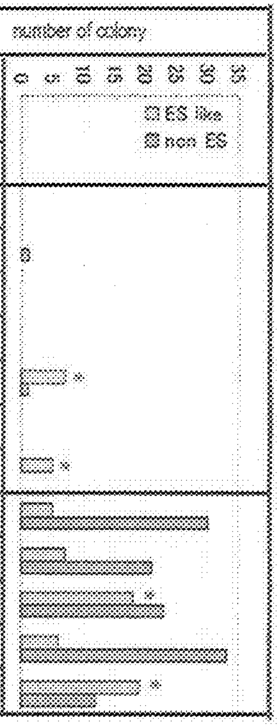

In addition, iPS cell induction experiments were performed with six factors (Klf4, c-Myc, Oct3/4, Sox2, Nanog, and Lin28) and two different combinations of four factors (Klf4, c-Myc, Oct3/4 and Sox2, referred to as Y4F in FIG. 49; and Oct3/4, Sox2, Nanog, and Lin-28, referred to as T4F in FIG. 49). The second combination of four factors, T4F, is the same combination as disclosed in Yu et al. *Science* 318:1917-1920, 2007. In these experiments, use of the six factors and the Y4F combination of four factors generated colonies having a similar morphology as ES-like cell colony, whereas the T4F combination generated no colonies having a similar morphology as ES-like cell colony (FIG. 49).

Example 23: Increased Efficiency of iPS Cell Generation with Sall4

Experiments performed with mouse embryonic fibroblasts and adult human dermal fibroblasts showed that iPS cell induction with three factors (Klf4, Oct3/4, and Sox2) is more efficient when Sall4 is added to the combination, that is when Klf4, Oct3/4, Sox2, and Sall4 are used (FIGS. 50A-C and FIG. 51). More ES like colonies were also observed when Sall4 was added to the four factors (Klf4, Oct3/4, Sox2, and c-Myc) or the three factors (Klf4, Oct3/4, Sox2) under the experimental conditions used. These experiments show that addition of Sall4 to the nuclear reprogramming factor can improve iPS induction efficiency.

Example 24: Improved iPS Cell Generation with Mouse Sall4 and/or Mouse Sall1

In accordance with the method described in Takahashi et al. *Cell* 131:861-872, 2007, 4 factors (Y4F, i.e., OCT3/4, SOX2, KLF4, c-MYC) or 3 factors (Y3F, i.e., OCT3/4, SOX2, KLF4) derived from human, along with mouse Sall4 (mSall4) and/or mouse Sall1 (mSall1) were transduced with retroviruses into adult human dermal fibroblasts (HDFs) expressing mouse ecotropic receptor Slc7a, which was transduced with lentivirus.

Figure 52:
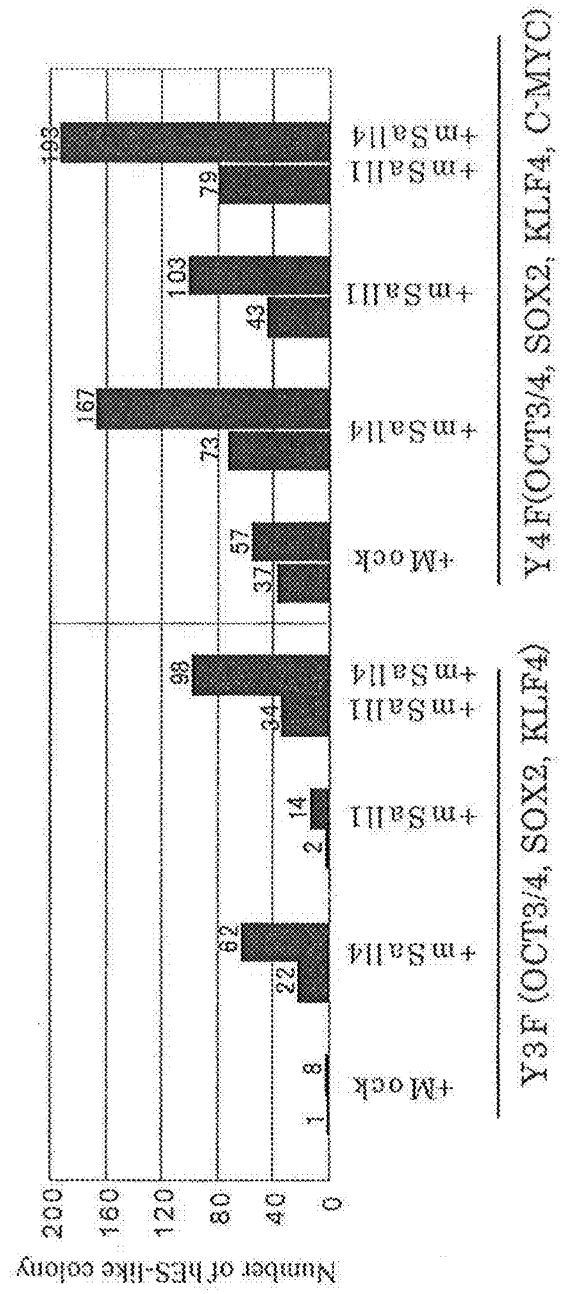
FIG. 52 shows the number of colonies confirmed on the $32^{nd}$ day (d32; left bar) and the $40^{th}$ day (d40; right bar) after the infection in which 4 factors (Y4F, i.e., OCT3/4, SOX2, KLF4, c-MYC) or 3 factors (Y3F, i.e., OCT3/4, SOX2, KLF4) derived from human, and either mouse Sall4 (mSall4), mouse Sall1 (mSall1) or both mSall4 and mSall1 were transduced with retroviruses into adult human dermal fibroblasts (HDFs) expressing Slc7a. "+Mock" shows the group in the case where a retrovirus derived from a vector containing neither mSall4 nor mSall1 together with Y3F or Y4F were transduced; "+mSall4" shows the group in the case where mSall4 together with Y3F or Y4F were transduced; "+mSall1" shows the group in the case where mSall1 together with Y3F or Y4F were transduced; and "+mSall4+mSall1" shows the group in the case where both of mSall4 and mSall1 together with Y3F or Y4F were transduced. The vertical axis shows the number of human ES-like colonies confirmed on a 10 cm culture plate. The same experiment was repeated three times. The total number of colonies of each experiment is shown above each bar of the graph.

On the sixth day after the transduction, HDFs were harvested once. Then, $5\times10^5$ HDFs were plated on $1.5\times10^6$ STO cells treated with mitomycin C. From the next day, HDFs were cultured with the medium for primate ES cells (ReproCELL) containing 4 ng/ml recombinant human bFGF (WAKO). FIG. 52 shows the number of ES-like colonies at the $32^{nd}$ day and the $40^{th}$ day after the infection.

On the $32^{nd}$ day after the infection, the number of colonies in the case where Y3F and Mock were transduced was 1, and the number of colonies in the case where Y4F and Mock were transduced was 37. Whereas, the number of colonies in the case where Y3F and mSall4 were transduced was 22 on the $32^{nd}$ day after infection, and the number of colonies in the case where Y4F and mSall4 were transduced was 73 on the $32^{nd}$ day after infection.

In the case where Y3F and mSall1 were transduced, the number of colonies was 2 on the $32^{nd}$ day after infection, and the number of colonies in the case where Y4F and mSall1 were transduced was 43 on the $32^{nd}$ day after infection. Where mSall1 was transduced together with Y3F or Y4F, the number of colonies on the $32^{nd}$ day after infection was about the same as when only Y3F or Y4F was transduced. Furthermore, in the case where both mSall4 and mSall1 together with Y3F were transduced, the number of colonies was 34 on the $32^{nd}$ day after infection; whereas in the case where both mSall4 and mSall1 together with Y4F were transduced, the number of colonies was 79 on the $32^{nd}$ day after infection.

On the $40^{th}$ day after the infection, the number of colonies in the case where Y3F and Mock were transduced was 8, and the number of colonies in the case where Y4F and Mock were transduced was 57. Whereas, in the case where mSall4 together with Y3F were transduced, the number of colonies was 62 on the $40^{th}$ day after infection, and the number of colonies in the case where Y4F and mSall4 were transduced was 167 on the $40^{th}$ day after infection. In the case where mSall1 together with Y3F were transduced, the number of colonies was 14 on the $40^{th}$ day after infection, and the number of colonies in the case where Y4F together with mSall1 were transduced was 103 on the $40^{th}$ day after infection. Furthermore, in the case where Y3F, mSall4 and mSall1 were transduced together, the number of colonies on the $40^{th}$ day after infection was 98, while the number of colonies on the $40^{th}$ day after infection in the case where Y4F, mSall4 and mSall1 were transduced was 193.

As shown by the above, human ES-like colonies were obtained 20 to 100 times more efficiently in the case where mSall4 or both mSall4 and mSall1, together with Y3F, were transduced. In addition, human ES-like colonies were obtained 2 to 4 times more efficiently in the case where mSall4 or both mSall4 and mSall1, together with Y4F, were transduced.

Example 25: Improved iPS Cell Generation with Mouse Sall4 and/or Mouse Sall1

In accordance with the method described in Takahashi et al. *Cell* 131:861-872, 2007, 4 factors (T4F, i.e., OCT3/4, SOX2, NANOG, LIN-28) or 3 factors (T3F, i.e., OCT3/4, SOX2, NANOG) derived from human, along with and mouse Sall4 (mSall4), mouse Sall1 (mSall1) or both mSall4 and mSall1 were transduced with retroviruses into adult human dermal fibroblasts (HDFs) expressing mouse ecotropic receptor Slc7a, which was transduced with lentivirus.

Figure 53:
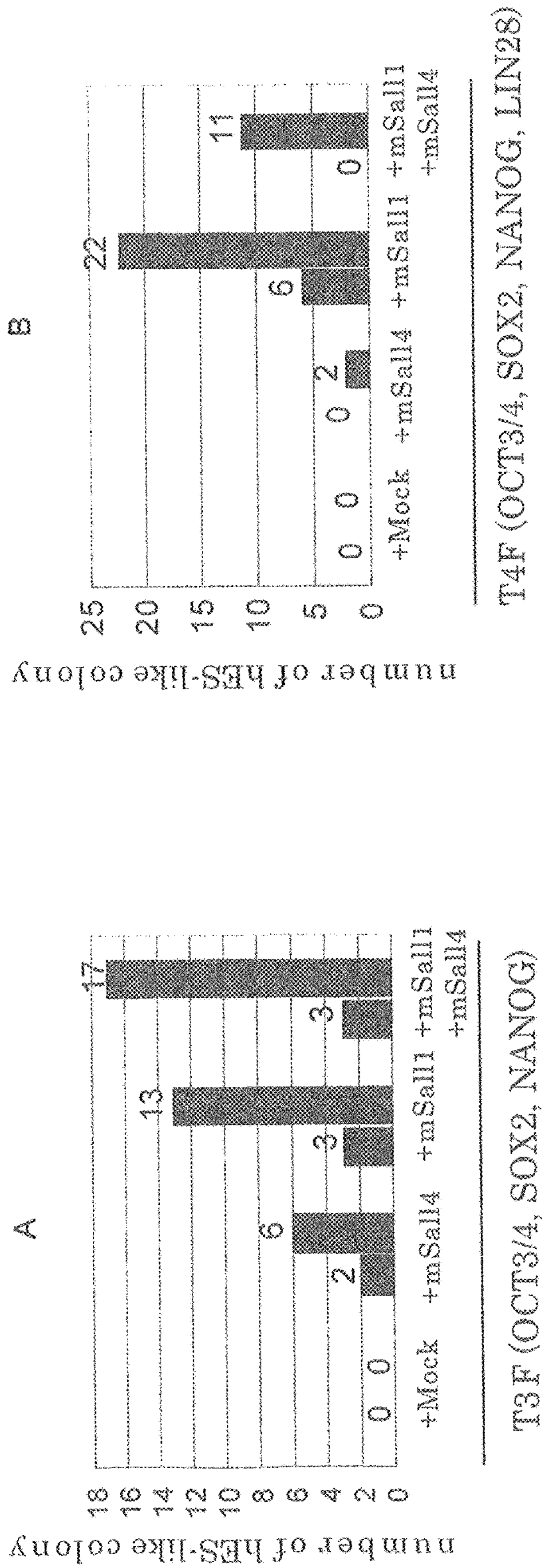
FIG. 53 shows the number of colonies confirmed on the $32^{nd}$ day (d32; left bar) and the $40^{th}$ day (d40; right bar) after the infection in which (A) 3 factors (T3F, i.e., OCT3/4, SOX2, NANOG) or (B) 4 factors (T4F, i.e, OCT3/4, SOX2, NANOG, LIN-28) derived from human, and either mouse Sall4 (mSall4), mouse Sall1 (mSall1) or both mSall4 and mSall1 were transduced with retroviruses into adult human dermal fibroblasts (HDFs) expressing Slc7a. "+Mock" shows the group in the case where a retrovirus derived from a vector containing neither mSall4 nor mSall1 together with T3F or T4F were transduced; "+mSall4" shows the group in the case where mSall4 together with T3F or T4F were transduced; "+mSall1" shows the group in the case where mSall1 together with T3F or T4F were transduced; and "+mSall4+mSall1" shows the group in the case where both mSall4 and mSall1 together with T3F or T4F were transduced. Vertical axes show the number of human ES-like colonies confirmed on a 10 cm culture plate. The same experiment was repeated twice. The total number of colonies of each experiment is shown above each bar of the graph.

On the sixth day after the introduction, HDFs were harvested once. Then, $5\times10^5$ HDFs were plated on $1.5\times10^6$ STO cells treated with mitomycin C. On the seventh day after the incubation, HDFs were cultured with the medium for primate ES cells (ReproCELL) containing 4 ng/ml recombinant human bFGF (WAKO). FIGS. 53A-B show the number of ES-like colonies at the $32^{nd}$ day and the $40^{th}$ day after the infection.

On the $32^{nd}$ day after the infection, the number of colonies in the case where T3F and Mock or T4F and Mock were transduced was 0. In the case where mSall4 together with T3F were transduced, the number of colonies was 2 on the $32^{nd}$ day after infection. However, on the $32^{nd}$ day after infection no ES-like colony could be confirmed in the case where T4F and mSall4 were transduced.

In the case where mSall1 together with T3F were transduced, the number of colonies was 3 on the $32^{nd}$ day after infection, and the number of colonies in the case where T4F and mSall1 were transduced was 6 on the $32^{nd}$ day after infection. Furthermore, in the case where both mSall4 and mSall1 together with T3F were transduced, the number of colonies was 3 on the $32^{nd}$ day after infection. However, on the $32^{nd}$ day after infection no ES-like colony could be confirmed in the case where T4F, mSall4 and mSall1 were transduced together.

On the $40^{th}$ day after the infection, the number of colonies in the case where T3F and Mock or T4F and Mock were transduced was 0. Whereas, in the case where mSall4 together with T3F were transduced, the number of colonies on the $40^{th}$ day after infection was 6, and the number of colonies on the $40^{th}$ day after infection in the case where T4F and mSall4 were transduced was 2.

In the case where mSall1 together with T3F were transduced, the number of colonies on the $40^{th}$ day after infection was 13, and the number of colonies in the case where T4F and mSall1 were transduced together was 22 on the $40^{th}$ day after infection. Furthermore, in the case where both mSall4 and mSall1 together with T3F were transduced, the number of colonies on the $40^{th}$ day after infection was 17. In the case where both mSall4 and mSall1 together with T4F were transduced, the number of colonies on the $40^{th}$ day after infection was 11.

In the case where T3F or T4F were transduced to establish iPS cells, it was observed that the addition of mSall4 had an improvement effect on the formation of human ES-like cell colonies. Furthermore, the addition of mSall1 improved the effect on the formation of human ES-like cell colonies more efficiently than mSall4. As shown by the above, the addition of mSall1 greatly enhanced the efficiency of human ES-like cell colony formation, and had a greater improvement effect on the formation of human ES-like cell colonies when used in combination with T3F or T4F than the addition of mSall4 did.

Furthermore, it was shown that the efficiency of human ES-like cell colony formation was much improved in the case where both mSall4 and mSall1 together with T3F or T4F were transduced.

Example 26: Improved iPS Cell Generation with Human Sall4

In accordance with the method described in Takahashi et al. *Cell* 131:861-872, 2007, adult human dermal fibroblasts (HDFs) expressing mouse ecotropic receptor Slc7a which was transduced with lentivirus were prepared. On the next day, 4 factors (Y4F, i.e., OCT3/4, SOX2, KLF4, c-MYC) or 3 factors (Y3F, i.e., OCT3/4, SOX2, KLF4) derived from human, and human SALL4 (hSALL4) were transduced with retroviruses into HDFs.

Figure 54:
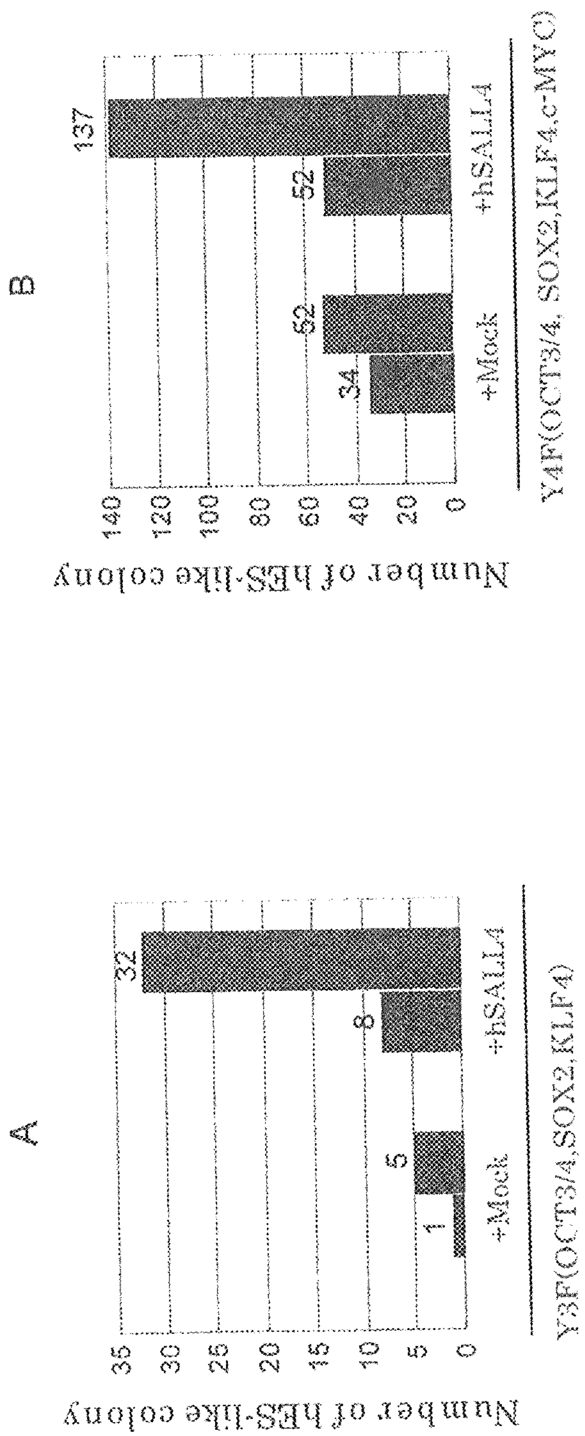
FIG. 54 shows the number of colonies confirmed on the $32^{nd}$ day (d32; left bar) and the $40^{th}$ day (d40; right bar) after the infection in which (A) 3 factors (Y3F, i.e., OCT3/4, SOX2, KLF4) or (B) 4 factors (Y4F, i.e., OCT3/4, SOX2, KLF4, c-MYC) derived from human, and human SALL4 (hSALL4) were transduced with retroviruses into adult human dermal fibroblasts (HDFs) expressing Slc7a. "+Mock" shows the group in the case where a retrovirus derived from a vector containing no hSALL4 together with Y3F or Y4F were transduced; "+hSALL4" shows the group in the case where hSALL4 together with Y3F or Y4F were transduced. Vertical axes show the number of human ES like colonies confirmed on a 10 cm culture plate. The same experiment was repeated twice or three times. The total number of colonies of each experiment is shown above each bar of the graph.

On the sixth day after the transduction, HDFs were harvested once. Then, $5\times10^5$ HDF cells were plated on $1.5\times10^6$ STO cells treated with mitomycin C. From the next day, HDFs were cultured with the medium for primate ES cells (ReproCELL) containing 4 ng/ml recombinant human bFGF (WAKO). FIGS. 54A-B show the number of ES-like colonies at the $32^{nd}$ day and the $40^{th}$ day after the infection.

On the $32^{nd}$ day after the infection, the number of colonies in the case where Y3F and Mock were transduced was 1, and the number of colonies in the case where Y4F and Mock were transduced was 34. Whereas, in the case where hSALL4 together with Y3F were transduced, the number of colonies was 8 on the $32^{nd}$ day after infection, and the number of colonies in the case where Y4F and hSALL4 were transduced was 52 on the $32^{nd}$ day after infection.

On the $40^{th}$ day after the infection, the number of colonies in the case where Y3F and Mock were transduced was 5, and the number of colonies in the case where Y4F and Mock were transduced was 52. Whereas, in the case where hSALL4 together with Y3F were transduced, the number of colonies was 32 on the $40^{th}$ day after infection, and the number of colonies in the case where Y4F and hSALL4 were transduced was 137 on the $40^{th}$ day after infection.

As shown by the above, human ES-like colonies were obtained 6 to 8 times more efficiently in the case where hSALL4 together with Y3F were transduced. In addition, the formation of human ES-like colonies was improved 1.5 to 2.5 times more efficiently in the case where hSALL4 together with Y4F were transduced.

Example 27: Effect of L-Myc (a) Nuclear Reprogramming by Transduction of 4 Genes (Oct3/4, Klf4, Sox2, and L-Myc)

(1) Effect on Establishment of Human iPS Cells

Figure 55:
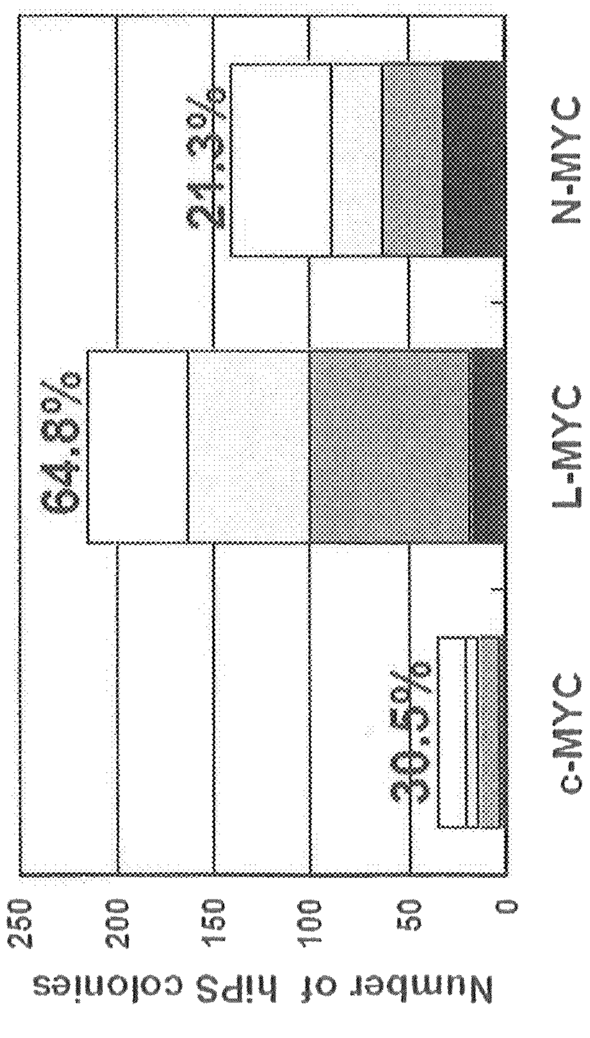
FIG. 55 is a graph which shows the result of counting of the colony number of human iPS cells which were established by transducing 4 genes (OCT3/4, KLF4, and SOX2 and any one of c-MYC, L-MYC or N-MYC) into aHDF-Slc7a1 by retrovirus. The values on each graph show the ratio of the iPS colony number to total colony number.

Adult human dermal fibroblasts (aHDF-Slc7a1) expressing mouse ecotropic virus receptor (Slc7a1) were prepared in accordance with the method described in Takahashi et al. *Cell* 131:861-872, 2007. The aHDF-Slc7a1 cells were plated at $3\times10^5$ cells/60 mm dish. On the next day, 4 genes derived from human (OCT3/4, KLF4 and SOX2 plus either L-MYC1 (hereinafter referred to as L-MYC), c-MYC or N-MYC) were transduced by retrovirus in accordance with the method described in Takahashi et al. *Cell* 131:861-872, 2007. On the sixth day after virus infection, the cells were recovered, and were plated again on MSTO cells at $5\times10^5$ cells/100 mm dish. From the next date, the cells were cultured in a medium obtained by adding 4 ng/ml recombinant human bFGF (WAKO) to the medium for primate ES cells (ReproCELL). On the $37^{th}$ day after retrovirus infection, the number of human iPS colonies (ES-like colonies) which were appearing was counted. TABLE 18 and FIG. 55 show the results of four experiments. FIG. 55 is a graph of the results of TABLE 18. The values on the graph show the ratio of the iPS colony number to the total colony number.

TABLE 18

< Number of hiPS colonies >

| | | ES-like | Total | % |
|---|---|---|---|---|
| h32 | c-MYC | 3 | 38 | 7.89 |
| ■ | L-MYC | 18 | 35 | 51.4 |
| | N-MYC | 32 | 431 | 7.42 |
| h44 | c-MYC | 11 | 14 | 78.6 |
| ▣ | L-MYC | 82 | 100 | 82.0 |
| | N-MYC | 31 | 63 | 49.2 |
| h51 | c-MYC | 7 | 69 | 10.1 |
| □ | L-MYC | 62 | 124 | 50.0 |
| | N-MYC | 25 | 225 | 11.1 |
| h58 | c-MYC | 14 | 55 | 25.5 |
| □ | L-MYC | 53 | 70 | 75.7 |
| | N-MYC | 52 | 298 | 17.4 |

As shown in TABLE 18 and FIG. 55, the efficacy of establishment of iPS colonies was increased 6 times by using L-MYC, as compared with the case of using c-Myc. Also, the ratio of the iPS colony (ES-like colony) number to the total colony number was increased 2 times by using L-MYC, as compared with the case of using c-MYC. Further, the efficacy of establishment of iPS colony was increased by using N-MYC as compared with the case of using c-MYC, although the increase of the efficacy was lower than that in the case of using L-MYC.

It has been reported that there is no difference in efficacy between c-MYC and L-MYC in the establishment of iPS cells derived from mouse fibroblast cells (MEF) (Nakagawa et al. *Nature Biotechnology* 26 (1): 101-106, 2008). As mentioned above, it has been revealed that the efficacy of establishment of human iPS cells is remarkably increased by using L-MYC in place of c-MYC.

(2) In Vitro Differentiation Induction

Figure 56:
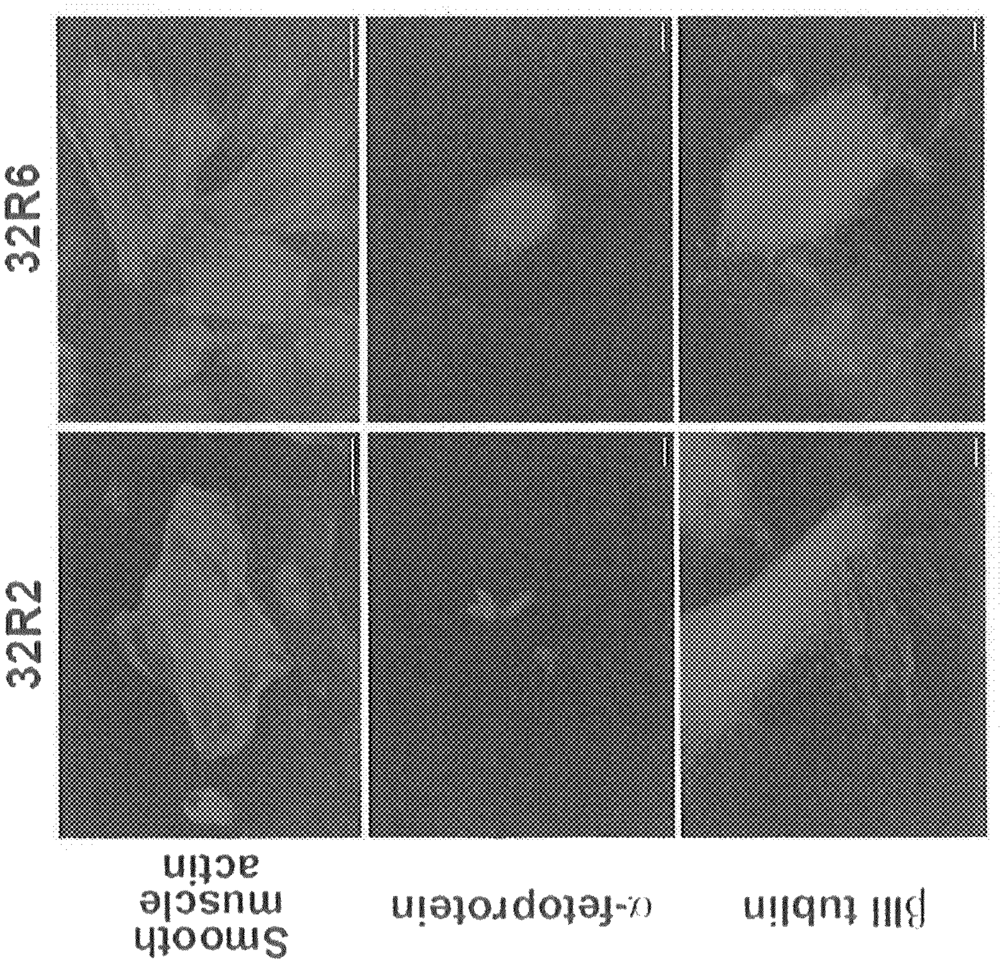
FIG. 56 is a photograph which shows the result of staining of cells differentiated from human iPS cells using an anti-smooth muscle actin antibody, anti-α-fetoprotein antibody or anti-βIII-tubulin antibody. It was confirmed that the human iPS cells (32R2 and 32R6) which were established by transducing 4 genes (OCT3/4, SOX2, KLF4, and L-MYC) into aHDF-Slc7a1 by retrovirus have an ability to differentiate into three germ layers.
Figure 57:
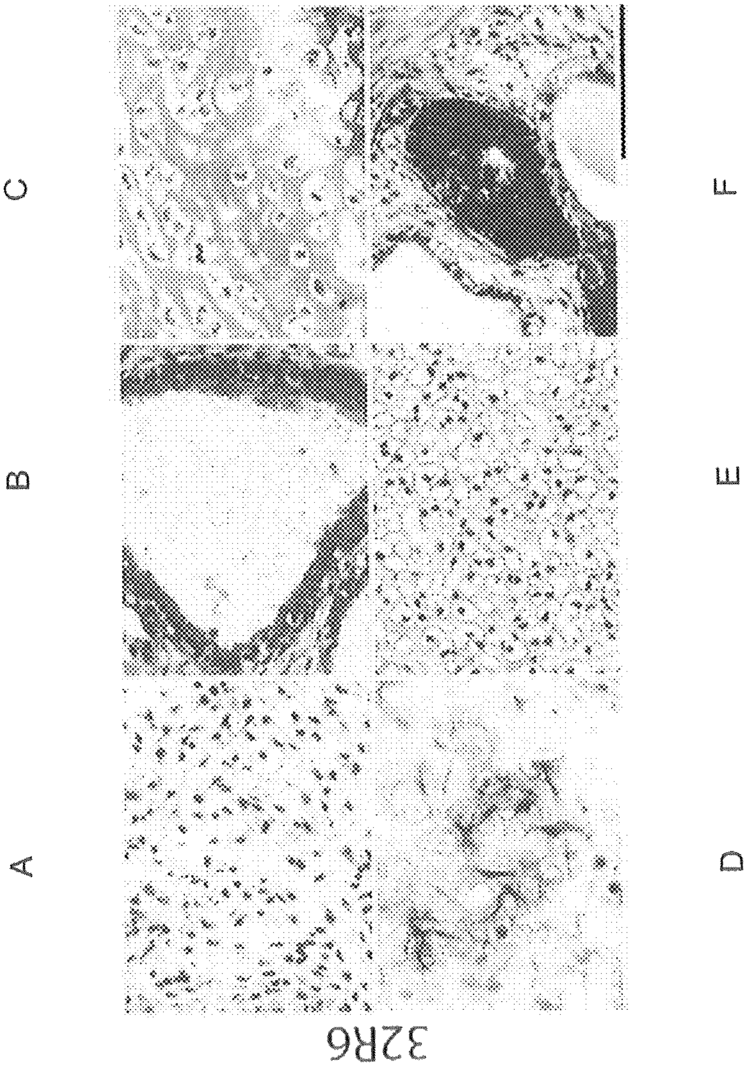
FIG. 57 shows tissue-stained images (hematoxylin-eosin staining) of teratomas which were obtained by injecting the human iPS cell (32R6) which was established by transduction of 4 genes (OCT3/4, SOX2, KLF4, and L-MYC) into a testis of SCID mouse. The upper row of images shows the tissue image of nerve tissue (A), bowel-like tissue (B), and cartilage tissue (C), respectively, from the left. The lower row of images shows the tissue image of hair tissue (D), adipose tissue (E), and pigment tissue (F), respectively, from the left.

Human iPS cells (32R2, 32R6) which were established by transduction of 4 genes (OCT3/4, KLF4, SOX2, and L-MYC) were plated on a low-binding dish, and embryoid bodies (EB) were formed on 100 mm dish in accordance with the method described in Takahashi et al. *Cell* 131:861-872, 2007. After culturing for 2 weeks, the cells were stained using an antibody against each of α-fetoprotein (R&D systems) which is a differentiation marker for endodermal cells, smooth muscle actin (DAKO) which is a differentiation marker for mesodermal cells, and βIII-tubulin (Chemicon) which is a differentiation marker for ectodermal cells. The results are shown in FIG. 56. The expression of each marker was confirmed by staining. It was confirmed that the established human iPS cells have an ability to differentiate into three germ layers.

(3) Teratoma Forming Ability

Human iPS cells (32R6) which were established by transduction of 4 genes (OCT3/4, KLF4, SOX2, and L-MYC) were cultured in the medium for primate ES cells (ReproCELL) containing recombinant human bFGF (4 ng/ml) and Rho kinase inhibitor Y-27632 (10 μM). After 1 hour, the cells were collected by treatment with collagen IV. Then, the cells were centrifuged and collected, and were suspended in DMEM/F12 containing Y-27632 (10 μM). A quarter of the confluent cells on 100 mm dish was injected into testis of SCID mouse. After two to three months, the tumor was cut into pieces and was fixed in PBS(−) containing 4% formaldehyde. Paraffin-embedded tissue was sliced and was stained with hematoxylin-eosin. The results are shown in FIGS. 57A-F. Histogenetically, the tumor is composed of several types of cells. Nerve tissues, bowel-like tissue, cartilage tissue, hair tissue, adipose cell and pigment tissue were observed. Thus, pluripotential ability of the iPS cell was demonstrated.

(4) Effect on Tumorigenesis of Chimera Mouse

MEFs (MEF-Ng) were isolated from a mouse having Nanog reporter which was prepared by inserting EGFP gene and puromycin-resistance gene into Nanog locus (Okita et al. *Nature* 448:313-17, 2007). Similarly, MEFs (MEF-Fbx) were isolated from a mouse having Fbx15 reporter which was prepared by inserting β-geo gene into Fbx15 locus (Takahashi et al. *Cell* 126:663-676, 2006). Four genes (Oct3/4, Klf4, Sox2, and L-Myc) were transduced into these MEFs by retrovirus. MEF-Ng was selected by puromycin, and MEF-Fbx was selected by G418. Thus, iPS cells, each of which is referred to as Nanog-iPS and Fbx-iPS, were established. These iPS cells were transplanted into blastocyst of C57BL/6 mouse to create a chimera mouse. The tumorigenesis in the chimera mouse and F1 mouse was evaluated. As a result, the mice are currently surviving for the period shown in TABLE 19, below, and no tumorgenesis was observed in any surviving mice.

TABLE 19

Summary of Tumorigenesis in Chimera Mice

| Mouse Type | Surviving Mice/Total Number of Mice | Days Surviving |
|---|---|---|
| Chimera Fbx-iPS | 19/19 | 349 |
| Chimera Nanog-iPS | 15/16 | 363 |
| F1 Nanog-iPS | 1/1 | 255 |
| F1 Nanog-iPS | 3/3 | 181 |
| F1 Nanog-iPS | 1/1 | 132 |
| Chimera Nanog-iPS | 30/30 | 63 |
| Chimera Nanog-iPS | 12/14 | 62 |

In case of using iPS cell which was obtained by reprogramming with 4 genes (Oct3/4, Klf4, Sox2, and c-Myc), 6 chimera mice among 37 mice died due to tumor within 100 days after birth (Nakagawa et al. *Nature Biotechnology* 26 (1): 101-106, 2008). On the other hand, it was revealed that, when L-Myc was used in place of c-Myc as mentioned above, the survival time was increased and the tumorigenesis was significantly decreased.

(B) Nuclear Reprogramming by Transduction of 3 Genes (Oct3/4, Klf4, and L-Myc)

(1) Formation of iPS Colony

Establishment of iPS cells was attempted by transduction of 3 genes (Oct3/4, Klf4, L-Myc) in accordance with the method described in Nakagawa et al. *Nature Biotechnology* 26 (1): 101-106, 2008. The MEF-Ng described in (A)(4) above were plated on gelatin-coated 6-well culture plates at $1.3\times10^5$ cells/well. 24 hours later, three mouse-derived genes (Oct3/4, Klf4, and L-Myc) were transduced by retrovirus.

Figure 58:
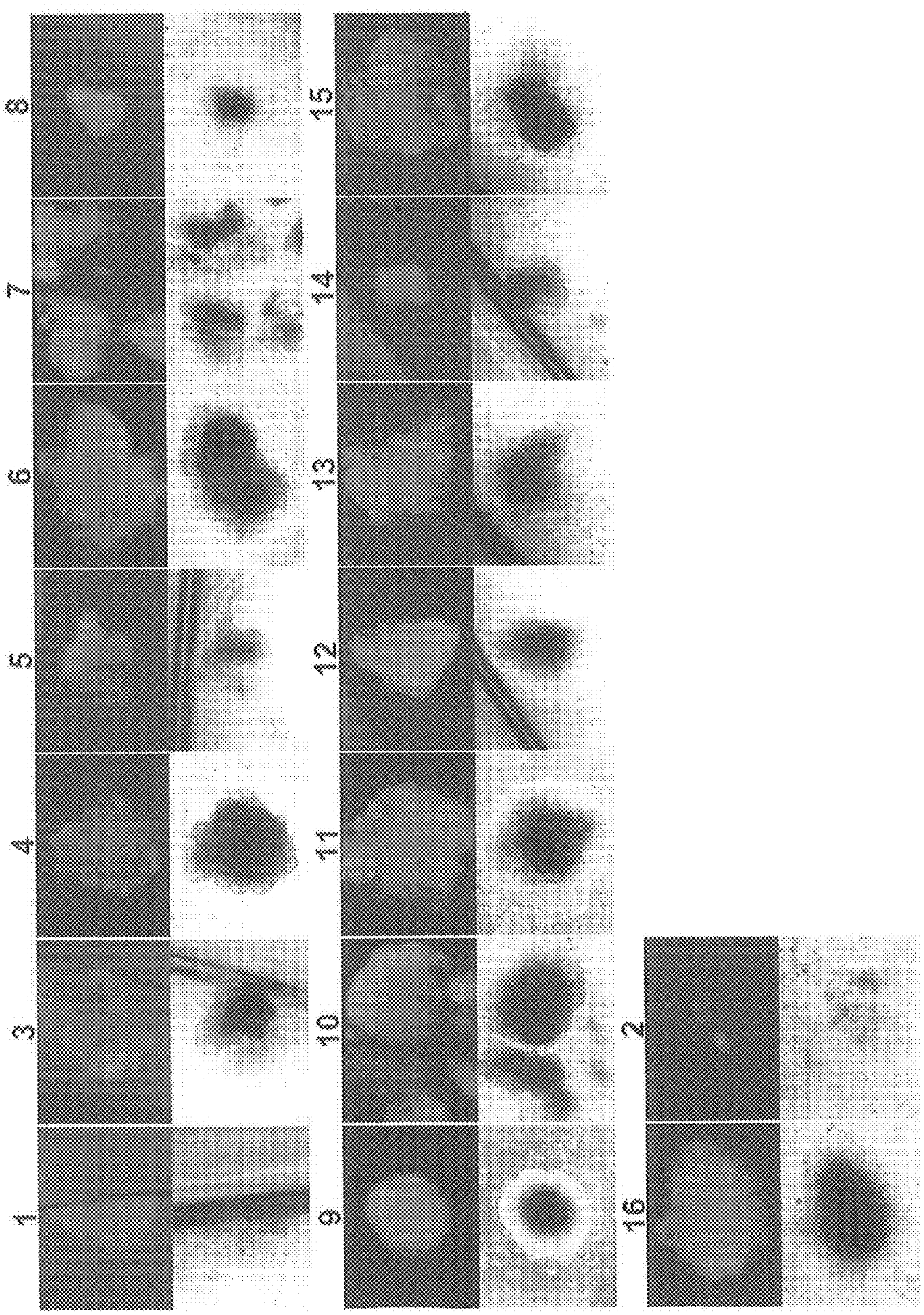
FIG. 58 is a photograph which shows the morphology of sixteen GFP-positive colonies (iPS-MEF-Ng-443-3) which were obtained by transducing 3 genes (Oct3/4, Klf4, and L-Myc) into MEF-Ng by retrovirus. The upper row of images shows GFP-positive colonies, and the lower row of images shows phase-contrast images.
Figure 59:
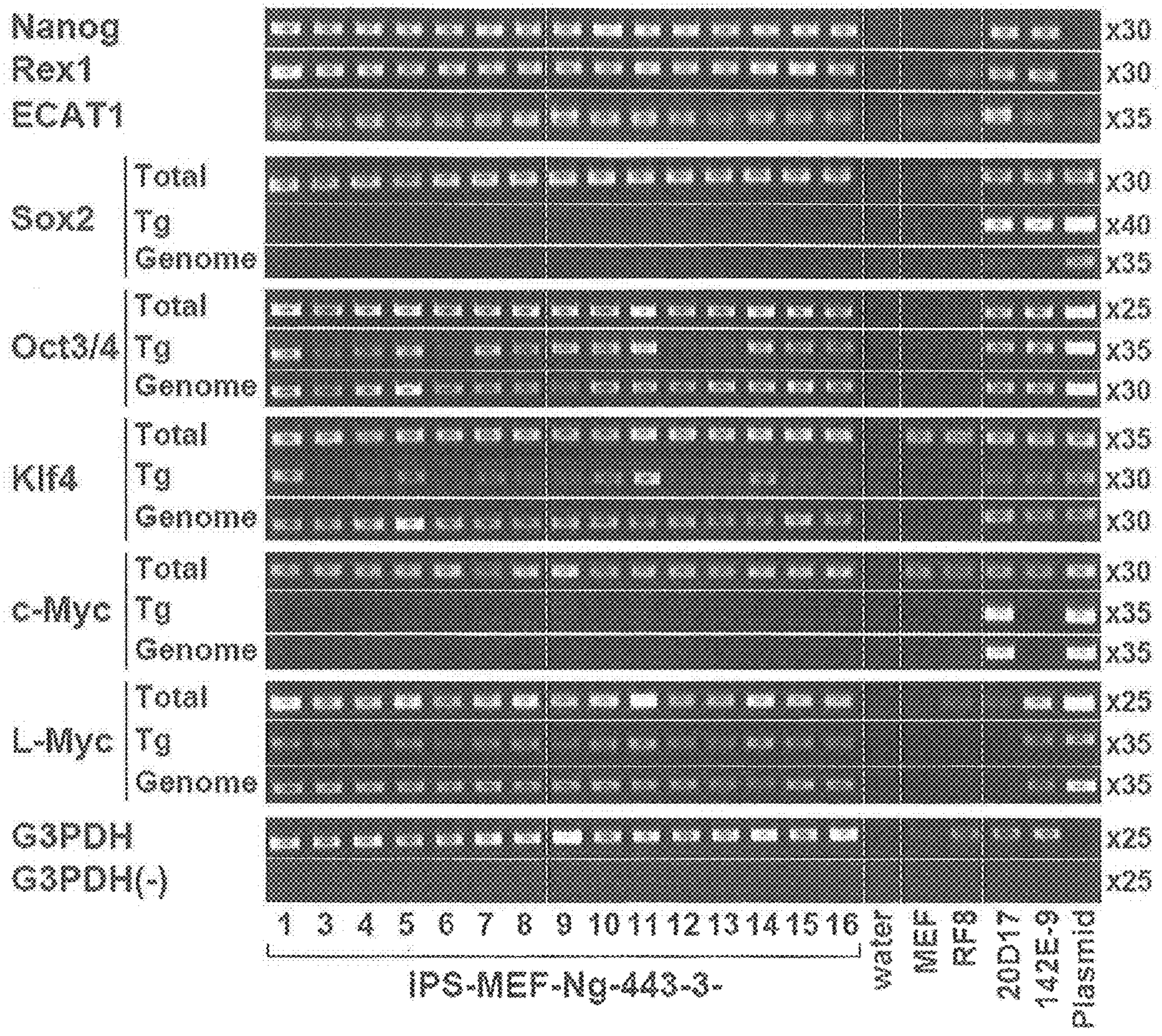
FIG. 59 is a photograph which shows the result of RT-PCR and genomic PCR using a clone derived from a GFP-positive colony (iPS-MEF-Ng-443-3). "Total" shows the result of detection of expression of endogenous gene and retrovirus-derived gene using specific primers for each factor. "Tg" shows the result of detection of expression of retrovirus-derived gene using specific primers for each factor. "Genome" shows the result of detection of presence of retrovirus-derived gene integrated into the genome DNA using specific primers for each factor. The numbers on the right side of the photograph indicate the cycle number of PCR. In the figure, "RF8" shows the result of the similar experiment using ES cell as a control, "20D17" shows the result of the similar experiment using Nanog-iPS (Okita et al. *Nature* 448:313-17, 2007), and "142E-9" shows the result of the similar experiment using iPS cell (Fbx-iPS) which was obtained by transducing 4 genes (Oct3/4, Klf4, L-Myc, and Sox2) into MEF-Fbx. In the figure, "Plasmid" shows the result obtained by using plasmid of each factor (pMXs-Sox2, pMXs-Oct3/4, pMXs-Klf4, pMXs-c-Myc, and pMXs-L-Myc).

On the fourth day after virus infection, the cells were recovered, and plated again on MSTO cells at $1.5\times10^5$ cells/6-well plate. From the next date, the cells were cultured in a culture medium for ES cells (which was obtained by adding, to DMEM (Nacarai tesque), 15% fetal bovine serum, 2 mM L-glutamine (Invitrogen), 100 μM non-essential amino acids (Invitrogen), 100 μM 2-mercaptoethanol (Invitrogen), 50 U/mL penicillin (Invitrogen) and 50 mg/mL streptomycin (Invitrogen)) supplemented with LIF. On the $46^{th}$ day after virus infection, GFP positive colonies were picked up (iPS-MEF-Ng-443-3 clone). The photograph of the 16 picked-up cells is shown in FIG. 58. All the cells were GFP-positive iPS colonies. Using these GFP-positive iPS colony-derived clones, RT-PCR and genomic PCR were carried out to analyze the gene expression. The results are shown in FIG. 59. Nanog, Rex1 and ECAT1, which are marker genes for ES cells, were expressed in all the clones. Also, the three transduced genes (Oct3/4, Klf4, L-Myc) were integrated into the genome in all of the iPS colonies which were examined. In some clones, the expression of mRNA was not detected, possibly due to silencing.

(2) In Vitro Differentiation Induction

Figure 60:
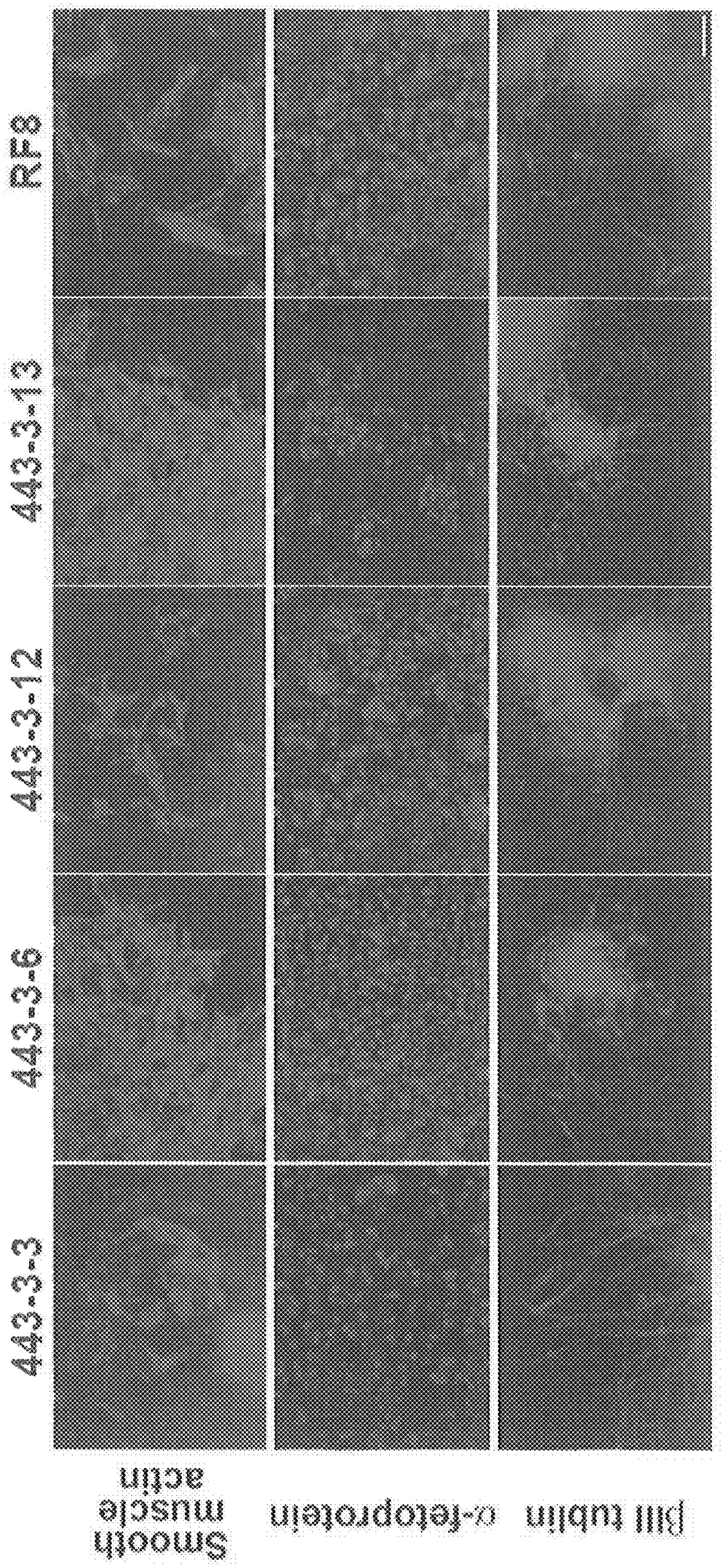
FIG. 60 is a photograph which shows the result of staining of cells differentiated from mouse iPS cells using an anti-smooth muscle actin antibody, anti-α-fetoprotein antibody or anti-βIII-tubulin antibody. It was confirmed that the mouse iPS cells (443-3-3, 443-3-6, 443-3-12, and 443-3-13) which were established by transduction of 3 genes (Oct3/4, Klf4 and L-Myc) have an ability to differentiate into three germ layers. RF8 is a control ES cell.

The four clones (IPS-MEF-Ng-443-3-3, iPS-MEF-Ng-443-3-6, iPS-MEF-Ng-443-3-12, and iPS-MEF-Ng-443-3-13) which were established in (1) above, were plated on a low-binding dish at $2\times10^6$ cells/6-well plate to form embryoid bodies (EB). The cells were cultured for 2 weeks in the culture medium for ES cells, and were then stained using an antibody against each of α-fetoprotein (R&D systems) which is a differentiation marker for endodermal cells, smooth muscle actin (DAKO) which is a differentiation marker for mesodermal cells, and βIII-tubulin (Chemicon) which is a differentiation marker for ectodermal cells. The results are shown in FIG. 60. The expression of each marker was confirmed by staining. It was confirmed that the established mouse iPS cells have an ability to differentiate into three germ layers.

(3) Teratoma Forming Ability

Figure 61:
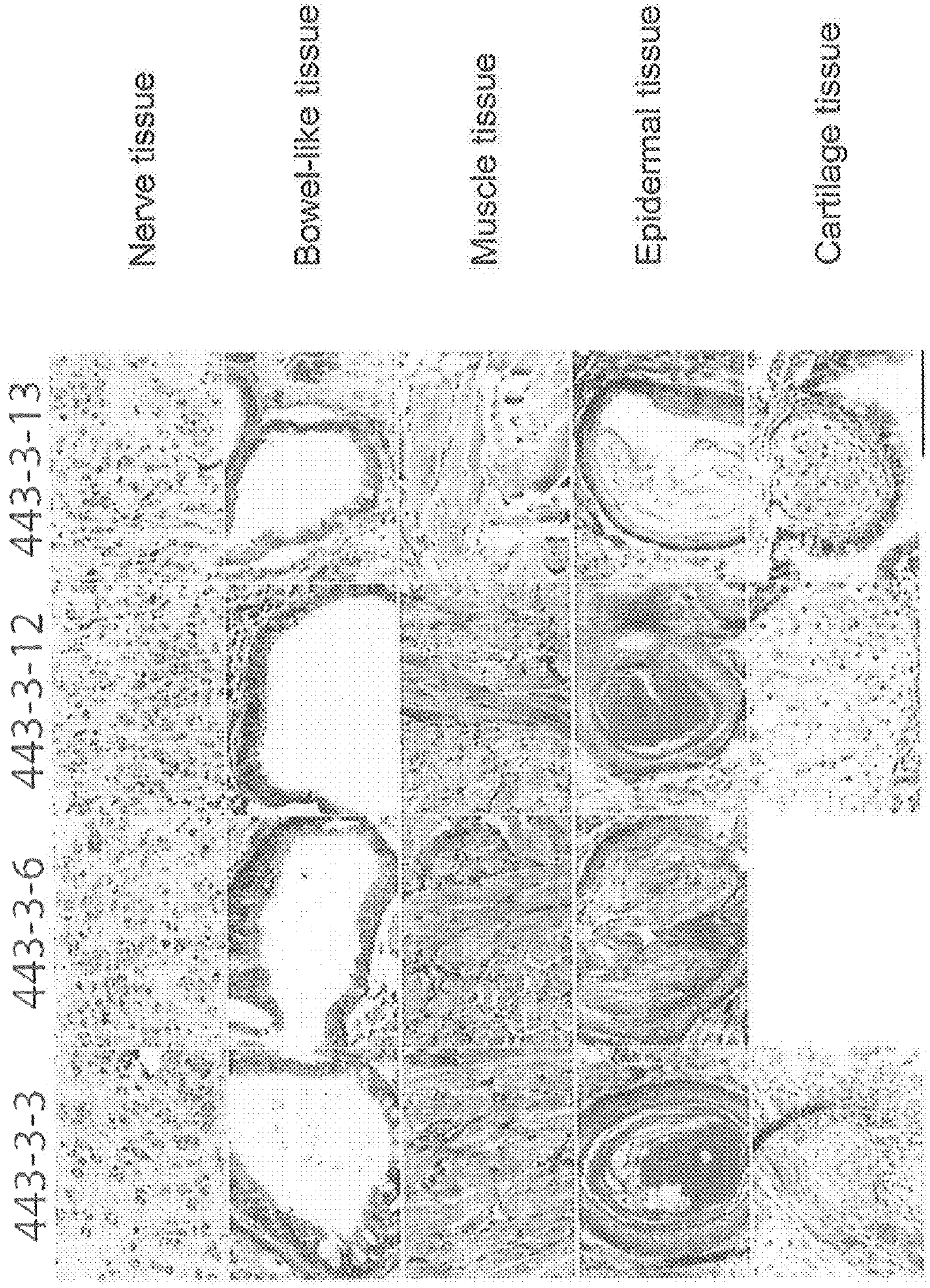
FIG. 61 is a tissue-stained image (hematoxylin-eosin staining) of teratoma which was obtained by subcutaneously injecting the mouse iPS cells (443-3-3, 443-3-6, 443-3-12, and 443-3-13) which were established by transduction of 3 genes (Oct3/4, Klf4, and L-Myc) into a nude mouse. The figure shows the tissue image of nerve tissue, bowel-like tissue, muscle tissue, epidermal tissue and cartilage tissue, respectively, from the top.

The four clones (iPS-MEF-Ng-443-3-3, iPS-MEF-Ng-443-3-6, iPS-MEF-Ng-443-3-12, iPS-MEF-Ng-443-3-13) which were established in (1) above, were subcutaneously injected into a nude mouse, respectively. After 4 weeks, teratoma formation was observed in all the cases. Histogenetically, the tumor is composed of several types of cells. Nerve tissues, bowel-like tissue, muscle tissue, epidermal tissue and cartilage tissue were observed (FIG. 61). Thus, pluripotential ability of the iPS cell was demonstrated.

Example 28: Effect of L-MYC and LIN28 on Induction of Human iPS Cells

Adult human dermal fibroblasts (aHDF-Slc7a1) expressing mouse ecotropic virus receptor (Slc7a1) were prepared in accordance with the method described in Takahashi et al. *Cell* 131:861-872, 2007. The aHDF-Slc7a1 cells were plated at $3\times10^5$ cells/60 mm dish. On the next day, the following human-derived 3 genes, 4 genes or 5 genes were transduced by retrovirus in accordance with the method described in Takahashi et al. *Cell* 131:861-872, 2007.

1. SOX2, OCT3/4, KLF4
2. SOX2, OCT3/4, KLF4, c-MYC
3. SOX2, OCT3/4, KLF4, L-MYC
4. SOX2, OCT3/4, KLF4, LIN28
5. SOX2, OCT3/4, KLF4, c-MYC, LIN28
6. SOX2, OCT3/4, KLF4, L-MYC, LIN28.

On the sixth day after virus infection, the cells were recovered, and were plated again on MSTO cells at $5\times10^5$ cells/100 mm dish. From the next date, the cells were cultured in a medium obtained by adding 4 ng/ml recombinant human bFGF (WAKO) to a medium for primate ES cells (ReproCELL).

Figure 62:
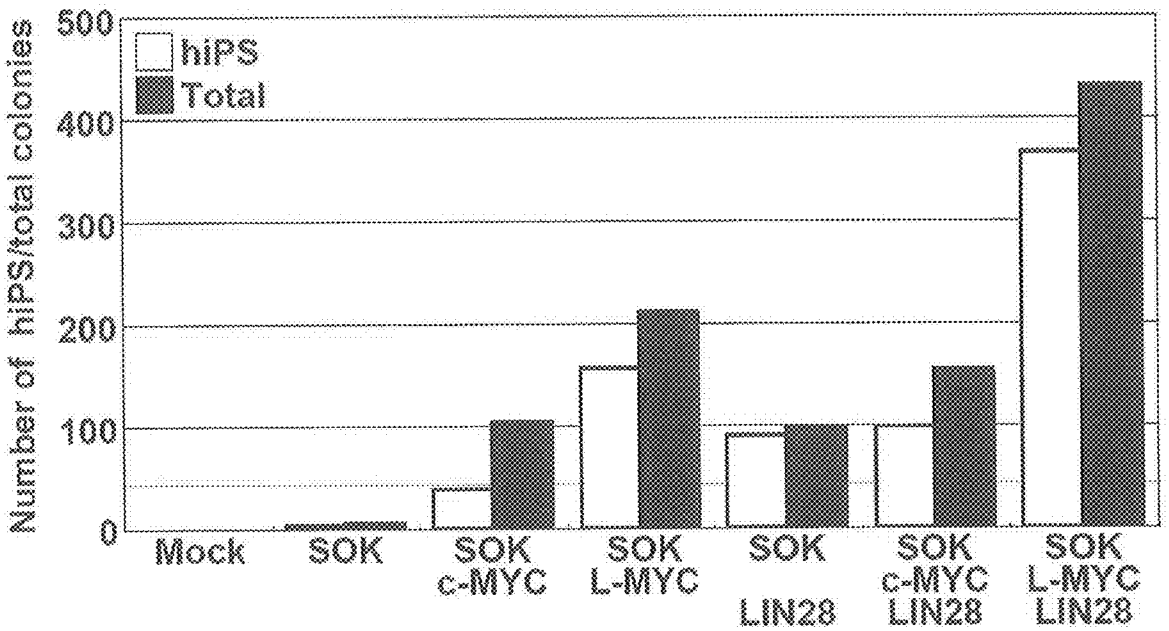
FIG. 62 is a graph which shows the results of counting the number of colonies of human iPS cells which were established by transducing 3 genes (OCT3/4, KLF4, and SOX2), and the c-MYC, L-MYC and/or LIN28 gene into aHDF-Slc7a1 cells by retrovirus. The black bar shows the total number of colonies, and the white bar shows the total number of iPS colonies.

On the 37$^{th}$ day after retrovirus infection, the numbers of the total colonies which appeared and the number of human iPS colonies (hiPS colony) were counted. The results are shown in TABLE 20 and FIG. 62. FIG. 62 is a graph of the result of TABLE 20.

TABLE 20

Summary of hiPS Cell Induction Results with L-MYC and LIN28)

| | | | | | | | hiPS colonies | Total colonies | hiPS (%) |
|---|---|---|---|---|---|---|---|---|---|
| 1 | Mock | DsRed | Mock | Mock | Mock | A | 0 | 0 | 0 |
| 2 | SOX2 | OCT4 | KLF4 | Mock | Mock | D | 3 | 5 | 60.0 |
| 3 | SOX2 | OCT4 | KLF4 | c-MYC | Mock | B | 38 | 103 | 36.9 |
| 4 | SOX2 | OCT4 | KLF4 | L-MYC | Mock | C | 156 | 211 | 73.9 |
| 5 | SOX2 | OCT4 | KLF4 | Mock | LIN28 | G | 90 | 97 | 92.8 |
| 6 | SOX2 | OCT4 | KLF4 | c-MYC | LIN28 | E | 98 | 154 | 63.6 |
| 7 | SOX2 | OCT4 | KLF4 | L-MYC | LIN28 | F | 366 | 432 | 84.7 |

By adding LIN28 to the 4 genes (SOX2, OCT3/4, KLF4 and L-MYC), the number of iPS colonies was significantly increased. The number of iPS colonies was much higher than the number of colonies in the case of adding LIN28 to the 4 genes (SOX2, OCT3/4, KLF4 and c-MYC). Further, LIN28 showed a synergistic effect when used in combination with the above-described 4 genes which included c-MYC, and showed an even stronger synergistic effect when used in combination with the above-described 4 genes which included L-MYC (TABLE 20). Further, the ratio of the iPS colony number to the total colony number was 84.7% which is a very high value, when five genes (SOX2, OCT3/4, KLF4, L-MYC, and LIN28) were used. From the aforementioned result, it was revealed that a combination of 5 genes (SOX2, OCT3/4, KLF4, L-MYC, and LIN28) was extremely effective for increasing the efficacy of establishment of human iPS cells.

Example 29: Effect of Chimeric and Mutant Myc Genes on Induction of Human iPS Cells Various Myc chimera genes (Ms-cL-Myc, Ms-Lc-Myc, Ms-cLc-Myc, Ms-LcL-Myc, Ms-ccL-Myc, Ms-cLL-Myc, Ms-LLc-Myc, and Ms-Lcc-Myc) and Myc point-mutated genes (c-MycW135E, c-MycV394D, c-MycL420P, L-MycW96E, L-MycV325D and L-MycL351P) were constructed. Regarding the Myc point-mutants, c-Myc W135E comprises an amino acid substitution within a domain essential for interaction with a nuclear factor that is required for E1A-mediated cell transformation (Brough et al. *Molecular and Cellular Biology* 15 (3): 1536-1544, 1995, which is herein incorporated by reference in its entirety). Another Myc point-mutant, c-Myc L420P, loses its ability to bind to MAX protein (Blackwood et al. *Science* 251 (4998): 1211-17, 1991, which is herein incorporated by reference in its entirety). Yet another Myc point-mutant, c-Myc V394D, loses its ability to bind to MIZ-1 protein (Herold et al. *Mol. Cell* 10 (3): 509-21, 2002, which is herein incorporated by reference in its entirety). L-MycW96E, L-MycV325D and L-MycL351P are corresponding point mutants of c-Myc W135E, c-Myc V394D, and c-Myc L420P.

TABLE 21 discloses the amino acid and nucleic acid sequences of the Myc constructs:

TABLE 21

| Myc, Myc Chimera, and Myc Variant Amino Acid and Nucleotide Sequences | |
|---|---|
| Ms-c-Myc | MPLNVNFTNRNYDLDYDSVQPYFICDEEENFYHQQQQSELQPPAPSEDIWK<br>KFELLPTPPLSPSRRSGLCSPSYVAVATSFSPREDDDGGGGNFSTADQLEM<br>MTELLGGDMVNQSFICDPDDETFIKNIIIQDCMWSGFSAAAKLVSEKLASY<br>QAARKDSTSLSPARGHSVCSTSSLYLQDLTAAASECIDPSVVFPYPLNDSS<br>SPKSCTSSDSTAFSPSSDSLLSSESSPRASPEPLVLHEETPPTTSSDSEEE<br>QEDEEEIDVVSVEKRQTPAKRSESGSSPSRGHSKPPHSPLVLKRCHVSTHQ<br>HNYAAPPSTRKDYPAAKRAKLDSGRVLKQISNNRKCSSPRSSDTEENDKRR<br>THNVLERQRRNELKRSFFALRDQIPELENNEKAPKVVILKKATAYILSIQA<br>DEHKLTSEKDLLRKRREQLKHKLEQLRNSGA (SEQ ID NO: 134)<br>ATGCCCCTCAACGTGAACTTCACCAACAGGAACTATGACCTCGACTACGAC<br>TCCGTACAGCCCTATTTCATCTGCGACGAGGAAGAGAATTTCTATCACCAG<br>CAACAGCAGAGCGAGCTGCAGCCGCCCGCGCCCAGTGAGGATATCTGGAAG |

TABLE 21-continued

| Myc, Myc Chimera, and Myc Variant Amino Acid and Nucleotide Sequences | |
|---|---|
| | AAATTCGAGCTGCTTCCCACCCCGCCCCTGTCCCCGAGCCGCCGCTCCGGG<br>CTCTGCTCTCCATCCTATGTTGCGGTCGCTACGTCCTTCTCCCCAAGGGAA<br>GACGATGACGGCGGCGGTGGCAACTTCTCCACCGCCGATCAGCTGGAGATG<br>ATGACCGAGTTACTTGGAGGAGACATGGTGAACCAGAGCTTCATCTGCGAT<br>CCTGACGACGAGACCTTCATCAAGAACATCATCATCCAGGACTGTATGTGG<br>AGCGGTTTCTCAGCCGCTGCCAAGCTGGTCTCGGAGAAGCTGGCCTCCTAC<br>CAGGCTGCGCGCAAAGACAGCACCAGCCTGAGCCCCGCCCGCGGGCACAGC<br>GTCTGCTCCACCTCCAGCCTGTACCTGCAGGACCTCACCGCCGCCGCGTCC<br>GAGTGCATTGACCCCTCAGTGGTCTTTCCCTACCCGCTCAACGACAGCAGC<br>TCGCCCAAATCCTGTACCTCGTCCGATTCCACGGCCTTCTCTCCTTCCTCG<br>GACTCGCTGCTGTCCTCCGAGTCCTCCCCACGGGCCAGCCCTGAGCCCCTA<br>GTGCTGCATGAGGAGACACCGCCCACCACCAGCAGCGACTCTGAAGAAGAG<br>CAAGAAGATGAGGAAGAAATTGATGTGGTGTCTGTGGAGAAGAGGCAAACC<br>CCTGCCAAGAGGTCGGAGTCGGGCTCATCTCCATCCCGAGGCCACAGCAAA<br>CCTCCGCACAGCCCACTGGTCCTCAAGAGGTGCCACGTCTCCACTCACCAG<br>CACAACTACGCCGCACCCCCCTCCACAAGGAAGGACTATCCAGCTGCCAAG<br>AGGGCCAAGTTGGACAGTGGCAGGGTCCTGAAGCAGATCAGCAACAACCGC<br>AAGT (SEQ ID NO: 135) |
| Ms-L-Myc | MDFDSYQHYFYDYDCGEDFYRSTAPSEDIWKKFELVPSPPTSPPWGSGPGA<br>VDPASGINPGEPWPGGGAGDEAESRGHSKAWGRNYASIIRRDCMWSGFSAR<br>ERLERVVSDRLAPGAPRGNPPKAPATPDGTPSLEASNPAPATQCQLGEPKT<br>QACSGSESPSDSEGEEIDVVTVEKRRSLDIRKPVTITVRADPLDPCMKHFH<br>ISIHQQQHNYAARFPPESCSQEGDPEPGPQEEAPEIEAPKEKEEEEEEEEE<br>EEIVSPPPVGSEAPQSCHPKPVSSDTEDVTKRKNHNFLERKRRNDLRSRFL<br>ALRDQVPTLASCSKAPKVVILSKALEYLQALVGAEKKMATEKRQLRCRQQQ<br>LQKRIAYLSGY (SEQ ID NO: 136)<br>ATGGACTTCGACTCGTATCAGCACTATTTCTACGACTATGACTGCGGAGAG<br>GATTTCTACCGCTCCACGGCGCCCAGCGAGGACATCTGGAAGAAATTCGAG<br>CTGGTGCCGTCGCCCCCCACGTCGCCGCCCTGGGGCTCCGGTCCCGGCGCC<br>GTGGACCCAGCCTCTGGGATTAATCCCGGGGAGCCGTGGCCTGGAGGGGGT<br>GCCGGGGACGAGGCGGAATCTCGGGGCCATTCGAAAGCCTGGGGCAGGAAT<br>TATGCTTCCATCATTCGCCGTGACTGCATGTGGAGCGGCTTCTCCGCCCGA<br>GAACGGCTGGAGAGAGTGGTGAGCGACAGGCTGGCCCCAGGCGCGCCCCGG<br>GGGAACCCGCCCAAAGCGCCCGCTACCCCGGACGGCACTCCTAGTCTGGAA<br>GCCAGTAACCCGGCGCCCGCCACCCAATGTCAGCTGGGCGAGCCCAAGACT<br>CAGGCCTGCTCCGGGTCCGAGAGCCCCAGCGATTCTGAAGGTGAAGAGATT<br>GACGTGGTGACCGTGGAGAAGAGGCGATCTCTGGACATCCGAAAGCCAGTC<br>ACCATCACGGTGCGAGCAGACCCCCTGGACCCCTGCATGAAGCACTTCCAT<br>ATCTCTATCCACCAACAGCAGCATAACTATGCTGCCCGTTTTCCTCCAGAA<br>AGTTGCTCTCAAGAGGGGGATCCTGAGCCAGGTCCCCAGGAAGAGGCTCCG<br>GAGATAGAAGCTCCCAAGGAGAAAGAGGAGGAGGAAGAGGAAGAGGAGGAA<br>GAAGAGATTGTGAGCCCCCCACCTGTCGGAAGTGAGGCTCCCCAGTCCTGC<br>CACCCCAAACCTGTCAGTTCTGACACTGAGGACGTGACCAAGAGGAAGAAC<br>CATAACTTCTTGGAACGAAAAAGGAGGAATGACCTCCGCTCCCGGTTCCTA<br>GCCCTGCGGGACCAGGTTCCCACCCTGGCCAGCTGCTCTAAGGCCCCCAAA<br>GTCGTGATCCTCAGCAAGGCGTTAGAATACTTGCAGGCTTTGGTGGGGGCT<br>GAAA (SEQ ID NO: 137) |
| Ms-cL-Myc | MPLNVNFTNRNYDLDYDSVQPYFICDEEENFYHQQQSELQPPAPSEDIWK<br>KFELLPTPPLSPSRRSGLCSPSYVAVATSFSPREDDDGGGGNFSTADQLEM<br>MTELLGGDMVNQSFICDPDDETFIKNIIIQDCMWSGFSAAAKLVSEKLASY<br>QAARKDSTSLSPARGHSVCSTSSLYLQDLTAAASECIDPSVVFPYPLNDSS<br>SPKSCTSSDSTAFSSDSEGEEIDVVTVEKRRSLDIRKPVTITVRADPLDPC<br>MKHFHISIHQQQHNYAARFPPESCSQEGDPEPGPQEEAPEIEAPKEKEEEE<br>EEEEEEEIVSPPPVGSEAPQSCHPKPVSSDTEDVTKRKNHNFLERKRRNDL<br>RSRFLALRDQVPTLASCSKAPKVVILSKALEYLQALVGAEKKMATEKRQLR<br>CRQQQLQKRIAYLSGY (SEQ ID NO: 138)<br>ATGCCCCTCAACGTGAACTTCACCAACAGGAACTATGACCTCGACTACGAC<br>TCCGTACAGCCCTATTTCATCTGCGACGAGGAAGAGAATTTCTATCACCAG<br>CAACAGCAGAGCGAGCTGCAGCCGCCCGCGCCCAGTGAGGATATCTGGAAG<br>AAATTCGAGCTGCTTCCCACCCCGCCCCTGTCCCCGAGCCGCCGCTCCGGG<br>CTCTGCTCTCCATCCTATGTTGCGGTCGCTACGTCCTTCTCCCCAAGGGAA<br>GACGATGACGGCGGCGGTGGCAACTTCTCCACCGCCGATCAGCTGGAGATG<br>ATGACCGAGTTACTTGGAGGAGACATGGTGAACCAGAGCTTCATCTGCGAT<br>CCTGACGACGAGACCTTCATCAAGAACATCATCATCCAGGACTGTATGTGG<br>AGCGGTTTCTCAGCCGCTGCCAAGCTGGTCTCGGAGAAGCTGGCCTCCTAC<br>CAGGCTGCGCGCAAAGACAGCACCAGCCTGAGCCCCGCCCGCGGGCACAGC<br>GTCTGCTCCACCTCCAGCCTGTACCTGCAGGACCTCACCGCCGCCGCGTCC<br>GAGTGCATTGACCCCTCAGTGGTCTTTCCCTACCCGCTCAACGACAGCAGC<br>TCGCCCAAATCCTGTACCTCGTCCGATTCCACGGCCTTCTCTAGCGATTCT<br>GAAGGTGAAGAGATTGACGTGGTGACCGTGGAGAAGAGGCGATCTCTGGAC<br>ATCCGAAAGCCAGTCACCATCACGGTGCGAGCAGACCCCCTGGACCCCTGC<br>ATGAAGCACTTCCATATCTCTATCCACCAACAGCAGCATAACTATGCTGCC<br>CGTTTTCCTCCAGAAAGTTGCTCTCAAGAGGGGGATCCTGAGCCAGGTCCC |

TABLE 21-continued

| Myc, Myc Chimera, and Myc Variant Amino Acid and Nucleotide Sequences | |
|---|---|
| | CAGGAAGAGGCTCCGGAGATAGAAGCTCCCAAGGAGAAAGAGGAGGAGGAA<br>GAGGAAGAGGAGGAAGAAGAGATTGTGAGCCCCCCACCTGTCGGAAGTGAG<br>GCTCCCCAGTCCTGCCACCCCAAACCTGTCAGTTCTGACACTGAGGACGTG<br>ACCA (SEQ ID NO: 139) |
| Ms-Lc-Myc | MDFDSYQHYFYDYDCGEDFYRSTAPSEDIWKKFELVPSPPTSPPWGSGPGA<br>VDPASGINPGEPWPGGGAGDEAESRGHSKAWGRNYASIIRRDCMWSGFSAR<br>ERLERVVSDRLAPGAPRGNPPKAPATPDGTPSLEASNPAPATQCQLGEPKT<br>QACSGSESPSDSLLSSESSPRASPEPLVLHEETPPTTSSDSEEEQEDEEEI<br>DVVSVEKRQTPAKRSESGSSPSRGHSKPPHSPLVLKRCHVSTHQHNYAAPP<br>STRKDYPAAKRAKLDSGRVLKQISNNRKCSSPRSSDTEENDKRRTHNVLER<br>QRRNELKRSFFALRDQIPELENNEKAPKVVILKKATAYILSIQADEHKLTS<br>EKDLLRKRREQLKHKLEQLRNSGA (SEQ ID NO: 140)<br>ATGGACTTCGACTCGTATCAGCACTATTTCTACGACTATGACTGCGGAGAG<br>GATTTCTACCGCTCCACGGCGCCCAGCGAGGACATCTGGAAGAAATTCGAG<br>CTGGTGCCGTCGCCCCCCACGTCGCCGCCCTGGGGCTCCGGTCCCGGCGCC<br>GTGGACCCAGCCTCTGGGATTAATCCCGGGGAGCCGTGGCCTGGAGGGGGT<br>GCCGGGGACGAGGCGGAATCTCGGGGCCATTCGAAAGCCTGGGGCAGGAAT<br>TATGCTTCCATCATTCGCCGTGACTGCATGTGGAGCGGCTTCTCCGCCCGA<br>GAACGGCTGGAGAGAGTGGTGAGCGACAGGCTGGCCCCAGGCGCGCCCCGG<br>GGGAACCCGCCCAAAGCGCCCGCTACCCCGGACGGCACTCCTAGTCTGGAA<br>GCCAGTAACCCGGCGCCCGCCACCCAATGTCAGCTGGGCGAGCCCAAGACT<br>CAGGCCTGCTCCGGGTCCGAGAGCCCCTCGGACTCGCTGCTGTCCTCCGAG<br>TCCTCCCCACGGGCCAGCCCTGAGCCCCTAGTGCTGCATGAGGAGACACCG<br>CCCACCACCAGCAGCGACTCTGAAGAAGAGCAAGAAGATGAGGAAGAAATT<br>GATGTGGTGTCTGTGGAGAAGAGGCAAACCCCTGCCAAGAGGTCGGAGTCG<br>GGCTCATCTCCATCCCGAGGCCACAGCAAACCTCCGCACAGCCCACTGGTC<br>CTCAAGAGGTGCCACGTCTCCACTCACCAGCACAACTACGCCGCACCCCCC<br>TCCACAAGGAAGGACTATCCAGCTGCCAAGAGGGCCAAGTTGGACAGTGGC<br>AGGGTCCTGAAGCAGATCAGCAACAACCGCAAGTGCTCCAGCCCCAGGTCC<br>TCAGACACGGAGGAAAACGACAAGAGGCGGACACACAACGTCTTGGAACGT<br>CAGAGGAGGAACGAGCTGAAGCGCAGCTTTTTTGCCCTGCGTGACCAGATC<br>CCTGAATTGGAAAACAACGAAAAGGCCCCCAAGGTAGTGATCCTCAAAAAA<br>GCCA (SEQ ID NO: 141) |
| Ms-cLc-Myc | MPLNVNFTNRNYDLDYDSVQPYFICDEEENFYHQQQSELQPPAPSEDIWK<br>KFELLPTPPLSPSRRSGLCSPSYVAVATSFSPREDDDGGGGNFSTADQLEM<br>MTELLGGDMVNQSFICDPDDETFIKNIIIQDCMWSGFSAAAKLERVVSDRL<br>APGAPRGNPPKAPATPDGTPSLEASNPAPATQCQLGEPKTQACSGSESPSD<br>SEGEEIDVVTVEKRRSLDIRKPVTITVRADPLDPCMKHFHISIHQQQHNYA<br>ARFPPESCSQEGDPEPGPQEEAPEIEAPKEKEEEEEEEEEEIVSPPPVGS<br>EAPQSCHPKPVSSDTEENDKRRTHNVLERQRRNELKRSFFALRDQIPELEN<br>NEKAPKVVILKKATAYILSIQADEHKLTSEKDLLRKRREQLKHKLEQLRNS<br>GA (SEQ ID NO: 142)<br>ATGCCCCTCAACGTGAACTTCACCAACAGGAACTATGACCTCGACTACGAC<br>TCCGTACAGCCCTATTTCATCTGCGACGAGGAAGAGAATTTCTATCACCAG<br>CAACAGCAGAGCGAGCTGCAGCCGCCCGCGCCCAGTGAGGATATCTGGAAG<br>AAATTCGAGCTGCTTCCCACCCCGCCCCTGTCCCCGAGCCGCCGCTCCGGG<br>CTCTGCTCTCCATCCTATGTTGCGGTCGCTACGTCCTTCTCCCCAAGGGAA<br>GACGATGACGGCGGCGGTGGCAACTTCTCCACCGCCGATCAGCTGGAGATG<br>ATGACCGAGTTACTTGGAGGAGACATGGTGAACCAGAGCTTCATCTGCGAT<br>CCTGACGACGAGACCTTCATCAAGAACATCATCATCCAGGACTGTATGTGG<br>AGCGGTTTCTCAGCCGCTGCCAAGCTGGAGAGAGTGGTGAGCGACAGGCTG<br>GCCCCAGGCGCGCCCCGGGGGAACCCGCCCAAAGCGCCCGCTACCCCGGAC<br>GGCACTCCTAGTCTGGAAGCCAGTAACCCGGCGCCCGCCACCCAATGTCAG<br>CTGGGCGAGCCCAAGACTCAGGCCTGCTCCGGGTCCGAGAGCCCCAGCGAT<br>TCTGAAGGTGAAGAGATTGACGTGGTGACCGTGGAGAAGAGGCGATCTCTG<br>GACATCCGAAAGCCAGTCACCATCACGGTGCGAGCAGACCCCCTGGACCCC<br>TGCATGAAGCACTTCCATATCTCTATCCACCAACAGCAGCATAACTATGCT<br>GCCCGTTTTCCTCCAGAAAGTTGCTCTCAAGAGGGGGATCCTGAGCCAGGT<br>CCCCAGGAAGAGGCTCCGGAGATAGAAGCTCCCAAGGAGAAAGAGGAGGAG<br>GAAGAGGAAGAGGAGGAAGAAGAGATTGTGAGCCCCCCACCTGTCGGAAGT<br>GAGGCTCCCCAGTCCTGCCACCCCAAACCTGTCTCCTCAGACACGGAGGAA<br>AACGACAAGAGGCGGACACACAACGTCTTGGAACGTCAGAGGAGGAACGAG<br>CTGA (SEQ ID NO: 143) |
| Ms-LcL-Myc | MDFDSYQHYFYDYDCGEDFYRSTAPSEDIWKKFELVPSPPTSPPWGSGPGA<br>VDPASGINPGEPWPGGGAGDEAESRGHSKAWGRNYASIIRRDCMWSGFSAR<br>ERLVSEKLASYQAARKDSTSLSPARGHSVCSTSSLYLQDLTAAASECIDPS<br>VVFPYPLNDSSSPKSCTSSDSTAFSPSSDSLLSSESSPRASPEPLVLHEET<br>PPTTSSDSEEEQEDEEEIDVVSVEKRQTPAKRSESGSSPSRGHSKPPHSPL<br>VLKRCHVSTHQHNYAAPPSTRKDYPAAKRAKLDSGRVLKQISNNRKCSSPR<br>SSDTEDVTKRKNHNFLERKRRNDLRSRFLALRDQVPTLASCSKAPKVVILS<br>KALEYLQALVGAEKKMATEKRQLRCRQQQLQKRIAYLSGY (SEQ ID<br>NO: 144)<br>ATGGACTTCGACTCGTATCAGCACTATTTCTACGACTATGACTGCGGAGAG<br>GATTTCTACCGCTCCACGGCGCCCAGCGAGGACATCTGGAAGAAATTCGAG |

TABLE 21-continued

| Myc, Myc Chimera, and Myc Variant Amino Acid and Nucleotide Sequences | |
|---|---|
| | CTGGTGCCGTCGCCCCCCACGTCGCCGCCCTGGGGCTCCGGTCCCGGCGCC<br>GTGGACCCAGCCTCTGGGATTAATCCCGGGGAGCCGTGGCCTGGAGGGGGT<br>GCCGGGGACGAGGCGGAATCTCGGGGCCATTCGAAAGCCTGGGGCAGGAAT<br>TATGCTTCCATCATTCGCCGTGACTGCATGTGGAGCGGCTTCTCCGCCCGA<br>GAACGGCTGGTCTCGGAGAAGCTGGCCTCCTACCAGGCTGCGCGCAAAGAC<br>AGCACCAGCCTGAGCCCCGCCCGCGGGCACAGCGTCTGCTCCACCTCCAGC<br>CTGTACCTGCAGGACCTCACCGCCGCCGCGTCCGAGTGCATTGACCCCTCA<br>GTGGTCTTTCCCTACCCGCTCAACGACAGCAGCTCGCCCAAATCCTGTACC<br>TCGTCCGATTCCACGGCCTTCTCTCCTTCCTCGGACTCGCTGCTGTCCTCC<br>GAGTCCTCCCCACGGGCCAGCCCTGAGCCCCTAGTGCTGCATGAGGAGACA<br>CCGCCCACCACCAGCAGCGACTCTGAAGAAGAGCAAGAAGATGAGGAAGAA<br>ATTGATGTGGTGTCTGTGGAGAAGAGGCAAACCCCTGCCAAGAGGTCGGAG<br>TCGGGCTCATCTCCATCCCGAGGCCACAGCAAACCTCCGCACAGCCCACTG<br>GTCCTCAAGAGGTGCCACGTCTCCACTCACCAGCACAACTACGCCGCACCC<br>CCCTCCACAAGGAAGGACTATCCAGCTGCCAAGAGGGCCAAGTTGGACAGT<br>GGCAGGGTCCTGAAGCAGATCAGCAACAACCGCAAGTGCTCCAGCCCCAGG<br>AGTTCTGACACTGAGGACGTGACCAAGAGGAAGAACCATAACTTCTTGGAA<br>CGAAAAAGGAGGAATGACCTCCGCTCCCGGTTCCTAGCCCTGCGGGACCAG<br>GTTC (SEQ ID NO: 145) |
| Ms-ccL-Myc | MPLNVNFTNRNYDLDYDSVQPYFICDEEENFYHQQQSELQPPAPSEDIWK<br>KFELLPTPPLSPSRRSGLCSPSYVAVATSFSPREDDDGGGGNFSTADQLEM<br>MTELLGGDMVNQSFICDPDDETFIKNIIIQDCMWSGFSAAAKLVSEKLASY<br>QAARKDSTSLSPARGHSVCSTSSLYLQDLTAAASECIDPSVVFPYPLNDSS<br>SPKSCTSSDSTAFSPSSDSLLSSESSPRASPEPLVLHEETPPTTSSDSEEE<br>QEDEEEIDVVSVEKRQTPAKRSESGSSPSRGHSKPPHSPLVLKRCHVSTHQ<br>HNYAAPPSTRKDYPAAKRAKLDSGRVLKQISNNRKCSSPRSSDTEDVTKRK<br>NHNFLERKRRNDLRSRFLALRDQVPTLASCSKAPKVVILSKALEYLQALVG<br>AEKKMATEKRQLRCRQQQLQKRIAYLSGY (SEQ ID NO: 146)<br>ATGCCCCTCAACGTGAACTTCACCAACAGGAACTATGACCTCGACTACGAC<br>TCCGTACAGCCCTATTTCATCTGCGACGAGGAAGAGAATTTCTATCACCAG<br>CAACAGCAGAGCGAGCTGCAGCCGCCCGCGCCCAGTGAGGATATCTGGAAG<br>AAATTCGAGCTGCTTCCCACCCCGCCCCTGTCCCCGAGCCGCCGCTCCGGG<br>CTCTGCTCTCCATCCTATGTTGCGGTCGCTACGTCCTTCTCCCCAAGGGAA<br>GACGATGACGGCGGCGGTGGCAACTTCTCCACCGCCGATCAGCTGGAGATG<br>ATGACCGAGTTACTTGGAGGAGACATGGTGAACCAGAGCTTCATCTGCGAT<br>CCTGACGACGAGACCTTCATCAAGAACATCATCATCCAGGACTGTATGTGG<br>AGCGGTTTCTCAGCCGCTGCCAAGCTGGTCTCGGAGAAGCTGGCCTCCTAC<br>CAGGCTGCGCGCAAAGACAGCACCAGCCTGAGCCCCGCCCGCGGGCACAGC<br>GTCTGCTCCACCTCCAGCCTGTACCTGCAGGACCTCACCGCCGCCGCGTCC<br>GAGTGCATTGACCCCTCAGTGGTCTTTCCCTACCCGCTCAACGACAGCAGC<br>TCGCCCAAATCCTGTACCTCGTCCGATTCCACGGCCTTCTCTCCTTCCTCG<br>GACTCGCTGCTGTCCTCCGAGTCCTCCCCACGGGCCAGCCCTGAGCCCCTA<br>GTGCTGCATGAGGAGACACCGCCCACCACCAGCAGCGACTCTGAAGAAGAG<br>CAAGAAGATGAGGAAGAAATTGATGTGGTGTCTGTGGAGAAGAGGCAAACC<br>CCTGCCAAGAGGTCGGAGTCGGGCTCATCTCCATCCCGAGGCCACAGCAAA<br>CCTCCGCACAGCCCACTGGTCCTCAAGAGGTGCCACGTCTCCACTCACCAG<br>CACAACTACGCCGCACCCCCCTCCACAAGGAAGGACTATCCAGCTGCCAAG<br>AGGGCCAAGTTGGACAGTGGCAGGGTCCTGAAGCAGATCAGCAACAACCGC<br>AAGT (SEQ ID NO: 147) |
| Ms-cLL-Myc | MPLNVNFTNRNYDLDYDSVQPYFICDEEENFYHQQQSELQPPAPSEDIWK<br>KFELLPTPPLSPSRRSGLCSPSYVAVATSFSPREDDDGGGGNFSTADQLEM<br>MTELLGGDMVNQSFICDPDDETFIKNIIIQDCMWSGFSAAAKLERVVSDRL<br>APGAPRGNPPKAPATPDGTPSLEASNPAPATQCQLGEPKTQACSGSESPSD<br>SEGEEIDVVTVEKRRSLDIRKPVTITVRADPLDPCMKHFHISIHQQQHNYA<br>ARFPPESCSQEGDPEPGPQEEAPEIEAPKEKEEEEEEEEEEEIVSPPPVGS<br>EAPQSCHPKPVSSDTEDVTKRKNHNFLERKRRNDLRSRFLALRDQVPTLAS<br>CSKAPKVVILSKALEYLQALVGAEKKMATEKRQLRCRQQQLQKRIAYLBGY<br>(SEQ ID NO: 148)<br>ATGCCCCTCAACGTGAACTTCACCAACAGGAACTATGACCTCGACTACGAC<br>TCCGTACAGCCCTATTTCATCTGCGACGAGGAAGAGAATTTCTATCACCAG<br>CAACAGCAGAGCGAGCTGCAGCCGCCCGCGCCCAGTGAGGATATCTGGAAG<br>AAATTCGAGCTGCTTCCCACCCCGCCCCTGTCCCCGAGCCGCCGCTCCGGG<br>CTCTGCTCTCCATCCTATGTTGCGGTCGCTACGTCCTTCTCCCCAAGGGAA<br>GACGATGACGGCGGCGGTGGCAACTTCTCCACCGCCGATCAGCTGGAGATG<br>ATGACCGAGTTACTTGGAGGAGACATGGTGAACCAGAGCTTCATCTGCGAT<br>CCTGACGACGAGACCTTCATCAAGAACATCATCATCCAGGACTGTATGTGG<br>AGCGGTTTCTCAGCCGCTGCCAAGCTGGAGAGAGTGGTGAGCGACAGGCTG<br>GCCCCAGGCGCGCCCCGGGGGAACCCGCCCAAAGCGCCCGCTACCCCGGAC<br>GGCACTCCTAGTCTGGAAGCCAGTAACCCGGCGCCCGCCACCCAATGTCAG<br>CTGGGCGAGCCCAAGACTCAGGCCTGCTCCGGGTCCGAGAGCCCCAGCGAT<br>TCTGAAGGTGAAGAGATTGACGTGGTGACCGTGGAGAAGAGGCGATCTCTG<br>GACATCCGAAAGCCAGTCACCATCACGGTGCGAGCAGACCCCCTGGACCCC<br>TGCATGAAGCACTTCCATATCTCTATCCACCAACAGCAGCATAACTATGCT<br>GCCCGTTTTCCTCCAGAAAGTTGCTCTCAAGAGGGGGATCCTGAGCCAGGT<br>CCCCAGGAAGAGGCTCCGGAGATAGAAGCTCCCAAGGAGAAAGAGGAGGAG |

TABLE 21-continued

| Myc, Myc Chimera, and Myc Variant Amino Acid and Nucleotide Sequences | |
|---|---|
| | GAAGAGGAAGAGGAGGAAGAAGAGATTGTGAGCCCCCCACCTGTCGGAAGT<br>GAGGCTCCCCAGTCCTGCCACCCCAAACCTGTCAGTTCTGACACTGAGGAC<br>GTGACCAAGAGGAAGAACCATAACTTCTTGGAACGAAAAGGAGGAATGAC<br>CTCC (SEQ ID NO: 149) |
| Ms-LLc-Myc | MDFDSYQHYFYDYDCGEDFYRSTAPSEDIWKKFELVPSPPTSPPWGSGPGA<br>VDPASGINPGEPWPGGGAGDEAESRGHSKAWGRNYASIIRRDCMWSGFSAR<br>ERLERVVSDRLAPGAPRGNPPKAPATPDGTPSLEASNPAPATQCQLGEPKT<br>QACSGSESPSDSEGEEIDVVTVEKRRSLDIRKPVTITVRADPLDPCMKHFH<br>ISIHQQQHNYAARFPPESCSQEGDPEPGPQEEAPEIEAPKEKEEEEEEEEE<br>EEIVSPPPVGSEAPQSCHPKPVSSDTEENDKRRTHNVLERQRRNELKRSFF<br>ALRDQIPELENNEKAPKVVILKKATAYILSIQADEHKLTSEKDLLRKRREQ<br>LKHKLEQLRNSGA (SEQ ID NO: 150)<br>ATGGACTTCGACTCGTATCAGCACTATTTCTACGACTATGACTGCGGAGAG<br>GATTTCTACCGCTCCACGGCGCCCAGCGAGGACATCTGGAAGAAATTCGAG<br>CTGGTGCCGTCGCCCCCCACGTCGCCGCCCTGGGGCTCCGGTCCCGGCGCC<br>GTGGACCCAGCCTCTGGGATTAATCCCGGGGAGCCGTGGCCTGGAGGGGGT<br>GCCGGGGACGAGGCGGAATCTCGGGGCCATTCGAAAGCCTGGGGCAGGAAT<br>TATGCTTCCATCATTCGCCGTGACTGCATGTGGAGCGGCTTCTCCGCCCGA<br>GAACGGCTGGAGAGAGTGGTGAGCGACAGGCTGGCCCCAGGCGCGCCCCGG<br>GGGAACCCGCCCAAAGCGCCCGCTACCCCGGACGGCACTCCTAGTCTGGAA<br>GCCAGTAACCCGGCGCCCGCCACCCAATGTCAGCTGGGCGAGCCCAAGACT<br>CAGGCCTGCTCCGGGTCCGAGAGCCCCAGCGATTCTGAAGGTGAAGAGATT<br>GACGTGGTGACCGTGGAGAAGAGGCGATCTCTGGACATCCGAAAGCCAGTC<br>ACCATCACGGTGCGAGCAGACCCCCTGGACCCCTGCATGAAGCACTTCCAT<br>ATCTCTATCCACCAACAGCAGCATAACTATGCTGCCCGTTTTCCTCCAGAA<br>AGTTGCTCTCAAGAGGGGGATCCTGAGCCAGGTCCCCAGGAAGAGGCTCCG<br>GAGATAGAAGCTCCCAAGGAGAAAGAGGAGGAGGAAGAGGAAGAGGAGGAA<br>GAAGAGATTGTGAGCCCCCCACCTGTCGGAAGTGAGGCTCCCCAGTCCTGC<br>CACCCCAAACCTGTCTCCTCAGACACGGAGGAAAACGACAAGAGGCGGACA<br>CACAACGTCTTGGAACGTCAGAGGAGGAACGAGCTGAAGCGCAGCTTTTTT<br>GCCCTGCGTGACCAGATCCCTGAATTGGAAAACAACGAAAAGGCCCCCAAG<br>GTAGTGATCCTCAAAAAAGCCACCGCCTACATCCTGTCCATTCAAGCAGAC<br>GAGC (SEQ ID NO: 151) |
| Ms-Lcc-Myc | MDFDSYQHYFYDYDCGEDFYRSTAPSEDIWKKFELVPSPPTSPPWGSGPGA<br>VDPASGINPGEPWPGGGAGDEAESRGHSKAWGRNYASIIRRDCMWSGFSAR<br>ERLVSEKLASYQAARKDSTSLSPARGHSVCSTSSLYLQDLTAAASECIDPS<br>VVFPYPLNDSSSPKSCTSSDSTAFSPSSDSLLSSESSPRASPEPLVLHEET<br>PPTTSSDSEEEQEDEEEIDVVSVEKRQTPAKRSESGSSPSRGHSKPPHSPL<br>VLKRCHVSTHQHNYAAPPSTRKDYPAAKRAKLDSGRVLKQISNNRKCSSPR<br>SSDTEENDKRRTHNVLERQRRNELKRSFFALRDQIPELENNEKAPKVVILK<br>KATAYILSIQADEHKLTSEKDLLRKRREQLKHKLEQLRNSGA (SEQ ID<br>NO: 152)<br>ATGGACTTCGACTCGTATCAGCACTATTTCTACGACTATGACTGCGGAGAG<br>GATTTCTACCGCTCCACGGCGCCCAGCGAGGACATCTGGAAGAAATTCGAG<br>CTGGTGCCGTCGCCCCCCACGTCGCCGCCCTGGGGCTCCGGTCCCGGCGCC<br>GTGGACCCAGCCTCTGGGATTAATCCCGGGGAGCCGTGGCCTGGAGGGGGT<br>GCCGGGGACGAGGCGGAATCTCGGGGCCATTCGAAAGCCTGGGGCAGGAAT<br>TATGCTTCCATCATTCGCCGTGACTGCATGTGGAGCGGCTTCTCCGCCCGA<br>GAACGGCTGGTCTCGGAGAAGCTGGCCTCCTACCAGGCTGCGCGCAAAGAC<br>AGCACCAGCCTGAGCCCCGCCCGCGGGCACAGCGTCTGCTCCACCTCCAGC<br>CTGTACCTGCAGGACCTCACCGCCGCCGCGTCCGAGTGCATTGACCCCTCA<br>GTGGTCTTTCCCTACCCGCTCAACGACAGCAGCTCGCCCAAATCCTGTACC<br>TCGTCCGATTCCACGGCCTTCTCTCCTTCCTCGGACTCGCTGCTGTCCTCC<br>GAGTCCTCCCCACGGGCCAGCCCTGAGCCCCTAGTGCTGCATGAGGAGACA<br>CCGCCCACCACCAGCAGCGACTCTGAAGAAGAGCAAGAAGATGAGGAAGAA<br>ATTGATGTGGTGTCTGTGGAGAAGAGGCAAACCCCTGCCAAGAGGTCGGAG<br>TCGGGCTCATCTCCATCCCGAGGCCACAGCAAACCTCCGCACAGCCCACTG<br>GTCCTCAAGAGGTGCCACGTCTCCACTCACCAGCACAACTACGCCGCACCC<br>CCCTCCACAAGGAAGGACTATCCAGCTGCCAAGAGGGCCAAGTTGGACAGT<br>GGCAGGGTCCTGAAGCAGATCAGCAACAACCGCAAGTGCTCCAGCCCCAGG<br>TCCTCAGACACGGAGGAAAACGACAAGAGGCGGACACACAACGTCTTGGAA<br>CGTCAGAGGAGGAACGAGCTGAAGCGCAGCTTTTTTGCCCTGCGTGACCAG<br>ATCC (SEQ ID NO: 153) |
| c-MycW135E | MPLNVNFTNRNYDLDYDSVQPYFICDEEENFYHQQQQSELQPPAPSEDIWK<br>KFELLPTPPLSPSRRSGLCSPSYVAVATSFSPREDDDGGGGNFSTADQLEM<br>MTELLGGDMVNQSFICDPDDETFIKNIIIQDCMESGFSAAAKLVSEKLASY<br>QAARKDSTSLSPARGHSVCSTSSLYLQDLTAAASECIDPSVVFPYPLNDSS<br>SPKSCTSSDSTAFSPSSDSLLSSESSPRASPEPLVLHEETPPTTSSDSEEE<br>QEDEEEIDVVSVEKRQTPAKRSESGSSPSRGHSKPPHSPLVLKRCHVSTHQ<br>HNYAAPPSTRKDYPAAKRAKLDSGRVLKQISNNRKCSSPRSSDTEENDKRR<br>THNVLERQRRNELKRSFFALRDQIPELENNEKAPKVVILKKATAYILSIQA<br>DEHKLTSEKDLLRKRREQLKHKLEQLRNSGA (SEQ ID NO: 154)<br>ATGCCCCTCAACGTGAACTTCACCAACAGGAACTATGACCTCGACTACGAC<br>TCCGTACAGCCCTATTTCATCTGCGACGAGGAAGAGAATTTCTATCACCAG |

TABLE 21-continued

| Myc, Myc Chimera, and Myc Variant Amino Acid and Nucleotide Sequences | |
|---|---|
| | CAACAGCAGAGCGAGCTGCAGCCGCCCGCGCCCAGTGAGGATATCTGGAAG<br>AAATTCGAGCTGCTTCCCACCCCGCCCCTGTCCCCGAGCCGCCGCTCCGGG<br>CTCTGCTCTCCATCCTATGTTGCGGTCGCTACGTCCTTCTCCCCAAGGGAA<br>GACGATGACGGCGGCGGTGGCAACTTCTCCACCGCCGATCAGCTGGAGATG<br>ATGACCGAGTTACTTGGAGGAGACATGGTGAACCAGAGCTTCATCTGCGAT<br>CCTGACGACGAGACCTTCATCAAGAACATCATCATCCAGGACTGTATGGAG<br>AGCGGTTTCTCAGCCGCTGCCAAGCTGGTCTCGGAGAAGCTGGCCTCCTAC<br>CAGGCTGCGCGCAAAGACAGCACCAGCCTGAGCCCCGCCCGCGGGCACAGC<br>GTCTGCTCCACCTCCAGCCTGTACCTGCAGGACCTCACCGCCGCCGCGTCC<br>GAGTGCATTGACCCCTCAGTGGTCTTTCCCTACCCGCTCAACGACAGCAGC<br>TCGCCCAAATCCTGTACCTCGTCCGATTCCACGGCCTTCTCTCCTTCCTCG<br>GACTCGCTGCTGTCCTCCGAGTCCTCCCCACGGGCCAGCCCTGAGCCCCTA<br>GTGCTGCATGAGGAGACACCGCCCACCACCAGCAGCGACTCTGAAGAAGAG<br>CAAGAAGATGAGGAAGAAATTGATGTGGTGTCTGTGGAGAAGAGGCAAACC<br>CCTGCCAAGAGGTCGGAGTCGGGCTCATCTCCATCCCGAGGCCACAGCAAA<br>CCTCCGCACAGCCCACTGGTCCTCAAGAGGTGCCACGTCTCCACTCACCAG<br>CACAACTACGCCGCACCCCCCTCCACAAGGAAGGACTATCCAGCTGCCAAG<br>AGGGCCAAGTTGGACAGTGGCAGGGTCCTGAAGCAGATCAGCAACAACCGC<br>AAGT (SEQ ID NO: 155) |
| c-MycV394D | MPLNVNFTNRNYDLDYDSVQPYFICDEEENFYHQQQSELQPPAPSEDIWK<br>KFELLPTPPLSPSRRSGLCSPSYVAVATSFSPREDDDGGGNFSTADQLEM<br>MTELLGGDMVNQSFICDPDDETFIKNIIIQDCMWSGFSAAAKLVSEKLASY<br>QAARKDSTSLSPARGHSVCSTSSLYLQDLTAAASECIDPSVVFPYPLNDSS<br>SPKSCTSSDSTAFSPSSDSLLSSESSPRASPEPLVLHEETPPTTSSDSEEE<br>QEDEEEIDVVSVEKRQTPAKRSESGSSPSRGHSKPPHSPLVLKRCHVSTHQ<br>HNYAAPPSTRKDYPAAKRAKLDSGRVLKQISNNRKCSSPRSSDTEENDKRR<br>THNVLERQRRNELKRSFFALRDQIPELENNEKAPKVDILKKATAYILSIQA<br>DEHKLTSEKDLLRKRREQLKHKLEQLRNSGA (SEQ ID NO: 156)<br>ATGCCCCTCAACGTGAACTTCACCAACAGGAACTATGACCTCGACTACGAC<br>TCCGTACAGCCCTATTTCATCTGCGACGAGGAAGAGAATTTCTATCACCAG<br>CAACAGCAGAGCGAGCTGCAGCCGCCCGCGCCCAGTGAGGATATCTGGAAG<br>AAATTCGAGCTGCTTCCCACCCCGCCCCTGTCCCCGAGCCGCCGCTCCGGG<br>CTCTGCTCTCCATCCTATGTTGCGGTCGCTACGTCCTTCTCCCCAAGGGAA<br>GACGATGACGGCGGCGGTGGCAACTTCTCCACCGCCGATCAGCTGGAGATG<br>ATGACCGAGTTACTTGGAGGAGACATGGTGAACCAGAGCTTCATCTGCGAT<br>CCTGACGACGAGACCTTCATCAAGAACATCATCATCCAGGACTGTATGTGG<br>AGCGGTTTCTCAGCCGCTGCCAAGCTGGTCTCGGAGAAGCTGGCCTCCTAC<br>CAGGCTGCGCGCAAAGACAGCACCAGCCTGAGCCCCGCCCGCGGGCACAGC<br>GTCTGCTCCACCTCCAGCCTGTACCTGCAGGACCTCACCGCCGCCGCGTCC<br>GAGTGCATTGACCCCTCAGTGGTCTTTCCCTACCCGCTCAACGACAGCAGC<br>TCGCCCAAATCCTGTACCTCGTCCGATTCCACGGCCTTCTCTCCTTCCTCG<br>GACTCGCTGCTGTCCTCCGAGTCCTCCCCACGGGCCAGCCCTGAGCCCCTA<br>GTGCTGCATGAGGAGACACCGCCCACCACCAGCAGCGACTCTGAAGAAGAG<br>CAAGAAGATGAGGAAGAAATTGATGTGGTGTCTGTGGAGAAGAGGCAAACC<br>CCTGCCAAGAGGTCGGAGTCGGGCTCATCTCCATCCCGAGGCCACAGCAAA<br>CCTCCGCACAGCCCACTGGTCCTCAAGAGGTGCCACGTCTCCACTCACCAG<br>CACAACTACGCCGCACCCCCCTCCACAAGGAAGGACTATCCAGCTGCCAAG<br>AGGGCCAAGTTGGACAGTGGCAGGGTCCTGAAGCAGATCAGCAACAACCGC<br>AAGT (SEQ ID NO: 157) |
| c-MycL420P | MPLNVNFTNRNYDLDYDSVQPYFICDEEENFYHQQQSELQPPAPSEDIWK<br>KFELLPTPPLSPSRRSGLCSPSYVAVATSFSPREDDDGGGNFSTADQLEM<br>MTELLGGDMVNQSFICDPDDETFIKNIIIQDCMWSGFSAAAKLVSEKLASY<br>QAARKDSTSLSPARGHSVCSTSSLYLQDLTAAASECIDPSVVFPYPLNDSS<br>SPKSCTSSDSTAFSPSSDSLLSSESSPRASPEPLVLHEETPPTTSSDSEEE<br>QEDEEEIDVVSVEKRQTPAKRSESGSSPSRGHSKPPHSPLVLKRCHVSTHQ<br>HNYAAPPSTRKDYPAAKRAKLDSGRVLKQISNNRKCSSPRSSDTEENDKRR<br>THNVLERQRRNELKRSFFALRDQIPELENNEKAPKVVILKKATAYILSIQA<br>DEHKLTSEKDLPRKRREQLKHKLEQLRNSGA (SEQ ID NO: 158)<br>ATGCCCCTCAACGTGAACTTCACCAACAGGAACTATGACCTCGACTACGAC<br>TCCGTACAGCCCTATTTCATCTGCGACGAGGAAGAGAATTTCTATCACCAG<br>CAACAGCAGAGCGAGCTGCAGCCGCCCGCGCCCAGTGAGGATATCTGGAAG<br>AAATTCGAGCTGCTTCCCACCCCGCCCCTGTCCCCGAGCCGCCGCTCCGGG<br>CTCTGCTCTCCATCCTATGTTGCGGTCGCTACGTCCTTCTCCCCAAGGGAA<br>GACGATGACGGCGGCGGTGGCAACTTCTCCACCGCCGATCAGCTGGAGATG<br>ATGACCGAGTTACTTGGAGGAGACATGGTGAACCAGAGCTTCATCTGCGAT<br>CCTGACGACGAGACCTTCATCAAGAACATCATCATCCAGGACTGTATGTGG<br>AGCGGTTTCTCAGCCGCTGCCAAGCTGGTCTCGGAGAAGCTGGCCTCCTAC<br>CAGGCTGCGCGCAAAGACAGCACCAGCCTGAGCCCCGCCCGCGGGCACAGC<br>GTCTGCTCCACCTCCAGCCTGTACCTGCAGGACCTCACCGCCGCCGCGTCC<br>GAGTGCATTGACCCCTCAGTGGTCTTTCCCTACCCGCTCAACGACAGCAGC<br>TCGCCCAAATCCTGTACCTCGTCCGATTCCACGGCCTTCTCTCCTTCCTCG<br>GACTCGCTGCTGTCCTCCGAGTCCTCCCCACGGGCCAGCCCTGAGCCCCTA<br>GTGCTGCATGAGGAGACACCGCCCACCACCAGCAGCGACTCTGAAGAAGAG<br>CAAGAAGATGAGGAAGAAATTGATGTGGTGTCTGTGGAGAAGAGGCAAACC<br>CCTGCCAAGAGGTCGGAGTCGGGCTCATCTCCATCCCGAGGCCACAGCAAA |

TABLE 21-continued

| Myc, Myc Chimera, and Myc Variant Amino Acid and Nucleotide Sequences | |
|---|---|
| | CCTCCGCACAGCCCACTGGTCCTCAAGAGGTGCCACGTCTCCACTCACCAG<br>CACAACTACGCCGCACCCCCCTCCACAAGGAAGGACTATCCAGCTGCCAAG<br>AGGGCCAAGTTGGACAGTGGCAGGGTCCTGAAGCAGATCAGCAACAACCGC<br>AAGT (SEQ ID NO: 159) |
| L-MycW96E | MDFDSYQHYFYDYDCGEDFYRSTAPSEDIWKKFELVPSPPTSPPWGSGPGA<br>VDPASGINPGEPWPGGGAGDEAESRGHSKAWGRNYASIIRRDCMESGFSAR<br>ERLERVVSDRLAPGAPRGNPPKAPATPDGTPSLEASNPAPATQCQLGEPKT<br>QACSGSESPSDSEGEEIDVVTVEKRRSLDIRKPVTITVRADPLDPCMKHFH<br>ISIHQQQHNYAARFPPESCSQEGDPEPGPQEEAPEIEAPKEKEEEEEEEEE<br>EEIVSPPPVGSEAPQSCHPKPVSSDTEDVTKRKNHNFLERKRRNDLRSRFL<br>ALRDQVPTLASCSKAPKVVILSKALEYLQALVGAEKKMATEKRQLRCRQQQ<br>LQKRIAYLSGY (SEQ ID NO: 160)<br>ATGGACTTCGACTCGTATCAGCACTATTTCTACGACTATGACTGCGGAGAG<br>GATTTCTACCGCTCCACGGCGCCCAGCGAGGACATCTGGAAGAAATTCGAG<br>CTGGTGCCGTCGCCCCCCACGTCGCCGCCCTGGGGCTCCGGTCCCGGCGCC<br>GTGGACCCAGCCTCTGGGATTAATCCCGGGGAGCCGTGGCCTGGAGGGGGT<br>GCCGGGGACGAGGCGGAATCTCGGGGCCATTCGAAAGCCTGGGGCAGGAAT<br>TATGCTTCCATCATTCGCCGTGACTGCATGGAGAGCGGCTTCTCCGCCCGA<br>GAACGGCTGGAGAGAGTGGTGAGCGACAGGCTGGCCCCAGGCGCGCCCCGG<br>GGGAACCCGCCCAAAGCGCCCGCTACCCCGGACGGCACTCCTAGTCTGGAA<br>GCCAGTAACCCGGCGCCCGCCACCCAATGTCAGCTGGGCGAGCCCAAGACT<br>CAGGCCTGCTCCGGGTCCGAGAGCCCCAGCGATTCTGAAGGTGAAGAGATT<br>GACGTGGTGACCGTGGAGAAGAGGCGATCTCTGGACATCCGAAAGCCAGTC<br>ACCATCACGGTGCGAGCAGACCCCCTGGACCCCTGCATGAAGCACTTCCAT<br>ATCTCTATCCACCAACAGCAGCATAACTATGCTGCCCGTTTTCCTCCAGAA<br>AGTTGCTCTCAAGAGGGGGATCCTGAGCCAGGTCCCCAGGAAGAGGCTCCG<br>GAGATAGAAGCTCCCAAGGAGAAAGAGGAGGAGGAAGAGGAAGAGGAGGAA<br>GAAGAGATTGTGAGCCCCCCACCTGTCGGAAGTGAGGCTCCCCAGTCCTGC<br>CACCCCAAACCTGTCAGTTCTGACACTGAGGACGTGACCAAGAGGAAGAAC<br>CATAACTTCTTGGAACGAAAAAGGAGGAATGACCTCCGCTCCCGGTTCCTA<br>GCCCTGCGGGACCAGGTTCCCACCCTGGCCAGCTGCTCTAAGGCCCCCAAA<br>GTCGTGATCCTCAGCAAGGCGTTAGAATACTTGCAGGCTTTGGTGGGGGCT<br>GAAA (SEQ ID NO: 161) |
| L-MycV325D | MDFDSYQHYFYDYDCGEDFYRSTAPSEDIWKKFELVPSPPTSPPWGSGPGA<br>VDPASGINPGEPWPGGGAGDEAESRGHSKAWGRNYASIIRRDCMWSGFSAR<br>ERLERVVSDRLAPGAPRGNPPKAPATPDGTPSLEASNPAPATQCQLGEPKT<br>QACSGSESPSDSEGEEIDVVTVEKRRSLDIRKPVTITVRADPLDPCMKHFH<br>ISIHQQQHNYAARFPPESCSQEGDPEPGPQEEAPEIEAPKEKEEEEEEEEE<br>EEIVSPPPVGSEAPQSCHPKPVSSDTEDVTKRKNHNFLERKRRNDLRSRFL<br>ALRDQVPTLASCSKAPKVDILSKALEYLQALVGAEKKMATEKRQLRCRQQQ<br>LQKRIAYLSGY (SEQ ID NO: 162)<br>ATGGACTTCGACTCGTATCAGCACTATTTCTACGACTATGACTGCGGAGAG<br>GATTTCTACCGCTCCACGGCGCCCAGCGAGGACATCTGGAAGAAATTCGAG<br>CTGGTGCCGTCGCCCCCCACGTCGCCGCCCTGGGGCTCCGGTCCCGGCGCC<br>GTGGACCCAGCCTCTGGGATTAATCCCGGGGAGCCGTGGCCTGGAGGGGGT<br>GCCGGGGACGAGGCGGAATCTCGGGGCCATTCGAAAGCCTGGGGCAGGAAT<br>TATGCTTCCATCATTCGCCGTGACTGCATGTGGAGCGGCTTCTCCGCCCGA<br>GAACGGCTGGAGAGAGTGGTGAGCGACAGGCTGGCCCCAGGCGCGCCCCGG<br>GGGAACCCGCCCAAAGCGCCCGCTACCCCGGACGGCACTCCTAGTCTGGAA<br>GCCAGTAACCCGGCGCCCGCCACCCAATGTCAGCTGGGCGAGCCCAAGACT<br>CAGGCCTGCTCCGGGTCCGAGAGCCCCAGCGATTCTGAAGGTGAAGAGATT<br>GACGTGGTGACCGTGGAGAAGAGGCGATCTCTGGACATCCGAAAGCCAGTC<br>ACCATCACGGTGCGAGCAGACCCCCTGGACCCCTGCATGAAGCACTTCCAT<br>ATCTCTATCCACCAACAGCAGCATAACTATGCTGCCCGTTTTCCTCCAGAA<br>AGTTGCTCTCAAGAGGGGGATCCTGAGCCAGGTCCCCAGGAAGAGGCTCCG<br>GAGATAGAAGCTCCCAAGGAGAAAGAGGAGGAGGAAGAGGAAGAGGAGGAA<br>GAAGAGATTGTGAGCCCCCCACCTGTCGGAAGTGAGGCTCCCCAGTCCTGC<br>CACCCCAAACCTGTCAGTTCTGACACTGAGGACGTGACCAAGAGGAAGAAC<br>CATAACTTCTTGGAACGAAAAAGGAGGAATGACCTCCGCTCCCGGTTCCTA<br>GCCCTGCGGGACCAGGTTCCCACCCTGGCCAGCTGCTCTAAGGCCCCCAAA<br>GTCGACATCCTCAGCAAGGCGTTAGAATACTTGCAGGCTTTGGTGGGGGCT<br>GAAA (SEQ ID NO: 163) |
| L-MycL351P | MDFDSYQHYFYDYDCGEDFYRSTAPSEDIWKKFELVPSPPTSPPWGSGPGA<br>VDPASGINPGEPWPGGGAGDEAESRGHSKAWGRNYASIIRRDCMWSGFSAR<br>ERLERVVSDRLAPGAPRGNPPKAPATPDGTPSLEASNPAPATQCQLGEPKT<br>QACSGSESPSDSEGEEIDVVTVEKRRSLDIRKPVTITVRADPLDPCMKHFH<br>ISIHQQQHNYAARFPPESCSQEGDPEPGPQEEAPEIEAPKEKEEEEEEEEE<br>EEIVSPPPVGSEAPQSCHPKPVSSDTEDVTKRKNHNFLERKRRNDLRSRFL<br>ALRDQVPTLASCSKAPKVVILSKALEYLQALVGAEKKMATEKRQPRCRQQQ<br>LQKRIAYLSGY (SEQ ID NO: 164)<br>ATGGACTTCGACTCGTATCAGCACTATTTCTACGACTATGACTGCGGAGAG<br>GATTTCTACCGCTCCACGGCGCCCAGCGAGGACATCTGGAAGAAATTCGAG<br>CTGGTGCCGTCGCCCCCCACGTCGCCGCCCTGGGGCTCCGGTCCCGGCGCC<br>GTGGACCCAGCCTCTGGGATTAATCCCGGGGAGCCGTGGCCTGGAGGGGGT |

TABLE 21-continued

| Myc, Myc Chimera, and Myc Variant Amino Acid and Nucleotide Sequences |
|---|
| GCCGGGGACGAGGCGGAATCTCGGGGCCATTCGAAAGCCTGGGGCAGGAAT<br>TATGCTTCCATCATTCGCCGTGACTGCATGTGGAGCGGCTTCTCCGCCCGA<br>GAACGGCTGGAGAGAGTGGTGAGCGACAGGCTGGCCCCAGGCGCGCCCCGG<br>GGGAACCCGCCCAAAGCGCCCGCTACCCCGGACGGCACTCCTAGTCTGGAA<br>GCCAGTAACCCGGCGCCCGCCACCCAATGTCAGCTGGGCGAGCCCAAGACT<br>CAGGCCTGCTCCGGGTCCGAGAGCCCCAGCGATTCTGAAGGTGAAGAGATT<br>GACGTGGTGACCGTGGAGAAGAGGCGATCTCTGGACATCCGAAAGCCAGTC<br>ACCATCACGGTGCGAGCAGACCCCCTGGACCCCTGCATGAAGCACTTCCAT<br>ATCTCTATCCACCAACAGCAGCATAACTATGCTGCCCGTTTTCCTCCAGAA<br>AGTTGCTCTCAAGAGGGGGATCCTGAGCCAGGTCCCCAGGAAGAGGCTCCG<br>GAGATAGAAGCTCCCAAGGAGAAAGAGGAGGAGGAAGAGGAAGAGGAGGAA<br>GAAGAGATTGTGAGCCCCCCACCTGTCGGAAGTGAGGCTCCCCAGTCCTGC<br>CACCCCAAACCTGTCAGTTCTGACACTGAGGACGTGACCAAGAGGAAGAAC<br>CATAACTTCTTGGAACGAAAAAGGAGGAATGACCTCCGCTCCCGGTTCCTA<br>GCCCTGCGGGACCAGGTTCCCACCCTGGCCAGCTGCTCTAAGGCCCCCAAA<br>GTCGTGATCCTCAGCAAGGCGTTAGAATACTTGCAGGCTTTGGTGGGGGCT<br>GAAA (SEQ ID NO: 165) |

Figure 63:
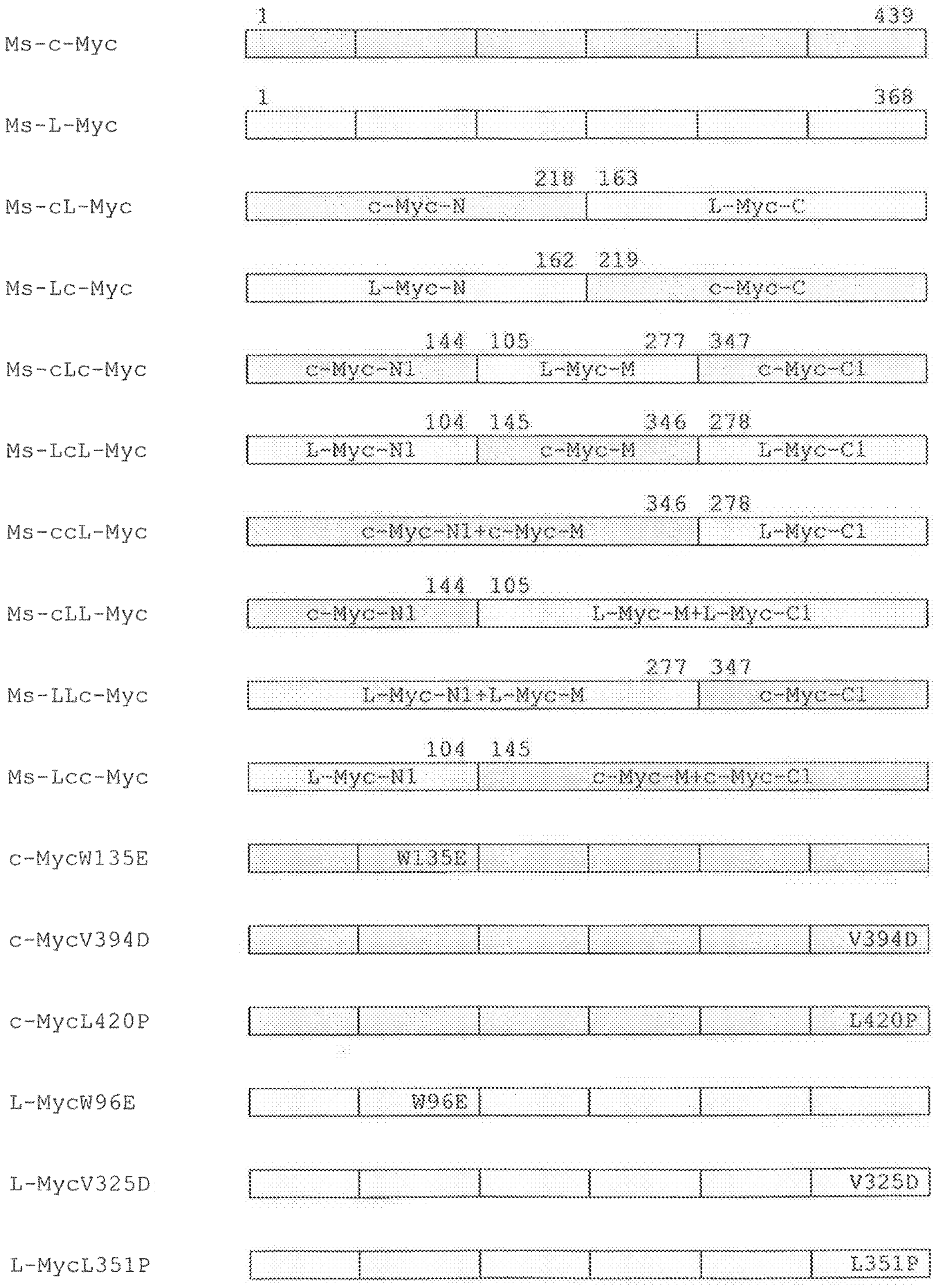
FIG. 63 schematically shows the structure of various Myc chimera genes and mutated genes.
Figure 64:
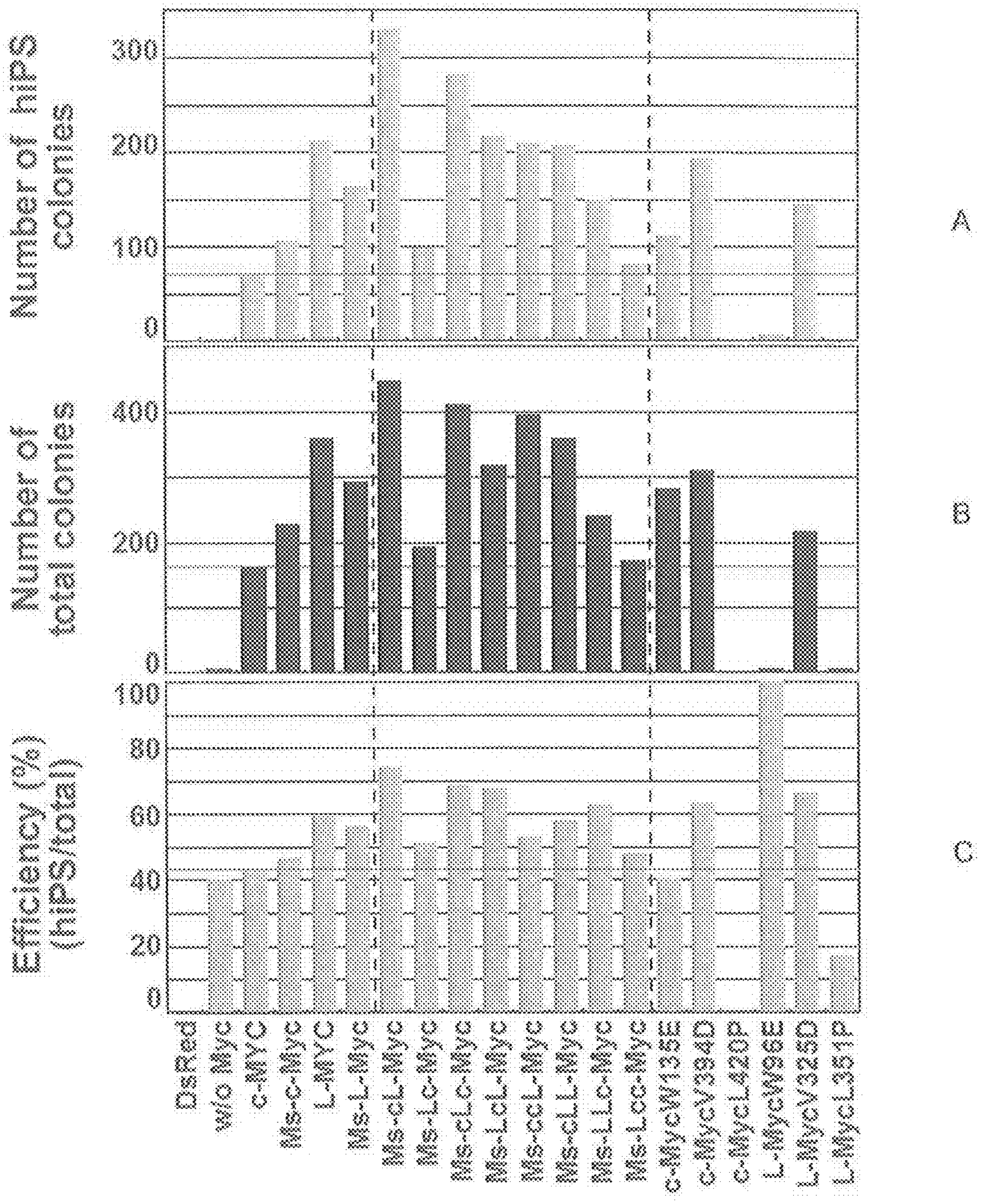
FIG. 64 shows the results of counting the number of colonies of human iPS cells which were established by transducing various Myc chimera genes and mutated genes into aHDF-Slc7a1 cells by retrovirus. (A) shows the number of hiPS cell colonies; (B) shows the total number of colonies; and (C) shows the ratio (%) of the iPS cell colony number to the total colony number.

The Myc chimeras and variants were constructed as described below (see also FIG. 63). At first, mouse c-Myc (Ms-c-Myc) and L-Myc (Ms-L-Myc) were respectively inserted into pENTR-D-TOPO (Invitrogen) to prepare pENTR-D-TOPO-Ms-c-Myc and pENTR-D-TOPO-Ms-L-Myc. Then, primers for introducing a point mutation shown in FIG. 63 were prepared based on the sequence information of mouse c-Myc (NCBI Acc. No. NM_010849) and L-Myc (NCBI Acc. No. NM_008506), and PCR was carried out with these primers using pENTR-D-TOPO-Ms-c-Myc and pENTR-D-TOPO-Ms-L-Myc as a template. After confirmation of each mutation by sequencing, the PCR product was subcloned into a retrovirus vector pMXs by LR reaction. Each fragment of chimera Myc shown in FIG. 63 was amplified by PCR. Then, PCR was carried out using a mixture of combinations of each fragment as a template. The obtained PCR product was subcloned into a retrovirus vector pMXs as mentioned above. The thus obtained each retrovirus, and each retrovirus vector of SOX2, OCT3/4, and KLF4 used in Example 28 were transduced into adult human dermal fibroblast (aHDF-Slc7a1) in the same way as in Example 28. On the 31$^{st}$ day after retrovirus infection, the number of total colonies and the number of human iPS colonies (hiPS colony) which appeared were counted. The results are shown in TABLE 22 and FIGS. 64A-C. FIGS. 64A-C are graphs of the results presented in TABLE 22.

TABLE 22

Summary of hiPS Cell Induction with Chimeric and Mutant Myc

| | | | | | | hiPS colonies | Total colonies | hiPS (%) |
|---|---|---|---|---|---|---|---|---|
| 1 | Neck | CCT4 | Mock | Mock | A | 0 | 0 | 0 |
| 2 | SOX2 | CCT4 | KLF4 | -MYC | B | 2 | 5 | 40 |
| 3 | SOX2 | CCT4 | KLF4 | c-MYC | C | 70 | 162 | 43.2 |
| 4 | SOX2 | CCT4 | KLF4 | Ms-c-Myc | D | 106 | 228 | 46.5 |
| 5 | SOX2 | CCT4 | KLF4 | L-MYC | E | 212 | 358 | 59.2 |
| 6 | SOX2 | CCT4 | KLF4 | Ms-L-Myc | F | 164 | 292 | 56.2 |
| 13 | SOX2 | CCT4 | KLF4 | Ms-cL-Myc | M | 330 | 446 | 74.0 |
| 14 | SOX2 | CCT4 | KLF4 | Ms-Lc-Myc | N | 98 | 192 | 51.0 |
| 15 | SOX2 | CCT4 | KLF4 | Ms-cLc-Myc | O | 282 | 410 | 68.8 |
| 16 | SOX2 | CCT4 | KLF4 | Ms-LcL-Myc | P | 216 | 318 | 67.9 |
| 17 | SOX2 | CCT4 | KLF4 | MS-ccL-Myc | Q | 209 | 394 | 53.0 |
| 18 | SOX2 | CCT4 | KLF4 | Ms-cLL-Myc | R | 208 | 359 | 57.9 |
| 19 | SOX2 | CCT4 | KLF4 | Ms-LLC-Myc | S | 150 | 240 | 62.5 |
| 20 | SOX2 | CCT4 | KLF4 | Ms-Lcc-Myc | T | 81 | 170 | 47.6 |
| 7 | SOX2 | CCT4 | KLF4 | Ms-c-Myc-W135E | G | 112 | 280 | 40.0 |
| 8 | SOX2 | CCT4 | KLF4 | Ms-c-Myc-V394D | H | 194 | 308 | 63.0 |

TABLE 22-continued

Summary of hiPS Cell Induction with Chimeric and Mutant Myc

| | | | | | | hiPS colonies | Total colonies | hiPS (%) |
|---|---|---|---|---|---|---|---|---|
| 9 | SOX2 | CCT4 | KLF4 | Ms-c-Myc-L420D | I | 0 | 0 | 0.0 |
| 10 | SOX2 | CCT4 | KLF4 | Ms-L-Myc-W96E | J | 6 | 6 | 100.0 |
| 11 | SOX2 | CCT4 | KLF4 | Ms-L-Myc-V325D | K | 144 | 216 | 66.7 |
| 12 | SOX2 | CCT4 | KLF4 | Ms-L-Nyc-L351P | L | 1 | 6 | 16.7 |

c-Myc and L-Myc have approximately 100% identity at the amino acid level between human and mouse. As shown in FIGS. 64A-C and TABLE 22, human iPS colonies were generated when mouse genes (Ms-c-Myc and Ms-L-Myc) were used, in the same way as in the case where human genes (c-MYC and L-MYC) were used. Therefore, it was confirmed that mouse c-Myc and L-Myc had the same function as that of human c-MYC and L-MYC.

The results obtained by using various Myc chimera genes and point-mutated genes were compared with those obtained by using wild-type Myc. As a result, it was found that the iPS colony number was increased when Ms-cL-Myc or Ms-cLc-Myc was used, as compared with the wild-type L-Myc (L-MYC), and that the best result was obtained when Ms-cL-Myc was used. Also, from the result obtained by using the point-mutated genes, it was revealed that one amino acid at the C-terminus (c-MycL420P and L-MycL351P) of c-Myc and L-Myc were very important. From the aforementioned results, it was suggested that the functional regions of Myc which were important for establishment of human iPS cells included the N-terminal third of c-Myc, the central region of L-Myc, and the C-terminal region of c/L-Myc. L Kits of the Present Invention.

One aspect of the present invention includes kits designed for use in the preparation and induction of iPS cells. Another aspect of the invention comprises kits for the prevention or treatment of a medical condition or disease through the use of an NRF, an iPS cell or a cell derived from an iPS cell by induction of differentiation. It is also an object of the present invention to provide compositions and methods useful for in vitro transfection, in vivo transfection, ex vivo transfection, in situ labeling, diagnostic tests, genetic therapy, gene therapy, treatment of medical conditions, and the creation of transgenic animals. One aspect of the present invention comprises kits designed for in vitro transfection, in vivo transfection, ex vivo transfection, in situ labeling, diagnostic tests, genetic therapy, gene therapy, treatment of medical conditions, and the creation of transgenic animals. Accordingly, the present invention includes a composition comprising one or more NRFs, one or more iPS cells, one or more cells derived from an iPS cell or cells, and combinations thereof.

Utility and Practical Applications

By using the nuclear reprogramming factor provided by the present invention, reprogramming of differentiated cell nuclei can be conveniently and highly reproducibly induced without using embryos or ES cells, and induced pluripotent stem cells as undifferentiated cells having differentiation ability, pluripotency and growth ability similar to those of ES cells can be established.

Uses of the induced pluripotent stem cells prepared by the method of the present invention are not particularly limited. The cells can be used for any experiments and research conducted with ES cells, therapeutic treatments utilizing ES cells and the like. For example, desired differentiated cells (e.g., nerve cells, cardiac muscle cells, hemocyte cells and the like) can be derived by treating induced pluripotent stem cells obtained by the method of the present invention with retinoic acid, growth factors such as EGF, glucocorticoid or the like, and stem cell therapy based on cellular auto-transplantation can be achieved by returning the differentiated cells obtained as described above to the patient. However, uses of the induced pluripotent stem cells of the present invention are not limited to the aforementioned specific embodiments.

Thus, the present invention has enabled the generation of iPS cells from adult human dermal fibroblasts and other human somatic cells, which are indistinguishable from human ES cells in their differentiation potential in vitro and in teratomas. Furthermore, the instant invention allows for the generation of patient- and disease-specific pluripotent stem cells. Even with the presence of retroviral integration, human iPS cells are useful for understanding disease mechanisms, drug screening, and toxicology. For example, hepatocytes derived from iPS cells with various genetic and disease backgrounds can be utilized in predicting liver toxicity of drug candidates. Human iPS cells may overcome the ethical issues that hES cells confront.

Reference is made to the following documents: Takahashi, et al. *Cell* 131:861-872, 2007; Nakagawa et al. *Nature Biotechnology* 26 (1): 101-106, 2008; Takahashi et al. *Cell* 126:663-676, 2006; Okita et al. *Nature* 448:313-17, 2007; Takahashi et al. *Nature Protocols* 2 (12): 3081-89, 2007; and the supplementary figures and data associated with these documents, all of which are incorporated by reference herein in their entireties.

Although the present invention has been described in considerable detail with regard to certain versions thereof, other versions are possible, and alterations, permutations, and equivalents of the versions shown will become apparent to those skilled in the art upon a reading of the specification and study of the drawings. Also, the various features of the versions herein can be combined in various ways to provide additional versions of the present invention. Furthermore, certain terminology has been used for the purposes of descriptive clarity, and not to limit the present invention. Therefore, any appended claims should not be limited to the description of the preferred versions contained herein and should include all such alterations, permutations, and equivalents as fall within the true spirit and scope of the present invention.

Having now fully described this invention, it will be understood to those of ordinary skill in the art that the methods of the present invention can be carried out with a wide and equivalent range of conditions, formulations, and other parameters without departing from the scope of the invention or any embodiments thereof.

The attached Sequence Listing includes those sequences disclosed in U.S. patent application Ser. No. 12/213,035, which is incorporated by reference herein in its entirety.

What is claimed is:

1. A single recombinant vector, a set of two recombinant vectors or a set of three recombinant vectors, wherein the single recombinant vector, set of two recombinant vectors or set of three recombinant vectors collectively comprise the following three genes:

an Oct family gene, a Klf family gene, and a Myc family gene, wherein the single recombinant vector comprises all of the three genes inserted in the single recombinant vector, wherein one of the three genes is inserted in a first recombinant vector of the set of two recombinant vectors and the other two of the three genes are inserted in a second recombinant vector of the set of two recombinant vectors, or wherein a first of the three genes is inserted in a first recombinant vector of the set of three recombinant vectors, a second of the three genes is inserted in a second recombinant vector of the set of three recombinant vectors and a third of the three genes is inserted in a third recombinant vector of the set of three recombinant vectors.

2. A method for preparing a single recombinant vector, a set of two recombinant vectors or a set of three recombinant vectors, wherein the single recombinant vector, set of two recombinant vectors or set of three recombinant vectors collectively comprise the following three genes:

an Oct family gene, a Klf family gene, and a Myc family gene, the method comprising:

obtaining a single vector, a set of two vectors or a set of three vectors, and inserting each of the three genes into the single vector, the set of two vectors or the set of three vectors, wherein the single recombinant vector comprises all of the three genes inserted in the single recombinant vector, wherein one of the three genes is inserted in a first recombinant vector of the set of two recombinant vectors and the other two of the three genes are inserted in a second recombinant vector of the set of two recombinant vectors, or wherein a first of the three genes is inserted in a first recombinant vector of the set of three recombinant vectors, a second of the three genes is inserted in a second recombinant vector of the set of three recombinant vectors and a third of the three genes is inserted in a third recombinant vector of the set of three recombinant vectors.

3. The method according to claim 2, wherein the three genes are: Oct3/4, Klf4, and c-Myc.

4. The method according to claim 2, further comprising inserting a Sox family gene into one of the vectors of the single vector, the set of two vectors or the set of three vectors.

5. The method according to claim 4, wherein the Sox family gene is Sox2 gene.

6. The method according to claim 2, wherein the three genes are Oct3/4, Klf4, and either L-Myc or N-Myc.

7. The single recombinant vector, the set of two recombinant vectors or the set of three recombinant vectors according to claim 1, wherein the three genes are: Oct3/4, Klf2, and c-Myc.

8. The method according to claim 4, wherein the Sox family gene is Sox1, Sox3, Sox15 or Sox17.

9. The single recombinant vector, the set of two recombinant vectors or the set of three recombinant vectors according to claim 1, wherein one of the single recombinant vector, the set of two recombinant vectors or the set of three recombinant vectors further comprises a Sox family gene.

10. A single recombinant vector, a set of two recombinant vectors, a set of three recombinant vectors or a set of four recombinant vectors, said single recombinant vector, set of two recombinant vectors, set of three recombinant vectors or set of four recombinant vectors collectively comprise the following four genes:

an Oct family gene, a Klf family gene, a Myc family gene and a Sox family gene, wherein the single recombinant vector comprises all of the four genes inserted in the single recombinant vector, wherein one of the four genes is inserted in a first recombinant vector of the set of two recombinant vectors and the other three of the four genes are inserted in a second recombinant vector of the set of two recombinant vectors, wherein two of the four genes are inserted in a first recombinant vector of the set of two recombinant vectors and two of the four genes inserted in a second recombinant vector of the set of two recombinant vectors, wherein a first of the four genes is inserted in a first recombinant vector of the set of three recombinant vectors, a second of the four genes is inserted in a second recombinant vector of the set of three recombinant vectors, and a third and fourth of the four genes are inserted in a third recombinant vector of the set of three recombinant vectors, or wherein a first of the four genes is inserted in a first recombinant vector of the set of four recombinant vectors, a second of the four genes is inserted in a second recombinant vector of the set of three recombinant vectors, a third of the four genes is inserted in a third recombinant vector of the set of four recombinant vectors, and a fourth of the four genes is inserted in a fourth recombinant vector of the set of four recombinant vectors.

11. A method for preparing a single recombinant vector, a set of two recombinant vectors, a set of three recombinant vectors or a set of four recombinant vectors, wherein the single recombinant vector, the set of two recombinant vectors, the set of three recombinant vectors or the set of four recombinant vectors collectively comprise the following four genes:

an Oct family gene, a Klf family gene, a Myc family gene and a Sox family gene, the method comprising:

obtaining a single vector, a set of two vectors, a set of three vectors or a set of four vectors, and inserting each of the four genes into the single vector, the set of two vectors, the set of three vectors or the set of four vectors, wherein the single recombinant vector comprises all of the four genes inserted in the single recombinant vector, wherein one of the four genes is inserted in a first recombinant vector of the set of two recombinant vectors and the other three of the four genes are inserted in a second recombinant vector of the set of two recombinant vectors, wherein two of the four genes are inserted in a first recombinant vector of the set of two recombinant vectors and two of the four genes are inserted in a second recombinant vector of the set of two recombinant vectors, wherein a first of the four genes is inserted in a first recombinant vector of the set of three recombinant vectors, a second of the four genes is inserted in a second recombinant vector of the set of three recombinant vectors, and a third and a fourth of the four genes are inserted in a third recombinant vector of the set of three recombinant vectors, or wherein a first of the four genes is inserted in a first recombinant vector of the set of four recombinant vectors, a second of the four genes is inserted in a second recombinant vector of the set of four recombinant vectors, a third of the four genes is inserted in a third recombinant vector of the set of four recombinant vectors and a fourth of the four genes is inserted in a fourth recombinant vector of the set of four recombinant vectors.

12. The method according to claim 11, wherein the Oct family gene is Oct3/4, the KLF family gene is Klf4, and the Myc family gene is c-Myc.

13. The method according to claim 11, wherein the Sox family gene is Sox2 gene.

14. The method according to claim 11, wherein the Sox family gene is selected from the group consisting of Sox1, Sox3, Sox15 and Sox17.

15. The method according to claim 11, wherein the Myc family gene is L-Myc or N-Myc gene.

16. The method according to claim 11, wherein the Sox family gene is Sox2 and the Klf family gene is Klf4.

17. The single recombinant vector, the set of two recombinant vectors, the set of three recombinant vectors or the set of four recombinant vectors according to claim 10, wherein the Sox family gene is Sox2.

18. The single recombinant vector, the set of two recombinant vectors or the set of three recombinant vectors according to claim 1, wherein the three genes are Oct3/4, Klf4, and either L-Myc or N-Myc.

19. The single recombinant vector, the set of two recombinant vectors, the set of three recombinant vectors or the set of four recombinant vectors according to claim 10, wherein the Sox family gene is Sox1, Sox3, Sox15 or Sox17.

20. A set of two recombinant vectors or a set of three recombinant vectors according to claim 1.

21. A set of two recombinant vectors, a set of three recombinant vectors or a set of four recombinant vectors according to claim 10.

22. A set of two recombinant vectors according to claim 1.

23. A set of two recombinant vectors or a set of three recombinant vectors according to claim 10.

* * * * *

SEQUENCE LISTING

```
<160> NUMBER OF SEQ ID NOS: 165

<210> SEQ ID NO 1
<211> LENGTH: 28
<212> TYPE: DNA
<213> ORGANISM: Artificial Sequence
<220> FEATURE:
<223> OTHER INFORMATION: oligonucleotide

<400> SEQUENCE: 1

tgtggggccc tgaaaggcga gctgagat                                         28


<210> SEQ ID NO 2
<211> LENGTH: 28
<212> TYPE: DNA
<213> ORGANISM: Artificial Sequence
<220> FEATURE:
<223> OTHER INFORMATION: oligonucleotide

<400> SEQUENCE: 2

atgggccgcc atacgacgac gctcaact                                         28


<210> SEQ ID NO 3
<211> LENGTH: 24
<212> TYPE: DNA
<213> ORGANISM: Artificial Sequence
```

<220> FEATURE:
<223> OTHER INFORMATION: oligonucleotide

<400> SEQUENCE: 3
gaagtctggt tccttggcag gatg 24

<210> SEQ ID NO 4
<211> LENGTH: 20
<212> TYPE: DNA
<213> ORGANISM: Artificial Sequence
<220> FEATURE:
<223> OTHER INFORMATION: oligonucleotide

<400> SEQUENCE: 4
actcgataca ctggcctagc 20

<210> SEQ ID NO 5
<211> LENGTH: 20
<212> TYPE: DNA
<213> ORGANISM: Artificial Sequence
<220> FEATURE:
<223> OTHER INFORMATION: oligonucleotide

<400> SEQUENCE: 5
caggtgtttg agggtagctc 20

<210> SEQ ID NO 6
<211> LENGTH: 20
<212> TYPE: DNA
<213> ORGANISM: Artificial Sequence
<220> FEATURE:
<223> OTHER INFORMATION: oligonucleotide

<400> SEQUENCE: 6
cggttcatca tggtacagtc 20

<210> SEQ ID NO 7
<211> LENGTH: 24
<212> TYPE: DNA
<213> ORGANISM: Artificial Sequence
<220> FEATURE:
<223> OTHER INFORMATION: oligonucleotide

<400> SEQUENCE: 7
actgcccctc atcagactgc tact 24

<210> SEQ ID NO 8
<211> LENGTH: 24
<212> TYPE: DNA
<213> ORGANISM: Artificial Sequence
<220> FEATURE:
<223> OTHER INFORMATION: oligonucleotide

<400> SEQUENCE: 8
cactgccttg tactcgggta gctg 24

<210> SEQ ID NO 9
<211> LENGTH: 24
<212> TYPE: DNA
<213> ORGANISM: Artificial Sequence
<220> FEATURE:
<223> OTHER INFORMATION: oligonucleotide

<400> SEQUENCE: 9
gttccaacct gtgcctcgcg tctt 24

<210> SEQ ID NO 10
<211> LENGTH: 26
<212> TYPE: DNA
<213> ORGANISM: Artificial Sequence
<220> FEATURE:
<223> OTHER INFORMATION: oligonucleotide

<400> SEQUENCE: 10
agcgaggcat ggagagagcg gagcag 26

<210> SEQ ID NO 11
<211> LENGTH: 23
<212> TYPE: DNA
<213> ORGANISM: Artificial Sequence
<220> FEATURE:
<223> OTHER INFORMATION: oligonucleotide

<400> SEQUENCE: 11
cgtggtgagc atcttcggag tgg 23

<210> SEQ ID NO 12
<211> LENGTH: 23
<212> TYPE: DNA
<213> ORGANISM: Artificial Sequence
<220> FEATURE:
<223> OTHER INFORMATION: oligonucleotide

<400> SEQUENCE: 12
ccttcttggt ccgcccgttc tta 23

<210> SEQ ID NO 13
<211> LENGTH: 30
<212> TYPE: DNA
<213> ORGANISM: Artificial Sequence
<220> FEATURE:
<223> OTHER INFORMATION: oligonucleotide

<400> SEQUENCE: 13
atggacgcaa ctgtgaacat gatgttcgca 30

<210> SEQ ID NO 14
<211> LENGTH: 30
<212> TYPE: DNA
<213> ORGANISM: Artificial Sequence
<220> FEATURE:
<223> OTHER INFORMATION: oligonucleotide

<400> SEQUENCE: 14
ctttgaggtc ctggtccatc acgtgaccat 30

<210> SEQ ID NO 15
<211> LENGTH: 24
<212> TYPE: DNA
<213> ORGANISM: Artificial Sequence
<220> FEATURE:
<223> OTHER INFORMATION: oligonucleotide

<400> SEQUENCE: 15
ccattagggg ccatcatcgc tttc 24

<210> SEQ ID NO 16
<211> LENGTH: 24
<212> TYPE: DNA
<213> ORGANISM: Artificial Sequence
<220> FEATURE:
<223> OTHER INFORMATION: oligonucleotide

<400> SEQUENCE: 16
cactgctcac tggagggggc ttgc 24

<210> SEQ ID NO 17
<211> LENGTH: 24
<212> TYPE: DNA
<213> ORGANISM: Artificial Sequence
<220> FEATURE:
<223> OTHER INFORMATION: oligonucleotide

<400> SEQUENCE: 17
tgctgcggtc caggccatca agag 24

<210> SEQ ID NO 18
<211> LENGTH: 24
<212> TYPE: DNA
<213> ORGANISM: Artificial Sequence
<220> FEATURE:
<223> OTHER INFORMATION: oligonucleotide

<400> SEQUENCE: 18
gggcactgtt cagttcagcg gatc 24

<210> SEQ ID NO 19
<211> LENGTH: 23
<212> TYPE: DNA
<213> ORGANISM: Artificial Sequence
<220> FEATURE:
<223> OTHER INFORMATION: oligonucleotide

<400> SEQUENCE: 19
tctttccacc aggcccccgg ctc 23

<210> SEQ ID NO 20
<211> LENGTH: 23
<212> TYPE: DNA
<213> ORGANISM: Artificial Sequence
<220> FEATURE:
<223> OTHER INFORMATION: oligonucleotide

<400> SEQUENCE: 20
tgcgggcgga catggggaga tcc 23

<210> SEQ ID NO 21
<211> LENGTH: 30
<212> TYPE: DNA
<213> ORGANISM: Artificial Sequence
<220> FEATURE:
<223> OTHER INFORMATION: oligonucleotide

<400> SEQUENCE: 21
attcttcgtt gtcaagccgc caaagtggag 30

<210> SEQ ID NO 22
<211> LENGTH: 30
<212> TYPE: DNA
<213> ORGANISM: Artificial Sequence
<220> FEATURE:
<223> OTHER INFORMATION: oligonucleotide

<400> SEQUENCE: 22
agttgtttgc tgcggagttg tcatctcgtc 30

<210> SEQ ID NO 23

```
<211> LENGTH: 2127
<212> TYPE: DNA
<213> ORGANISM: Artificial Sequence
<220> FEATURE:
<223> OTHER INFORMATION: oligonucleotide

<400> SEQUENCE: 23

atggataaag ttttaaacag agaggaatct ttgcagctaa tggaccttct aggtcttgaa     60

aggagtgcct gggggaatat tcctctgatg agaaaggcat atttaaaaaa atgcaaggag    120

tttcatcctg ataaaggagg agatgaagaa aaaatgaaga aaatgaatac tctgtacaag    180

aaaatggaag atggagtaaa atatgctcat caacctgact ttggaggctt ctgggatgca    240

actgagattc caacctatgg aactgatgaa tgggagcagt ggtggaatgc ctttaatgag    300

gaaaacctgt tttgctcaga agaaatgcca tctagtgatg atgaggctac tgctgactct    360

caacattcta ctcctccaaa aaagaagaga aaggtagaag accccaagga ctttccttca    420

gaattgctaa gtttttgag tcatgctgtg tttagtaata gaactcttgc ttgctttgct    480

atttacacca caaaggaaaa agctgcactg ctatacaaga aaattatgga aaaatattct    540

gtaaccttta taagtaggca taacagttat aatcataaca tactgttttt tcttactcca    600

cacaggcata gagtgtctgc tattaataac tatgctcaaa aattgtgtac ctttagcttt    660

ttaatttgta aaggggttaa taaggaatat ttgatgtata gtgccttgac tagagatcca    720

ttttctgtta ttgaggaaag tttgccaggt gggttaaagg agcatgattt taatccagaa    780

gaagcagagg aaactaaaca agtgtcctgg aagcttgtaa cagagtatgc aatggaaaca    840

aaatgtgatg atgtgttgtt attgcttggg atgtacttgg aatttcagta cagttttgaa    900

atgtgtttaa aatgtattaa aaaagaacag cccagccact ataagtacca tgaaaagcat    960

tatgcaaatg ctgctatatt tgctgacagc aaaaaccaaa aaaccatatg ccaacaggct   1020

gttgatactg ttttagctaa aaagcgggtt gatagcctac aattaactag agaacaaatg   1080

ttaacaaaca gatttaatga tcttttggat aggatggata taatgtttgg ttctacaggc   1140

tctgctgaca tagaagaatg gatggctgga gttgcttggc tacactgttt gttgcccaaa   1200

atggattcag tggtgtatga ctttttaaaa tgcatggtgt acaacattcc taaaaaaaga   1260

tactggctgt ttaaaggacc aattgatagt ggtaaaacta cattagcagc tgctttgctt   1320

gaattatgtg gggggaaagc tttaaatgtt aatttgccct tggacaggct gaactttgag   1380

ctaggagtag ctattgacca gtttttagta gtttttgagg atgtaaaggg cactggaggg   1440

gagtccagag atttgccttc aggtcaggga attaataacc tggacaattt aagggattat   1500

ttggatggca gtgttaaggt aaacttagaa aagaaacacc taaataaaag aactcaaata   1560

tttcccccctg gaatagtcac catgaatgag tacagtgtgc ctaaaacact gcaggccaga   1620

tttgtaaaac aaatagattt taggcccaaa gattatttaa agcattgcct ggaacgcagt   1680

gagtttttgt tagaaaagag aataattcaa agtggcattg ctttgcttct tatgttaatt   1740

tggtacagac ctgtggctga gtttgctcaa agtattcaga gcagaattgt ggagtggaaa   1800

gagagattgg acaaagagtt tagtttgtca gtgtatcaaa aaatgaagtt taatgtggct   1860

atgggaattg gagttttaga ttggctaaga aacagtgatg atgatgatga agacagccag   1920

gaaaatgctg ataaaaatga agatggtggg gagaagaaca tggaagactc agggcatgaa   1980

acaggcattg attcacagtc ccaaggctca tttcaggccc ctcagtcctc acagtctgtt   2040

catgatcata atcagccata ccacatttgt agaggtttta cttgctttaa aaaacctccc   2100

acacctcccc ctgaacctga aacataa                                       2127
```

<210> SEQ ID NO 24
<211> LENGTH: 456
<212> TYPE: DNA
<213> ORGANISM: Artificial Sequence
<220> FEATURE:
<223> OTHER INFORMATION: oligonucleotide

<400> SEQUENCE: 24
atgtttcagg acccacagga gcgacccaga aagttaccac agttatgcac agagctgcaa 60
acaactatac atgatataat attagaatgt gtgtactgca agcaacagtt actgcgacgt 120
gaggtatatg actttgcttt tcgggattta tgcatagtat atagagatgg gaatccatat 180
gctgtatgtg ataaatgttt aaagttttat tctaaaatta gtgagtatag acattattgt 240
tatagtttgt atggaacaac attagaacag caatacaaca aaccgttgtg tgatttgtta 300
attaggtgta ttaactgtca aaagccactg tgtcctgaag aaaagcaaag acatctggac 360
aaaaagcaaa gattccataa tataaggggt cggtggaccg gtcgatgtat gtcttgttgc 420
agatcatcaa gaacacgtag agaaacccag ctgtaa 456

<210> SEQ ID NO 25
<211> LENGTH: 297
<212> TYPE: DNA
<213> ORGANISM: Artificial Sequence
<220> FEATURE:
<223> OTHER INFORMATION: oligonucleotide

<400> SEQUENCE: 25
atgcatggag atacacctac attgcatgaa tatatgttag atttgcaacc agagacaact 60
gatctctact gttatgagca attaaatgac agctcagagg aggaggatga aatagatggt 120
ccagctggac aagcagaacc ggacagagcc cattacaata ttgtaacctt ttgttgcaag 180
tgtgactcta cgcttcggtt gtgcgtacaa agcacacacg tagacattcg tactttggaa 240
gacctgttaa tgggcacact aggaattgtg tgccccatct gttctcagaa accataa 297

<210> SEQ ID NO 26
<211> LENGTH: 23
<212> TYPE: DNA
<213> ORGANISM: Artificial Sequence
<220> FEATURE:
<223> OTHER INFORMATION: oligonucleotide

<400> SEQUENCE: 26
ccccagggcc ccattttggt acc 23

<210> SEQ ID NO 27
<211> LENGTH: 26
<212> TYPE: DNA
<213> ORGANISM: Artificial Sequence
<220> FEATURE:
<223> OTHER INFORMATION: oligonucleotide

<400> SEQUENCE: 27
ggcacccctg gcatggctct tggctc 26

<210> SEQ ID NO 28
<211> LENGTH: 25
<212> TYPE: DNA
<213> ORGANISM: Artificial Sequence
<220> FEATURE:
<223> OTHER INFORMATION: oligonucleotide

<400> SEQUENCE: 28
acgatcgtgg ccccggaaaa ggacc 25

<210> SEQ ID NO 29
<211> LENGTH: 27
<212> TYPE: DNA
<213> ORGANISM: Artificial Sequence
<220> FEATURE:
<223> OTHER INFORMATION: oligonucleotide

<400> SEQUENCE: 29
caacaaccga aaatgcacca gccccag 27

<210> SEQ ID NO 30
<211> LENGTH: 24
<212> TYPE: DNA
<213> ORGANISM: Artificial Sequence
<220> FEATURE:
<223> OTHER INFORMATION: oligonucleotide

<400> SEQUENCE: 30
ttatcgtcga ccactgtgct gctg 24

<210> SEQ ID NO 31
<211> LENGTH: 24
<212> TYPE: DNA
<213> ORGANISM: Artificial Sequence
<220> FEATURE:
<223> OTHER INFORMATION: oligonucleotide

<400> SEQUENCE: 31 cccttttctct ggagactaaa taaa 24

<210> SEQ ID NO 32
<211> LENGTH: 24
<212> TYPE: DNA
<213> ORGANISM: Artificial Sequence
<220> FEATURE:
<223> OTHER INFORMATION: oligonucleotide

<400> SEQUENCE: 32
gacaggggga ggggaggagc tagg 24

<210> SEQ ID NO 33
<211> LENGTH: 26
<212> TYPE: DNA
<213> ORGANISM: Artificial Sequence
<220> FEATURE:
<223> OTHER INFORMATION: oligonucleotide

<400> SEQUENCE: 33
cttccctcca accagttgcc ccaaac 26

<210> SEQ ID NO 34
<211> LENGTH: 26
<212> TYPE: DNA
<213> ORGANISM: Artificial Sequence
<220> FEATURE:
<223> OTHER INFORMATION: oligonucleotide

<400> SEQUENCE: 34
gggaaatggg aggggtgcaa aagagg 26

<210> SEQ ID NO 35
<211> LENGTH: 26

<212> TYPE: DNA
<213> ORGANISM: Artificial Sequence
<220> FEATURE:
<223> OTHER INFORMATION: oligonucleotide

<400> SEQUENCE: 35
ttgcgtgagt gtggatggga ttggtg 26

<210> SEQ ID NO 36
<211> LENGTH: 25
<212> TYPE: DNA
<213> ORGANISM: Artificial Sequence
<220> FEATURE:
<223> OTHER INFORMATION: oligonucleotide

<400> SEQUENCE: 36
cagccccgat tcttccacca gtccc 25

<210> SEQ ID NO 37
<211> LENGTH: 25
<212> TYPE: DNA
<213> ORGANISM: Artificial Sequence
<220> FEATURE:
<223> OTHER INFORMATION: oligonucleotide

<400> SEQUENCE: 37
cggaagattc ccagtcgggt tcacc 25

<210> SEQ ID NO 38
<211> LENGTH: 24
<212> TYPE: DNA
<213> ORGANISM: Artificial Sequence
<220> FEATURE:
<223> OTHER INFORMATION: oligonucleotide

<400> SEQUENCE: 38
cttatgctac gtaaaggagc tggg 24

<210> SEQ ID NO 39
<211> LENGTH: 24
<212> TYPE: DNA
<213> ORGANISM: Artificial Sequence
<220> FEATURE:
<223> OTHER INFORMATION: oligonucleotide

<400> SEQUENCE: 39
gtgccaaccc aggtcccgga agtt 24

<210> SEQ ID NO 40
<211> LENGTH: 24
<212> TYPE: DNA
<213> ORGANISM: Artificial Sequence
<220> FEATURE:
<223> OTHER INFORMATION: oligonucleotide

<400> SEQUENCE: 40
cagatcctaa acagctcgca gaat 24

<210> SEQ ID NO 41
<211> LENGTH: 23
<212> TYPE: DNA
<213> ORGANISM: Artificial Sequence
<220> FEATURE:
<223> OTHER INFORMATION: oligonucleotide

<400> SEQUENCE: 41
gcgtacgcaa attaaagtcc aga 23

<210> SEQ ID NO 42
<211> LENGTH: 23
<212> TYPE: DNA
<213> ORGANISM: Artificial Sequence
<220> FEATURE:
<223> OTHER INFORMATION: oligonucleotide

<400> SEQUENCE: 42
ctacaacgcc tacgagtcct aca 23

<210> SEQ ID NO 43
<211> LENGTH: 24
<212> TYPE: DNA
<213> ORGANISM: Artificial Sequence
<220> FEATURE:
<223> OTHER INFORMATION: oligonucleotide

<400> SEQUENCE: 43
gttgcaccag aaaagtcaga gttg 24

<210> SEQ ID NO 44
<211> LENGTH: 24
<212> TYPE: DNA
<213> ORGANISM: Artificial Sequence
<220> FEATURE:
<223> OTHER INFORMATION: oligonucleotide

<400> SEQUENCE: 44
atatcccgcc gtgggtgaaa gttc 24

<210> SEQ ID NO 45
<211> LENGTH: 24
<212> TYPE: DNA
<213> ORGANISM: Artificial Sequence
<220> FEATURE:
<223> OTHER INFORMATION: oligonucleotide

<400> SEQUENCE: 45
actcagccat ggactggagc atcc 24

<210> SEQ ID NO 46
<211> LENGTH: 24
<212> TYPE: DNA
<213> ORGANISM: Artificial Sequence
<220> FEATURE:
<223> OTHER INFORMATION: oligonucleotide

<400> SEQUENCE: 46
ggagccgcct gccctggaaa attc 24

<210> SEQ ID NO 47
<211> LENGTH: 24
<212> TYPE: DNA
<213> ORGANISM: Artificial Sequence
<220> FEATURE:
<223> OTHER INFORMATION: oligonucleotide

<400> SEQUENCE: 47
tttttcctga tattctattc ccat 24

<210> SEQ ID NO 48
<211> LENGTH: 24
<212> TYPE: DNA
<213> ORGANISM: Artificial Sequence
<220> FEATURE:
<223> OTHER INFORMATION: oligonucleotide

<400> SEQUENCE: 48
ccgtccccgc aatctccttc catc 24

<210> SEQ ID NO 49
<211> LENGTH: 24
<212> TYPE: DNA
<213> ORGANISM: Artificial Sequence
<220> FEATURE:
<223> OTHER INFORMATION: oligonucleotide

<400> SEQUENCE: 49
atgatgccaa catggctccc ggtg 24

<210> SEQ ID NO 50
<211> LENGTH: 26
<212> TYPE: DNA
<213> ORGANISM: Artificial Sequence
<220> FEATURE:
<223> OTHER INFORMATION: oligonucleotide

<400> SEQUENCE: 50
cctgctcaag ctgactcgac accgtg 26

<210> SEQ ID NO 51
<211> LENGTH: 25
<212> TYPE: DNA
<213> ORGANISM: Artificial Sequence
<220> FEATURE:
<223> OTHER INFORMATION: oligonucleotide

<400> SEQUENCE: 51
ggaaaagctg gccctggggt ggagc 25

<210> SEQ ID NO 52
<211> LENGTH: 28
<212> TYPE: DNA
<213> ORGANISM: Artificial Sequence
<220> FEATURE:
<223> OTHER INFORMATION: oligonucleotide

<400> SEQUENCE: 52
tgattgtagt gctttctggc tgggctcc 28

<210> SEQ ID NO 53
<211> LENGTH: 26
<212> TYPE: DNA
<213> ORGANISM: Artificial Sequence
<220> FEATURE:
<223> OTHER INFORMATION: oligonucleotide

<400> SEQUENCE: 53
gcgtcctggg aagggagatc cggagc 26

<210> SEQ ID NO 54
<211> LENGTH: 26
<212> TYPE: DNA
<213> ORGANISM: Artificial Sequence
<220> FEATURE:
<223> OTHER INFORMATION: oligonucleotide

<400> SEQUENCE: 54
ttgaggggca tcgtcgcggg aggctg 26

<210> SEQ ID NO 55
<211> LENGTH: 24
<212> TYPE: DNA
<213> ORGANISM: Artificial Sequence
<220> FEATURE:
<223> OTHER INFORMATION: oligonucleotide

<400> SEQUENCE: 55
cgagaggacc ccgtggatgc agag 24

<210> SEQ ID NO 56
<211> LENGTH: 24
<212> TYPE: DNA
<213> ORGANISM: Artificial Sequence
<220> FEATURE:
<223> OTHER INFORMATION: oligonucleotide

<400> SEQUENCE: 56
ggcggccatc ttcagcttct ccag 24

<210> SEQ ID NO 57
<211> LENGTH: 26
<212> TYPE: DNA
<213> ORGANISM: Artificial Sequence
<220> FEATURE:
<223> OTHER INFORMATION: oligonucleotide

<400> SEQUENCE: 57
gccctctccc tcccctccac gcacag 26

<210> SEQ ID NO 58
<211> LENGTH: 26
<212> TYPE: DNA
<213> ORGANISM: Artificial Sequence
<220> FEATURE:
<223> OTHER INFORMATION: oligonucleotide

<400> SEQUENCE: 58
cggcgccgtt gctcacagac cacagg 26

<210> SEQ ID NO 59
<211> LENGTH: 26
<212> TYPE: DNA
<213> ORGANISM: Artificial Sequence
<220> FEATURE:
<223> OTHER INFORMATION: oligonucleotide

<400> SEQUENCE: 59
ggcccgccac ttgcaggagt accagg 26

<210> SEQ ID NO 60
<211> LENGTH: 26
<212> TYPE: DNA
<213> ORGANISM: Artificial Sequence
<220> FEATURE:
<223> OTHER INFORMATION: oligonucleotide

<400> SEQUENCE: 60
cttctgctcg ggcccctcat gagacg 26

<210> SEQ ID NO 61
<211> LENGTH: 28
<212> TYPE: DNA
<213> ORGANISM: Artificial Sequence
<220> FEATURE:
<223> OTHER INFORMATION: oligonucleotide

<400> SEQUENCE: 61
acccattatc cagatgtgtt tgcccgag 28

<210> SEQ ID NO 62
<211> LENGTH: 26
<212> TYPE: DNA
<213> ORGANISM: Artificial Sequence
<220> FEATURE:
<223> OTHER INFORMATION: oligonucleotide

<400> SEQUENCE: 62
atggtgaagc tgggcatagg cggcag 26

<210> SEQ ID NO 63
<211> LENGTH: 26
<212> TYPE: DNA
<213> ORGANISM: Artificial Sequence
<220> FEATURE:
<223> OTHER INFORMATION: oligonucleotide

<400> SEQUENCE: 63
tgggagcggt gaagatggaa gggcac 26

<210> SEQ ID NO 64
<211> LENGTH: 26
<212> TYPE: DNA
<213> ORGANISM: Artificial Sequence
<220> FEATURE:
<223> OTHER INFORMATION: oligonucleotide

<400> SEQUENCE: 64
tcatgccagc gcccacgtac gacgac 26

<210> SEQ ID NO 65
<211> LENGTH: 26
<212> TYPE: DNA
<213> ORGANISM: Artificial Sequence
<220> FEATURE:
<223> OTHER INFORMATION: oligonucleotide

<400> SEQUENCE: 65
cgctttcatg gtgtgggcta aggacg 26

<210> SEQ ID NO 66
<211> LENGTH: 26
<212> TYPE: DNA
<213> ORGANISM: Artificial Sequence
<220> FEATURE:
<223> OTHER INFORMATION: oligonucleotide

<400> SEQUENCE: 66
tagttggggt ggtcctgcat gtgctg 26

<210> SEQ ID NO 67
<211> LENGTH: 26
<212> TYPE: DNA
<213> ORGANISM: Artificial Sequence
<220> FEATURE:
<223> OTHER INFORMATION: oligonucleotide

<400> SEQUENCE: 67
cgccaggatc cccgctttga aatctg 26

<210> SEQ ID NO 68

<211> LENGTH: 26
<212> TYPE: DNA
<213> ORGANISM: Artificial Sequence
<220> FEATURE:
<223> OTHER INFORMATION: oligonucleotide

<400> SEQUENCE: 68
tcggccgcca gctctttgat gtgttc 26

<210> SEQ ID NO 69
<211> LENGTH: 24
<212> TYPE: DNA
<213> ORGANISM: Artificial Sequence
<220> FEATURE:
<223> OTHER INFORMATION: oligonucleotide

<400> SEQUENCE: 69
ggaggcgtgg agctcagcga cacc 24

<210> SEQ ID NO 70
<211> LENGTH: 24
<212> TYPE: DNA
<213> ORGANISM: Artificial Sequence
<220> FEATURE:
<223> OTHER INFORMATION: oligonucleotide

<400> SEQUENCE: 70
cggggagctc gctgacggag tctg 24

<210> SEQ ID NO 71
<211> LENGTH: 30
<212> TYPE: DNA
<213> ORGANISM: Artificial Sequence
<220> FEATURE:
<223> OTHER INFORMATION: oligonucleotide

<400> SEQUENCE: 71
caggtggcgg acgtgtgaaa attgagagtg 30

<210> SEQ ID NO 72
<211> LENGTH: 26
<212> TYPE: DNA
<213> ORGANISM: Artificial Sequence
<220> FEATURE:
<223> OTHER INFORMATION: oligonucleotide

<400> SEQUENCE: 72
cacgctggat ctgcctgggg actgtg 26

<210> SEQ ID NO 73
<211> LENGTH: 26
<212> TYPE: DNA
<213> ORGANISM: Artificial Sequence
<220> FEATURE:
<223> OTHER INFORMATION: oligonucleotide

<400> SEQUENCE: 73
acagagggga ggtgcgccag ttcacg 26

<210> SEQ ID NO 74
<211> LENGTH: 26
<212> TYPE: DNA
<213> ORGANISM: Artificial Sequence
<220> FEATURE:
<223> OTHER INFORMATION: oligonucleotide

<400> SEQUENCE: 74
acggggtgga cctcgctgca cagatc 26

<210> SEQ ID NO 75
<211> LENGTH: 26
<212> TYPE: DNA
<213> ORGANISM: Artificial Sequence
<220> FEATURE:
<223> OTHER INFORMATION: oligonucleotide

<400> SEQUENCE: 75
ggcaccagca gcagcaggag cagcag 26

<210> SEQ ID NO 76
<211> LENGTH: 26
<212> TYPE: DNA
<213> ORGANISM: Artificial Sequence
<220> FEATURE:
<223> OTHER INFORMATION: oligonucleotide

<400> SEQUENCE: 76
ccacgtctga ggagccgagg aagcag 26

<210> SEQ ID NO 77
<211> LENGTH: 26
<212> TYPE: DNA
<213> ORGANISM: Artificial Sequence
<220> FEATURE:
<223> OTHER INFORMATION: oligonucleotide

<400> SEQUENCE: 77
gggccccatc aacttcaccg tcttcc 26

<210> SEQ ID NO 78
<211> LENGTH: 26
<212> TYPE: DNA
<213> ORGANISM: Artificial Sequence
<220> FEATURE:
<223> OTHER INFORMATION: oligonucleotide

<400> SEQUENCE: 78
tgtagtcgat gttccccgcc aggtcc 26

<210> SEQ ID NO 79
<211> LENGTH: 26
<212> TYPE: DNA
<213> ORGANISM: Artificial Sequence
<220> FEATURE:
<223> OTHER INFORMATION: oligonucleotide

<400> SEQUENCE: 79
atgagcggga gaaggagcgg cagaac 26

<210> SEQ ID NO 80
<211> LENGTH: 26
<212> TYPE: DNA
<213> ORGANISM: Artificial Sequence
<220> FEATURE:
<223> OTHER INFORMATION: oligonucleotide

<400> SEQUENCE: 80
tcaatggcca gcaccttcct cctctc 26

<210> SEQ ID NO 81
<211> LENGTH: 28
<212> TYPE: DNA

<213> ORGANISM: Artificial Sequence
<220> FEATURE:
<223> OTHER INFORMATION: oligonucleotide

<400> SEQUENCE: 81
tttaacaccg ccagcgctct tcaccttg 28

<210> SEQ ID NO 82
<211> LENGTH: 28
<212> TYPE: DNA
<213> ORGANISM: Artificial Sequence
<220> FEATURE:
<223> OTHER INFORMATION: oligonucleotide

<400> SEQUENCE: 82
tcgtggcgcg tgtgttgtgg gtatctcg 28

<210> SEQ ID NO 83
<211> LENGTH: 25
<212> TYPE: DNA
<213> ORGANISM: Artificial Sequence
<220> FEATURE:
<223> OTHER INFORMATION: oligonucleotide

<400> SEQUENCE: 83
ctggaggccg agcagaagcg caacg 25

<210> SEQ ID NO 84
<211> LENGTH: 25
<212> TYPE: DNA
<213> ORGANISM: Artificial Sequence
<220> FEATURE:
<223> OTHER INFORMATION: oligonucleotide

<400> SEQUENCE: 84
gtccgcccgc tcctctgcct catcc 25

<210> SEQ ID NO 85
<211> LENGTH: 20
<212> TYPE: DNA
<213> ORGANISM: Artificial Sequence
<220> FEATURE:
<223> OTHER INFORMATION: oligonucleotide

<400> SEQUENCE: 85
tttttttttt tttttttttt 20

<210> SEQ ID NO 86
<211> LENGTH: 27
<212> TYPE: DNA
<213> ORGANISM: Artificial Sequence
<220> FEATURE:
<223> OTHER INFORMATION: oligonucleotide

<400> SEQUENCE: 86
gccacagcaa acctcctcac agcccac 27

<210> SEQ ID NO 87
<211> LENGTH: 28
<212> TYPE: DNA
<213> ORGANISM: Artificial Sequence
<220> FEATURE:
<223> OTHER INFORMATION: oligonucleotide

<400> SEQUENCE: 87
ctcgtcgttt ccgcaacaag tcctcttc 28

<210> SEQ ID NO 88
<211> LENGTH: 26
<212> TYPE: DNA
<213> ORGANISM: Artificial Sequence
<220> FEATURE:
<223> OTHER INFORMATION: oligonucleotide

<400> SEQUENCE: 88
caccatggcg ggacacctgg cttcag 26

<210> SEQ ID NO 89
<211> LENGTH: 26
<212> TYPE: DNA
<213> ORGANISM: Artificial Sequence
<220> FEATURE:
<223> OTHER INFORMATION: oligonucleotide

<400> SEQUENCE: 89
acctcagttt gaatgcatgg gagagc 26

<210> SEQ ID NO 90
<211> LENGTH: 31
<212> TYPE: DNA
<213> ORGANISM: Artificial Sequence
<220> FEATURE:
<223> OTHER INFORMATION: oligonucleotide

<400> SEQUENCE: 90
caccatgtac aacatgatgg agacggagct g 31

<210> SEQ ID NO 91
<211> LENGTH: 26
<212> TYPE: DNA
<213> ORGANISM: Artificial Sequence
<220> FEATURE:
<223> OTHER INFORMATION: oligonucleotide

<400> SEQUENCE: 91
tcacatgtgt gagaggggca gtgtgc 26

<210> SEQ ID NO 92
<211> LENGTH: 30
<212> TYPE: DNA
<213> ORGANISM: Artificial Sequence
<220> FEATURE:
<223> OTHER INFORMATION: oligonucleotide

<400> SEQUENCE: 92
caccatggct gtcagtgacg cgctgctccc 30

<210> SEQ ID NO 93
<211> LENGTH: 30
<212> TYPE: DNA
<213> ORGANISM: Artificial Sequence
<220> FEATURE:
<223> OTHER INFORMATION: oligonucleotide

<400> SEQUENCE: 93
ttaaaaatgt ctcttcatgt gtaaggcgag 30

<210> SEQ ID NO 94
<211> LENGTH: 30
<212> TYPE: DNA
<213> ORGANISM: Artificial Sequence
<220> FEATURE:

<223> OTHER INFORMATION: oligonucleotide

<400> SEQUENCE: 94
caccatgccc ctcaacgtta gcttcaccaa 30

<210> SEQ ID NO 95
<211> LENGTH: 30
<212> TYPE: DNA
<213> ORGANISM: Artificial Sequence
<220> FEATURE:
<223> OTHER INFORMATION: oligonucleotide

<400> SEQUENCE: 95
tcacgcacaa gagttccgta gctgttcaag 30

<210> SEQ ID NO 96
<211> LENGTH: 27
<212> TYPE: DNA
<213> ORGANISM: Artificial Sequence
<220> FEATURE:
<223> OTHER INFORMATION: oligonucleotide

<400> SEQUENCE: 96
caccatgggc tgcaaaaacc tgctcgg 27

<210> SEQ ID NO 97
<211> LENGTH: 27
<212> TYPE: DNA
<213> ORGANISM: Artificial Sequence
<220> FEATURE:
<223> OTHER INFORMATION: oligonucleotide

<400> SEQUENCE: 97
tcatttgcac tggtccaagt tgctgtc 27

<210> SEQ ID NO 98
<211> LENGTH: 33
<212> TYPE: DNA
<213> ORGANISM: Artificial Sequence
<220> FEATURE:
<223> OTHER INFORMATION: oligonucleotide

<400> SEQUENCE: 98
attgtcgacg gggatttggc agggtcacag gac 33

<210> SEQ ID NO 99
<211> LENGTH: 32
<212> TYPE: DNA
<213> ORGANISM: Artificial Sequence
<220> FEATURE:
<223> OTHER INFORMATION: oligonucleotide

<400> SEQUENCE: 99
cccagatctc caatgccacc tcctcccaaa cg 32

<210> SEQ ID NO 100
<211> LENGTH: 32
<212> TYPE: DNA
<213> ORGANISM: Artificial Sequence
<220> FEATURE:
<223> OTHER INFORMATION: oligonucleotide

<400> SEQUENCE: 100
cactcgaggt ggaggagctg agggcactgt gg 32

<210> SEQ ID NO 101
<211> LENGTH: 32
<212> TYPE: DNA
<213> ORGANISM: Artificial Sequence
<220> FEATURE:
<223> OTHER INFORMATION: oligonucleotide

<400> SEQUENCE: 101
cacagatctg aaatgagggc ttgcgaaggg ac 32

<210> SEQ ID NO 102
<211> LENGTH: 30
<212> TYPE: DNA
<213> ORGANISM: Artificial Sequence
<220> FEATURE:
<223> OTHER INFORMATION: oligonucleotide

<400> SEQUENCE: 102
ggtttaaaag ggtaaatgtg attatattta 30

<210> SEQ ID NO 103
<211> LENGTH: 22
<212> TYPE: DNA
<213> ORGANISM: Artificial Sequence
<220> FEATURE:
<223> OTHER INFORMATION: oligonucleotide

<400> SEQUENCE: 103
caaactacaa ccacccatca ac 22

<210> SEQ ID NO 104
<211> LENGTH: 30
<212> TYPE: DNA
<213> ORGANISM: Artificial Sequence
<220> FEATURE:
<223> OTHER INFORMATION: oligonucleotide

<400> SEQUENCE: 104
gaggttggag tagaaggatt gttttggttt 30

<210> SEQ ID NO 105
<211> LENGTH: 30
<212> TYPE: DNA
<213> ORGANISM: Artificial Sequence
<220> FEATURE:
<223> OTHER INFORMATION: oligonucleotide

<400> SEQUENCE: 105
cccccctaac ccatcacctc caccacctaa 30

<210> SEQ ID NO 106
<211> LENGTH: 25
<212> TYPE: DNA
<213> ORGANISM: Artificial Sequence
<220> FEATURE:
<223> OTHER INFORMATION: oligonucleotide

<400> SEQUENCE: 106
tggttaggtt ggttttaaat ttttg 25

<210> SEQ ID NO 107
<211> LENGTH: 26
<212> TYPE: DNA
<213> ORGANISM: Artificial Sequence
<220> FEATURE:
<223> OTHER INFORMATION: oligonucleotide

<400> SEQUENCE: 107
aacccaccct tataaattct caatta 26

<210> SEQ ID NO 108
<211> LENGTH: 33
<212> TYPE: DNA
<213> ORGANISM: Artificial Sequence
<220> FEATURE:
<223> OTHER INFORMATION: oligonucleotide

<400> SEQUENCE: 108
caccatgtac agcatgatga tggagaccga cct 33

<210> SEQ ID NO 109
<211> LENGTH: 26
<212> TYPE: DNA
<213> ORGANISM: Artificial Sequence
<220> FEATURE:
<223> OTHER INFORMATION: oligonucleotide

<400> SEQUENCE: 109
ctagatatgc gtcaggggca ccgtgc 26

<210> SEQ ID NO 110
<211> LENGTH: 34
<212> TYPE: DNA
<213> ORGANISM: Artificial Sequence
<220> FEATURE:
<223> OTHER INFORMATION: oligonucleotide

<400> SEQUENCE: 110
caccatgtac agcctgctgg agactgaact caag 34

<210> SEQ ID NO 111
<211> LENGTH: 30
<212> TYPE: DNA
<213> ORGANISM: Artificial Sequence
<220> FEATURE:
<223> OTHER INFORMATION: oligonucleotide

<400> SEQUENCE: 111
tcagatgtgg gtcagcggca ccgttccatt 30

<210> SEQ ID NO 112
<211> LENGTH: 27
<212> TYPE: DNA
<213> ORGANISM: Artificial Sequence
<220> FEATURE:
<223> OTHER INFORMATION: oligonucleotide

<400> SEQUENCE: 112
cacctcggcc atggcctcgc tgctggg 27

<210> SEQ ID NO 113
<211> LENGTH: 27
<212> TYPE: DNA
<213> ORGANISM: Artificial Sequence
<220> FEATURE:
<223> OTHER INFORMATION: oligonucleotide

<400> SEQUENCE: 113
ctccattcct ccagctctat gacacac 27

<210> SEQ ID NO 114
<211> LENGTH: 28

<212> TYPE: DNA
<213> ORGANISM: Artificial Sequence
<220> FEATURE:
<223> OTHER INFORMATION: oligonucleotide

<400> SEQUENCE: 114
caccatggcg ctgaccagct cctcacaa 28

<210> SEQ ID NO 115
<211> LENGTH: 24
<212> TYPE: DNA
<213> ORGANISM: Artificial Sequence
<220> FEATURE:
<223> OTHER INFORMATION: oligonucleotide

<400> SEQUENCE: 115
ttaaaggtgg gttactggca tggg 24

<210> SEQ ID NO 116
<211> LENGTH: 26
<212> TYPE: DNA
<213> ORGANISM: Artificial Sequence
<220> FEATURE:
<223> OTHER INFORMATION: oligonucleotide

<400> SEQUENCE: 116
caccagagcc atgagcagcc cggatg 26

<210> SEQ ID NO 117
<211> LENGTH: 26
<212> TYPE: DNA
<213> ORGANISM: Artificial Sequence
<220> FEATURE:
<223> OTHER INFORMATION: oligonucleotide

<400> SEQUENCE: 117
cgtcaaatgt cggggtagtt gcaata 26

<210> SEQ ID NO 118
<211> LENGTH: 29
<212> TYPE: DNA
<213> ORGANISM: Artificial Sequence
<220> FEATURE:
<223> OTHER INFORMATION: oligonucleotide

<400> SEQUENCE: 118
caccatgcag agatcgccgc ccggctacg 29

<210> SEQ ID NO 119
<211> LENGTH: 30
<212> TYPE: DNA
<213> ORGANISM: Artificial Sequence
<220> FEATURE:
<223> OTHER INFORMATION: oligonucleotide

<400> SEQUENCE: 119
ctagcctgag atgcaagcac tgtaatagac 30

<210> SEQ ID NO 120
<211> LENGTH: 28
<212> TYPE: DNA
<213> ORGANISM: Artificial Sequence
<220> FEATURE:
<223> OTHER INFORMATION: oligonucleotide

<400> SEQUENCE: 120
caccatgaat aatccatcag aaaccaat 28

<210> SEQ ID NO 121
<211> LENGTH: 24
<212> TYPE: DNA
<213> ORGANISM: Artificial Sequence
<220> FEATURE:
<223> OTHER INFORMATION: oligonucleotide

<400> SEQUENCE: 121
gctctgcact cagctcactg tgcc 24

<210> SEQ ID NO 122
<211> LENGTH: 28
<212> TYPE: DNA
<213> ORGANISM: Artificial Sequence
<220> FEATURE:
<223> OTHER INFORMATION: oligonucleotide

<400> SEQUENCE: 122
caccatggcc accaccgcgc agtatctg 28

<210> SEQ ID NO 123
<211> LENGTH: 24
<212> TYPE: DNA
<213> ORGANISM: Artificial Sequence
<220> FEATURE:
<223> OTHER INFORMATION: oligonucleotide

<400> SEQUENCE: 123
ggaacccagt ccgcagggtc actg 24

<210> SEQ ID NO 124
<211> LENGTH: 29
<212> TYPE: DNA
<213> ORGANISM: Artificial Sequence
<220> FEATURE:
<223> OTHER INFORMATION: oligonucleotide

<400> SEQUENCE: 124
caccatgagg cagaagagag agaggaggc 29

<210> SEQ ID NO 125
<211> LENGTH: 30
<212> TYPE: DNA
<213> ORGANISM: Artificial Sequence
<220> FEATURE:
<223> OTHER INFORMATION: oligonucleotide

<400> SEQUENCE: 125
tcagaggtga cgcttcatgt gcagagctaa 30

<210> SEQ ID NO 126
<211> LENGTH: 30
<212> TYPE: DNA
<213> ORGANISM: Artificial Sequence
<220> FEATURE:
<223> OTHER INFORMATION: oligonucleotide

<400> SEQUENCE: 126
caccatggcg ctcagcgagc ctatcttgcc 30

<210> SEQ ID NO 127
<211> LENGTH: 30
<212> TYPE: DNA
<213> ORGANISM: Artificial Sequence
<220> FEATURE:
<223> OTHER INFORMATION: oligonucleotide

<400> SEQUENCE: 127
ctacatatgt cgcttcatgt gcaaggccag 30

<210> SEQ ID NO 128
<211> LENGTH: 28
<212> TYPE: DNA
<213> ORGANISM: Artificial Sequence
<220> FEATURE:
<223> OTHER INFORMATION: oligonucleotide

<400> SEQUENCE: 128
caccatgccc acgcgggtgc tgaccatg 28

<210> SEQ ID NO 129
<211> LENGTH: 24
<212> TYPE: DNA
<213> ORGANISM: Artificial Sequence
<220> FEATURE:
<223> OTHER INFORMATION: oligonucleotide

<400> SEQUENCE: 129
tcgctcagtt ctggtggcgc ttca 24

<210> SEQ ID NO 130
<211> LENGTH: 34
<212> TYPE: DNA
<213> ORGANISM: Artificial Sequence
<220> FEATURE:
<223> OTHER INFORMATION: oligonucleotide

<400> SEQUENCE: 130
caccatggac ttcgactcgt atcagcacta tttc 34

<210> SEQ ID NO 131
<211> LENGTH: 30
<212> TYPE: DNA
<213> ORGANISM: Artificial Sequence
<220> FEATURE:
<223> OTHER INFORMATION: oligonucleotide

<400> SEQUENCE: 131
ttagtagcca ctgaggtacg cgattctctt 30

<210> SEQ ID NO 132
<211> LENGTH: 30
<212> TYPE: DNA
<213> ORGANISM: Artificial Sequence
<220> FEATURE:
<223> OTHER INFORMATION: oligonucleotide

<400> SEQUENCE: 132
caccatgccc agctgcaccg cgtccaccat 30

<210> SEQ ID NO 133
<211> LENGTH: 26
<212> TYPE: DNA
<213> ORGANISM: Artificial Sequence
<220> FEATURE:
<223> OTHER INFORMATION: oligonucleotide

<400> SEQUENCE: 133
ttagcaagtc cgagcgtgtt cgatct 26

<210> SEQ ID NO 134
<211> LENGTH: 439
<212> TYPE: PRT
<213> ORGANISM: Artificial Sequence
<220> FEATURE:
<223> OTHER INFORMATION: peptide

<400> SEQUENCE: 134

Met Pro Leu Asn Val Asn Phe Thr Asn Arg Asn Tyr Asp Leu Asp Tyr
1 5 10 15

Asp Ser Val Gln Pro Tyr Phe Ile Cys Asp Glu Glu Glu Asn Phe Tyr
20 25 30

His Gln Gln Gln Gln Ser Glu Leu Gln Pro Pro Ala Pro Ser Glu Asp
35 40 45

Ile Trp Lys Lys Phe Glu Leu Leu Pro Thr Pro Pro Leu Ser Pro Ser
50 55 60

Arg Arg Ser Gly Leu Cys Ser Pro Ser Tyr Val Ala Val Ala Thr Ser
65 70 75 80

Phe Ser Pro Arg Glu Asp Asp Asp Gly Gly Gly Gly Asn Phe Ser Thr
85 90 95

Ala Asp Gln Leu Glu Met Met Thr Glu Leu Leu Gly Gly Asp Met Val
100 105 110

Asn Gln Ser Phe Ile Cys Asp Pro Asp Asp Glu Thr Phe Ile Lys Asn
115 120 125

Ile Ile Ile Gln Asp Cys Met Trp Ser Gly Phe Ser Ala Ala Ala Lys
130 135 140

Leu Val Ser Glu Lys Leu Ala Ser Tyr Gln Ala Ala Arg Lys Asp Ser
145 150 155 160

Thr Ser Leu Ser Pro Ala Arg Gly His Ser Val Cys Ser Thr Ser Ser
165 170 175

Leu Tyr Leu Gln Asp Leu Thr Ala Ala Ala Ser Glu Cys Ile Asp Pro
180 185 190

Ser Val Val Phe Pro Tyr Pro Leu Asn Asp Ser Ser Ser Pro Lys Ser
195 200 205

Cys Thr Ser Ser Asp Ser Thr Ala Phe Ser Pro Ser Ser Asp Ser Leu
210 215 220

Leu Ser Ser Glu Ser Ser Pro Arg Ala Ser Pro Glu Pro Leu Val Leu
225 230 235 240

His Glu Glu Thr Pro Pro Thr Thr Ser Ser Asp Ser Glu Glu Glu Gln
245 250 255

Glu Asp Glu Glu Glu Ile Asp Val Val Ser Val Glu Lys Arg Gln Thr
260 265 270

Pro Ala Lys Arg Ser Glu Ser Gly Ser Ser Pro Ser Arg Gly His Ser
275 280 285

Lys Pro Pro His Ser Pro Leu Val Leu Lys Arg Cys His Val Ser Thr
290 295 300

His Gln His Asn Tyr Ala Ala Pro Pro Ser Thr Arg Lys Asp Tyr Pro
305 310 315 320

Ala Ala Lys Arg Ala Lys Leu Asp Ser Gly Arg Val Leu Lys Gln Ile
325 330 335

Ser Asn Asn Arg Lys Cys Ser Ser Pro Arg Ser Ser Asp Thr Glu Glu
340 345 350

Asn Asp Lys Arg Arg Thr His Asn Val Leu Glu Arg Gln Arg Arg Asn
355 360 365

Glu Leu Lys Arg Ser Phe Phe Ala Leu Arg Asp Gln Ile Pro Glu Leu
370 375 380

Glu Asn Asn Glu Lys Ala Pro Lys Val Val Ile Leu Lys Lys Ala Thr
385 390 395 400

Ala Tyr Ile Leu Ser Ile Gln Ala Asp Glu His Lys Leu Thr Ser Glu
405 410 415

Lys Asp Leu Leu Arg Lys Arg Arg Glu Gln Leu Lys His Lys Leu Glu
420 425 430

Gln Leu Arg Asn Ser Gly Ala
435

<210> SEQ ID NO 135
<211> LENGTH: 1024
<212> TYPE: DNA
<213> ORGANISM: Artificial Sequence
<220> FEATURE:
<223> OTHER INFORMATION: oligonucleotide

<400> SEQUENCE: 135
atgcccctca acgtgaactt caccaacagg aactatgacc tcgactacga ctccgtacag 60
ccctatttca tctgcgacga ggaagagaat ttctatcacc agcaacagca gagcgagctg 120
cagccgcccg cgcccagtga ggatatctgg aagaaattcg agctgcttcc caccccgccc 180
ctgtccccga gccgccgctc cgggctctgc tctccatcct atgttgcggt cgctacgtcc 240
ttctccccaa gggaagacga tgacggcggc ggtggcaact tctccaccgc cgatcagctg 300
gagatgatga ccgagttact tggaggagac atggtgaacc agagcttcat ctgcgatcct 360
gacgacgaga ccttcatcaa gaacatcatc atccaggact gtatgtggag cggtttctca 420
gccgctgcca agctggtctc ggagaagctg gcctcctacc aggctgcgcg caaagacagc 480
accagcctga gccccgcccg cgggcacagc gtctgctcca cctccagcct gtacctgcag 540
gacctcaccg ccgccgcgtc cgagtgcatt gacccctcag tggtctttcc ctacccgctc 600
aacgacagca gctcgcccaa atcctgtacc tcgtccgatt ccacggcctt ctctccttcc 660
tcggactcgc tgctgtcctc cgagtcctcc ccacgggcca gccctgagcc cctagtgctg 720
catgaggaga caccgcccac caccagcagc gactctgaag aagagcaaga agatgaggaa 780
gaaattgatg tggtgtctgt ggagaagagg caaacccctg ccaagaggtc ggagtcgggc 840
tcatctccat cccgaggcca cagcaaacct ccgcacagcc cactggtcct caagaggtgc 900
cacgtctcca ctcaccagca caactacgcc gcaccccccct ccacaaggaa ggactatcca 960
gctgccaaga gggccaagtt ggacagtggc agggtcctga agcagatcag caacaaccgc 1020
aagt 1024

<210> SEQ ID NO 136
<211> LENGTH: 368
<212> TYPE: PRT
<213> ORGANISM: Artificial Sequence
<220> FEATURE:
<223> OTHER INFORMATION: peptide

<400> SEQUENCE: 136

Met Asp Phe Asp Ser Tyr Gln His Tyr Phe Tyr Asp Tyr Asp Cys Gly
1 5 10 15

Glu Asp Phe Tyr Arg Ser Thr Ala Pro Ser Glu Asp Ile Trp Lys Lys
20 25 30

Phe Glu Leu Val Pro Ser Pro Pro Thr Ser Pro Pro Trp Gly Ser Gly
35 40 45

```
Pro Gly Ala Val Asp Pro Ala Ser Gly Ile Asn Pro Gly Glu Pro Trp
    50                  55                  60

Pro Gly Gly Gly Ala Gly Asp Glu Ala Glu Ser Arg Gly His Ser Lys
65                  70                  75                  80

Ala Trp Gly Arg Asn Tyr Ala Ser Ile Ile Arg Arg Asp Cys Met Trp
                85                  90                  95

Ser Gly Phe Ser Ala Arg Glu Arg Leu Glu Arg Val Val Ser Asp Arg
            100                 105                 110

Leu Ala Pro Gly Ala Pro Arg Gly Asn Pro Pro Lys Ala Pro Ala Thr
        115                 120                 125

Pro Asp Gly Thr Pro Ser Leu Glu Ala Ser Asn Pro Ala Pro Ala Thr
    130                 135                 140

Gln Cys Gln Leu Gly Glu Pro Lys Thr Gln Ala Cys Ser Gly Ser Glu
145                 150                 155                 160

Ser Pro Ser Asp Ser Glu Gly Glu Glu Ile Asp Val Val Thr Val Glu
                165                 170                 175

Lys Arg Arg Ser Leu Asp Ile Arg Lys Pro Val Thr Ile Thr Val Arg
            180                 185                 190

Ala Asp Pro Leu Asp Pro Cys Met Lys His Phe His Ile Ser Ile His
        195                 200                 205

Gln Gln Gln His Asn Tyr Ala Ala Arg Phe Pro Pro Glu Ser Cys Ser
    210                 215                 220

Gln Glu Gly Asp Pro Glu Pro Gly Pro Gln Glu Glu Ala Pro Glu Ile
225                 230                 235                 240

Glu Ala Pro Lys Glu Lys Glu Glu Glu Glu Glu Glu Glu Glu Glu Glu
                245                 250                 255

Glu Ile Val Ser Pro Pro Pro Val Gly Ser Glu Ala Pro Gln Ser Cys
            260                 265                 270

His Pro Lys Pro Val Ser Ser Asp Thr Glu Asp Val Thr Lys Arg Lys
        275                 280                 285

Asn His Asn Phe Leu Glu Arg Lys Arg Arg Asn Asp Leu Arg Ser Arg
    290                 295                 300

Phe Leu Ala Leu Arg Asp Gln Val Pro Thr Leu Ala Ser Cys Ser Lys
305                 310                 315                 320

Ala Pro Lys Val Val Ile Leu Ser Lys Ala Leu Glu Tyr Leu Gln Ala
                325                 330                 335

Leu Val Gly Ala Glu Lys Lys Met Ala Thr Glu Lys Arg Gln Leu Arg
            340                 345                 350

Cys Arg Gln Gln Gln Leu Gln Lys Arg Ile Ala Tyr Leu Ser Gly Tyr
        355                 360                 365
```

<210> SEQ ID NO 137
<211> LENGTH: 1024
<212> TYPE: DNA
<213> ORGANISM: Artificial Sequence
<220> FEATURE:
<223> OTHER INFORMATION: oligonucleotide

<400> SEQUENCE: 137

```
atggacttcg actcgtatca gcactatttc tacgactatg actgcggaga ggatttctac      60

cgctccacgg cgcccagcga ggacatctgg aagaaattcg agctggtgcc gtcgcccccc     120

acgtcgccgc cctggggctc cggtcccggc gccgtggacc cagcctctgg gattaatccc     180

ggggagccgt ggcctggagg gggtgccggg gacgaggcgg aatctcgggg ccattcgaaa     240
```

```
gcctggggca ggaattatgc ttccatcatt cgccgtgact gcatgtggag cggcttctcc    300

gcccgagaac ggctggagag agtggtgagc gacaggctgg ccccaggcgc gccccggggg    360

aacccgccca aagcgcccgc taccccggac ggcactccta gtctggaagc cagtaacccg    420

gcgcccgcca cccaatgtca gctgggcgag cccaagactc aggcctgctc cgggtccgag    480

agccccagcg attctgaagg tgaagagatt gacgtggtga ccgtggagaa gaggcgatct    540

ctggacatcc gaaagccagt caccatcacg gtgcgagcag accccctgga cccctgcatg    600

aagcacttcc atatctctat ccaccaacag cagcataact atgctgcccg ttttcctcca    660

gaaagttgct ctcaagaggg ggatcctgag ccaggtcccc aggaagaggc tccggagata    720

gaagctccca aggagaaaga ggaggaggaa gaggaagagg aggaagaaga gattgtgagc    780

cccccacctg tcggaagtga ggctccccag tcctgccacc ccaaacctgt cagttctgac    840

actgaggacg tgaccaagag gaagaaccat aacttcttgg aacgaaaaag gaggaatgac    900

ctccgctccc ggttcctagc cctgcgggac caggttccca ccctggccag ctgctctaag    960

gcccccaaag tcgtgatcct cagcaaggcg ttagaatact tgcaggcttt ggtgggggct   1020

gaaa                                                                1024
```

```
<210> SEQ ID NO 138
<211> LENGTH: 424
<212> TYPE: PRT
<213> ORGANISM: Artificial Sequence
<220> FEATURE:
<223> OTHER INFORMATION: peptide

<400> SEQUENCE: 138

Met Pro Leu Asn Val Asn Phe Thr Asn Arg Asn Tyr Asp Leu Asp Tyr
1               5                   10                  15

Asp Ser Val Gln Pro Tyr Phe Ile Cys Asp Glu Glu Glu Asn Phe Tyr
            20                  25                  30

His Gln Gln Gln Ser Glu Leu Gln Pro Pro Ala Pro Ser Glu Asp
        35                  40                  45

Ile Trp Lys Lys Phe Glu Leu Leu Pro Thr Pro Pro Leu Ser Pro Ser
    50                  55                  60

Arg Arg Ser Gly Leu Cys Ser Pro Ser Tyr Val Ala Val Ala Thr Ser
65                  70                  75                  80

Phe Ser Pro Arg Glu Asp Asp Asp Gly Gly Gly Gly Asn Phe Ser Thr
                85                  90                  95

Ala Asp Gln Leu Glu Met Met Thr Glu Leu Leu Gly Gly Asp Met Val
            100                 105                 110

Asn Gln Ser Phe Ile Cys Asp Pro Asp Asp Glu Thr Phe Ile Lys Asn
        115                 120                 125

Ile Ile Ile Gln Asp Cys Met Trp Ser Gly Phe Ser Ala Ala Ala Lys
    130                 135                 140

Leu Val Ser Glu Lys Leu Ala Ser Tyr Gln Ala Ala Arg Lys Asp Ser
145                 150                 155                 160

Thr Ser Leu Ser Pro Ala Arg Gly His Ser Val Cys Ser Thr Ser Ser
                165                 170                 175

Leu Tyr Leu Gln Asp Leu Thr Ala Ala Ala Ser Glu Cys Ile Asp Pro
            180                 185                 190

Ser Val Val Phe Pro Tyr Pro Leu Asn Asp Ser Ser Ser Pro Lys Ser
        195                 200                 205

Cys Thr Ser Ser Asp Ser Thr Ala Phe Ser Ser Asp Ser Glu Gly Glu
    210                 215                 220
```

```
Glu Ile Asp Val Val Thr Val Glu Lys Arg Arg Ser Leu Asp Ile Arg
225                 230                 235                 240

Lys Pro Val Thr Ile Thr Val Arg Ala Asp Pro Leu Asp Pro Cys Met
                245                 250                 255

Lys His Phe His Ile Ser Ile His Gln Gln Gln His Asn Tyr Ala Ala
            260                 265                 270

Arg Phe Pro Pro Glu Ser Cys Ser Gln Glu Gly Asp Pro Glu Pro Gly
        275                 280                 285

Pro Gln Glu Glu Ala Pro Glu Ile Glu Ala Pro Lys Glu Lys Glu Glu
    290                 295                 300

Glu Glu Glu Glu Glu Glu Glu Glu Glu Ile Val Ser Pro Pro Pro Val
305                 310                 315                 320

Gly Ser Glu Ala Pro Gln Ser Cys His Pro Lys Pro Val Ser Ser Asp
                325                 330                 335

Thr Glu Asp Val Thr Lys Arg Lys Asn His Asn Phe Leu Glu Arg Lys
            340                 345                 350

Arg Arg Asn Asp Leu Arg Ser Arg Phe Leu Ala Leu Arg Asp Gln Val
        355                 360                 365

Pro Thr Leu Ala Ser Cys Ser Lys Ala Pro Lys Val Val Ile Leu Ser
    370                 375                 380

Lys Ala Leu Glu Tyr Leu Gln Ala Leu Val Gly Ala Glu Lys Lys Met
385                 390                 395                 400

Ala Thr Glu Lys Arg Gln Leu Arg Cys Arg Gln Gln Gln Leu Gln Lys
                405                 410                 415

Arg Ile Ala Tyr Leu Ser Gly Tyr
            420
```

<210> SEQ ID NO 139
<211> LENGTH: 1024
<212> TYPE: DNA
<213> ORGANISM: Artificial Sequence
<220> FEATURE:
<223> OTHER INFORMATION: oligonucleotide

<400> SEQUENCE: 139

```
atgcccctca acgtgaactt caccaacagg aactatgacc tcgactacga ctccgtacag      60

ccctatttca tctgcgacga ggaagagaat ttctatcacc agcaacagca gagcgagctg     120

cagccgcccg cgcccagtga ggatatctgg aagaaattcg agctgcttcc cacccgcccc     180

ctgtccccga gccgccgctc cggctctgc tctccatcct atgttgcggt cgctacgtcc      240

ttctccccaa gggaagacga tgacggcggc ggtggcaact tctccaccgc cgatcagctg     300

gagatgatga ccgagttact tggaggagac atggtgaacc agagcttcat ctgcgatcct     360

gacgacgaga ccttcatcaa gaacatcatc atccaggact gtatgtggag cggtttctca     420

gccgctgcca agctggtctc ggagaagctg gcctcctacc aggctgcgcg caaagacagc     480

accagcctga gccccgcccg cgggcacagc gtctgctcca cctccagcct gtacctgcag     540

gacctcaccg ccgccgcgtc cgagtgcatt gacccctcag tggtctttcc ctacccgctc     600

aacgacagca gctcgcccaa atcctgtacc tcgtccgatt ccacggcctt ctctagcgat     660

tctgaaggtg aagagattga cgtggtgacc gtggagaaga ggcgatctct ggacatccga     720

aagccagtca ccatcacggt gcgagcagac cccctggacc cctgcatgaa gcacttccat     780

atctctatcc accaacagca gcataactat gctgcccgtt ttcctccaga aagttgctct     840

caagaggggg atcctgagcc aggtccccag gaagaggctc cggagataga agctcccaag     900
```

gagaaagagg aggaggaaga ggaagaggag gaagaagaga ttgtgagccc cccacctgtc 960
ggaagtgagg ctccccagtc ctgccacccc aaacctgtca gttctgacac tgaggacgtg 1020
acca 1024

<210> SEQ ID NO 140
<211> LENGTH: 381
<212> TYPE: PRT
<213> ORGANISM: Artificial Sequence
<220> FEATURE:
<223> OTHER INFORMATION: peptide

<400> SEQUENCE: 140

Met Asp Phe Asp Ser Tyr Gln His Tyr Phe Tyr Asp Tyr Asp Cys Gly
1 5 10 15

Glu Asp Phe Tyr Arg Ser Thr Ala Pro Ser Glu Asp Ile Trp Lys Lys
20 25 30

Phe Glu Leu Val Pro Ser Pro Pro Thr Ser Pro Pro Trp Gly Ser Gly
35 40 45

Pro Gly Ala Val Asp Pro Ala Ser Gly Ile Asn Pro Gly Glu Pro Trp
50 55 60

Pro Gly Gly Gly Ala Gly Asp Glu Ala Glu Ser Arg Gly His Ser Lys
65 70 75 80

Ala Trp Gly Arg Asn Tyr Ala Ser Ile Ile Arg Arg Asp Cys Met Trp
85 90 95

Ser Gly Phe Ser Ala Arg Glu Arg Leu Glu Arg Val Val Ser Asp Arg
100 105 110

Leu Ala Pro Gly Ala Pro Arg Gly Asn Pro Pro Lys Ala Pro Ala Thr
115 120 125

Pro Asp Gly Thr Pro Ser Leu Glu Ala Ser Asn Pro Ala Pro Ala Thr
130 135 140

Gln Cys Gln Leu Gly Glu Pro Lys Thr Gln Ala Cys Ser Gly Ser Glu
145 150 155 160

Ser Pro Ser Asp Ser Leu Leu Ser Ser Glu Ser Ser Pro Arg Ala Ser
165 170 175

Pro Glu Pro Leu Val Leu His Glu Glu Thr Pro Pro Thr Thr Ser Ser
180 185 190

Asp Ser Glu Glu Glu Gln Glu Asp Glu Glu Glu Ile Asp Val Val Ser
195 200 205

Val Glu Lys Arg Gln Thr Pro Ala Lys Arg Ser Glu Ser Gly Ser Ser
210 215 220

Pro Ser Arg Gly His Ser Lys Pro Pro His Ser Pro Leu Val Leu Lys
225 230 235 240

Arg Cys His Val Ser Thr His Gln His Asn Tyr Ala Ala Pro Pro Ser
245 250 255

Thr Arg Lys Asp Tyr Pro Ala Ala Lys Arg Ala Lys Leu Asp Ser Gly
260 265 270

Arg Val Leu Lys Gln Ile Ser Asn Asn Arg Lys Cys Ser Ser Pro Arg
275 280 285

Ser Ser Asp Thr Glu Glu Asn Asp Lys Arg Arg Thr His Asn Val Leu
290 295 300

Glu Arg Gln Arg Arg Asn Glu Leu Lys Arg Ser Phe Phe Ala Leu Arg
305 310 315 320

Asp Gln Ile Pro Glu Leu Glu Asn Asn Glu Lys Ala Pro Lys Val Val
325 330 335

Ile Leu Lys Lys Ala Thr Ala Tyr Ile Leu Ser Ile Gln Ala Asp Glu
340 345 350

His Lys Leu Thr Ser Glu Lys Asp Leu Leu Arg Lys Arg Arg Glu Gln
355 360 365

Leu Lys His Lys Leu Glu Gln Leu Arg Asn Ser Gly Ala
370 375 380

<210> SEQ ID NO 141
<211> LENGTH: 1024
<212> TYPE: DNA
<213> ORGANISM: Artificial Sequence
<220> FEATURE:
<223> OTHER INFORMATION: oligonucleotide

<400> SEQUENCE: 141
atggacttcg actcgtatca gcactatttc tacgactatg actgcggaga ggatttctac 60
cgctccacgg cgcccagcga ggacatctgg aagaaattcg agctggtgcc gtcgcccccc 120
acgtcgccgc cctggggctc cggtcccggc gccgtggacc cagcctctgg gattaatccc 180
ggggagccgt ggcctggagg gggtgccggg gacgaggcgg aatctcgggg ccattcgaaa 240
gcctggggca ggaattatgc ttccatcatt cgccgtgact gcatgtggag cggcttctcc 300
gcccgagaac ggctggagag agtggtgagc gacaggctgg ccccaggcgc gccccggggg 360
aacccgccca aagcgcccgc taccccggac ggcactccta gtctggaagc cagtaacccg 420
gcgcccgcca cccaatgtca gctgggcgag cccaagactc aggcctgctc cgggtccgag 480
agcccctcgg actcgctgct gtcctccgag tcctccccac gggccagccc tgagccccta 540
gtgctgcatg aggagacacc gcccaccacc agcagcgact ctgaagaaga gcaagaagat 600
gaggaagaaa ttgatgtggt gtctgtggag aagaggcaaa cccctgccaa gaggtcggag 660
tcgggctcat ctccatcccg aggccacagc aaacctccgc acagcccact ggtcctcaag 720
aggtgccacg tctccactca ccagcacaac tacgccgcac ccccctccac aaggaaggac 780
tatccagctg ccaagagggc caagttggac agtggcaggg tcctgaagca gatcagcaac 840
aaccgcaagt gctccagccc caggtcctca gacacggagg aaaacgacaa gaggcggaca 900
cacaacgtct tggaacgtca gaggaggaac gagctgaagc gcagcttttt tgccctgcgt 960
gaccagatcc ctgaattgga aaacaacgaa aaggccccca aggtagtgat cctcaaaaaa 1020
gcca 1024

<210> SEQ ID NO 142
<211> LENGTH: 410
<212> TYPE: PRT
<213> ORGANISM: Artificial Sequence
<220> FEATURE:
<223> OTHER INFORMATION: oligonucleotide

<400> SEQUENCE: 142

Met Pro Leu Asn Val Asn Phe Thr Asn Arg Asn Tyr Asp Leu Asp Tyr
1 5 10 15

Asp Ser Val Gln Pro Tyr Phe Ile Cys Asp Glu Glu Glu Asn Phe Tyr
20 25 30

His Gln Gln Gln Gln Ser Glu Leu Gln Pro Pro Ala Pro Ser Glu Asp
35 40 45

Ile Trp Lys Lys Phe Glu Leu Leu Pro Thr Pro Pro Leu Ser Pro Ser
50 55 60

Arg Arg Ser Gly Leu Cys Ser Pro Ser Tyr Val Ala Val Ala Thr Ser

```
65                  70                  75                  80

Phe Ser Pro Arg Glu Asp Asp Asp Gly Gly Gly Gly Asn Phe Ser Thr
                85                  90                  95

Ala Asp Gln Leu Glu Met Met Thr Glu Leu Leu Gly Gly Asp Met Val
            100                 105                 110

Asn Gln Ser Phe Ile Cys Asp Pro Asp Asp Glu Thr Phe Ile Lys Asn
        115                 120                 125

Ile Ile Ile Gln Asp Cys Met Trp Ser Gly Phe Ser Ala Ala Ala Lys
    130                 135                 140

Leu Glu Arg Val Val Ser Asp Arg Leu Ala Pro Gly Ala Pro Arg Gly
145                 150                 155                 160

Asn Pro Pro Lys Ala Pro Ala Thr Pro Asp Gly Thr Pro Ser Leu Glu
                165                 170                 175

Ala Ser Asn Pro Ala Pro Ala Thr Gln Cys Gln Leu Gly Glu Pro Lys
            180                 185                 190

Thr Gln Ala Cys Ser Gly Ser Glu Ser Pro Ser Asp Ser Glu Gly Glu
        195                 200                 205

Glu Ile Asp Val Val Thr Val Glu Lys Arg Arg Ser Leu Asp Ile Arg
    210                 215                 220

Lys Pro Val Thr Ile Thr Val Arg Ala Asp Pro Leu Asp Pro Cys Met
225                 230                 235                 240

Lys His Phe His Ile Ser Ile His Gln Gln Gln His Asn Tyr Ala Ala
                245                 250                 255

Arg Phe Pro Pro Glu Ser Cys Ser Gln Glu Gly Asp Pro Glu Pro Gly
            260                 265                 270

Pro Gln Glu Glu Ala Pro Glu Ile Glu Ala Pro Lys Glu Lys Glu Glu
        275                 280                 285

Glu Glu Glu Glu Glu Glu Glu Glu Glu Ile Val Ser Pro Pro Pro Val
    290                 295                 300

Gly Ser Glu Ala Pro Gln Ser Cys His Pro Lys Pro Val Ser Ser Asp
305                 310                 315                 320

Thr Glu Glu Asn Asp Lys Arg Arg Thr His Asn Val Leu Glu Arg Gln
                325                 330                 335

Arg Arg Asn Glu Leu Lys Arg Ser Phe Phe Ala Leu Arg Asp Gln Ile
            340                 345                 350

Pro Glu Leu Glu Asn Asn Glu Lys Ala Pro Lys Val Val Ile Leu Lys
        355                 360                 365

Lys Ala Thr Ala Tyr Ile Leu Ser Ile Gln Ala Asp Glu His Lys Leu
    370                 375                 380

Thr Ser Glu Lys Asp Leu Leu Arg Lys Arg Arg Glu Gln Leu Lys His
385                 390                 395                 400

Lys Leu Glu Gln Leu Arg Asn Ser Gly Ala
                405                 410
```

<210> SEQ ID NO 143
<211> LENGTH: 1024
<212> TYPE: DNA
<213> ORGANISM: Artificial Sequence
<220> FEATURE:
<223> OTHER INFORMATION: oligonucleotide

<400> SEQUENCE: 143

```
atgcccctca acgtgaactt caccaacagg aactatgacc tcgactacga ctccgtacag      60

ccctatttca tctgcgacga ggaagagaat ttctatcacc agcaacagca gagcgagctg     120
```

```
cagccgcccg cgcccagtga ggatatctgg aagaaattcg agctgcttcc caccccgccc    180

ctgtccccga gccgccgctc cgggctctgc tctccatcct atgttgcggt cgctacgtcc    240

ttctccccaa gggaagacga tgacggcggc ggtggcaact tctccaccgc cgatcagctg    300

gagatgatga ccgagttact tggaggagac atggtgaacc agagcttcat ctgcgatcct    360

gacgacgaga ccttcatcaa gaacatcatc atccaggact gtatgtggag cggtttctca    420

gccgctgcca agctggagag agtggtgagc gacaggctgg ccccaggcgc gccccggggg    480

aacccgccca aagcgcccgc taccccggac ggcactccta gtctggaagc cagtaacccg    540

gcgcccgcca cccaatgtca gctgggcgag cccaagactc aggcctgctc cgggtccgag    600

agccccagcg attctgaagg tgaagagatt gacgtggtga ccgtggagaa gaggcgatct    660

ctggacatcc gaaagccagt caccatcacg gtgcgagcag accccctgga cccctgcatg    720

aagcacttcc atatctctat ccaccaacag cagcataact atgctgcccg ttttcctcca    780

gaaagttgct ctcaagaggg ggatcctgag ccaggtcccc aggaagaggc tccggagata    840

gaagctccca aggagaaaga ggaggaggaa gaggaagagg aggaagaaga gattgtgagc    900

cccccacctg tcggaagtga ggctccccag tcctgccacc ccaaacctgt ctcctcagac    960

acggaggaaa acgacaagag gcggacacac aacgtcttgg aacgtcagag gaggaacgag   1020

ctga                                                                1024


<210> SEQ ID NO 144
<211> LENGTH: 397
<212> TYPE: PRT
<213> ORGANISM: Artificial Sequence
<220> FEATURE:
<223> OTHER INFORMATION: peptide

<400> SEQUENCE: 144

Met Asp Phe Asp Ser Tyr Gln His Tyr Phe Tyr Asp Tyr Asp Cys Gly
1               5                   10                  15

Glu Asp Phe Tyr Arg Ser Thr Ala Pro Ser Glu Asp Ile Trp Lys Lys
            20                  25                  30

Phe Glu Leu Val Pro Ser Pro Pro Thr Ser Pro Pro Trp Gly Ser Gly
        35                  40                  45

Pro Gly Ala Val Asp Pro Ala Ser Gly Ile Asn Pro Gly Glu Pro Trp
    50                  55                  60

Pro Gly Gly Gly Ala Gly Asp Glu Ala Glu Ser Arg Gly His Ser Lys
65                  70                  75                  80

Ala Trp Gly Arg Asn Tyr Ala Ser Ile Ile Arg Arg Asp Cys Met Trp
                85                  90                  95

Ser Gly Phe Ser Ala Arg Glu Arg Leu Val Ser Glu Lys Leu Ala Ser
            100                 105                 110

Tyr Gln Ala Ala Arg Lys Asp Ser Thr Ser Leu Ser Pro Ala Arg Gly
        115                 120                 125

His Ser Val Cys Ser Thr Ser Ser Leu Tyr Leu Gln Asp Leu Thr Ala
    130                 135                 140

Ala Ala Ser Glu Cys Ile Asp Pro Ser Val Val Phe Pro Tyr Pro Leu
145                 150                 155                 160

Asn Asp Ser Ser Ser Pro Lys Ser Cys Thr Ser Ser Asp Ser Thr Ala
                165                 170                 175

Phe Ser Pro Ser Ser Asp Ser Leu Leu Ser Ser Glu Ser Ser Pro Arg
            180                 185                 190

Ala Ser Pro Glu Pro Leu Val Leu His Glu Glu Thr Pro Pro Thr Thr
```

```
        195                 200                 205

Ser Ser Asp Ser Glu Glu Glu Gln Glu Asp Glu Glu Glu Ile Asp Val
    210                 215                 220

Val Ser Val Glu Lys Arg Gln Thr Pro Ala Lys Arg Ser Glu Ser Gly
225                 230                 235                 240

Ser Ser Pro Ser Arg Gly His Ser Lys Pro Pro His Ser Pro Leu Val
                245                 250                 255

Leu Lys Arg Cys His Val Ser Thr His Gln His Asn Tyr Ala Ala Pro
            260                 265                 270

Pro Ser Thr Arg Lys Asp Tyr Pro Ala Ala Lys Arg Ala Lys Leu Asp
        275                 280                 285

Ser Gly Arg Val Leu Lys Gln Ile Ser Asn Asn Arg Lys Cys Ser Ser
    290                 295                 300

Pro Arg Ser Ser Asp Thr Glu Asp Val Thr Lys Arg Lys Asn His Asn
305                 310                 315                 320

Phe Leu Glu Arg Lys Arg Arg Asn Asp Leu Arg Ser Arg Phe Leu Ala
                325                 330                 335

Leu Arg Asp Gln Val Pro Thr Leu Ala Ser Cys Ser Lys Ala Pro Lys
            340                 345                 350

Val Val Ile Leu Ser Lys Ala Leu Glu Tyr Leu Gln Ala Leu Val Gly
        355                 360                 365

Ala Glu Lys Lys Met Ala Thr Glu Lys Arg Gln Leu Arg Cys Arg Gln
    370                 375                 380

Gln Gln Leu Gln Lys Arg Ile Ala Tyr Leu Ser Gly Tyr
385                 390                 395


<210> SEQ ID NO 145
<211> LENGTH: 1024
<212> TYPE: DNA
<213> ORGANISM: Artificial Sequence
<220> FEATURE:
<223> OTHER INFORMATION: oligonucleotide

<400> SEQUENCE: 145

atggacttcg actcgtatca gcactatttc tacgactatg actgcggaga ggatttctac     60

cgctccacgg cgcccagcga ggacatctgg aagaaattcg agctggtgcc gtcgcccccc    120

acgtcgccgc cctggggctc cggtcccggc gccgtggacc cagcctctgg gattaatccc    180

ggggagccgt ggcctggagg gggtgccggg gacgaggcgg aatctcgggg ccattcgaaa    240

gcctggggca ggaattatgc ttccatcatt cgccgtgact gcatgtggag cggcttctcc    300

gcccgagaac ggctggtctc ggagaagctg gcctcctacc aggctgcgcg caaagacagc    360

accagcctga gccccgcccg cgggcacagc gtctgctcca cctccagcct gtacctgcag    420

gacctcaccg ccgccgcgtc cgagtgcatt gacccctcag tggtctttcc ctacccgctc    480

aacgacagca gctcgcccaa atcctgtacc tcgtccgatt ccacggcctt ctctccttcc    540

tcggactcgc tgctgtcctc cgagtcctcc ccacgggcca gccctgagcc cctagtgctg    600

catgaggaga caccgcccac caccagcagc gactctgaag aagagcaaga agatgaggaa    660

gaaattgatg tggtgtctgt ggagaagagg caaacccctg ccaagaggtc ggagtcgggc    720

tcatctccat cccgaggcca cagcaaacct ccgcacagcc cactggtcct caagaggtgc    780

cacgtctcca ctcaccagca caactacgcc gcaccccct ccacaaggaa ggactatcca    840

gctgccaaga gggccaagtt ggacagtggc agggtcctga agcagatcag caacaaccgc    900

aagtgctcca gccccaggag ttctgacact gaggacgtga ccaagaggaa gaaccataac    960
```

ttcttggaac gaaaaaggag gaatgacctc cgctcccggt tcctagccct gcgggaccag 1020
gttc 1024

<210> SEQ ID NO 146
<211> LENGTH: 437
<212> TYPE: PRT
<213> ORGANISM: Artificial Sequence
<220> FEATURE:
<223> OTHER INFORMATION: oligonucleotide

<400> SEQUENCE: 146

Met Pro Leu Asn Val Asn Phe Thr Asn Arg Asn Tyr Asp Leu Asp Tyr
1 5 10 15

Asp Ser Val Gln Pro Tyr Phe Ile Cys Asp Glu Glu Glu Asn Phe Tyr
20 25 30

His Gln Gln Gln Gln Ser Glu Leu Gln Pro Pro Ala Pro Ser Glu Asp
35 40 45

Ile Trp Lys Lys Phe Glu Leu Leu Pro Thr Pro Pro Leu Ser Pro Ser
50 55 60

Arg Arg Ser Gly Leu Cys Ser Pro Ser Tyr Val Ala Val Ala Thr Ser
65 70 75 80

Phe Ser Pro Arg Glu Asp Asp Asp Gly Gly Gly Gly Asn Phe Ser Thr
85 90 95

Ala Asp Gln Leu Glu Met Met Thr Glu Leu Leu Gly Gly Asp Met Val
100 105 110

Asn Gln Ser Phe Ile Cys Asp Pro Asp Asp Glu Thr Phe Ile Lys Asn
115 120 125

Ile Ile Ile Gln Asp Cys Met Trp Ser Gly Phe Ser Ala Ala Ala Lys
130 135 140

Leu Val Ser Glu Lys Leu Ala Ser Tyr Gln Ala Ala Arg Lys Asp Ser
145 150 155 160

Thr Ser Leu Ser Pro Ala Arg Gly His Ser Val Cys Ser Thr Ser Ser
165 170 175

Leu Tyr Leu Gln Asp Leu Thr Ala Ala Ala Ser Glu Cys Ile Asp Pro
180 185 190

Ser Val Val Phe Pro Tyr Pro Leu Asn Asp Ser Ser Ser Pro Lys Ser
195 200 205

Cys Thr Ser Ser Asp Ser Thr Ala Phe Ser Pro Ser Ser Asp Ser Leu
210 215 220

Leu Ser Ser Glu Ser Ser Pro Arg Ala Ser Pro Glu Pro Leu Val Leu
225 230 235 240

His Glu Glu Thr Pro Pro Thr Thr Ser Ser Asp Ser Glu Glu Glu Gln
245 250 255

Glu Asp Glu Glu Glu Ile Asp Val Val Ser Val Glu Lys Arg Gln Thr
260 265 270

Pro Ala Lys Arg Ser Glu Ser Gly Ser Ser Pro Ser Arg Gly His Ser
275 280 285

Lys Pro Pro His Ser Pro Leu Val Leu Lys Arg Cys His Val Ser Thr
290 295 300

His Gln His Asn Tyr Ala Ala Pro Pro Ser Thr Arg Lys Asp Tyr Pro
305 310 315 320

Ala Ala Lys Arg Ala Lys Leu Asp Ser Gly Arg Val Leu Lys Gln Ile
325 330 335

Ser Asn Asn Arg Lys Cys Ser Ser Pro Arg Ser Ser Asp Thr Glu Asp

```
            340                 345                 350

Val Thr Lys Arg Lys Asn His Asn Phe Leu Glu Arg Lys Arg Arg Asn
        355                 360                 365

Asp Leu Arg Ser Arg Phe Leu Ala Leu Arg Asp Gln Val Pro Thr Leu
    370                 375                 380

Ala Ser Cys Ser Lys Ala Pro Lys Val Val Ile Leu Ser Lys Ala Leu
385                 390                 395                 400

Glu Tyr Leu Gln Ala Leu Val Gly Ala Glu Lys Lys Met Ala Thr Glu
                405                 410                 415

Lys Arg Gln Leu Arg Cys Arg Gln Gln Gln Leu Gln Lys Arg Ile Ala
            420                 425                 430

Tyr Leu Ser Gly Tyr
        435


<210> SEQ ID NO 147
<211> LENGTH: 1024
<212> TYPE: DNA
<213> ORGANISM: Artificial Sequence
<220> FEATURE:
<223> OTHER INFORMATION: oligonucleotide

<400> SEQUENCE: 147

atgcccctca acgtgaactt caccaacagg aactatgacc tcgactacga ctccgtacag     60

ccctatttca tctgcgacga ggaagagaat ttctatcacc agcaacagca gagcgagctg    120

cagccgcccg cgcccagtga ggatatctgg aagaaattcg agctgcttcc caccccgccc    180

ctgtccccga gccgccgctc cgggctctgc tctccatcct atgttgcggt cgctacgtcc    240

ttctccccaa gggaagacga tgacggcggc ggtggcaact tctccaccgc cgatcagctg    300

gagatgatga ccgagttact tggaggagac atggtgaacc agagcttcat ctgcgatcct    360

gacgacgaga ccttcatcaa gaacatcatc atccaggact gtatgtggag cggtttctca    420

gccgctgcca agctggtctc ggagaagctg gcctcctacc aggctgcgcg caaagacagc    480

accagcctga gccccgcccg cggcacagc gtctgctcca cctccagcct gtacctgcag    540

gacctcaccg ccgccgcgtc cgagtgcatt gacccctcag tggtctttcc ctacccgctc    600

aacgacagca gctcgcccaa atcctgtacc tcgtccgatt ccacggcctt ctctccttcc    660

tcggactcgc tgctgtcctc cgagtcctcc ccacgggcca gccctgagcc cctagtgctg    720

catgaggaga caccgcccac caccagcagc gactctgaag aagagcaaga agatgaggaa    780

gaaattgatg tggtgtctgt ggagaagagg caaacccctg ccaagaggtc ggagtcgggc    840

tcatctccat cccgaggcca cagcaaacct ccgcacagcc cactggtcct caagaggtgc    900

cacgtctcca ctcaccagca caactacgcc gcaccccct ccacaaggaa ggactatcca    960

gctgccaaga gggccaagtt ggacagtggc agggtcctga agcagatcag caacaaccgc   1020

aagt                                                                 1024


<210> SEQ ID NO 148
<211> LENGTH: 408
<212> TYPE: PRT
<213> ORGANISM: Artificial Sequence
<220> FEATURE:
<223> OTHER INFORMATION: peptide

<400> SEQUENCE: 148

Met Pro Leu Asn Val Asn Phe Thr Asn Arg Asn Tyr Asp Leu Asp Tyr
1               5                   10                  15
```

```
Asp Ser Val Gln Pro Tyr Phe Ile Cys Asp Glu Glu Glu Asn Phe Tyr
            20                  25                  30

His Gln Gln Gln Gln Ser Glu Leu Gln Pro Pro Ala Pro Ser Glu Asp
        35                  40                  45

Ile Trp Lys Lys Phe Glu Leu Leu Pro Thr Pro Pro Leu Ser Pro Ser
    50                  55                  60

Arg Arg Ser Gly Leu Cys Ser Pro Ser Tyr Val Ala Val Ala Thr Ser
65                  70                  75                  80

Phe Ser Pro Arg Glu Asp Asp Asp Gly Gly Gly Gly Asn Phe Ser Thr
                85                  90                  95

Ala Asp Gln Leu Glu Met Met Thr Glu Leu Leu Gly Gly Asp Met Val
            100                 105                 110

Asn Gln Ser Phe Ile Cys Asp Pro Asp Asp Glu Thr Phe Ile Lys Asn
        115                 120                 125

Ile Ile Ile Gln Asp Cys Met Trp Ser Gly Phe Ser Ala Ala Ala Lys
    130                 135                 140

Leu Glu Arg Val Val Ser Asp Arg Leu Ala Pro Gly Ala Pro Arg Gly
145                 150                 155                 160

Asn Pro Pro Lys Ala Pro Ala Thr Pro Asp Gly Thr Pro Ser Leu Glu
                165                 170                 175

Ala Ser Asn Pro Ala Pro Ala Thr Gln Cys Gln Leu Gly Glu Pro Lys
            180                 185                 190

Thr Gln Ala Cys Ser Gly Ser Glu Ser Pro Ser Asp Ser Glu Gly Glu
        195                 200                 205

Glu Ile Asp Val Val Thr Val Glu Lys Arg Arg Ser Leu Asp Ile Arg
    210                 215                 220

Lys Pro Val Thr Ile Thr Val Arg Ala Asp Pro Leu Asp Pro Cys Met
225                 230                 235                 240

Lys His Phe His Ile Ser Ile His Gln Gln Gln His Asn Tyr Ala Ala
                245                 250                 255

Arg Phe Pro Pro Glu Ser Cys Ser Gln Glu Gly Asp Pro Glu Pro Gly
            260                 265                 270

Pro Gln Glu Glu Ala Pro Glu Ile Glu Ala Pro Lys Glu Lys Glu Glu
        275                 280                 285

Glu Glu Glu Glu Glu Glu Glu Glu Glu Ile Val Ser Pro Pro Pro Val
    290                 295                 300

Gly Ser Glu Ala Pro Gln Ser Cys His Pro Lys Pro Val Ser Ser Asp
305                 310                 315                 320

Thr Glu Asp Val Thr Lys Arg Lys Asn His Asn Phe Leu Glu Arg Lys
                325                 330                 335

Arg Arg Asn Asp Leu Arg Ser Arg Phe Leu Ala Leu Arg Asp Gln Val
            340                 345                 350

Pro Thr Leu Ala Ser Cys Ser Lys Ala Pro Lys Val Val Ile Leu Ser
        355                 360                 365

Lys Ala Leu Glu Tyr Leu Gln Ala Leu Val Gly Ala Glu Lys Lys Met
    370                 375                 380

Ala Thr Glu Lys Arg Gln Leu Arg Cys Arg Gln Gln Gln Leu Gln Lys
385                 390                 395                 400

Arg Ile Ala Tyr Leu Ser Gly Tyr
                405
```

<210> SEQ ID NO 149
<211> LENGTH: 1024
<212> TYPE: DNA

<213> ORGANISM: Artificial Sequence
<220> FEATURE:
<223> OTHER INFORMATION: oligonucleotide

<400> SEQUENCE: 149
atgcccctca acgtgaactt caccaacagg aactatgacc tcgactacga ctccgtacag 60
ccctatttca tctgcgacga ggaagagaat ttctatcacc agcaacagca gagcgagctg 120
cagccgcccg cgcccagtga ggatatctgg aagaaattcg agctgcttcc caccccgccc 180
ctgtccccga gccgccgctc cgggctctgc tctccatcct atgttgcggt cgctacgtcc 240
ttctccccaa gggaagacga tgacggcggc ggtggcaact tctccaccgc cgatcagctg 300
gagatgatga ccgagttact tggaggagac atggtgaacc agagcttcat ctgcgatcct 360
gacgacgaga ccttcatcaa gaacatcatc atccaggact gtatgtggag cggtttctca 420
gccgctgcca agctggagag agtggtgagc gacaggctgg ccccaggcgc gccccggggg 480
aacccgccca aagcgcccgc taccccggac ggcactccta gtctggaagc cagtaacccg 540
gcgcccgcca cccaatgtca gctgggcgag cccaagactc aggcctgctc cgggtccgag 600
agccccagcg attctgaagg tgaagagatt gacgtggtga ccgtggagaa gaggcgatct 660
ctggacatcc gaaagccagt caccatcacg gtgcgagcag accccctgga cccctgcatg 720
aagcacttcc atatctctat ccaccaacag cagcataact atgctgcccg ttttcctcca 780
gaaagttgct ctcaagaggg ggatcctgag ccaggtcccc aggaagaggc tccggagata 840
gaagctccca aggagaaaga ggaggaggaa gaggaagagg aggaagaaga gattgtgagc 900
cccccacctg tcggaagtga ggctccccag tcctgccacc ccaaacctgt cagttctgac 960
actgaggacg tgaccaagag gaagaaccat aacttcttgg aacgaaaaag gaggaatgac 1020
ctcc 1024

<210> SEQ ID NO 150
<211> LENGTH: 370
<212> TYPE: PRT
<213> ORGANISM: Artificial Sequence
<220> FEATURE:
<223> OTHER INFORMATION: peptide

<400> SEQUENCE: 150

Met Asp Phe Asp Ser Tyr Gln His Tyr Phe Tyr Asp Tyr Asp Cys Gly
1 5 10 15

Glu Asp Phe Tyr Arg Ser Thr Ala Pro Ser Glu Asp Ile Trp Lys Lys
20 25 30

Phe Glu Leu Val Pro Ser Pro Pro Thr Ser Pro Pro Trp Gly Ser Gly
35 40 45

Pro Gly Ala Val Asp Pro Ala Ser Gly Ile Asn Pro Gly Glu Pro Trp
50 55 60

Pro Gly Gly Gly Ala Gly Asp Glu Ala Glu Ser Arg Gly His Ser Lys
65 70 75 80

Ala Trp Gly Arg Asn Tyr Ala Ser Ile Ile Arg Arg Asp Cys Met Trp
85 90 95

Ser Gly Phe Ser Ala Arg Glu Arg Leu Glu Arg Val Val Ser Asp Arg
100 105 110

Leu Ala Pro Gly Ala Pro Arg Gly Asn Pro Pro Lys Ala Pro Ala Thr
115 120 125

Pro Asp Gly Thr Pro Ser Leu Glu Ala Ser Asn Pro Ala Pro Ala Thr
130 135 140

```
Gln Cys Gln Leu Gly Glu Pro Lys Thr Gln Ala Cys Ser Gly Ser Glu
145                 150                 155                 160

Ser Pro Ser Asp Ser Glu Gly Glu Glu Ile Asp Val Val Thr Val Glu
                165                 170                 175

Lys Arg Arg Ser Leu Asp Ile Arg Lys Pro Val Thr Ile Thr Val Arg
            180                 185                 190

Ala Asp Pro Leu Asp Pro Cys Met Lys His Phe His Ile Ser Ile His
        195                 200                 205

Gln Gln Gln His Asn Tyr Ala Ala Arg Phe Pro Pro Glu Ser Cys Ser
    210                 215                 220

Gln Glu Gly Asp Pro Glu Pro Gly Pro Gln Glu Glu Ala Pro Glu Ile
225                 230                 235                 240

Glu Ala Pro Lys Glu Lys Glu Glu Glu Glu Glu Glu Glu Glu Glu Glu
                245                 250                 255

Glu Ile Val Ser Pro Pro Pro Val Gly Ser Glu Ala Pro Gln Ser Cys
            260                 265                 270

His Pro Lys Pro Val Ser Ser Asp Thr Glu Glu Asn Asp Lys Arg Arg
        275                 280                 285

Thr His Asn Val Leu Glu Arg Gln Arg Arg Asn Glu Leu Lys Arg Ser
    290                 295                 300

Phe Phe Ala Leu Arg Asp Gln Ile Pro Glu Leu Glu Asn Asn Glu Lys
305                 310                 315                 320

Ala Pro Lys Val Val Ile Leu Lys Lys Ala Thr Ala Tyr Ile Leu Ser
                325                 330                 335

Ile Gln Ala Asp Glu His Lys Leu Thr Ser Glu Lys Asp Leu Leu Arg
            340                 345                 350

Lys Arg Arg Glu Gln Leu Lys His Lys Leu Glu Gln Leu Arg Asn Ser
        355                 360                 365

Gly Ala
    370
```

<210> SEQ ID NO 151
<211> LENGTH: 1023
<212> TYPE: DNA
<213> ORGANISM: Artificial Sequence
<220> FEATURE:
<223> OTHER INFORMATION: oligonucleotide

<400> SEQUENCE: 151

```
atggacttcg actcgtatca gcactatttc tacgactaga ctgcggagag gatttctacc     60

gctccacggc gcccagcgag gacatctgga agaaattcga gctggtgccg tcgcccccca    120

cgtcgccgcc ctggggctcc ggtcccggcg ccgtggaccc agcctctggg attaatcccg    180

gggagccgtg gcctggaggg ggtgccgggg acgaggcgga atctcggggc cattcgaaag    240

cctggggcag gaattatgct tccatcattc gccgtgactg catgtggagc ggcttctccg    300

cccgagaacg gctggagaga gtggtgagcg acaggctggc cccaggcgcg ccccggggga    360

acccgcccaa agcgcccgct accccggacg gcactcctag tctggaagcc agtaacccgg    420

cgcccgccac ccaatgtcag ctgggcgagc ccaagactca ggcctgctcc gggtccgaga    480

gccccagcga ttctgaaggt gaagagattg acgtggtgac cgtggagaag aggcgatctc    540

tggacatccg aaagccagtc accatcacgg tgcgagcaga ccccctggac ccctgcatga    600

agcacttcca tatctctatc caccaacagc agcataacta tgctgcccgt tttcctccag    660

aaagttgctc tcaagagggg gatcctgagc caggtcccca ggaagaggct ccggagatag    720
```

-continued

```
aagctcccaa ggagaaagag gaggaggaag aggaagagga ggaagaagag attgtgagcc    780

ccccacctgt cggaagtgag gctccccagt cctgccaccc caaacctgtc tcctcagaca    840

cggaggaaaa cgacaagagg cggacacaca acgtcttgga acgtcagagg aggaacgagc    900

tgaagcgcag ctttttgcc ctgcgtgacc agatccctga attggaaaac aacgaaaagg    960

cccccaaggt agtgatcctc aaaaaagcca ccgcctacat cctgtccatt caagcagacg   1020

agc                                                                 1023
```

```
<210> SEQ ID NO 152
<211> LENGTH: 399
<212> TYPE: PRT
<213> ORGANISM: Artificial Sequence
<220> FEATURE:
<223> OTHER INFORMATION: peptide

<400> SEQUENCE: 152

Met Asp Phe Asp Ser Tyr Gln His Tyr Phe Tyr Asp Tyr Asp Cys Gly
1               5                   10                  15

Glu Asp Phe Tyr Arg Ser Thr Ala Pro Ser Glu Asp Ile Trp Lys Lys
            20                  25                  30

Phe Glu Leu Val Pro Ser Pro Pro Thr Ser Pro Pro Trp Gly Ser Gly
        35                  40                  45

Pro Gly Ala Val Asp Pro Ala Ser Gly Ile Asn Pro Gly Glu Pro Trp
    50                  55                  60

Pro Gly Gly Gly Ala Gly Asp Glu Ala Glu Ser Arg Gly His Ser Lys
65                  70                  75                  80

Ala Trp Gly Arg Asn Tyr Ala Ser Ile Ile Arg Arg Asp Cys Met Trp
                85                  90                  95

Ser Gly Phe Ser Ala Arg Glu Arg Leu Val Ser Glu Lys Leu Ala Ser
            100                 105                 110

Tyr Gln Ala Ala Arg Lys Asp Ser Thr Ser Leu Ser Pro Ala Arg Gly
        115                 120                 125

His Ser Val Cys Ser Thr Ser Ser Leu Tyr Leu Gln Asp Leu Thr Ala
    130                 135                 140

Ala Ala Ser Glu Cys Ile Asp Pro Ser Val Val Phe Pro Tyr Pro Leu
145                 150                 155                 160

Asn Asp Ser Ser Ser Pro Lys Ser Cys Thr Ser Ser Asp Ser Thr Ala
                165                 170                 175

Phe Ser Pro Ser Ser Asp Ser Leu Leu Ser Ser Glu Ser Ser Pro Arg
            180                 185                 190

Ala Ser Pro Glu Pro Leu Val Leu His Glu Glu Thr Pro Pro Thr Thr
        195                 200                 205

Ser Ser Asp Ser Glu Glu Glu Gln Glu Asp Glu Glu Glu Ile Asp Val
    210                 215                 220

Val Ser Val Glu Lys Arg Gln Thr Pro Ala Lys Arg Ser Glu Ser Gly
225                 230                 235                 240

Ser Ser Pro Ser Arg Gly His Ser Lys Pro Pro His Ser Pro Leu Val
                245                 250                 255

Leu Lys Arg Cys His Val Ser Thr His Gln His Asn Tyr Ala Ala Pro
            260                 265                 270

Pro Ser Thr Arg Lys Asp Tyr Pro Ala Ala Lys Arg Ala Lys Leu Asp
        275                 280                 285

Ser Gly Arg Val Leu Lys Gln Ile Ser Asn Asn Arg Lys Cys Ser Ser
    290                 295                 300
```

```
Pro Arg Ser Ser Asp Thr Glu Glu Asn Asp Lys Arg Arg Thr His Asn
305                 310                 315                 320

Val Leu Glu Arg Gln Arg Arg Asn Glu Leu Lys Arg Ser Phe Phe Ala
                325                 330                 335

Leu Arg Asp Gln Ile Pro Glu Leu Glu Asn Asn Glu Lys Ala Pro Lys
            340                 345                 350

Val Val Ile Leu Lys Lys Ala Thr Ala Tyr Ile Leu Ser Ile Gln Ala
        355                 360                 365

Asp Glu His Lys Leu Thr Ser Glu Lys Asp Leu Leu Arg Lys Arg Arg
    370                 375                 380

Glu Gln Leu Lys His Lys Leu Glu Gln Leu Arg Asn Ser Gly Ala
385                 390                 395


<210> SEQ ID NO 153
<211> LENGTH: 1024
<212> TYPE: DNA
<213> ORGANISM: Artificial Sequence
<220> FEATURE:
<223> OTHER INFORMATION: oligonucleotide

<400> SEQUENCE: 153

atggacttcg actcgtatca gcactatttc tacgactatg actgcggaga ggatttctac     60

cgctccacgg cgcccagcga ggacatctgg aagaaattcg agctggtgcc gtcgcccccc    120

acgtcgccgc cctggggctc cggtcccggc gccgtggacc cagcctctgg gattaatccc    180

ggggagccgt ggcctggagg gggtgccggg gacgaggcgg aatctcgggg ccattcgaaa    240

gcctggggca ggaattatgc ttccatcatt cgccgtgact gcatgtggag cggcttctcc    300

gcccgagaac ggctggtctc ggagaagctg gcctcctacc aggctgcgcg caaagacagc    360

accagcctga gccccgcccg cgggcacagc gtctgctcca cctccagcct gtacctgcag    420

gacctcaccg ccgccgcgtc cgagtgcatt gacccctcag tggtctttcc ctacccgctc    480

aacgacagca gctcgcccaa atcctgtacc tcgtccgatt ccacggcctt ctctccttcc    540

tcggactcgc tgctgtcctc cgagtcctcc ccacgggcca gccctgagcc cctagtgctg    600

catgaggaga caccgcccac caccagcagc gactctgaag aagagcaaga agatgaggaa    660

gaaattgatg tggtgtctgt ggagaagagg caaacccctg ccaagaggtc ggagtcgggc    720

tcatctccat cccgaggcca cagcaaacct ccgcacagcc cactggtcct caagaggtgc    780

cacgtctcca ctcaccagca caactacgcc gcaccccccct ccacaaggaa ggactatcca    840

gctgccaaga gggccaagtt ggacagtggc agggtcctga agcagatcag caacaaccgc    900

aagtgctcca gccccaggtc ctcagacacg gaggaaaacg acaagaggcg gacacacaac    960

gtcttggaac gtcagaggag gaacgagctg aagcgcagct tttttgccct gcgtgaccag   1020

atcc                                                                1024


<210> SEQ ID NO 154
<211> LENGTH: 439
<212> TYPE: PRT
<213> ORGANISM: Artificial Sequence
<220> FEATURE:
<223> OTHER INFORMATION: peptide

<400> SEQUENCE: 154

Met Pro Leu Asn Val Asn Phe Thr Asn Arg Asn Tyr Asp Leu Asp Tyr
1               5                   10                  15

Asp Ser Val Gln Pro Tyr Phe Ile Cys Asp Glu Glu Glu Asn Phe Tyr
            20                  25                  30
```

```
His Gln Gln Gln Gln Ser Glu Leu Gln Pro Pro Ala Pro Ser Glu Asp
        35                  40                  45

Ile Trp Lys Lys Phe Glu Leu Leu Pro Thr Pro Pro Leu Ser Pro Ser
    50                  55                  60

Arg Arg Ser Gly Leu Cys Ser Pro Ser Tyr Val Ala Val Ala Thr Ser
65                  70                  75                  80

Phe Ser Pro Arg Glu Asp Asp Asp Gly Gly Gly Gly Asn Phe Ser Thr
                85                  90                  95

Ala Asp Gln Leu Glu Met Met Thr Glu Leu Leu Gly Gly Asp Met Val
            100                 105                 110

Asn Gln Ser Phe Ile Cys Asp Pro Asp Asp Glu Thr Phe Ile Lys Asn
        115                 120                 125

Ile Ile Ile Gln Asp Cys Met Glu Ser Gly Phe Ser Ala Ala Ala Lys
    130                 135                 140

Leu Val Ser Glu Lys Leu Ala Ser Tyr Gln Ala Ala Arg Lys Asp Ser
145                 150                 155                 160

Thr Ser Leu Ser Pro Ala Arg Gly His Ser Val Cys Ser Thr Ser Ser
                165                 170                 175

Leu Tyr Leu Gln Asp Leu Thr Ala Ala Ala Ser Glu Cys Ile Asp Pro
            180                 185                 190

Ser Val Val Phe Pro Tyr Pro Leu Asn Asp Ser Ser Ser Pro Lys Ser
        195                 200                 205

Cys Thr Ser Ser Asp Ser Thr Ala Phe Ser Pro Ser Ser Asp Ser Leu
    210                 215                 220

Leu Ser Ser Glu Ser Ser Pro Arg Ala Ser Pro Glu Pro Leu Val Leu
225                 230                 235                 240

His Glu Glu Thr Pro Pro Thr Thr Ser Ser Asp Ser Glu Glu Glu Gln
                245                 250                 255

Glu Asp Glu Glu Glu Ile Asp Val Val Ser Val Glu Lys Arg Gln Thr
            260                 265                 270

Pro Ala Lys Arg Ser Glu Ser Gly Ser Ser Pro Ser Arg Gly His Ser
        275                 280                 285

Lys Pro Pro His Ser Pro Leu Val Leu Lys Arg Cys His Val Ser Thr
    290                 295                 300

His Gln His Asn Tyr Ala Ala Pro Pro Ser Thr Arg Lys Asp Tyr Pro
305                 310                 315                 320

Ala Ala Lys Arg Ala Lys Leu Asp Ser Gly Arg Val Leu Lys Gln Ile
                325                 330                 335

Ser Asn Asn Arg Lys Cys Ser Ser Pro Arg Ser Ser Asp Thr Glu Glu
            340                 345                 350

Asn Asp Lys Arg Arg Thr His Asn Val Leu Glu Arg Gln Arg Arg Asn
        355                 360                 365

Glu Leu Lys Arg Ser Phe Phe Ala Leu Arg Asp Gln Ile Pro Glu Leu
    370                 375                 380

Glu Asn Asn Glu Lys Ala Pro Lys Val Val Ile Leu Lys Lys Ala Thr
385                 390                 395                 400

Ala Tyr Ile Leu Ser Ile Gln Ala Asp Glu His Lys Leu Thr Ser Glu
                405                 410                 415

Lys Asp Leu Leu Arg Lys Arg Arg Glu Gln Leu Lys His Lys Leu Glu
            420                 425                 430

Gln Leu Arg Asn Ser Gly Ala
        435
```

<210> SEQ ID NO 155
<211> LENGTH: 1024
<212> TYPE: DNA
<213> ORGANISM: Artificial Sequence
<220> FEATURE:
<223> OTHER INFORMATION: oligonucleotide

<400> SEQUENCE: 155
atgcccctca acgtgaactt caccaacagg aactatgacc tcgactacga ctccgtacag 60
ccctatttca tctgcgacga ggaagagaat ttctatcacc agcaacagca gagcgagctg 120
cagccgcccg cgcccagtga ggatatctgg aagaaattcg agctgcttcc cacccccgccc 180 ctgtccccga gccgccgctc cgggctctgc tctccatcct atgttgcggt cgctacgtcc 240
ttctccccaa gggaagacga tgacggcggc ggtggcaact tctccaccgc cgatcagctg 300
gagatgatga ccgagttact tggaggagac atggtgaacc agagcttcat ctgcgatcct 360
gacgacgaga ccttcatcaa gaacatcatc atccaggact gtatggagag cggtttctca 420
gccgctgcca agctggtctc ggagaagctg gcctcctacc aggctgcgcg caaagacagc 480
accagcctga gccccgcccg cgggcacagc gtctgctcca cctccagcct gtacctgcag 540
gacctcaccg ccgccgcgtc cgagtgcatt gacccctcag tggtctttcc ctacccgctc 600
aacgacagca gctcgcccaa atcctgtacc tcgtccgatt ccacggcctt ctctccttcc 660
tcggactcgc tgctgtcctc cgagtcctcc ccacgggcca gccctgagcc cctagtgctg 720
catgaggaga caccgcccac caccagcagc gactctgaag aagagcaaga agatgaggaa 780
gaaattgatg tggtgtctgt ggagaagagg caaacccctg ccaagaggtc ggagtcgggc 840
tcatctccat cccgaggcca cagcaaacct ccgcacagcc cactggtcct caagaggtgc 900
cacgtctcca ctcaccagca caactacgcc gcaccccct ccacaaggaa ggactatcca 960
gctgccaaga gggccaagtt ggacagtggc agggtcctga agcagatcag caacaaccgc 1020
aagt 1024

<210> SEQ ID NO 156
<211> LENGTH: 439
<212> TYPE: PRT
<213> ORGANISM: Artificial Sequence
<220> FEATURE:
<223> OTHER INFORMATION: peptide

<400> SEQUENCE: 156

Met Pro Leu Asn Val Asn Phe Thr Asn Arg Asn Tyr Asp Leu Asp Tyr
1 5 10 15

Asp Ser Val Gln Pro Tyr Phe Ile Cys Asp Glu Glu Glu Asn Phe Tyr
20 25 30

His Gln Gln Gln Gln Ser Glu Leu Gln Pro Pro Ala Pro Ser Glu Asp
35 40 45

Ile Trp Lys Lys Phe Glu Leu Leu Pro Thr Pro Pro Leu Ser Pro Ser
50 55 60

Arg Arg Ser Gly Leu Cys Ser Pro Ser Tyr Val Ala Val Ala Thr Ser
65 70 75 80

Phe Ser Pro Arg Glu Asp Asp Asp Gly Gly Gly Gly Asn Phe Ser Thr
85 90 95

Ala Asp Gln Leu Glu Met Met Thr Glu Leu Leu Gly Gly Asp Met Val
100 105 110

Asn Gln Ser Phe Ile Cys Asp Pro Asp Asp Glu Thr Phe Ile Lys Asn
115 120 125

```
Ile Ile Ile Gln Asp Cys Met Trp Ser Gly Phe Ser Ala Ala Ala Lys
    130                 135                 140

Leu Val Ser Glu Lys Leu Ala Ser Tyr Gln Ala Ala Arg Lys Asp Ser
145                 150                 155                 160

Thr Ser Leu Ser Pro Ala Arg Gly His Ser Val Cys Ser Thr Ser Ser
                165                 170                 175

Leu Tyr Leu Gln Asp Leu Thr Ala Ala Ala Ser Glu Cys Ile Asp Pro
            180                 185                 190

Ser Val Val Phe Pro Tyr Pro Leu Asn Asp Ser Ser Ser Pro Lys Ser
        195                 200                 205

Cys Thr Ser Ser Asp Ser Thr Ala Phe Ser Pro Ser Ser Asp Ser Leu
    210                 215                 220

Leu Ser Ser Glu Ser Ser Pro Arg Ala Ser Pro Glu Pro Leu Val Leu
225                 230                 235                 240

His Glu Glu Thr Pro Pro Thr Thr Ser Ser Asp Ser Glu Glu Glu Gln
                245                 250                 255

Glu Asp Glu Glu Glu Ile Asp Val Val Ser Val Glu Lys Arg Gln Thr
            260                 265                 270

Pro Ala Lys Arg Ser Glu Ser Gly Ser Ser Pro Ser Arg Gly His Ser
        275                 280                 285

Lys Pro Pro His Ser Pro Leu Val Leu Lys Arg Cys His Val Ser Thr
    290                 295                 300

His Gln His Asn Tyr Ala Ala Pro Pro Ser Thr Arg Lys Asp Tyr Pro
305                 310                 315                 320

Ala Ala Lys Arg Ala Lys Leu Asp Ser Gly Arg Val Leu Lys Gln Ile
                325                 330                 335

Ser Asn Asn Arg Lys Cys Ser Ser Pro Arg Ser Ser Asp Thr Glu Glu
            340                 345                 350

Asn Asp Lys Arg Arg Thr His Asn Val Leu Glu Arg Gln Arg Arg Asn
        355                 360                 365

Glu Leu Lys Arg Ser Phe Phe Ala Leu Arg Asp Gln Ile Pro Glu Leu
    370                 375                 380

Glu Asn Asn Glu Lys Ala Pro Lys Val Asp Ile Leu Lys Lys Ala Thr
385                 390                 395                 400

Ala Tyr Ile Leu Ser Ile Gln Ala Asp Glu His Lys Leu Thr Ser Glu
                405                 410                 415

Lys Asp Leu Leu Arg Lys Arg Arg Glu Gln Leu Lys His Lys Leu Glu
            420                 425                 430

Gln Leu Arg Asn Ser Gly Ala
        435
```

<210> SEQ ID NO 157
<211> LENGTH: 1024
<212> TYPE: DNA
<213> ORGANISM: Artificial Sequence
<220> FEATURE:
<223> OTHER INFORMATION: oligonucleotide

<400> SEQUENCE: 157

```
atgcccctca acgtgaactt caccaacagg aactatgacc tcgactacga ctccgtacag     60

ccctatttca tctgcgacga ggaagagaat ttctatcacc agcaacagca gagcgagctg    120

cagccgcccg cgcccagtga ggatatctgg aagaaattcg agctgcttcc cacccccgccc    180

ctgtccccga gccgccgctc cgggctctgc tctccatcct atgttgcggt cgctacgtcc    240
```

```
ttctccccaa gggaagacga tgacggcggc ggtggcaact tctccaccgc cgatcagctg    300

gagatgatga ccgagttact tggaggagac atggtgaacc agagcttcat ctgcgatcct    360

gacgacgaga ccttcatcaa gaacatcatc atccaggact gtatgtggag cggtttctca    420

gccgctgcca agctggtctc ggagaagctg gcctcctacc aggctgcgcg caaagacagc    480

accagcctga gccccgcccg cgggcacagc gtctgctcca cctccagcct gtacctgcag    540

gacctcaccg ccgccgcgtc cgagtgcatt gacccctcag tggtctttcc ctacccgctc    600

aacgacagca gctcgcccaa atcctgtacc tcgtccgatt ccacggcctt ctctccttcc    660

tcggactcgc tgctgtcctc cgagtcctcc ccacgggcca gccctgagcc cctagtgctg    720

catgaggaga caccgcccac caccagcagc gactctgaag aagagcaaga agatgaggaa    780

gaaattgatg tggtgtctgt ggagaagagg caaacccctg ccaagaggtc ggagtcgggc    840

tcatctccat cccgaggcca cagcaaacct ccgcacagcc cactggtcct caagaggtgc    900

cacgtctcca ctcaccagca caactacgcc gcaccccccct ccacaaggaa ggactatcca    960

gctgccaaga gggccaagtt ggacagtggc agggtcctga agcagatcag caacaaccgc   1020

aagt                                                                1024
```

```
<210> SEQ ID NO 158
<211> LENGTH: 439
<212> TYPE: PRT
<213> ORGANISM: Artificial Sequence
<220> FEATURE:
<223> OTHER INFORMATION: peptide

<400> SEQUENCE: 158

Met Pro Leu Asn Val Asn Phe Thr Asn Arg Asn Tyr Asp Leu Asp Tyr
1               5                   10                  15

Asp Ser Val Gln Pro Tyr Phe Ile Cys Asp Glu Glu Glu Asn Phe Tyr
            20                  25                  30

His Gln Gln Gln Gln Ser Glu Leu Gln Pro Pro Ala Pro Ser Glu Asp
        35                  40                  45

Ile Trp Lys Lys Phe Glu Leu Leu Pro Thr Pro Pro Leu Ser Pro Ser
    50                  55                  60

Arg Arg Ser Gly Leu Cys Ser Pro Ser Tyr Val Ala Val Ala Thr Ser
65                  70                  75                  80

Phe Ser Pro Arg Glu Asp Asp Asp Gly Gly Gly Gly Asn Phe Ser Thr
                85                  90                  95

Ala Asp Gln Leu Glu Met Met Thr Glu Leu Leu Gly Gly Asp Met Val
            100                 105                 110

Asn Gln Ser Phe Ile Cys Asp Pro Asp Asp Glu Thr Phe Ile Lys Asn
        115                 120                 125

Ile Ile Ile Gln Asp Cys Met Trp Ser Gly Phe Ser Ala Ala Ala Lys
    130                 135                 140

Leu Val Ser Glu Lys Leu Ala Ser Tyr Gln Ala Ala Arg Lys Asp Ser
145                 150                 155                 160

Thr Ser Leu Ser Pro Ala Arg Gly His Ser Val Cys Ser Thr Ser Ser
                165                 170                 175

Leu Tyr Leu Gln Asp Leu Thr Ala Ala Ala Ser Glu Cys Ile Asp Pro
            180                 185                 190

Ser Val Val Phe Pro Tyr Pro Leu Asn Asp Ser Ser Ser Pro Lys Ser
        195                 200                 205

Cys Thr Ser Ser Asp Ser Thr Ala Phe Ser Pro Ser Ser Asp Ser Leu
    210                 215                 220
```

```
Leu Ser Ser Glu Ser Ser Pro Arg Ala Ser Pro Glu Pro Leu Val Leu
225                 230                 235                 240

His Glu Glu Thr Pro Pro Thr Thr Ser Ser Asp Ser Glu Glu Glu Gln
                245                 250                 255

Glu Asp Glu Glu Glu Ile Asp Val Val Ser Val Glu Lys Arg Gln Thr
            260                 265                 270

Pro Ala Lys Arg Ser Glu Ser Gly Ser Ser Pro Ser Arg Gly His Ser
        275                 280                 285

Lys Pro Pro His Ser Pro Leu Val Leu Lys Arg Cys His Val Ser Thr
    290                 295                 300

His Gln His Asn Tyr Ala Ala Pro Pro Ser Thr Arg Lys Asp Tyr Pro
305                 310                 315                 320

Ala Ala Lys Arg Ala Lys Leu Asp Ser Gly Arg Val Leu Lys Gln Ile
                325                 330                 335

Ser Asn Asn Arg Lys Cys Ser Ser Pro Arg Ser Ser Asp Thr Glu Glu
            340                 345                 350

Asn Asp Lys Arg Arg Thr His Asn Val Leu Glu Arg Gln Arg Arg Asn
        355                 360                 365

Glu Leu Lys Arg Ser Phe Phe Ala Leu Arg Asp Gln Ile Pro Glu Leu
    370                 375                 380

Glu Asn Asn Glu Lys Ala Pro Lys Val Val Ile Leu Lys Lys Ala Thr
385                 390                 395                 400

Ala Tyr Ile Leu Ser Ile Gln Ala Asp Glu His Lys Leu Thr Ser Glu
                405                 410                 415

Lys Asp Leu Pro Arg Lys Arg Arg Glu Gln Leu Lys His Lys Leu Glu
            420                 425                 430

Gln Leu Arg Asn Ser Gly Ala
        435
```

<210> SEQ ID NO 159
<211> LENGTH: 1024
<212> TYPE: DNA
<213> ORGANISM: Artificial Sequence
<220> FEATURE:
<223> OTHER INFORMATION: oligonucleotide

<400> SEQUENCE: 159

```
atgcccctca acgtgaactt caccaacagg aactatgacc tcgactacga ctccgtacag     60

ccctatttca tctgcgacga ggaagagaat ttctatcacc agcaacagca gagcgagctg    120

cagccgcccg cgcccagtga ggatatctgg aagaaattcg agctgcttcc cacccgccc    180

ctgtccccga gccgccgctc cgggctctgc tctccatcct atgttgcggt cgctacgtcc    240

ttctccccaa gggaagacga tgacggcggc ggtggcaact tctccaccgc cgatcagctg    300

gagatgatga ccgagttact tggaggagac atggtgaacc agagcttcat ctgcgatcct    360

gacgacgaga ccttcatcaa gaacatcatc atccaggact gtatgtggag cggtttctca    420

gccgctgcca agctggtctc ggagaagctg gcctcctacc aggctgcgcg caaagacagc    480

accagcctga gccccgcccg cgggcacagc gtctgctcca cctccagcct gtacctgcag    540

gacctcaccg ccgccgcgtc cgagtgcatt gacccctcag tggtctttcc ctacccgctc    600

aacgacagca gctcgcccaa atcctgtacc tcgtccgatt ccacggcctt ctctccttcc    660

tcggactcgc tgctgtcctc cgagtcctcc ccacgggcca gccctgagcc cctagtgctg    720

catgaggaga caccgcccac caccagcagc gactctgaag aagagcaaga agatgaggaa    780
```

-continued

```
gaaattgatg tggtgtctgt ggagaagagg caaacccctg ccaagaggtc ggagtcgggc    840

tcatctccat cccgaggcca cagcaaacct ccgcacagcc cactggtcct caagaggtgc    900

cacgtctcca ctcaccagca caactacgcc gcaccccct ccacaaggaa ggactatcca     960

gctgccaaga gggccaagtt ggacagtggc agggtcctga agcagatcag caacaaccgc   1020

aagt                                                                1024
```

```
<210> SEQ ID NO 160
<211> LENGTH: 368
<212> TYPE: PRT
<213> ORGANISM: Artificial Sequence
<220> FEATURE:
<223> OTHER INFORMATION: peptide

<400> SEQUENCE: 160

Met Asp Phe Asp Ser Tyr Gln His Tyr Phe Tyr Asp Tyr Asp Cys Gly
1               5                   10                  15

Glu Asp Phe Tyr Arg Ser Thr Ala Pro Ser Glu Asp Ile Trp Lys Lys
            20                  25                  30

Phe Glu Leu Val Pro Ser Pro Pro Thr Ser Pro Pro Trp Gly Ser Gly
        35                  40                  45

Pro Gly Ala Val Asp Pro Ala Ser Gly Ile Asn Pro Gly Glu Pro Trp
    50                  55                  60

Pro Gly Gly Gly Ala Gly Asp Glu Ala Glu Ser Arg Gly His Ser Lys
65                  70                  75                  80

Ala Trp Gly Arg Asn Tyr Ala Ser Ile Ile Arg Arg Asp Cys Met Glu
                85                  90                  95

Ser Gly Phe Ser Ala Arg Glu Arg Leu Glu Arg Val Val Ser Asp Arg
            100                 105                 110

Leu Ala Pro Gly Ala Pro Arg Gly Asn Pro Pro Lys Ala Pro Ala Thr
        115                 120                 125

Pro Asp Gly Thr Pro Ser Leu Glu Ala Ser Asn Pro Ala Pro Ala Thr
    130                 135                 140

Gln Cys Gln Leu Gly Glu Pro Lys Thr Gln Ala Cys Ser Gly Ser Glu
145                 150                 155                 160

Ser Pro Ser Asp Ser Glu Gly Glu Glu Ile Asp Val Val Thr Val Glu
                165                 170                 175

Lys Arg Arg Ser Leu Asp Ile Arg Lys Pro Val Thr Ile Thr Val Arg
            180                 185                 190

Ala Asp Pro Leu Asp Pro Cys Met Lys His Phe His Ile Ser Ile His
        195                 200                 205

Gln Gln Gln His Asn Tyr Ala Ala Arg Phe Pro Pro Glu Ser Cys Ser
    210                 215                 220

Gln Glu Gly Asp Pro Glu Pro Gly Pro Gln Glu Glu Ala Pro Glu Ile
225                 230                 235                 240

Glu Ala Pro Lys Glu Lys Glu Glu Glu Glu Glu Glu Glu Glu Glu Glu
                245                 250                 255

Glu Ile Val Ser Pro Pro Pro Val Gly Ser Glu Ala Pro Gln Ser Cys
            260                 265                 270

His Pro Lys Pro Val Ser Ser Asp Thr Glu Asp Val Thr Lys Arg Lys
        275                 280                 285

Asn His Asn Phe Leu Glu Arg Lys Arg Arg Asn Asp Leu Arg Ser Arg
    290                 295                 300

Phe Leu Ala Leu Arg Asp Gln Val Pro Thr Leu Ala Ser Cys Ser Lys
305                 310                 315                 320
```

Ala Pro Lys Val Val Ile Leu Ser Lys Ala Leu Glu Tyr Leu Gln Ala
325 330 335

Leu Val Gly Ala Glu Lys Lys Met Ala Thr Glu Lys Arg Gln Leu Arg
340 345 350

Cys Arg Gln Gln Gln Leu Gln Lys Arg Ile Ala Tyr Leu Ser Gly Tyr
355 360 365

<210> SEQ ID NO 161
<211> LENGTH: 1024
<212> TYPE: DNA
<213> ORGANISM: Artificial Sequence
<220> FEATURE:
<223> OTHER INFORMATION: oligonucleotide

<400> SEQUENCE: 161
atggacttcg actcgtatca gcactatttc tacgactatg actgcggaga ggatttctac 60
cgctccacgg cgcccagcga ggacatctgg aagaaattcg agctggtgcc gtcgcccccc 120
acgtcgccgc cctggggctc cggtcccggc gccgtggacc cagcctctgg gattaatccc 180
ggggagccgt ggcctggagg gggtgccggg gacgaggcgg aatctcgggg ccattcgaaa 240
gcctggggca ggaattatgc ttccatcatt cgccgtgact gcatggagag cggcttctcc 300
gcccgagaac ggctggagag agtggtgagc gacaggctgg ccccaggcgc gccccggggg 360
aacccgccca aagcgcccgc taccccggac ggcactccta gtctggaagc cagtaacccg 420
gcgcccgcca cccaatgtca gctgggcgag cccaagactc aggcctgctc cgggtccgag 480
agccccagcg attctgaagg tgaagagatt gacgtggtga ccgtggagaa gaggcgatct 540
ctggacatcc gaaagccagt caccatcacg gtgcgagcag acccccctgga cccctgcatg 600 aagcacttcc atatctctat ccaccaacag cagcataact atgctgcccg ttttcctcca 660
gaaagttgct ctcaagaggg ggatcctgag ccaggtcccc aggaagaggc tccggagata 720
gaagctccca aggagaaaga ggaggaggaa gaggaagagg aggaagaaga gattgtgagc 780
cccccacctg tcggaagtga ggctccccag tcctgccacc ccaaacctgt cagttctgac 840
actgaggacg tgaccaagag gaagaaccat aacttcttgg aacgaaaaag gaggaatgac 900
ctccgctccc ggttcctagc cctgcgggac caggttccca ccctggccag ctgctctaag 960
gcccccaaag tcgtgatcct cagcaaggcg ttagaatact tgcaggcttt ggtgggggct 1020
gaaa 1024

<210> SEQ ID NO 162
<211> LENGTH: 368
<212> TYPE: PRT
<213> ORGANISM: Artificial Sequence
<220> FEATURE:
<223> OTHER INFORMATION: peptide

<400> SEQUENCE: 162

Met Asp Phe Asp Ser Tyr Gln His Tyr Phe Tyr Asp Tyr Asp Cys Gly
1 5 10 15

Glu Asp Phe Tyr Arg Ser Thr Ala Pro Ser Glu Asp Ile Trp Lys Lys
20 25 30

Phe Glu Leu Val Pro Ser Pro Pro Thr Ser Pro Pro Trp Gly Ser Gly
35 40 45

Pro Gly Ala Val Asp Pro Ala Ser Gly Ile Asn Pro Gly Glu Pro Trp
50 55 60

Pro Gly Gly Gly Ala Gly Asp Glu Ala Glu Ser Arg Gly His Ser Lys

```
65                  70                  75                  80

Ala Trp Gly Arg Asn Tyr Ala Ser Ile Ile Arg Arg Asp Cys Met Trp
                85                  90                  95

Ser Gly Phe Ser Ala Arg Glu Arg Leu Glu Arg Val Val Ser Asp Arg
            100                 105                 110

Leu Ala Pro Gly Ala Pro Arg Gly Asn Pro Pro Lys Ala Pro Ala Thr
        115                 120                 125

Pro Asp Gly Thr Pro Ser Leu Glu Ala Ser Asn Pro Ala Pro Ala Thr
    130                 135                 140

Gln Cys Gln Leu Gly Glu Pro Lys Thr Gln Ala Cys Ser Gly Ser Glu
145                 150                 155                 160

Ser Pro Ser Asp Ser Glu Gly Glu Glu Ile Asp Val Val Thr Val Glu
                165                 170                 175

Lys Arg Arg Ser Leu Asp Ile Arg Lys Pro Val Thr Ile Thr Val Arg
            180                 185                 190

Ala Asp Pro Leu Asp Pro Cys Met Lys His Phe His Ile Ser Ile His
        195                 200                 205

Gln Gln Gln His Asn Tyr Ala Ala Arg Phe Pro Pro Glu Ser Cys Ser
    210                 215                 220

Gln Glu Gly Asp Pro Glu Pro Gly Pro Gln Glu Glu Ala Pro Glu Ile
225                 230                 235                 240

Glu Ala Pro Lys Glu Lys Glu Glu Glu Glu Glu Glu Glu Glu Glu Glu
                245                 250                 255

Glu Ile Val Ser Pro Pro Pro Val Gly Ser Glu Ala Pro Gln Ser Cys
            260                 265                 270

His Pro Lys Pro Val Ser Ser Asp Thr Glu Asp Val Thr Lys Arg Lys
        275                 280                 285

Asn His Asn Phe Leu Glu Arg Lys Arg Arg Asn Asp Leu Arg Ser Arg
    290                 295                 300

Phe Leu Ala Leu Arg Asp Gln Val Pro Thr Leu Ala Ser Cys Ser Lys
305                 310                 315                 320

Ala Pro Lys Val Asp Ile Leu Ser Lys Ala Leu Glu Tyr Leu Gln Ala
                325                 330                 335

Leu Val Gly Ala Glu Lys Lys Met Ala Thr Glu Lys Arg Gln Leu Arg
            340                 345                 350

Cys Arg Gln Gln Gln Leu Gln Lys Arg Ile Ala Tyr Leu Ser Gly Tyr
        355                 360                 365
```

<210> SEQ ID NO 163
<211> LENGTH: 1024
<212> TYPE: DNA
<213> ORGANISM: Artificial Sequence
<220> FEATURE:
<223> OTHER INFORMATION: oligonucleotide

<400> SEQUENCE: 163

```
atggacttcg actcgtatca gcactatttc tacgactatg actgcggaga ggatttctac      60

cgctccacgg cgcccagcga ggacatctgg aagaaattcg agctggtgcc gtcgcccccc     120

acgtcgccgc cctggggctc cggtcccggc gccgtggacc cagcctctgg gattaatccc     180

ggggagccgt ggcctggagg gggtgccggg gacgaggcgg aatctcgggg ccattcgaaa     240

gcctggggca ggaattatgc ttccatcatt cgccgtgact gcatgtggag cggcttctcc     300

gcccgagaac ggctggagag agtggtgagc gacaggctgg ccccaggcgc gccccggggg     360

aacccgccca aagcgcccgc taccccggac ggcactccta gtctggaagc cagtaacccg     420
```

```
gcgcccgcca cccaatgtca gctgggcgag cccaagactc aggcctgctc cgggtccgag    480

agccccagcg attctgaagg tgaagagatt gacgtggtga ccgtggagaa gaggcgatct    540

ctggacatcc gaaagccagt caccatcacg gtgcgagcag accccctgga cccctgcatg    600

aagcacttcc atatctctat ccaccaacag cagcataact atgctgcccg ttttcctcca    660

gaaagttgct ctcaagaggg ggatcctgag ccaggtcccc aggaagaggc tccggagata    720

gaagctccca aggagaaaga ggaggaggaa gaggaagagg aggaagaaga gattgtgagc    780

cccccacctg tcggaagtga ggctccccag tcctgccacc ccaaacctgt cagttctgac    840

actgaggacg tgaccaagag gaagaaccat aacttcttgg aacgaaaaag gaggaatgac    900

ctccgctccc ggttcctagc cctgcgggac caggttccca ccctggccag ctgctctaag    960

gcccccaaag tcgacatcct cagcaaggcg ttagaatact tgcaggcttt ggtgggggct   1020

gaaa                                                                1024
```

<210> SEQ ID NO 164
<211> LENGTH: 365
<212> TYPE: PRT
<213> ORGANISM: Artificial Sequence
<220> FEATURE:
<223> OTHER INFORMATION: peptide

<400> SEQUENCE: 164

```
Met Asp Phe Asp Ser Tyr Gln His Tyr Phe Tyr Asp Tyr Asp Cys Gly
1               5                   10                  15

Glu Asp Phe Tyr Arg Ser Thr Ala Pro Ser Glu Asp Ile Trp Lys Lys
            20                  25                  30

Phe Glu Leu Val Pro Ser Pro Pro Thr Ser Pro Pro Trp Gly Ser Gly
        35                  40                  45

Pro Gly Ala Val Asp Pro Ala Ser Gly Ile Asn Pro Gly Glu Pro Trp
    50                  55                  60

Pro Gly Gly Gly Ala Gly Asp Glu Ala Glu Ser Arg Gly His Ser Lys
65                  70                  75                  80

Ala Trp Gly Arg Asn Tyr Ala Ser Ile Ile Arg Arg Asp Cys Met Trp
                85                  90                  95

Ser Gly Phe Ser Ala Arg Glu Arg Leu Glu Arg Val Val Ser Asp Arg
            100                 105                 110

Leu Ala Pro Gly Ala Pro Arg Gly Asn Pro Pro Lys Ala Pro Ala Thr
        115                 120                 125

Pro Asp Gly Thr Pro Ser Leu Glu Ala Ser Asn Pro Ala Pro Ala Thr
    130                 135                 140

Gln Cys Gln Leu Gly Glu Pro Lys Thr Gln Ala Cys Ser Gly Ser Glu
145                 150                 155                 160

Ser Pro Ser Asp Ser Glu Gly Glu Glu Ile Asp Val Val Thr Val Glu
                165                 170                 175

Lys Arg Arg Ser Leu Asp Ile Arg Lys Pro Val Thr Ile Thr Val Arg
            180                 185                 190

Ala Asp Pro Leu Asp Pro Cys Met Lys His Phe His Ile Ser Ile His
        195                 200                 205

Gln Gln Gln His Asn Tyr Ala Ala Arg Phe Pro Pro Glu Ser Cys Ser
    210                 215                 220

Gln Glu Gly Asp Pro Glu Pro Gly Pro Gln Glu Glu Ala Pro Glu Ile
225                 230                 235                 240

Glu Ala Pro Lys Glu Lys Glu Glu Glu Glu Glu Glu Glu Glu Glu Glu
```

```
                245                 250                 255

Glu Ile Val Ser Pro Pro Pro Val Gly Ser Glu Ala Pro Gln Ser Cys
            260                 265                 270

His Pro Lys Pro Val Ser Ser Asp Thr Glu Asp Val Thr Lys Arg Lys
        275                 280                 285

Phe Leu Glu Arg Lys Arg Arg Asn Asp Leu Arg Ser Arg Phe Leu Ala
    290                 295                 300

Leu Arg Asp Gln Val Pro Thr Leu Ala Ser Cys Ser Lys Ala Pro Lys
305                 310                 315                 320

Val Val Ile Leu Ser Lys Ala Leu Glu Tyr Leu Gln Ala Leu Val Gly
                325                 330                 335

Ala Glu Lys Lys Met Ala Thr Glu Lys Arg Gln Pro Arg Cys Arg Gln
            340                 345                 350

Gln Gln Leu Gln Lys Arg Ile Ala Tyr Leu Ser Gly Tyr
        355                 360                 365
```

<210> SEQ ID NO 165
<211> LENGTH: 1024
<212> TYPE: DNA
<213> ORGANISM: Artificial Sequence
<220> FEATURE:
<223> OTHER INFORMATION: oligonucleotide

<400> SEQUENCE: 165

```
atggacttcg actcgtatca gcactatttc tacgactatg actgcggaga ggatttctac      60

cgctccacgg cgcccagcga ggacatctgg aagaaattcg agctggtgcc gtcgccccc      120

acgtcgccgc cctggggctc cggtcccggc gccgtggacc cagcctctgg gattaatccc     180

ggggagccgt ggcctggagg gggtgccggg gacgaggcgg aatctcgggg ccattcgaaa     240

gcctggggca ggaattatgc ttccatcatt cgccgtgact gcatgtggag cggcttctcc     300

gcccgagaac ggctggagag agtggtgagc gacaggctgg ccccaggcgc gccccggggg     360

aacccgccca aagcgcccgc taccccggac ggcactccta gtctggaagc cagtaacccg     420

gcgcccgcca cccaatgtca gctgggcgag cccaagactc aggcctgctc cgggtccgag     480

agccccagcg attctgaagg tgaagagatt gacgtggtga ccgtggagaa gaggcgatct     540

ctggacatcc gaaagccagt caccatcacg gtgcgagcag acccccctgga cccctgcatg    600

aagcacttcc atatctctat ccaccaacag cagcataact atgctgcccg ttttcctcca     660

gaaagttgct ctcaagaggg ggatcctgag ccaggtcccc aggaagaggc tccggagata     720

gaagctccca aggagaaaga ggaggaggaa gaggaagagg aggaagaaga gattgtgagc     780

cccccacctg tcggaagtga ggctccccag tcctgccacc ccaaacctgt cagttctgac     840

actgaggacg tgaccaagag gaagaaccat aacttcttgg aacgaaaaag gaggaatgac     900

ctccgctccc ggttcctagc cctgcgggac caggttccca ccctggccag ctgctctaag     960

gcccccaaag tcgtgatcct cagcaaggcg ttagaatact tgcaggcttt ggtgggggct    1020

gaaa                                                                 1024
```